(12) United States Patent
Shepard et al.

(10) Patent No.: US 12,006,320 B2
(45) Date of Patent: *Jun. 11, 2024

(54) HETEROCYCLIC DERIVATIVES AS PI3K INHIBITORS

(71) Applicant: Incyte Corporation, Wilmington, DE (US)

(72) Inventors: Stacey Shepard, Wilmington, DE (US); Yanran Ai, West Chester, PA (US); Andrew P. Combs, Kennett Square, PA (US); Nikoo Falahatpisheh, Wilmington, DE (US); Lixin Shao, Wilmington, DE (US); Artem Shvartsbart, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 233 days.

This patent is subject to a terminal disclaimer.

(21) Appl. No.: 17/356,986

(22) Filed: Jun. 24, 2021

(65) Prior Publication Data

US 2021/0395258 A1 Dec. 23, 2021

Related U.S. Application Data

(63) Continuation of application No. 16/681,014, filed on Nov. 12, 2019, now Pat. No. 11,078,204.

(60) Provisional application No. 62/760,515, filed on Nov. 13, 2018.

(51) Int. Cl.
| | | |
|---|---|---|
| *A61K 31/4985* | (2006.01) | |
| *A61K 31/53* | (2006.01) | |
| *A61P 9/00* | (2006.01) | |
| *A61P 25/00* | (2006.01) | |
| *A61P 35/00* | (2006.01) | |
| *A61P 37/00* | (2006.01) | |
| *C07D 407/04* | (2006.01) | |
| *C07D 487/04* | (2006.01) | |
| *C07D 519/00* | (2006.01) | |

(52) U.S. Cl.
CPC ......... *C07D 487/04* (2013.01); *C07D 519/00* (2013.01)

(58) Field of Classification Search
CPC ....... A61K 31/4985; A61K 31/53; A61P 9/00; A61P 25/00; A61P 35/00; A61P 37/00; C07D 407/04; C07D 519/00
See application file for complete search history.

(56) References Cited

U.S. PATENT DOCUMENTS

| | | | |
|---|---|---|---|
| 5,521,184 | A | 5/1996 | Zimmerman |
| 8,377,940 | B2 | 2/2013 | Clayton et al. |
| 8,748,426 | B2 | 6/2014 | Jadhav et al. |
| 11,078,204 | B2 | 8/2021 | Shepard et al. |
| 11,161,838 | B2 | 11/2021 | Shepard et al. |
| 11,396,502 | B2 | 7/2022 | Shepard et al. |
| 2007/0105864 | A1 | 5/2007 | Guzi et al. |
| 2007/0225286 | A1 | 10/2007 | Ren et al. |
| 2011/0245247 | A1 | 10/2011 | Braje et al. |
| 2013/0203995 | A1 | 8/2013 | Boyd et al. |
| 2017/0145002 | A1 | 5/2017 | Duggan |
| 2018/0086737 | A1 | 3/2018 | Argiriadi et al. |
| 2020/0148667 | A1 | 5/2020 | Shepard et al. |
| 2020/0148671 | A1 | 5/2020 | Shepard et al. |
| 2020/0148689 | A1 | 5/2020 | Shepard et al. |
| 2022/0340544 | A1 | 10/2022 | Shepard et al. |

FOREIGN PATENT DOCUMENTS

| | | |
|---|---|---|
| CN | 107417738 | 12/2017 |
| WO | WO 00/09495 | 2/2000 |
| WO | WO 00/053595 | 9/2000 |
| WO | WO 01/014402 | 3/2001 |
| WO | WO 01/064655 | 9/2001 |
| WO | WO 2002/000196 | 1/2002 |
| WO | WO 03/037347 | 5/2003 |
| WO | WO 03/024967 | 9/2003 |
| WO | WO 03/099771 | 12/2003 |
| WO | WO 04/005281 | 1/2004 |
| WO | WO 04/046120 | 8/2004 |
| WO | WO 04/080980 | 9/2004 |

(Continued)

OTHER PUBLICATIONS

Atzrodt et al., "The Renaissance of H/D Exchange," Angew. Chem. Int. Ed., 2007, 46:7744-7765.

(Continued)

*Primary Examiner* — Brenda L Coleman
(74) *Attorney, Agent, or Firm* — Fish & Richardson P.C.

(57) ABSTRACT

This application relates to compounds of Formula (I):

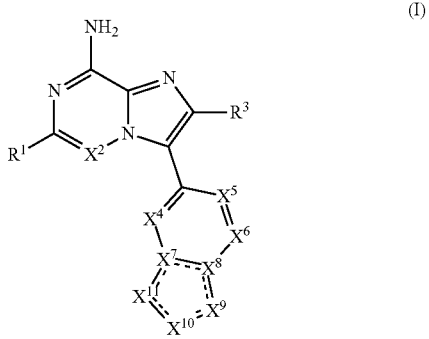

or pharmaceutically acceptable salts thereof, which are inhibitors of PI3K-γ which are useful for the treatment of disorders such as autoimmune diseases, cancer, cardiovascular diseases, and neurodegenerative diseases.

33 Claims, No Drawings

(56) References Cited

FOREIGN PATENT DOCUMENTS

| WO | WO 04/056786 | 10/2004 |
|---|---|---|
| WO | WO 05/028444 | 3/2005 |
| WO | WO 2005/047280 | 5/2005 |
| WO | WO 2006/020879 | 2/2006 |
| WO | WO 2006/038041 | 4/2006 |
| WO | WO 2006/056399 | 6/2006 |
| WO | WO 2007/016674 | 2/2007 |
| WO | WO 2007/021308 | 2/2007 |
| WO | WO 2007/021309 | 2/2007 |
| WO | WO 2007/095024 | 8/2007 |
| WO | WO 2008/047831 | 4/2008 |
| WO | WO 2008/130853 | 10/2008 |
| WO | WO 2008/150232 | 12/2008 |
| WO | WO 2008/150233 | 12/2008 |
| WO | WO 2009/100130 | 8/2009 |
| WO | WO 2009/148403 | 12/2009 |
| WO | WO 2010/019899 | 2/2010 |
| WO | WO 2010/136723 | 12/2010 |
| WO | WO 2010/148074 | 12/2010 |
| WO | WO 2011/008487 | 1/2011 |
| WO | WO 2011/006794 | 5/2011 |
| WO | WO 2011/075630 | 6/2011 |
| WO | WO 2011/075643 | 6/2011 |
| WO | WO 2011/080718 | 7/2011 |
| WO | WO 2011/084098 | 7/2011 |
| WO | WO 2011/087776 | 7/2011 |
| WO | WO 2011/130342 | 10/2011 |
| WO | WO 2011/143365 | 11/2011 |
| WO | WO 2013/000994 | 1/2013 |
| WO | WO 2013/033569 | 3/2013 |
| WO | WO 2013/151975 | 10/2013 |
| WO | WO 2014/028968 | 2/2014 |
| WO | WO 2014/075387 | 5/2014 |
| WO | WO 2014/154760 | 10/2014 |
| WO | WO 2016/012930 | 1/2016 |
| WO | WO 2016/130501 | 8/2016 |
| WO | WO 2016/176457 | 11/2016 |
| WO | WO 2017/055305 | 4/2017 |
| WO | WO 2017/153527 | 9/2017 |
| WO | WO 2017/223414 | 12/2017 |
| WO | WO 2018/055040 | 3/2018 |

OTHER PUBLICATIONS

Barber et al., "PI3Kgamma inhibition blocks glomerulonephritis and extends lifespan in a mouse model of systemic lupus," Nat. Medicine, 2005, 9:933-935.

Berod et al., "PI3Kγ deficiency delays the onset of experimental autoimmune encephalomyelitis and ameliorates its clinical outcome," Euro. J Immunol., 2011, 41:833-844.

Blom et al., "Optimizing Preparative LC-MS Configurations and Methods for Parallel Synthesis Purification," J Combi. Chem., 2003, 5:670-683.

Blom et al., "Preparative LC-MS Purification: Improved Compound Specific Method Optimization," J Combi. Chem., 2004, 6:874-883.

Blom et al., "Two-Pump At col. Dilution Configuration for Preparative LC-MS," J Combi. Chem., 2002, 4(4):295-301.

Brock et al., "Roles of G beta gamma in membrane recruitment and activation of p110 gamma/p101 phosphoinositide 3-kinase gamma," J Cell Biol., 2003, 160(1):89-99.

Camps et al., "Blockade of PI3Kγ suppresses joint inflammation and damage in mouse models of rheumatoid arthritis," Nat. Medicine, Sep. 2005, 11(9):936-943.

Cantley, "The phosphoinositide 3-kinase pathway," Science, 2002, 296(5573): 1655-7.

Carter et al., "Prioritization of driver mutations in pancreatic cancer using cancer-specific high-throughput annotation of somatic mutations (CHASM)," Cancer Biol. Ther., 2010, 10:582-587.

Comerford et al., "PI3Kγ drives priming and survival of autoreactive CD4(+) T cells during experimental autoimmune encephalomyelitis," PLOS one, 2012, 7(9):e45095.

Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol. Exp Ther. 2009, 328:758-765.

Doukas et al., "Phosphoinositide 3-kinase gamma/delta inhibition limits infarct size after myocardial ischemia/reperfusion injury," Proc. Natl. Acad. Sci. USA, 2006, 103:19866-19871.

El Khoury et al., "Ccr2 deficiency impairs microglial accumulation and accelerates progression of Alzheimer-like disease," Nat. Med., 2007, 13:432-438.

Falasca and Maffucci, "Targeting p110gamma in gastrointestinal cancers: attack on multiple fronts," Frontiers in Physiology, 2014, 5:1-10.

Giri et al., "Mechanism of amyloid peptide induced CCR5 expression in monocytes and its inhibition by siRNA for Egr-1," Am. J. Physiol. Cell Physiol., 2005, 289:C264-C276.

Gonzalez-Garcia et al., "Phosphatidylinositol 3-Kinase γ Inhibition Ameliorates Inflammation and Tumor Growth in a Model of Colitis-Associated Cancer," Gastroenterology, 2010, 138:1373-1384.

Hanahan and Weinberg, "Hallmarks of Cancer: The Next Generation," Cell, 2011, 144:646-674.

Hayer et al., "PI3Kgamma regulates cartilage damage in chronic inflammatory arthritis," FASB J, 2009, 23(12):4288-4298.

International Search Report and Written Opinion in International Application No. PCT/US2019/060852, dated May 6, 2020, 15 pages.

International Search Report and Written Opinion in International Application No. PCT/US2019/060923, dated Mar. 9, 2020, 15 pages.

International Search Report and Written Opinion in International Application No. PCT/US2019/060955, dated May 7, 2020, 17 pages.

International Preliminary Report on Patentability in International Application No. PCT/US2019/060923, dated May 27, 2021, 8 pages.

International Preliminary Report on Patentability in International Application No. PCTUS/2019/060955, dated May 27, 2021, 8 pages.

International Preliminary Report on Patentability in International Application No. PCT/US2019/060852, dated May 27, 2021, 8 pages.

Jimenez et al., "The p85 regulatory subunit controls sequential activation of phosphoinositide 3-kinase by Tyr kinases and Ras," J Biol Chem., 2002, 277(44):41556-62.

Kaneda et al., "Abstract 3650: PI3-kinase gamma controls the macrophage M1-M2 switch, thereby promoting tumor immunosuppression and progression," Cancer Res., Oct. 1, 2014, 74:(Suppl 19:Abstact 3650).

Kerekes et al., "Aurora kinase inhibitors based on the imidazo[1,2-a]pyrazine core: fluorine and deuterium incorporation improve oral absorption and exposure," J Med. Chem. 2011, 54:201-210.

Kolb et al., "Catalytic Asymmetric Dihydroxylation," Chem. Rev., 1994, 94(8):2483-2547.

Laffargue et al., "Phosphoinositide 3-kinase gamma is an essential amplifier of mast cell function," Immunity, 2002, 16:441-451.

Leahy et al., "Discovery of a novel series of potent and orally bioavailable phosphoinositide 3-kinase γ inhibitors," J Med Chem., Jun. 14, 2012, 55(11):5467-5482.

Li et al., "PI3Kγ inhibition alleviates symptoms and increases axon number in experimental autoimmune encephalomyelitis mice," Neuroscience, 2013, 253:89-99.

Lupia et al., "Ablation of phosphoinositide 3-kinase-gamma reduces the severity of acute pancreatitis," Am. J. Pathology, 2004, 165:2003-2011.

Martin et al., "PI3Kγ mediates Kaposi's sarcoma-associated herpes virus vGPCR-induced sarcomagenesis," Cancer Cell, 2011, 19:805-813.

Mejdrova et al., "Highly Selective Phosphatidylinositol 4-Kinase IIIb Inhibitors and Structural Insight into Their Mode of Action," J Med Chem., 2015, 58:3767-3793.

Moreno-Dorado et al., "Enantioselective synthesis of arylmethoxyacetic acid derivatives," Tetrahedron: Asymmetry, 2003, 14:503-510.

(56) References Cited

OTHER PUBLICATIONS

Passos et al., "Involvement of phosphoinositide 3-kinase gamma in the neuro-inflammatory response and cognitive impairments induced by beta-amyloid 1-40 peptide in mice," Brain Behav. Immun. 2010, 24:493-501.
Pemberton et al., "Discovery of Highly Isoform Selective Orally Bioavailable Phosphoinositide 3-Kinase (PI3K)-γ Inhibitors," J Med Chem., Jun. 28, 2018, 61(12):5435-5441.
Pinho et al., "Phosphoinositide-3 kinases critically regulate the recruitment and survival of eosinophils in vivo: importance for the resolution of allergic inflammation," Leukocyte Biology, 2005, 77:800-810.
Prete et al., "Defective dendritic cell migration and activation of adaptive immunity in PI3Kgamma-deficient mice," The EMBO Journal, 2004, 23:3505-3515.
Randis et al., "Role of PI3Kdelta and PI3Kgamma in inflammatory arthritis and tissue localization of neutrophils," Eur. J Immunol, 2008, 38:1215-1224.
Rodrigues et al., "Absence of PI3K gamma leads to increased leukocyte apoptosis and diminished severity of experimental auto-immune encephalomyelitis," J Neuroimmunol. 2010, 222:90-94.
Ruckle et al., "PI3Kgamma inhibition: towards an 'aspirin of the 21st century'?" Nat. Rev. Drug Discovery, 2006, 5:903-918.
Schmid et al., "Receptor tyrosine kinases and TLR/ILIRs unexpectedly activate myeloid cell PI3kγ, a single convergent point promoting tumor inflammation and progression," Cancer Cell, 2011, 19:715-727.
Schmidt et al., "Abstract 411: PI3 Kinase gamma control of Arginase-1 expression promotes tumor immunosuppression," Cancer Res., 2012, 72(Suppl 1): Abstract 411.
Sharpless, "The Osmium-Catalyzed Asymmetric Dihydroxylation: A New Ligand Class and a Process Improvement," J Org. Chem., 1992, 57(10):2768-2771.
Spicer et al., "Benzenesulphonamide inhibitors of the cytolytic protein perforin," Bioorg Med Chem Lett., Feb. 15, 2017, 27(4):1050-1054.
Subramaniam et al., "Targeting Nonclassical Oncogenes for Therapy in T-ALL," Cancer Cell, 2012, 21:459-472.
Thomas et al., "Airway inflammation: chemokine-induced neutrophilia and the class I phosphoinositide 3-kinases," Eur. J Immunol. 2005, 35:1283-1291.
Vanhaesebroeck et al., "Signalling by PI3k isoforms: insights from Gene-targeted mice," Trends Biochem Sci., 2005, 30(4):194-204.
Vecchione et al., "Protection from angiotensin II-mediated vasculotoxic and hypertensive response in mice lacking PI3K," J Exp. Med., 2005, 201:1217-1228.
Xu et al., "Design, synthesis and biological evaluation of deuterated nintedanib for improving pharmacokinetic properties," Label Compd. Radiopharm. 2015, 58:308-312.
Sigmaaldrich.com, "L-α-Phosphatidyl-D-myo-inositol 4,5-diphosphate, dioctanoyl," CAS 204858-53-7, retrieved from URL <https://www.sigmaaldrich.com/US/en/product/sigma/p3584?context=product>.

HETEROCYCLIC DERIVATIVES AS PI3K INHIBITORS

TECHNICAL FIELD

The present disclosure provides derivatives of heterocyclic compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knock-out or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., Nat. Rev. Drug Discovery, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinopohils to airways and degranulation of mast cells (see e.g. Laffargue et al., Immunity, 2002, 16, 441-451; Prete et al., The EMBO Journal, 2004, 23, 3505-3515; Pinho et al., L. Leukocyte Biology, 2005, 77, 800-810; Thomas et al., Eur. J. Immunol. 2005, 35, 1283-1291; Doukas et al., J. Pharmacol. Exp Ther. 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., Am. J. Pathology, 2004, 165, 2003-2011). PI3Kγ$^{-/-}$ mice were largely protected in four different models of rheumatoid arthritis (CIA, α-CII-IA, K/BxN serum transfer and TNF transgenic) and PI3Kγ inhibition suppressed the progression of joint inflammation and damage in the CIA and α-CII-IA models (see e.g., Camps et al., Nat. Medicine, 2005, 11, 939-943; Randis et al., Eur. J. Immunol, 2008, 38, 1215-1224; Hayer et al., FASB J., 2009, 4288-4298). In the MRL-lpr mouse model of human systemic lupus erythematous, inhibition of PI3Kγ reduced glomerulonephritis and prolonged life span (Barber et al., Nat. Medicine, 2005, 9, 933-935).

There is evidence suggesting that chronic inflammation due to infiltration by myeloid-derived cells is a key component in the progression of neurodegeneration diseases, such as Alzheimer's disease (AD) (Gir et al., Am. J. Physiol. Cell Physiol., 2005, 289, C264-C276; El Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced cognitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., J. Neuroimmunol. 2010, 222, 90-94; Berod et al., Euro. J. Immunol. 2011, 41, 833-844; Comerford et al., PLOS one, 2012, 7, e45095; Li et al., Neuroscience, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., Cancer Cell, 2011, 19, 715-727). A further study reported that PI3Kγ deficiency could ameliorate inflammation and tumor growth in mice having colitis-associated colon cancer, (Gonzalez-Garcia et al., Gastroenterology, 2010, 138, 1373-1384). Detailed mechanistic analysis indicates that tumor infiltration by CD11b$^+$ myeloid cells can cause protumorigenic inflammation at tumor sites and PI3Kγ in the myeloid cells is critical in mediating signaling of various chemoattractants in bring the cells to the tumor (Schmid et al., Cancer Cell, 2011, 19, 715-727). Other studies suggest that PI3Kγ is also required for differentiation of naïve myeloid cells into M2 macrophges at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., *Cancer Res.* 2012, 72 (Suppl 1: Abstract, 411; Kaneda et al., *Cancer Res.,* 74 (Suppl 19: Abstract 3650)).

In addition to its potential role in promoting protumorigenic microenvironment, PI3Kγ may play a direct role in cancer cells. PI3Kγ is reported to be required for signaling from the Kaposi's sarcoma-associated herpevirus encoded vGPCR oncogene and tumor growth in a mouse model of sarcoma (Martin et al., *Cancer Cell,* 2011, 19, 805-813). PI3Kγ was also suggested to be required for growth of T-ALL (Subramanjam et al., *Cancer Cell,* 2012, 21, 459-472), PDAC and HCC cells (Falasca and Maffucci, *Frontiers in Physiology,* 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., *Cancer Biol. Ther.* 2010, 10, 582-587).

Finally, PI3Kγ deficiency also has been reported to offer protection to experimental animals in different cardiovascular disease models. For examples, lack of PI3Kγ would reduce angiotension-evoked smooth muscle contraction and, therefore, protect mice from angiotension-induced hypertension (Vecchione et al., *J Exp. Med.* 2005, 201, 1217-1228). In rigorous animal myocardial infarction models, PI3Kγ inhibition provided potent cardioprotection, reducing infarct development and preserving myocardial function (Doukas et al., *Proc. Natl. Acad. Sci. USA,* 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present disclosure relates to, inter alia, compounds of Formula (I):

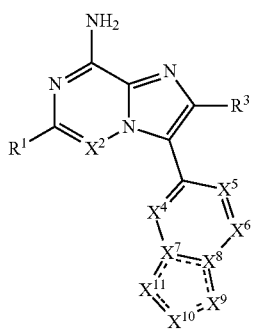

or a pharmaceutically acceptable salt thereof, wherein constituent members are defined herein.

The present disclosure further provides pharmaceutical compositions comprising a compound of Formula (I), or a pharmaceutically acceptable salt thereof, and a pharmaceutically acceptable carrier.

The present disclosure further provides methods of inhibiting an activity of PI3Kγ kinase comprising contacting the kinase with a compound of Formula (I), or a pharmaceutically acceptable salt thereof.

The present disclosure further provides methods of treating a disease or a disorder associated with abnormal PI3Kγ kinase expression or activity in a patient by administering to said patient a therapeutically effective amount of a compound of Formula (I), or a pharmaceutically acceptable salt thereof.

The present disclosure further provides a compound of Formula (I), or a pharmaceutically acceptable salt thereof, for use in any of the methods described herein.

The present disclosure further provides use of a compound of Formula (I), or a pharmaceutically acceptable salt thereof, for the preparation of a medicament for use in any of the methods described herein.

DETAILED DESCRIPTION

Compounds

The present application provides, inter alia, compounds of Formula (I):

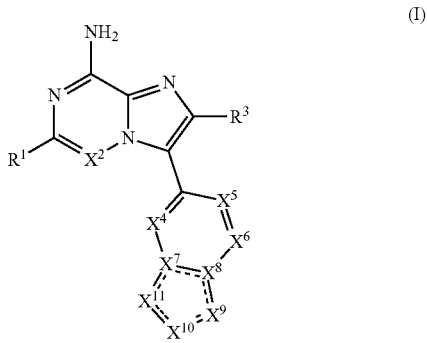

or a pharmaceutically acceptable salt thereof; wherein:
each bond symbol represented by ══ is independently a single or double bond;
$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOH)R^{b1}$, $C(=NCN)R^{b1}$, $C(=NR^{e1})NR^{c1}R^{d1}$, $NR^{c1}C(=NR^{e1})NR^{c1}R^{d1}$, $NR^{c1}C(=NOH)NR^{c1}R^{d1}$, $NR^{c1}C(=NCN)NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $S(O)(=NR^{e1})R^{b1}$, $OS(O)(=NR^{e1})R^{b1}$, $OS(O)_2R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{14}$ substituents;
each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, 4, 5, 6, 7, or 8 independently selected $R^{1A}$ substituents;

or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{1A}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f1}$ and $R^{g1}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterocycloalkyl;

each $R^{1A}$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NOH)R^{b11}$, $C(=NCN)R^{b11}$, $C(=NR^{e11})NR^{c11}R^{d11}$, $NR^{c11}C(=NR^{e11})NR^{c11}R^{d11}$, $NR^{c11}C(=NOH)NR^{c11}R^{d11}$, $NR^{c11}C(=NCN)NR^{c11}R^{d11}$, $NR^{c11}C(=NR^{e11})R^{b11}$, $NR^{c11}S(O)NR^{c11}R^{d11}$, $NR^{c11}S(O)R^{b11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $S(O)(=NR^{e11})R^{b11}$, $OS(O)(=NR^{e11})R^{b11}$, $OS(O)_2R^{b11}$, $SF_5$, $P(O)R^{f1}R^{g1}$, $OP(O)(OR^{h11})(OR^{i11})$, $P(O)(OR^{h11})(OR^{i11})$, and $BR^{j11}R^{k11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^{1B}$ substituents;

each $R^{a11}$, $R^{b11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{b11}$, $R^{c11}$ and $R^{d11}$ are each optionally substituted with 1, 2, 3, 4, 5, 6, 7, or 8 independently selected $R^{1B}$ substituents;

or, any $R^{c11}$ and $R^{d11}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{1B}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f11}$ and $R^{g11}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{1B}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NOH)R^{b12}$, $C(=NCN)R^{b12}$, $C(=NR^{e12})NR^{c12}R^{d12}$, $NR^{c12}C(=NR^{e12})NR^{c12}R^{d12}$, $NR^{c12}C(=NOH)NR^{c12}R^{d12}$, $NR^{c12}C(=NCN)NR^{c12}R^{d12}$, $NR^{c12}C(=NR^{e12})R^{b12}$, $NR^{c12}S(O)NR^{c12}R^{d12}$, $NR^{c12}S(O)R^{b12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $S(O)(=NR^{e12})R^{b12}$, $OS(O)(=NR^{e12})R^{b12}$, $OS(O)_2R^{b12}$, $SF_5$, $P(O)R^{f12}R^{g12}$, $OP(O)(OR^{h12})(OR^{i12})$, $P(O)(OR^{h12})(OR^{i12})$, and $BR^{j12}R^{k12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, 4, 5, 6, 7, or 8 independently selected $R^{1C}$ substituents;

each $R^{a12}$, $R^{b12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a12}$, $R^{b12}$, $R^{c12}$ and $R^{d12}$ are each optionally substituted with 1, 2, 3, 4, 5, 6, 7, or 8 independently selected $R^{1C}$ substituents;

or, any $R^{c12}$ and $R^{d12}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{1C}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f12}$ and $R^{g12}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h12}$ and $R^{k12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j12}$ and $R^{k12}$ is independently selected from OH, $C_{1-6}$ alkoxy, and $C_{1-6}$ haloalkoxy;

or any $R^{j12}$ and $R^{k12}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{1C}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a13}$, $SR^{a13}$, $NHOR^{a13}$, $C(O)R^{b13}$, $C(O)NR^{c13}R^{d13}$, $C(O)NR^{c13}(OR^{a13})$, $C(O)OR^{a13}$, $OC(O)R^{b13}$, $OC(O)NR^{c13}R^{d13}$, $NR^{c13}R^{d13}$, $NR^{c13}NR^{c13}R^{d13}$, $NR^{c13}C(O)R^{b13}$, $NR^{c13}C(O)OR^{a13}$, $NR^{c13}C(O)NR^{c13}R^{d13}$, $C(=NR^{e13})R^{b13}$, $C(=NOH)R^{b13}$, $C(=NCN)R^{b13}$, $C(=NR^{e13})NR^{c13}R^{d13}$, $NR^{c13}C(=NR^{e13})NR^{c13}R^{d13}$, $NR^{c13}C(=NOH)NR^{c13}R^{d13}$, $NR^{c13}C(=NCN)NR^{c13}R^{d13}$, $NR^{c13}C(=NR^{e13})R^{b13}$, $NR^{c13}S(O)NR^{c13}R^{d13}$, $NR^{c13}S(O)R^{b13}$, $NR^{c13}S(O)_2R^{b13}$, $NR^{c13}S(O)(=NR^{e13})R^{b13}$, $NR^{c13}S(O)_2NR^{c13}R^{d13}$, $S(O)R^{b13}$, $S(O)NR^{c13}R^{d13}$, $S(O)_2R^{b13}$, $S(O)_2NR^{c13}R^{d13}$, $S(O)(=NR^{e13})R^{b13}$, $OS(O)(=NR^{e13})R^{b13}$, $OS(O)_2R^{b13}$, $SF_5$, $P(O)R^{f13}R^{g13}$, $OP(O)(OR^{h13})(OR^{i13})$, $P(O)(OR^{h13})(OR^{i13})$, and $BR^{j13}R^{k13}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{1C}$ are each optionally substituted with 1, 2, 3, or 4 independently selected $R^M$ substituents;

each $R^{a13}$, $R^{b13}$, $R^{c13}$, and $R^{d13}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a13}$, $R^{b13}$, $R^{c13}$ and $R^{d13}$ are each optionally substituted with 1, 2, 3, or 4 independently selected $R^M$ substituents;

or, any $R^{c13}$ and $R^{d13}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e13}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f13}$ and $R^{g13}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h13}$ and $R^{i13}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j13}$ and $R^{k13}$ is independently selected from OH, $C_{1-6}$ alkoxy, and $C_{1-6}$ haloalkoxy;

or any $R^{j13}$ and $R^{k13}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^M$ is independently selected from D, OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-6}$ cycloalkyl, C$_{1-3}$ alkoxy, C$_{1-3}$ haloalkoxy, amino, C$_{1-3}$ alkylamino, di(C$_{1-3}$ alkyl) amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-4}$ alkoxycarbonyl, C$_{1-3}$ alkylcarbonylamino, C$_{1-3}$ alkoxycarbonylamino, C$_{1-3}$ alkylcarbonyloxy, aminocarbonyloxy, C$_{1-3}$ alkylaminocarbonyloxy, di(C$_{1-3}$ alkyl)aminocarbonyloxy, C$_{1-3}$ alkylsulfonylamino, aminosulfonyl, C$_{1-3}$ alkylaminosulfonyl, di(C$_{1-3}$ alkyl) aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino;

$X^2$ is N or CR$^2$;

$R^2$ is selected from H, D, halo, CN, OH, NH$_2$, C$_{1-6}$ alkyl, C$_{2-6}$ alkenyl, C$_{2-6}$ alkynyl, C$_{1-6}$ haloalkyl, and C$_{3-7}$ cycloalkyl;

$X^4$ is N or CR$^4$;

$X^5$ is N or CR$^5$;

$R^3$, $R^4$ and $R^5$ are each independently selected from H, D, halo, CN, OH, NH$_2$, C$_{1-6}$ alkyl, C$_{2-6}$ alkenyl, C$_{2-6}$ alkynyl, C$_{1-6}$ alkoxy, C$_{1-6}$ haloalkyl, C$_{1-6}$ haloalkoxy, cyano-C$_{1-6}$ alkyl, HO—C$_{1-6}$ alkyl, C$_{1-6}$ alkoxy-C$_{1-6}$ alkyl, C$_{3-6}$ cycloalkyl, C$_{1-6}$ alkylamino, di(C$_{1-6}$ alkyl) amino, and C(O)NR$^{a3}$R$^{b3}$;

each R$^{a3}$ and R$^{b3}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a3}$ and R$^{b3}$ are each optionally substituted with 1, 2, 3 or 4 independently selected R$^M$ substituents;

or, any R$^{a3}$ and R$^{b3}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected R$^M$ substituents;

$X^6$ is N or CR$^6$;

$R^6$ is selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a6}$, SR$^{a6}$, NHOR$^{a6}$, C(O)R$^{b6}$, C(O)NR$^{c6}$R$^{d6}$, C(O)NR$^{c6}$(OR$^{a6}$), C(O)OR$^{a6}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O) OR$^{a6}$, NR$^{c6}$C(O)NR$^{c6}$R$^{d6}$, C(=NR$^{e6}$)R$^{b6}$, C(=NOH) R$^{b6}$, C(=NCN)R$^{b6}$, C(=NR$^{e6}$)NR$^{c6}$R$^{d6}$, NR$^{c6}$C (=NR$^{e6}$)NR$^{c6}$R$^{d6}$, NR$^{c6}$C(=NOH)NR$^{c6}$R$^{d6}$, NR$^{c6}$C (=NCN)NR$^{c6}$R$^{d6}$, NR$^{c6}$C(=NR$^{e6}$)R$^{b6}$, NR$^{c6}$S(O) NR$^{c6}$R$^{d6}$, NR$^{c6}$S(O)R$^{b6}$, NR$^{c6}$S(O)$_2$R$^{b6}$, NR$^{c6}$S(O) (=NR$^{e6}$)R$^{b6}$, NR$^{c6}$S(O)$_2$NR$^{c6}$R$^{d6}$, S(O)R$^{b6}$, S(O) NR$^{c6}$R$^{d6}$, S(O)$_2$R$^{b6}$, S(O)$_2$NR$^{c6}$R$^{d6}$, S(O)(=NR$^{e6}$) R$^{b6}$, OS(O)(=NR$^{c6}$)R$^{d6}$, OS(O)$_2$R$^{b6}$, SF$_5$, P(O) R$^{f6}$R$^{g6}$, OP(O)(OR$^{h6}$)(OR$^{i6}$), P(O)(OR$^{h6}$)(OR$^{i6}$), and BR$^{j6}$R$^{k6}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^6$ are each optionally substituted with 1, 2, 3, 4, 5, 6, 7, or 8 independently selected R$^{6A}$ substituents;

each R$^{a6}$, R$^{b6}$, R$^{c6}$, and R$^{d6}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a6}$, R$^{b6}$, R$^{c6}$ and R$^{d6}$ are each optionally substituted with 1, 2, 3, 4, 5, 6, 7, or 8 independently selected R$^{6A}$ substituents;

or, any R$^{c6}$ and R$^{d6}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{6A}$ substituents;

each R$^{e6}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{f6}$ and R$^{g6}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{h6}$ and R$^{i6}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{j6}$ and R$^{k6}$ is independently selected from OH, C$_{1-6}$ alkoxy, and C$_{1-6}$ haloalkoxy;

or any R$^{j6}$ and R$^{k6}$ attached to the same B atom, together with the B atom to which they are attached, form a 5- or 6-membered heterocycloalkyl group optionally substituted with 1, 2, 3, or 4 substituents independently selected from C$_{1-6}$ alkyl, C$_{1-6}$ haloalkyl, C$_{3-10}$ cycloalkyl, and 4-10 membered heterocycloalkyl;

each R$^{6A}$ is selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a61}$, SR$^{a61}$, NHOR$^{a61}$, C(O)R$^{b61}$, C(O) NR$^{c61}$R$^{d61}$, C(O)NR$^{c61}$(OR$^{a61}$), C(O)OR$^{a61}$, OC(O) R$^{b61}$, OC(O)NR$^{c61}$R$^{d61}$, NR$^{c61}$R$^{d61}$, NR$^{c61}$NR$^{c61}$R$^{d61}$, NR$^{c61}$C(O)R$^{b61}$, NR$^{c61}$C(O)OR$^{a61}$, NR$^{c61}$C(O)

NR$^{c61}$R$^{d61}$, C(=NR$^{e61}$)R$^{b61}$, C(=NOH)R$^{b61}$, C(=NCN)R$^{b61}$, C(=NR$^{e61}$)NR$^{c61}$R$^{d61}$, NR$^{c61}$C(=NR$^{e61}$)NR$^{c61}$R$^{d61}$, NR$^{c61}$C(=NOH)NR$^{c61}$R$^{d61}$, NR$^{c61}$C(=NCN)NR$^{c61}$R$^{d61}$, NR$^{c61}$C(=NR$^{e61}$)R$^{b61}$, NR$^{c61}$S(O)NR$^{c61}$R$^{d61}$, NR$^{c61}$S(O)R$^{b61}$, NR$^{c61}$S(O)$_2$R$^{b61}$, NR$^{c61}$S(O)(=NR$^{e61}$)R$^{b61}$, NR$^{c61}$S(O)$_2$NR$^{c61}$R$^{d61}$, S(O)R$^{b61}$, S(O)NR$^{c61}$R$^{d61}$, S(O)$_2$R$^{b61}$, S(O)$_2$NR$^{c61}$R$^{d61}$, S(O)(=NR$^{e61}$)R$^{b61}$, OS(O)(=NR$^{e61}$)R$^{b61}$, OS(O)$_2$R$^{b61}$, SF$_5$, P(O)R$^{f61}$R$^{g61}$, OP(O)(OR$^{h61}$)(OR$^{i61}$), P(O)(OR$^{h61}$)(OR$^{i61}$), and BR$^{j61}$R$^{k61}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{6A}$ are each optionally substituted with 1, 2, 3, 4, 5, 6, 7, or 8 independently selected R$^{6B}$ substituents;

each R$^{a61}$, R$^{b61}$, R$^{c61}$, and R$^{d61}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a61}$, R$^{b61}$, R$^{c61}$ and R$^{d61}$ are each optionally substituted with 1, 2, 3, 4, 5, 6, 7, or 8 independently selected R$^{6B}$ substituents;

or, any R$^{c61}$ and R$^{d61}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{6B}$ substituents;

each R$^{e61}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{f61}$ and R$^{g61}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered hetereocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered hetereocycloalkyl)-C$_{1-6}$ alkyl-;

each R$^{h61}$ and R$^{i61}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered hetereocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered hetereocycloalkyl)-C$_{1-6}$ alkyl-;

each R$^{j61}$ and R$^{k61}$ is independently selected from OH, C$_{1-6}$ alkoxy, and C$_{1-6}$ haloalkoxy;

or any R$^{j61}$ and R$^{k61}$ attached to the same B atom, together with the B atom to which they are attached, form a 5- or 6-membered heterocycloalkyl group optionally substituted with 1, 2, 3, or 4 substituents independently selected from C$_{1-6}$ alkyl, C$_{1-6}$ haloalkyl, C$_{3-10}$ cycloalkyl, and 4-10 membered heterocycloalkyl;

each R$^{6B}$ is selected from H, D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a62}$, SR$^{a62}$, NHOR$^{a62}$, C(O)R$^{b62}$, C(O)NR$^{c62}$R$^{d62}$, C(O)NR$^{c62}$(OR$^{a62}$), C(O)OR$^{a62}$, OC(O)R$^{b62}$, OC(O)NR$^{c62}$R$^{d62}$, NR$^{c62}$R$^{d62}$, NR$^{c62}$NR$^{c62}$R$^{d62}$, NR$^{c62}$C(O)R$^{b62}$, NR$^{c62}$C(O)OR$^{a62}$, NR$^{c62}$C(O)NR$^{c62}$R$^{d62}$, C(=NR$^{e62}$)R$^{b62}$, C(=NOH)R$^{b62}$, C(=NCN)R$^{b62}$, C(=NR$^{e62}$)NR$^{c62}$R$^{d62}$, NR$^{c62}$C(=NR$^{e62}$)NR$^{c62}$R$^{d62}$, NR$^{c62}$C(=NOH)NR$^{c62}$R$^{d62}$, NR$^{c62}$C(=NCN)NR$^{c62}$R$^{d62}$, NR$^{c62}$C(=NR$^{e62}$)R$^{b62}$, NR$^{c62}$S(O)NR$^{c62}$R$^{d62}$, NR$^{c62}$S(O)R$^{b62}$, NR$^{c62}$S(O)$_2$R$^{b62}$, NR$^{c62}$S(O)(=NR$^{e62}$)R$^{b62}$, NR$^{c62}$S(O)$_2$NR$^{c62}$R$^{d62}$, S(O)R$^{b62}$, S(O)NR$^{c62}$R$^{d62}$, S(O)$_2$R$^{b62}$, S(O)$_2$NR$^{c62}$R$^{d62}$, S(O)(=NR$^{e62}$)R$^{b62}$, OS(O)(=NR$^{e62}$)R$^{b62}$, OS(O)$_2$R$^{b62}$, SF$_5$, P(O)R$^{f62}$R$^{g62}$, OP(O)(OR$^{h62}$)(OR$^{i62}$), P(O)(OR$^{h62}$)(OR$^{i62}$), and BR$^{j62}$R$^{k62}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{6B}$ are each optionally substituted with 1, 2, 3, 4, 5, 6, 7, or 8 independently selected R$^{6C}$ substituents;

each R$^{a62}$, R$^{b62}$, R$^{c62}$, and R$^{d62}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a62}$, R$^{b62}$, R$^{c62}$ and R$^{d62}$ are each optionally substituted with 1, 2, 3, 4, 5, 6, 7, or 8 independently selected R$^{6C}$ substituents;

or, any R$^{c62}$ and R$^{d62}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{6C}$ substituents;

each R$^{d62}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{f62}$ and R$^{g62}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered hetereocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered hetereocycloalkyl)-C$_{1-6}$ alkyl-;

each R$^{h62}$ and R$^{i62}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered hetereocycloalkyl)-C$_{1-6}$ alkyl-;

each R$^{j62}$ and R$^{k62}$ is independently selected from OH, C$_{1-6}$ alkoxy, and C$_{1-6}$ haloalkoxy;

or any $R^{j62}$ and $R^{k62}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{6C}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a63}$, $SR^{a63}$, $NHOR^{a63}$, $C(O)R^{b63}$, $C(O)NR^{c63}R^{d63}$, $C(O)NR^{c63}(OR^{a63})$, $C(O)OR^{a63}$, $OC(O)R^{b63}$, $OC(O)NR^{c63}R^{d63}$, $NR^{c63}R^{d63}$, $NR^{c63}NR^{c63}R^{d63}$, $NR^{c63}C(O)R^{b63}$, $NR^{c63}C(O)OR^{a63}$, $NR^{c63}C(O)NR^{c63}R^{d63}$, $C(=NR^{e63})R^{b63}$, $C(=NOH)R^{b63}$, $C(=NCN)R^{b63}$, $C(=NR^{e63})NR^{c63}R^{d63}$, $NR^{c63}C(=NR^{e63})NR^{c63}R^{d63}$, $NR^{c63}C(=NOH)NR^{c63}R^{d63}$, $NR^{c63}C(=NCN)NR^{c63}R^{d63}$, $NR^{c63}C(=NR^{e63})R^{b63}$, $NR^{c63}S(O)NR^{c63}R^{d63}$, $NR^{c63}S(O)R^{b63}$, $NR^{c63}S(O)_2R^{b63}$, $NR^{c63}S(O)(=NR^{e63})R^{b63}$, $NR^{c63}S(O)_2NR^{c63}R^{d63}$, $S(O)R^{b63}$, $S(O)NR^{c63}R^{d63}$, $S(O)_2R^{b63}$, $S(O)_2NR^{c63}R^{d63}$, $S(O)(=NR^{e63})R^{b63}$, $OS(O)(=NR^{e63})R^{b63}$, $OS(O)_2R^{b63}$, $SF_5$, $P(O)R^{f63}R^{g63}$, $OP(O)(OR^{h63})(OR^{i63})$, $P(O)(OR^{h63})(OR^{i63})$, and $BR^{j63}R^{k63}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{6C}$ are each optionally substituted with 1, 2, 3, or 4 independently selected $R^M$ substituents;

each $R^{a63}$, $R^{b63}$, $R^{c63}$, and $R^{d63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a63}$, $R^{b63}$, $R^{c63}$ and $R^{d63}$ are each optionally substituted with 1, 2, 3, or 4 independently selected $R^M$ substituents;

or, any $R^{c63}$ and $R^{d63}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e63}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f63}$ and $R^{g63}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h63}$ and $R^{i63}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j63}$ and $R^{k63}$ is independently selected from OH, $C_{1-6}$ alkoxy, and $C_{1-6}$ haloalkoxy;

or any $R^{j63}$ and $R^{k63}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

$X^7$ is N, CH, or C;

$X^8$ is N, CH, or C;

$X^9$ is N, $NR^{9N}$, O, S, S(O), $S(O)_2$, $CR^9$, or $C(R^9)_2$;

$X^{10}$ is N, $NR^{10N}$, O, S, $CR^{10}$, or $C(R^{10})_2$;

$X^{11}$ is N, $NR^{11N}$, O, S, $CR^{11}$, $C(R^{11})_2$;

wherein no more than three of $X^4$, $X^5$, $X^6$, $X^7$, and $X^8$ are simultaneously N; and at least two of $X^7$, $X^8$, $X^9$, $X^{10}$, and $X^{11}$ are independently selected from C, CH, $CR^9$, $C(R^9)_2$, $CR^{10}$, $C(R^{10})_2$, $CR^{11}$, and $C(R^{11})_2$; and no two adjacent members of $X^9$, $X^{10}$, and $X^{11}$ are simultaneously O, S, S(O), or $S(O)_2$;

provided that (a) when $X^7$ is N, then $X^8$ is C; or (b) when $X^7$ is C, then $X^8$ is N;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b9N}$, $C(O)NR^{c9N}R^{d9N}$, $C(O)OR^{a9N}$, $C(=NR^{e9N})R^{b9N}$, $C(=NR^{e9N})NR^{c9N}R^{d9N}$, $C(=NCN)NR^{c9N}R^{d9N}$, $C(=NOR^{a9N})NR^{c9N}$, $S(O)_2R^{b9N}$, $S(O)(=NR^{c9N})R^{d9N}$, and $S(O)_2NR^{c9N}R^{d9N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, 4, 5, 6, 7, or 8 independently selected $R^{9NA}$ substituents;

each $R^{a9N}$, $R^{b9N}$, $R^{c9N}$, and $R^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9N}$, $R^{b9N}$, $R^{c9N}$, and $R^{d9N}$ are each optionally substituted with 1, 2, 3, 4, 5, 6, 7, or 8 independently selected $R^{9NA}$ substituents;

or, any $R^{c9N}$ and $R^{d9N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9NA}$ substituents;

each $R^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a9N2}$, $SR^{a9N2}$, $NHOR^{a9N2}$, $C(O)R^{b9N2}$, $C(O)NR^{c9N2}R^{d9N2}$, $C(O)NR^{c9N2}(OR^{a9N2})$, $C(O)OR^{a9N2}$, $OC(O)R^{b9N2}$, $OC(O)NR^{c9N2}R^{d9N2}$, $NR^{c9N2}R^{d9N2}$, $NR^{c9N2}NR^{c9N2}R^{d9N2}$, $NR^{c9N2}C(O)R^{b9N2}$, $NR^{c9N2}C(O)OR^{a9N2}$, $NR^{c9N2}C(O)NR^{c9N2}R^{d9N2}$, $C(=NR^{e9N2})R^{b9N2}$, $C(=NOH)R^{b9N2}$, $C(=NCN)R^{b9N2}$, $C(=NR^{e9N2})NR^{c9N2}R^{d9N2}$, $NR^{c9N2}C(=NR^{e9N2})NR^{c9N2}R^{d9N2}$, $NR^{c9N2}C(=NOH)NR^{c9N2}R^{d9N2}$, $NR^{c9N2}C(=NCN)NR^{c9N2}R^{d9N2}$, $NR^{c9N2}C(=NR^{e9N2})R^{b9N2}$, $NR^{c9N2}S(O)NR^{c9N2}R^{d9N2}$, $NR^{c9N2}S(O)R^{b9N2}$, $NR^{c9N2}S(O)_2R^{b9N2}$, $NR^{c9N2}S(O)(=NR^{e9N2})R^{b9N2}$, $NR^{c9N2}S(O)_2NR^{c9N2}R^{d9N2}$, $S(O)R^{b9N2}$, $S(O)NR^{c9N2}R^{d9N2}$, $S(O)_2R^{b9N2}$, $S(O)_2NR^{c9N2}R^{d9N2}$, $S(O)(=NR^{e9N2})R^{b9N2}$, $OS(O)(=NR^{e9N2})R^{b9N2}$, $OS(O)_2R^{b9N2}$, $SF_5$, $P(O)R^{f9N2}R^{g9N2}$, $OP(O)(OR^{h9N2})(OR^{i9N2})$, $P(O)(OR^{h9N2})(OR^{i9N2})$, and $BR^{j9N2}R^{k9N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9NA}$ are each optionally substituted with 1, 2, 3, or 4 independently selected $R^M$ substituents;

each $R^{a9N2}$, $R^{b9N2}$, $R^{c9N2}$, and $R^{d9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a9N2}$, $R^{b9N2}$, $R^{c9N2}$ and $R^{d9N2}$ are each optionally substituted with 1, 2, 3, or 4 independently selected $R^M$ substituents;

or, any $R^{c9N2}$ and $R^{d9N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e9N2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f9N2}$ and $R^{g9N2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h9N2}$ and $R^{i9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j9N2}$ and $R^{k9N2}$ is independently selected from OH, $C_{1-6}$ alkoxy, and $C_{1-6}$ haloalkoxy;

or any $R^{j9N2}$ and $R^{k9N2}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^9$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, $NR^{c91}C(O)NR^{c91}R^{d91}$, $C(=NR^{e91})R^{b91}$, $C(=NOH)R^{b91}$, $C(=NCN)R^{b91}$, $C(=NR^{e91})NR^{c91}R^{d91}$, $NR^{c91}C(=NR^{e91})NR^{c91}R^{d91}$, $NR^{c91}C(=NOH)NR^{c91}R^{d91}$, $NR^{c91}C(=NCN)NR^{c91}R^{d91}$, $NR^{c91}C(=NR^{e91})R^{b91}$, $NR^{c91}S(O)NR^{c91}R^{d91}$, $NR^{c91}S(O)R^{b91}$, $NR^{c91}S(O)_2R^{b91}$, $NR^{c91}S(O)(=NR^{e91})R^{b91}$, $NR^{c91}S(O)_2NR^{c91}R^{d91}$, $S(O)R^{b91}$, $S(O)NR^{c91}R^{d91}$, $S(O)_2R^{b91}$, $S(O)_2NR^{c91}R^{d91}$, $S(O)(=NR^{e91})R^{b91}$, $OS(O)(=NR^{e91})R^{b91}$, $OS(O)_2R^{b91}$, $SF_5$, $P(O)R^{f91}R^{g91}$, $OP(O)(OR^{h91})(OR^{i91})$, $P(O)(OR^{h91})(OR^{i91})$, and $BR^{j91}R^{k91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

or, alternatively, two $R^9$ groups together form an oxo group;

each $R^{a91}$, $R^{b91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a91}$, $R^{b91}$, $R^{c91}$ and $R^{d91}$ are each optionally substituted with 1, 2, 3, 4, 5, 6, 7, or 8 independently selected $R^{9A}$ substituents;

or, any $R^{c91}$ and $R^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9A}$ substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f91}$ and $R^{g91}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h91}$ and $R^{i91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j91}$ and $R^{k91}$ is independently selected from OH, $C_{1-6}$ alkoxy, and $C_{1-6}$ haloalkoxy;

or any $R^{j91}$ and $R^{k91}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, $NR^{c92}C(O)NR^{c92}R^{d92}$, $C(=NR^{e92})R^{b92}$, $C(=NOH)R^{b92}$, $C(=NCN)R^{b92}$, $C(=NR^{e92})NR^{c92}R^{d92}$, $NR^{c92}C(=NR^{e92})NR^{c92}R^{d92}$, $NR^{c92}C(=NOH)NR^{c92}R^{d92}$, $NR^{c92}C(=NCN)NR^{c92}R^{d92}$, $NR^{c92}C(=NR^{e92})R^{b92}$, $NR^{c92}S(O)NR^{c92}R^{d92}$, $NR^{c92}S(O)R^{b92}$, $NR^{c92}S(O)_2R^{b92}$, $NR^{c92}S(O)(=NR^{e92})R^{b92}$, $NR^{c92}S(O)_2NR^{c92}R^{d92}$, $S(O)R^{b92}$, $S(O)NR^{c92}R^{d92}$, $S(O)_2R^{b92}$, $S(O)_2NR^{c92}R^{d92}$, $S(O)(=NR^{e92})R^{b92}$, $OS(O)(=NR^{e92})R^{b92}$, $OS(O)_2R^{b92}$, $SF_5$, $P(O)R^{f92}R^{g92}$, $OP(O)(OR^{h92})(OR^{i92})$, $P(O)(OR^{h92})(OR^{i92})$, and $BR^{j92}R^{k92}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a92}$, $R^{b92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a92}$, $R^{b92}$, $R^{c92}$ and $R^{d92}$ are each optionally substituted with 1, 2, 3, or 4 independently selected $R^M$ substituents;

or, any $R^{c92}$ and $R^{d92}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e92}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f62}$ and $R^{g92}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h92}$ and $R^{i92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j92}$ and $R^{k92}$ is independently selected from OH, $C_{1-6}$ alkoxy, and $C_{1-6}$ haloalkoxy;

or any $R^{j92}$ and $R^{k92}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b10N}$, $C(O)NR^{c10N}R^{d10N}$, $C(O)OR^{a10N}$, $C(=NR^{e10N})R^{b10N}$, $C(=NR^{e10N})NR^{c10N}R^{d10N}$, $C(=NCN)NR^{c10N}R^{d10N}$, $C(=NOR^{a10N})NR^{c10N}$, $S(O)_2R^{b10N}$, $S(O)(=NR^{c10N})R^{d10N}$, and $S(O)_2NR^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, 4, 5, 6, 7, or 8 independently selected $R^{10NA}$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, 4, 5, 6, 7, or 8 independently selected $R^{10NA}$ substituents;

or, any $R^{c10N}$ and $R^{d10N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10NA}$ substituents;

each $R^{e10N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a10N2}$, $SR^{a10N2}$, $NHOR^{a10N2}$, $C(O)R^{b10N2}$, $C(O)NR^{c10N2}R^{d10N2}$, $C(O)NR^{c10N2}(OR^{a10N2})$, $C(O)OR^{a10N2}$, $OC(O)R^{b10N2}$, $OC(O)NR^{c10N2}R^{d10N2}$, $NR^{c10N2}R^{d10N2}$, $NR^{c10N2}NR^{c10N2}R^{d10N2}$, $NR^{c10N2}C(O)R^{b10N2}$, $NR^{c10N2}C(O)OR^{a10N2}$, $NR^{c10N2}C(O)NR^{c10N2}R^{d10N2}$, $C(=NR^{e10N2})R^{b10N2}$, $C(=NOH)R^{b10N2}$, $C(=NCN)R^{b10N2}$, $C(=NR^{e10N2})NR^{c10N2}R^{d10N2}$, $NR^{c10N2}C(=NR^{e10N2})NR^{c10N2}R^{d10N2}$, $NR^{c10N2}C(=NOH)NR^{c10N2}R^{d10N2}$, $NR^{c10N2}C(=NCN)NR^{c10N2}R^{d10N2}$, $NR^{c10N2}C(=NR^{e10N2})R^{b10N2}$, $NR^{c10N2}S(O)NR^{c10N2}R^{d10N2}$, $NR^{c10N2}S(O)R^{b10N2}$, $NR^{c10N2}S(O)_2R^{b10N2}$, $NR^{c10N2}S(O)(=NR^{e10N2})R^{b10N2}$, $NR^{c10N2}S(O)_2NR^{c10N2}R^{d10N2}$, $S(O)R^{b10N2}$, $S(O)NR^{c10N2}R^{d10N2}$, $S(O)_2R^{b10N2}$, $S(O)_2NR^{c10N2}R^{d10N2}$, $S(O)(=NR^{e10N2})R^{b10N2}$, $OS(O)(=NR^{e10N2})R^{b10N2}$, $OS(O)_2R^{b10N2}$, $SF_5$, $P(O)R^{f10N2}R^{g10N2}$, $OP(O)(OR^{h10N2})(OR^{i10N2})$, $P(O)(OR^{h10N2})(OR^{i10N2})$, and $BR^{10N2}R^{k10N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10NA}$ are each optionally substituted with 1, 2, 3, or 4 independently selected $R^M$ substituents;

each $R^{a10N2}$, $R^{b10N2}$, $R^{c10N2}$, and $R^{d10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a10N2}$, $R^{b10N2}$, $R^{c10N2}$ and $R^{d10N2}$ are each optionally substituted with 1, 2, 3, or 4 independently selected $R^M$ substituents;

or, any $R^{c10N2}$ and $R^{d10N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e10N2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f10N2}$ and $R^{g10N2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h10N2}$ and $R^{i10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j10N2}$ and $R^{k10N2}$ is independently selected from OH, $C_{1-6}$ alkoxy, and $C_{1-6}$ haloalkoxy;

or any $R^{j10N2}$ and $R^{k10N2}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{10}$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a101}$, $SR^{a101}$, $NHOR^{a101}$, $C(O)R^{b101}$, $C(O)NR^{c101}R^{d101}$, $C(O)NR^{c101}(OR^{a101})$, $C(O)OR^{a101}$, $OC(O)R^{b101}$, $OC(O)NR^{c101}R^{d101}$, $NR^{c101}R^{d101}$, $NR^{c101}NR^{c101}R^{d101}$, $NR^{c101}C(O)R^{b101}$, $NR^{c101}C(O)OR^{a101}$, $NR^{c101}C(O)NR^{c101}R^{d101}$, $C(=NR^{e101})R^{b101}$, $C(=NOH)R^{b101}$, $C(=NCN)R^{b101}$, $C(=NR^{e101})NR^{c101}R^{d101}$, $NR^{c101}C(=NR^{e101})NR^{c101}R^{d101}$, $NR^{c101}C(=NOH)NR^{c101}R^{d101}$, $NR^{c101}C(=NCN)NR^{c101}R^{d101}$, $NR^{c101}C(=NR^{e101})R^{b101}$, $NR^{c101}S(O)NR^{c101}R^{d101}$, $NR^{c101}S(O)R^{b101}$, $NR^{c101}S(O)_2R^{b101}$, $NR^{c101}S(O)(=NR^{e101})R^{b101}$, $NR^{c101}S(O)_2NR^{c101}R^{d101}$, $S(O)R^{b101}$, $S(O)NR^{c101}R^{d101}$, $S(O)_2R^{b101}$, $S(O)_2NR^{c101}R^{d101}$, $S(O)(=NR^{e101})R^{b101}$, $OS(O)(=NR^{e101})R^{b101}$, $OS(O)_2R^{b101}$, $SF_5$, $P(O)R^{f101}R^{g101}$, $OP(O)(OR^{h101})(OR^{i101})$, $P(O)(OR^{h101})(OR^{i101})$, and $BR^{j101}R^{k101}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{10}$ are each optionally substituted with 1, 2, 3, 4, 5, 6, 7, or 8 independently selected $R^{10A}$ substituents;

each $R^{a101}$, $R^{b101}$, $R^{c101}$, and $R^{d101}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a101}$, $R^{b101}$, $R^{c101}$ and $R^{d101}$ are each optionally substituted with 1, 2, 3, 4, 5, 6, 7, or 8 independently selected $R^{10A}$ substituents;

or, any $R^{c101}$ and $R^{d101}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10A}$ substituents;

each $R^{e101}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f101}$ and $R^{g101}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h101}$ and $R^{i101}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j101}$ and $R^{k101}$ is independently selected from OH, $C_{1-6}$ alkoxy, and $C_{1-6}$ haloalkoxy;

or any $R^{j101}$ and $R^{k101}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{10A}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a102}$, $SR^{a102}$, $NHOR^{a102}$, $C(O)R^{b102}$, $C(O)NR^{c102}R^{d102}$, $C(O)NR^{c102}(OR^{a102})$, $C(O)OR^{a102}$, $OC(O)R^{b102}$, $OC(O)NR^{c102}R^{d102}$, $NR^{c102}$, $NR^{c102}NR^{c102}R^{d102}$, $NR^{c102}C(O)R^{b102}$, $NR^{c102}C(O)OR^{a102}$, $NR^{c102}C(O)NR^{c102}R^{d102}$, $C(=NR^{e102})R^{b102}$, $C(=NOH)R^{b102}$, $C(=NCN)R^{b102}$, $C(=NR^{e102})NR^{c102}R^{d102}$, $NR^{c102}R^{d102}$, $NR^{c102}C(=NR^{e102})NR^{c102}R^{d102}$, $NR^{c102}C(=NOH)NR^{c102}R^{d102}$, $NR^{c102}C(=NCN)NR^{c102}R^{d102}$, $NR^{c102}C(=NR^{e102})R^{b102}$, $NR^{c102}S(O)NR^{c102}R^{d102}$, $NR^{c102}S(O)R^{b102}$, $NR^{c102}S(O)_2R^{b102}$, $NR^{c102}S(O)(=NR^{e102})R^{b102}$, $NR^{c102}S(O)_2NR^{c102}R^{d102}$, $S(O)R^{b102}$, $S(O)NR^{c102}R^{d102}$, $S(O)_2R^{b102}$, $S(O)_2NR^{c102}R^{d102}$, $S(O)(=NR^{e102})R^{b102}$, $OS(O)(=NR^{e102})R^{b102}$, $OS(O)_2R^{b102}$, $SF_5$, $P(O)R^{f102}R^{g102}$, $OP(O)(OR^{h102})(OR^{i102})$, $P(O)(OR^{h102})(OR^{i102})$, and $BR^{j102}R^{k102}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10A}$ are each optionally substituted with 1, 2, 3, or 4 independently selected $R^M$ substituents;

each $R^{a102}$, $R^{b102}$, $R^{c102}$, and $R^{d102}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a102}$, $R^{b102}$, $R^{c102}$ and $R^{d102}$ are each optionally substituted with 1, 2, 3, or 4 independently selected $R^M$ substituents;

or, any $R^{c102}$ and $R^{d102}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e102}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f102}$ and $R^{g102}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h102}$ and $R^{i102}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j102}$ and $R^{k102}$ is independently selected from OH, $C_{1-6}$ alkoxy, and $C_{1-6}$ haloalkoxy;

or any $R^{j102}$ and $R^{k102}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl; $R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b11N}$, $C(O)NR^{c11N}R^{d11N}$, $C(O)OR^{a11N}$, $C(=NR^{e11N})R^{b11N}$, $C(=NR^{e11N})NR^{c11N}R^{d11N}$, $C(=NCN)NR^{c11N}R^{d11N}$, $C(=NOR^{a11N})NR^{c11N}$, $S(O)_2R^{b11N}$, $S(O)(=NR^{c11N})R^{d11N}$, and $S(O)_2NR^{c11N}R^{d11N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{11N}$ are each optionally substituted with 1, 2, 3, 4, 5, 6, 7, or 8 independently selected $R^{11NA}$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^{11NA}$ substituents;

or, any $R^{c11N}$ and $R^{d11N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11NA}$ substituents;

each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11NA}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a11N2}$, $SR^{a11N2}$, $NHOR^{a11N2}$, $C(O)R^{b11N2}$, $C(O)NR^{c11N2}R^{d11N2}$, $C(O)NR^{c11N2}(OR^{a11N2})$, $C(O)OR^{a11N2}$, $OC(O)R^{b11N2}$, $OC(O)NR^{c11N2}R^{d11N2}$, $NR^{c11N2}R^{d11N2}$, $NR^{c11N2}NR^{c11N2}R^{d11N2}$, $NR^{c11N2}C(O)R^{b11N2}$, $NR^{c11N2}C(O)OR^{a11N2}$, $NR^{c11N2}C(O)NR^{c11N2}R^{d11N2}$, $C(=NR^{e11N2})R^{b11N2}$, $C(=NOH)R^{b11N2}$, $C(=NCN)R^{b11N2}$, $C(=NR^{e11N2})NR^{c11N2}R^{d11N2}$, $NR^{c11N2}C(=NR^{e11N2})NR^{c11N2}R^{d11N2}$, $NR^{c11N2}C(=NOH)NR^{c11N2}R^{d11N2}$, $NR^{c11N2}C(=NCN)NR^{c11N2}R^{d11N2}$, $NR^{c11N2}C(=NR^{e11N2})R^{b11N2}$, $NR^{c11N2}S(O)NR^{c11N2}R^{d11N2}$, $NR^{c11N2}S(O)R^{b11N2}$, $NR^{c11N2}S(O)_2R^{b11N2}$, $NR^{c11N2}S(O)(=NR^{e11N2})R^{b11N2}$, $NR^{c11N2}S(O)_2NR^{c11N2}R^{d11N2}$, $S(O)R^{b11N2}$, $S(O)NR^{c11N2}R^{d11N2}$, $S(O)_2R^{b11N2}$, $S(O)_2NR^{c11N2}R^{d11N2}$, $S(O)(=NR^{e11N2})R^{b11N2}$, $OS(O)(=NR^{e11N2})R^{b11N2}$, $OS(O)_2R^{b11N2}$, $SF_5$, $P(O)R^{f11N2}R^{g11N2}$, $OP(O)(OR^{h11N2})(OR^{i11N2})$, $P(O)(OR^{h11N2})(OR^{i11N2})$, and $BR^{11N2}R^{k11N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11NA}$ are each optionally substituted with 1, 2, 3, or 4 independently selected $R^M$ substituents;

each $R^{a11N2}$, $R^{b11N2}$, $R^{c11N2}$, and $R^{d11N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a11N2}$, $R^{b11N2}$, $R^{c11N2}$ and $R^{d11N2}$ are each optionally substituted with 1, 2, 3, or 4 independently selected $R^M$ substituents;

or, any $R^{c11N2}$ and $R^{d11N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e11N2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f11N2}$ and $R^{g11N2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h11N2}$ and $R^{i11N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j11N2}$ and $R^{k11N}$ is independently selected from OH, $C_{1-6}$ alkoxy, and $C_{1-6}$ haloalkoxy;

or any $R^{j11N2}$ and $R^{k11N2}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{11}$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a111}$, $SR^{a111}$, $NHOR^{a111}$, $C(O)R^{b111}$, $C(O)NR^{c111}R^{d111}$, $C(O)NR^{c111}(OR^{a111})$, $C(O)OR^{a111}$, $OC(O)R^{b111}$, $OC(O)NR^{c111}R^{d111}$, $NR^{c111}R^{d111}$, $NR^{c111}NR^{c111}R^{d111}$, $NR^{c111}C(O)R^{b111}$, $NR^{c111}C(O)OR^{a111}$, $NR^{c111}C(O)NR^{c111}R^{d111}$, $C(=NR^{e111})R^{b111}$, $C(=NOH)R^{b111}$, $C(=NCN)R^{b111}$, $C(=NR^{e111})NR^{c111}R^{d111}$, $NR^{cm}C(=NR^{e111})NR^{c111}R^{d111}$, $NR^{c111}C(=NOH)NR^{c111}R^{d111}$, $NR^{c111}C(=NCN)NR^{c111}R^{d111}$, $NR^{c111}C(=NR^{e111})R^{b111}$, $NR^{c111}S(O)NR^{c111}R^{d111}$, $NR^{c111}S(O)R^{b111}$, $NR^{c111}S(O)_2R^{b111}$, $NR^{c111}S(O)(=NR^{e111})R^{b111}$, $NR^{c111}S(O)_2NR^{c111}R^{d111}$, $S(O)R^{b111}$, $S(O)NR^{c111}R^{d111}$, $S(O)_2R^{b111}$, $S(O)_2NR^{c111}R^{d111}$, $S(O)(=NR^{e111})R^{b111}$, $OS(O)(=NR^{e111})R^{b111}$, $OS(O)_2R^{b111}$, $SF_5$, $P(O)R^{f111}R^{g111}$, $OP(O)(OR^{h111})(OR^{i111})$, $P(O)(OR^{h111})(OR^{i111})$, and $BR^{j111}R^{k111}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^{11A}$ substituents;

each $R^{a111}$, $R^{b111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a111}$, $R^{b111}$, $R^{c111}$ and $R^{d111}$ are each optionally substituted with 1, 2, 3, 4, 5, 6, 7, or 8 independently selected $R^{11A}$ substituents;

or, any $R^{c111}$ and $R^{d111}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11A}$ substituents;

each $R^{e111}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f111}$ and $R^{g111}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h111}$ and $R^{i111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j111}$ and $R^{k111}$ is independently selected from OH, $C_{1-6}$ alkoxy, and $C_{1-6}$ haloalkoxy;

or any $R^{j111}$ and $R^{k111}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterocycloalkyl; and each $R^{11A}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a112}$, $SR^{a112}$, $NHOR^{a112}$, $C(O)R^{b112}$, $C(O)NR^{c112}R^{d112}$, $C(O)NR^{c112}(OR^{a112})$, $C(O)OR^{a112}$, $OC(O)R^{b112}$, $OC(O)NR^{c112}R^{d112}$, $NR^{c112}R^{d112}$, $NR^{c112}NR^{c112}R^{d112}$, $NR^{c112}C(O)R^{b112}$, $NR^{c112}C(O)OR^{a112}$, $NR^{c112}C(O)NR^{c112}R^{d112}$, $C(=NR^{e112})R^{b112}$, $C(=NOH)R^{b112}$, $C(=NCN)R^{b112}$, $C(=NR^{e112})NR^{c112}R^{d112}$, $NR^{c112}C(=NR^{e112})NR^{c112}R^{d112}$, $NR^{c112}C(=NOH)NR^{c112}R^{d112}$, $NR^{c112}C(=NCN)NR^{c112}R^{d112}$, $NR^{c112}C(=NR^{e112})R^{b112}$, $NR^{c112}S(O)NR^{c112}R^{d112}$, $NR^{c112}S(O)R^{b112}$, $NR^{c112}S(O)_2R^{b112}$, $NR^{c112}S(O)(=NR^{e112})R^{b112}$, $NR^{c112}S(O)_2NR^{c112}R^{d112}$, $S(O)R^{b112}$, $S(O)NR^{c112}R^{d112}$, $S(O)_2R^{b112}$, $S(O)_2NR^{c112}R^{d112}$, $S(O)(=NR^{e112})R^{b112}$, $OS(O)(=NR^{e112})R^{b112}$, $OS(O)_2R^{b112}$, $SF_5$, $P(O)R^{f112}R^{g112}$, $OP(O)(OR^{h112})(OR^{i112})$, $P(O)(OR^{h112})(OR^{i112})$, and $BR^{j112}R^{k112}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11A}$ are each optionally substituted with 1, 2, 3, or 4 independently selected $R^M$ substituents;

each $R^{a112}$, $R^{b112}$, $R^{c112}$, and $R^{d112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a112}$, $R^{b112}$, $R^{c112}$ and $R^{d112}$ are each optionally substituted with 1, 2, 3, or 4 independently selected $R^M$ substituents;

or, any $R^{c112}$ and $R^{d112}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e112}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f112}$ and $R^{g112}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h112}$ and $R^{i112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j112}$ and $R^{k112}$ is independently selected from OH, $C_{1-6}$ alkoxy, and $C_{1-6}$ haloalkoxy;

or any $R^{j112}$ and $R^{k112}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterocycloalkyl.

In some embodiments:

$R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOH)R^{b1}$, $C(=NCN)R^{b1}$, $C(=NR^{e1})NR^{c1}R^{d1}$, $NR^{c1}C(=NR^{e1})NR^{c1}R^{d1}$, $NR^{c1}C(=NOH)NR^{c1}R^{d1}$, $NR^{c1}C(=NCN)NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $S(O)(=NR^{e1})R^{b1}$, $OS(O)(=NR^{e1})R^{b1}$, $OS(O)_2R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, 4, 5, 6, 7, or 8 independently selected $R^{1A}$ substituents;

or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{1A}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f1}$ and $R^{g1}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocyclyl)-$C_{1-6}$ alkyl-;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{1A}$ is independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NOH)R^{b11}$, $C(=NCN)R^{b11}$, $C(=NR^{e11})NR^{c11}R^{d11}$, $NR^{c11}C(=NR^{e11})NR^{c11}R^{d11}$, $NR^{c11}C(=NOH)NR^{c11}R^{d11}$, $NR^{c11}C(=NCN)NR^{c11}R^{d11}$, $NR^{c11}C(=NR^{e11})R^{b11}$, $NR^{c11}S(O)NR^{c11}R^{d11}$, $NR^{c11}S(O)R^{b11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $S(O)(=NR^{e11})R^{b11}$, $OS(O)(=NR^{e11})R^{b11}$, $OS(O)_2R^{b11}$, $SF_5$, $P(O)R^{f11}R^{g11}$, $OP(O)(OR^{h11})(OR^{i11})$, $P(O)(OR^{h11})(OR^{i11})$, and $BR^{j11}R^{k11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3 or 4 independently selected $R^M$ substituents;

each $R^{a11}$, $R^{b11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{b11}$, $R^{c11}$ and $R^{d11}$ are each optionally substituted with 1, 2, 3 or 4 independently selected $R^M$ substituents;

or, any $R^{c11}$ and $R^{d11}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, or 4 independently selected $R^M$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f11}$ and $R^{g11}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$X^2$ is N or $CR^2$;

$R^2$ is selected from H, D, halo, CN, OH, $NH_2$, $C_{1-6}$ alkyl, $C_{2-6}$ alkenyl, $C_{2-6}$ alkynyl, $C_{1-6}$ haloalkyl, and $C_{3-7}$ cycloalkyl;

$X^4$ is N or $CR^4$;

$X^5$ is N or $CR^5$;

$R^3$, $R^4$ and $R^5$ are each independently selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^{a3}R^{b3}$;

each $R^{a3}$ and $R^{b3}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a3}$ and $R^{b3}$ are each optionally substituted with 1, 2, 3 or 4 independently selected $R^M$ substituents;

or, any $R^{a3}$ and $R^{b3}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$X^6$ is N or $CR^6$;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NOH)NR^{c6}R^{d6}$, $NR^{c6}C(=NCN)NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $S(O)(=NR^{e6})R^{b6}$, $OS(O)(=NR^{e6})R^{d6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, 4, 5, 6, 7, or 8 independently selected $R^{6A}$ substituents;

or, any $R^{c6}$ and $R^{d6}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NR^{e61})R^{b61}$, $C(=NOH)R^{b61}$, $C(=NCN)R^{b61}$, $C(=NR^{e61})NR^{c61}R^{d61}$, $NR^{c61}C(=NR^{e61})NR^{c61}R^{d61}$, $NR^{c61}C(=NOH)NR^{c61}R^{d61}$, $NR^{c61}C(=NCN)NR^{c61}R^{d61}$, $NR^{c61}C(=NR^{e61})R^{b61}$, $NR^{c61}S(O)NR^{c61}R^{d61}$, $NR^{c61}S(O)R^{b61}$, $NR^{c61}S(O)_2R^{b61}$, $NR^{c61}S(O)(=NR^{e61})R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, $S(O)(=NR^{e61})R^{b61}$, $OS(O)(=NR^{e61})R^{b61}$, $OS(O)_2R^{b61}$, $SF_5$, $P(O)R^{f61}R^{g61}$, $OP(O)(OR^{h61})(OR^{i61})$, $P(O)(OR^{h61})(OR^{i61})$, and $BR^{j61}R^{k61}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{6A}$ are each optionally substituted with 1, 2, 3, or 4 independently selected $R^M$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{b61}$, $R^{c61}$ and $R^{d61}$ are each optionally substituted with 1, 2, 3, or 4 independently selected $R^M$ substituents;

or, any $R^{c61}$ and $R^{d61}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, or 4 independently selected $R^M$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f61}$ and $R^{g61}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h61}$ and $R^{i61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j61}$ and $R^{k61}$ is independently selected from OH, $C_{1-6}$ alkoxy, and $C_{1-6}$ haloalkoxy;

or any $R^{j61}$ and $R^{k61}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

$X^7$ is N, CH, or C;

$X^8$ is N, CH, or C;

$X^9$ is N, $NR^{9N}$, O, S, S(O), $S(O)_2$, $CR^9$, or $C(R^9)_2$;

$X^{10}$ is N, $NR^{10N}$, O, S, $CR^{10}$, or $C(R^{10})_2$;

$X^{11}$ is N, $NR^{11N}$, O, S, $CR^{11}$, $C(R^{11})_2$;

wherein no more than three of $X^4$, $X^5$, $X^6$, $X^7$, and $X^8$ are simultaneously N; and at least two of $X^7$, $X^8$, $X^9$, $X^{10}$, and $X^{11}$ are independently selected from C, CH, $CR^9$, $C(R^9)_2$, $CR^{10}$, $C(R^{10})_2$, $CR^{11}$, and $C(R^{11})_2$; and no two adjacent members of $X^9$, $X^{10}$, and $X^{11}$ are simultaneously O, S, S(O), or $S(O)_2$;

provided that (a) when $X^7$ is N, then $X^8$ is C; or (b) when $X^7$ is C, then $X^8$ is N;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b9N}$, $C(O)NR^{c9N}R^{d9N}$, $C(O)OR^{a9N}$, $C(=NR^{e9N})R^{b9N}$, $C(=NR^{e9N})NR^{c9N}R^{d9N}$, $C(=NCN)NR^{c9N}R^{d9N}$, $C(=NOR^{a9N})NR^{c9N}$, $S(O)_2R^{b9N}$, $S(O)(=NR^{c9N})R^{d9N}$, and $S(O)_2NR^{c9N}R^{d9N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, 4, 5, 6, 7, or 8 independently selected $R^{9NA}$ substituents;

each $R^{a9N}$, $R^{b9N}$, $R^{c9N}$, and $R^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9N}$, $R^{b9N}$, $R^{c9N}$, and $R^{d9N}$ are each optionally substituted with 1, 2, 3, 4, 5, 6, 7, or 8 independently selected $R^{9NA}$ substituents;

or, any $R^{c9N}$ and $R^{d9N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9NA}$ substituents;

each $R^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a9N2}$, $SR^{a9N2}$, $NHOR^{a9N2}$, $C(O)R^{b9N2}$, $C(O)NR^{c9N2}R^{d9N2}$, $C(O)NR^{c9N2}(OR^{a9N2})$, $C(O)OR^{a9N2}$, $OC(O)R^{b9N2}$, $OC(O)NR^{c9N2}R^{d9N2}$, $NR^{c9N2}R^{d9N2}$, $NR^{c9N2}NR^{c9N2}R^{d9N2}$, $NR^{c9N2}C(O)R^{b9N2}$, $NR^{c9N2}C(O)OR^{a9N2}$, $NR^{c9N2}C(O)NR^{c9N2}R^{d9N2}$, $C(=NR^{e9N2})R^{b9N2}$, $C(=NOH)R^{b9N2}$, $C(=NCN)R^{b9N2}$, $C(=NR^{e9N2})NR^{c9N2}R^{d9N2}$, $NR^{c9N2}C(=NR^{e9N2})NR^{c9N2}R^{d9N2}$, $NR^{c9N2}R^{d9N2}$, $NR^{c9N2}C(=NOH)NR^{c9N2}R^{d9N2}$, $NR^{c9N2}C(=NCN)NR^{c9N2}R^{d9N2}$, $NR^{c9N2}C(=NR^{e9N2})R^{b9N2}$, $NR^{c9N2}S(O)NR^{c9N2}R^{d9N2}$, $NR^{c9N2}S(O)R^{b9N2}$, $NR^{c9N2}S(O)_2R^{b9N2}$, $NR^{c9N2}S(O)(=NR^{e9N2})R^{b9N2}$, $NR^{c9N2}S(O)_2NR^{c9N2}R^{d9N2}$, $S(O)R^{b9N2}$, $S(O)NR^{c9N2}R^{d9N2}$, $S(O)_2R^{b9N2}$, $S(O)_2NR^{c9N2}R^{d9N2}$, $S(O)(=NR^{e9N2})R^{b9N2}$, $OS(O)(=NR^{e9N2})R^{b9N2}$, $OS(O)_2R^{b9N2}$, $SF_5$, $P(O)R^{f9N2}R^{g9N2}$, $OP(O)(OR^{h9N2})(OR^{i9N2})$, $P(O)(OR^{h9N2})(OR^{i9N2})$, and $BR^{j9N2}R^{k9N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9NA}$ are each optionally substituted with 1, 2, 3, or 4 independently selected $R^M$ substituents;

each $R^{a9N2}$, $R^{b9N2}$, $R^{c9N2}$, and $R^{d9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a9N2}$, $R^{b9N2}$, $R^{c9N2}$ and $R^{d9N2}$ are each optionally substituted with 1, 2, 3, or 4 independently selected $R^M$ substituents;

or, any $R^{c9N2}$ and $R^{d9N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e9N2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f9N2}$ and $R^{g9N2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h9N2}$ and $R^{i9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j9N2}$ and $R^{k9N2}$ is independently selected from OH, $C_{1-6}$ alkoxy, and $C_{1-6}$ haloalkoxy;

or any $R^{j9N2}$ and $R^{k9N2}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterecycloalkyl;

$R^9$ is selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, $NR^{c91}C(O)NR^{c91}R^{d91}$, $C(=NR^{e91})R^{b91}$, $C(=NOH)R^{b91}$, $C(=NCN)R^{b91}$, $C(=NR^{e91})NR^{c91}R^{d91}$, $NR^{c91}C(=NR^{e91})NR^{c91}R^{d91}$, $NR^{c91}C(=NOH)NR^{c91}R^{d91}$, $NR^{c91}C(=NCN)NR^{c91}R^{d91}$, $NR^{c91}C(=NR^{e91})R^{b91}$, $NR^{c91}S(O)NR^{c91}R^{d91}$, $NR^{c91}S(O)R^{b91}$, $NR^{c91}S(O)_2R^{b91}$, $NR^{c91}S(O)(=NR^{e91})R^{b91}$, $NR^{c91}S(O)_2NR^{c91}R^{d91}$, $S(O)R^{b91}$, $S(O)NR^{c91}R^{d91}$, $S(O)_2R^{b91}$, $S(O)_2NR^{c91}R^{d91}$, $S(O)(=NR^{e91})R^{b91}$, $OS(O)(=NR^{e91})R^{b91}$, $OS(O)_2R^{b91}$, $SF_5$, $P(O)R^{f91}R^{g91}$, $OP(O)(OR^{h91})(OR^{i91})$, $P(O)(OR^{h91})(OR^{i91})$, and $BR^{j91}R^{k91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

or, alternatively, two $R^9$ groups together form an oxo group;

each $R^{a91}$, $R^{b91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a91}$, $R^{b91}$, $R^{c91}$ and $R^{d91}$ are each optionally substituted with 1, 2, 3, 4, 5, 6, 7, or 8 independently selected $R^{9A}$ substituents;

or, any $R^{c91}$ and $R^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9A}$ substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f91}$ and $R^{g91}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterecycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterecycloalkyl)-$C_{1-6}$ alkyl-;

each $R^{h91}$ and $R^{i91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterecycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterecycloalkyl)-$C_{1-6}$ alkyl-;

each $R^{j91}$ and $R^{k91}$ is independently selected from OH, $C_{1-6}$ alkoxy, and $C_{1-6}$ haloalkoxy;

or any $R^{j91}$ and $R^{k91}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{9A}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, $NR^{c92}C(O)NR^{c92}R^{d92}$, $C(=NR^{e92})R^{b92}$, $C(=NOH)R^{b92}$, $C(=NCN)R^{b92}$, $C(=NR^{e92})NR^{c92}R^{d92}$, $NR^{c92}C(=NR^{e92})NR^{c92}R^{d92}$, $NR^{c92}C(=NOH)NR^{c92}R^{d92}$, $NR^{c92}C(=NCN)NR^{c92}R^{d92}$, $NR^{c92}C(=NR^{e92})R^{b92}$, $NR^{c92}S(O)NR^{c92}R^{d92}$, $NR^{c92}S(O)R^{b92}$, $NR^{c92}S(O)_2R^{b92}$, $NR^{c92}S(O)(=NR^{e92})R^{b92}$, $NR^{c92}S(O)_2NR^{c92}R^{d92}$, $S(O)R^{b92}$, $S(O)NR^{c92}R^{d92}$, $S(O)_2R^{b92}$, $S(O)_2NR^{c92}R^{d92}$, $S(O)(=NR^{e92})R^{b92}$, $OS(O)(=NR^{e92})R^{b92}$, $OS(O)_2R^{b92}$, $SF_5$, $P(O)R^{f92}R^{g92}$, $OP(O)(OR^{h92})(OR^{i92})$, $P(O)(OR^{h92})(OR^{i92})$, and $BR^{j92}R^{k92}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a92}$, $R^{b92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a92}$, $R^{b92}$, $R^{c92}$ and $R^{d92}$ are each optionally substituted with 1, 2, 3, or 4 independently selected $R^M$ substituents;

or, any $R^{c92}$ and $R^{d92}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e92}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f92}$ and $R^{g92}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h92}$ and $R^{i92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j92}$ and $R^{k92}$ is independently selected from OH, $C_{1-6}$ alkoxy, and $C_{1-6}$ haloalkoxy;

or any $R^{j92}$ and $R^{k92}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b10N}$, $C(O)NR^{c10N}R^{d10N}$, $C(O)OR^{a10N}$, $C(=NR^{e10N})R^{b10N}$, $C(=NR^{e10N})NR^{c10N}R^{d10N}$, $C(=NCN)NR^{c10N}R^{d10N}$, $C(=NOR^{a10N})NR^{c10N}$, $S(O)_2R^{b10N}$, $S(O)(=NR^{c10N})R^{d10N}$, and $S(O)_2NR^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, 4, 5, 6, 7, or 8 independently selected $R^{10NA}$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, 4, 5, 6, 7, or 8 independently selected $R^{10NA}$ substituents;

or, any $R^{c10N}$ and $R^{d10N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10NA}$ substituents;

each $R^{e10N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a10N2}$, $SR^{a10N2}$, $NHOR^{a10N2}$, $C(O)R^{b10N2}$, $C(O)NR^{c10N2}R^{d10N2}$, $C(O)NR^{c10N2}(OR^{a10N2})$, $C(O)OR^{a10N2}$, $OC(O)R^{b10N2}$, $OC(O)NR^{c10N2}R^{d10N2}$, $NR^{c10N2}R^{d10N2}$, $NR^{c10N2}NR^{c10N2}R^{d10N2}$, $NR^{c10N2}C(O)R^{b10N2}$, $NR^{c10N2}C(O)OR^{a10N2}$, $NR^{c10N2}C(O)NR^{c10N2}R^{d10N2}$, $C(=NR^{e10N2})R^{b10N2}$, $C(=NOH)R^{b10N2}$, $C(=NCN)R^{b10N2}$, $C(=NR^{e10N2})$ $NR^{c10N2}R^{d10N2}$, $NR^{c10N2}C(=NR^{e10N2})$ $NR^{c10N2}R^{d10N2}$, $NR^{c10N2}C(=NOH)NR^{c10N2}R^{d10N2}$, $NR^{c10N2}C(=NCN)NR^{c10N2}R^{d10N2}$, $NR^{c10N2}C(=NR^{e10N2})R^{b10N2}$, $NR^{c10N2}S(O)NR^{c10N2}R^{d10N2}$, $NR^{c10N2}S(O)R^{b10N2}$, $NR^{c10N2}S(O)_2R^{b10N2}$, $NR^{c10N2}S(O)(=NR^{e10N2})R^{b10N2}$, $NR^{c10N2}S(O)_2NR^{c10N2}R^{d10N2}$, $S(O)R^{b10N2}$, $S(O)NR^{c10N2}R^{d10N2}$, $S(O)_2R^{b10N2}$, $S(O)_2NR^{c10N2}R^{d10N2}$, $S(O)(=NR^{e10N2})R^{b10N2}$, $OS(O)(=NR^{e10N2})R^{b10N2}$, $OS(O)_2R^{b10N2}$, $SF_5$, $P(O)R^{f10N2}R^{g10N2}$, $OP(O)(OR^{h10N2})(OR^{i10N2})$, $P(O)(OR^{h10N2})(OR^{i10N2})$, and $BR^{10N2}R^{k10N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10NA}$ are each optionally substituted with 1, 2, 3, or 4 independently selected $R^M$ substituents;

each $R^{a10N2}$, $R^{b10N2}$, $R^{c10N2}$, and $R^{d10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a10N2}$, $R^{b10N2}$, $R^{c10N2}$ and $R^{d10N2}$ are each optionally substituted with 1, 2, 3, or 4 independently selected $R^M$ substituents;

or, any $R^{c10N2}$ and $R^{d10N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e10N2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f10N2}$ and $R^{g10N2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h10N2}$ and $R^{i10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j10N2}$ and $R^{k10N2}$ independently selected from OH, $C_{1-6}$ alkoxy, and $C_{1-6}$ haloalkoxy;

or any $R^{j10N2}$ and $R^{k10N2}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{10}$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a101}$, $SR^{a101}$, $NHOR^{a101}$, $C(O)R^{b101}$, $C(O)NR^{c101}R^{d101}$, $C(O)NR^{c101}(OR^{a101})$, $C(O)OR^{a101}$, $OC(O)R^{b101}$, $OC(O)NR^{c101}R^{d101}$, $NR^{c101}R^{d101}$, $NR^{c101}NR^{c101}R^{d101}$, $NR^{c101}C(O)R^{b101}$, $NR^{c101}C(O)OR^{a101}$, $NR^{c101}C(O)NR^{c101}R^{d101}$, $C(=NR^{e101})R^{b101}$, $C(=NOH)R^{b101}$, $C(=NCN)R^{b101}$, $C(=NR^{e101})NR^{c101}R^{d101}$, $NR^{c101}C(=NR^{e101})NR^{c101}R^{d101}$, $NR^{c101}C(=NOH)NR^{c101}R^{d101}$, $NR^{c101}C(=NCN)NR^{c101}R^{d101}$, $NR^{c101}C(=NR^{e101})R^{b101}$, $NR^{c101}S(O)NR^{c101}R^{d101}$, $NR^{c101}S(O)R^{b101}$, $NR^{c101}S(O)_2R^{b101}$, $NR^{c101}S(O)(=NR^{e101})R^{b101}$, $NR^{c101}S(O)_2NR^{c101}R^{d101}$, $S(O)R^{b101}$, $S(O)NR^{c101}R^{d101}$, $S(O)_2R^{b101}$, $S(O)_2NR^{c101}R^{d101}$, $S(O)(=NR^{e101})R^{b101}$, $OS(O)(=NR^{e101})R^{b101}$, $OS(O)_2R^{b101}$, $SF_5$, $P(O)R^{f101}R^{g101}$, $OP(O)(OR^{h101})(OR^{i101})$, $P(O)(OR^{h101})(OR^{i101})$, and $BR^{j101}R^{k101}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{10}$ are each optionally substituted with 1, 2, 3, 4, 5, 6, 7, or 8 independently selected $R^{10A}$ substituents;

each $R^{a101}$, $R^{b101}$, $R^{c101}$, and $R^{d101}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a101}$, $R^{b101}$, $R^{c101}$ and $R^{d101}$ are each optionally substituted with 1, 2, 3, 4, 5, 6, 7, or 8 independently selected $R^{10A}$ substituents;

or, any $R^{c101}$ and $R^{d101}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10A}$ substituents;

each $R^{e101}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f101}$ and $R^{g101}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h101}$ and $R^{i101}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j101}$ and $R^{k101}$ is independently selected from OH, $C_{1-6}$ alkoxy, and $C_{1-6}$ haloalkoxy;

or any $R^{j101}$ and $R^{k101}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

each $R^{104}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a102}$, $SR^{a102}$, $NHOR^{a102}$, $C(O)R^{b102}$, $C(O)NR^{c102}R^{d102}$, $C(O)NR^{c102}(OR^{a102})$, $C(O)OR^{a102}$, $OC(O)R^{b102}$, $OC(O)NR^{c102}R^{d102}$, $NR^{c102}R^{d102}$, $NR^{c102}NR^{c102}R^{d102}$, $NR^{c102}C(O)R^{b102}$, $NR^{c102}C(O)OR^{a102}$, $NR^{c102}C(O)NR^{c102}R^{d102}$, $C(=NR^{e102})R^{b102}$, $C(=NOH)R^{b102}$, $C(=NCN)R^{b102}$, $C(=NR^{e102})NR^{c102}R^{d102}$, $NR^{c102}C(=NR^{e102})NR^{c102}R^{d102}$, $NR^{c102}C(=NOH)NR^{c102}R^{d102}$, $NR^{c102}C(=NCN)NR^{c102}R^{d102}$, $NR^{c102}C(=NR^{e102})R^{b102}$, $NR^{c102}S(O)NR^{c102}R^{d102}$, $NR^{c102}S(O)R^{b102}$, $NR^{c102}S(O)_2R^{b102}$, $NR^{c102}S(O)(=NR^{e102})R^{b102}$, $NR^{c102}S(O)_2NR^{c102}R^{d102}$, $S(O)R^{b102}$, $S(O)NR^{c102}R^{d102}$, $S(O)_2R^{b102}$, $S(O)_2NR^{c102}R^{d102}$, $S(O)(=NR^{e102})R^{b102}$, $OS(O)(=NR^{e102})R^{b102}$, $OS(O)_2R^{b102}$, $SF_5$, $P(O)R^{f102}R^{g102}$, $OP(O)(OR^{h102})(OR^{i102})$, $P(O)(OR^{h102})(OR^{i102})$, and $BR^{j102}R^{k102}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{104}$ are each optionally substituted with 1, 2, 3, or 4 independently selected $R^M$ substituents;

each $R^{a102}$, $R^{b102}$, $R^{c102}$, and $R^{d102}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a102}$, $R^{b102}$, $R^{c102}$ and $R^{d102}$ are each optionally substituted with 1, 2, 3, or 4 independently selected $R^M$ substituents;

or, any $R^{c102}$ and $R^{d102}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e102}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f102}$ and $R^{g102}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h102}$ and $R^{i102}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j102}$ and $R^{k102}$ is independently selected from OH, $C_{1-6}$ alkoxy, and $C_{1-6}$ haloalkoxy;

or any $R^{j102}$ and $R^{k102}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered hetereocycloalkyl;

$R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b11N}$, $C(O)NR^{c11N}R^{d11N}$, $C(O)OR^{a11N}$, $C(=NR^{e11N})R^{b11N}$, $C(=NR^{e11N})NR^{c11N}R^{d11N}$, $C(=NCN)NR^{c11N}R^{d11N}$, $C(=NOR^{a11N})NR^{c11N}$, $S(O)_2R^{b11N}$, $S(O)(=NR^{c11N})R^{d11N}$, and $S(O)_2NR^{c11N}R^{d11N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{11N}$ are each optionally substituted with 1, 2, 3, 4, 5, 6, 7, or 8 independently selected $R^{11NA}$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^{11NA}$ substituents;

or, any $R^{c11N}$ and $R^{d11N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11NA}$ substituents;

each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11NA}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a11N2}$, SR$^{a11N2}$, NHOR$^{a11N2}$, C(O)R$^{b11N2}$, C(O)NR$^{c11N2}$R$^{d11N2}$, C(O)NR$^{c11N2}$(OR$^{a11N2}$), C(O)OR$^{a11N2}$, OC(O)R$^{b11N2}$, OC(O)NR$^{c11N2}$R$^{d11N2}$, NR$^{c11N2}$R$^{d11N2}$, NR$^{c11N2}$NR$^{c11N2}$R$^{d11N2}$, NR$^{c11N2}$C(O)R$^{b11N2}$, NR$^{c11N2}$C(O)OR$^{a11N2}$, NR$^{c11N2}$C(O)NR$^{c11N2}$R$^{d11N2}$, C(=NR$^{e11N2}$)R$^{b11N2}$, C(=NOH)R$^{b11N2}$, C(=NCN)R$^{b11N2}$, C(=NR$^{e11N2}$)NR$^{c11N2}$R$^{d11N2}$, NR$^{c11N2}$C(=NR$^{e11N2}$)NR$^{c11N2}$R$^{d11N2}$, NR$^{c11N2}$C(=NOH)NR$^{c11N2}$R$^{d11N2}$, NR$^{c11N2}$C(=NCN)NR$^{c11N2}$R$^{d11N2}$, NR$^{c11N2}$C(=NR$^{e11N2}$)R$^{b11N2}$, NR$^{c11N2}$S(O)NR$^{c11N2}$R$^{d11N2}$, NR$^{c11N2}$S(O)R$^{b11N2}$, NR$^{c11N2}$S(O)$_2$R$^{b11N2}$, NR$^{c11N2}$S(O)(=NR$^{e11N2}$)R$^{b11N2}$, NR$^{c11N2}$S(O)$_2$NR$^{c11N2}$R$^{d11N2}$, S(O)R$^{b11N2}$, S(O)NR$^{c11N2}$R$^{d11N2}$, S(O)$_2$R$^{b11N2}$, S(O)$_2$NR$^{c11N2}$R$^{d11N2}$, S(O)(=NR$^{e11N2}$)R$^{b11N2}$, OS(O)(=NR$^{e11N2}$)R$^{b11N2}$, OS(O)$_2$R$^{b11N2}$, SF$_5$, P(O)R$^{f11N2}$R$^{g11N2}$, OP(O)(OR$^{h11N2}$)(OR$^{i11N2}$), P(O)(OR$^{h11N2}$)(OR$^{i11N2}$), and BR$^{j11N2}$R$^{k11N2}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{11NA}$ are each optionally substituted with 1, 2, 3, or 4 independently selected R$^M$ substituents;

each R$^{a11N2}$, R$^{b11N2}$, R$^{c11N2}$, and R$^{d11N2}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a11N2}$, R$^{b11N2}$, R$^{c11N2}$ and R$^{d11N2}$ are each optionally substituted with 1, 2, 3, or 4 independently selected R$^M$ substituents;

or, any R$^{c11N2}$ and R$^{d11N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected R$^M$ substituents;

each R$^{e11N2}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{f11N2}$ and R$^{g11N2}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

each R$^{h11N2}$ and R$^{i11N2}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

each R$^{j11N2}$ and R$^{k11N2}$ is independently selected from OH, C$_{1-6}$ alkoxy, and C$_{1-6}$ haloalkoxy;

or any R$^{j11N2}$ and R$^{k11N2}$ attached to the same B atom, together with the B atom to which they are attached, form a 5- or 6-membered heterocycloalkyl group optionally substituted with 1, 2, 3, or 4 substituents independently selected from C$_{1-6}$ alkyl, C$_{1-6}$ haloalkyl, C$_{3-10}$ cycloalkyl, and 4-10 membered heterocycloalkyl;

R$^{11}$ is selected from H, D, halo, oxo, $_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a111}$, SR$^{a111}$, NHOR$^{a111}$, C(O)R$^{b111}$, C(O)NR$^{c111}$R$^{d111}$, C(O)NR$^{c111}$(OR$^{a111}$), C(O)OR$^{a111}$, OC(O)R$^{b111}$, OC(O)NR$^{c111}$R$^{d111}$, NR$^{c111}$R$^{d111}$, NR$^{c111}$NR$^{c111}$R$^{d111}$, NR$^{c111}$C(O)R$^{b111}$, NR$^{c111}$C(O)OR$^{d111}$, NR$^{c111}$C(O)NR$^{c111}$R$^{d111}$, C(=NR$^{e111}$)R$^{b111}$, C(=NOH)R$^{b111}$, C(=NCN)R$^{b111}$, C(=NR$^{e111}$)NR$^{c111}$R$^{d111}$, NR$^{c111}$C(=NR$^{e111}$)NR$^{c111}$R$^{d111}$, NR$^{c111}$C(=NOH)NR$^{c111}$R$^{d111}$, NR$^{c111}$C(=NCN)NR$^{c111}$R$^{d111}$, NR$^{c111}$C(=NR$^{e111}$)R$^{b111}$, NR$^{c111}$S(O)NR$^{c111}$R$^{d111}$, NR$^{c111}$S(O)R$^{b111}$, NR$^{c111}$S(O)$_2$R$^{b111}$, NR$^{c111}$S(O)(=NR$^{e111}$)R$^{b111}$, NR$^{c111}$S(O)$_2$NR$^{c111}$R$^{d111}$, S(O)R$^{b111}$, S(O)NR$^{c111}$R$^{d111}$, S(O)$_2$R$^{b111}$, S(O)$_2$NR$^{c111}$R$^{d111}$, S(O)(=NR$^{e111}$)R$^{b111}$, OS(O)(=NR$^{e111}$)R$^{b111}$, OS(O)$_2$R$^{b111}$, SF$_5$, P(O)R$^{f111}$R$^{g111}$, OP(O)(OR$^{h111}$)(OR$^{i111}$), P(O)(OR$^{h111}$)(OR$^{i111}$), and BR$^{j111}$R$^{k111}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{11}$ are each optionally substituted with 1, 2, 3, 4, 5, 6, 7, or 8 independently selected R$^{11A}$ substituents;

each R$^{a111}$, R$^{b111}$, R$^{c111}$, and R$^{d111}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a111}$, R$^{b111}$, R$^{c111}$ and R$^{d111}$ are each optionally substituted with 1, 2, 3, 4, 5, 6, 7, or 8 independently selected R$^{11A}$ substituents;

or, any R$^{c111}$ and R$^{d111}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{11A}$ substituents;

each R$^{e111}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, and C$_{2-6}$ alkynyl;

each R$^{f111}$ and R$^{g111}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered hetereocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered hetereocycloalkyl)-C$_{1-6}$ alkyl-;

each $R^{h111}$ and $R^{i111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterecycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j111}$ and $R^{k111}$ is independently selected from OH, $C_{1-6}$ alkoxy, and $C_{1-6}$ haloalkoxy;

or any $R^{j111}$ and $R^{k111}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterecycloalkyl; and each $R^{11A}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a112}$, $SR^{a112}$, $NHOR^{a112}$, $C(O)R^{b112}$, $C(O)NR^{c112}R^{d112}$, $C(O)NR^{c112}(OR^{a112})$, $C(O)OR^{a112}$, $OC(O)R^{b112}$, $OC(O)NR^{c112}R^{d112}$, $NR^{c112}R^{d112}$, $NR^{c112}NR^{c112}R^{d112}$, $NR^{c112}C(O)R^{b112}$, $NR^{c112}C(O)OR^{a112}$, $NR^{c112}C(O)NR^{c112}R^{d112}$, $C(=NR^{e112})R^{b112}$, $C(=NOH)R^{b112}$, $C(=NCN)R^{b112}$, $C(=NR^{e112})NR^{c112}R^{d112}$, $NR^{c112}C(=NR^{e112})NR^{c112}R^{d112}$, $NR^{c112}C(=NOH)NR^{c112}R^{d112}$, $NR^{c112}C(=NCN)NR^{c112}R^{d112}$, $NR^{c112}C(=NR^{e112})R^{b112}$, $NR^{c112}S(O)NR^{c112}R^{d112}$, $NR^{c112}S(O)R^{b112}$, $NR^{c112}S(O)_2R^{b112}$, $NR^{c112}S(O)(=NR^{e112})R^{b112}$, $NR^{c112}S(O)_2NR^{c112}R^{d112}$, $S(O)R^{b112}$, $S(O)NR^{c112}R^{d112}$, $S(O)_2R^{b112}$, $S(O)_2NR^{c112}R^{d112}$, $S(O)(=NR^{e112})R^{b112}$, $OS(O)(=NR^{e112})R^{b112}$, $OS(O)_2R^{b112}$, $SF_5$, $P(O)R^{f112}R^{g112}$, $OP(O)(OR^{h112})(OR^{i112})$, $P(O)(OR^{h112})(OR^{i112})$, and $BR^{j112}R^{k112}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11A}$ are each optionally substituted with 1, 2, 3, or 4 independently selected $R^M$ substituents;

each $R^{a112}$, $R^{b112}$, $R^{c112}$, and $R^{d112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a112}$, $R^{b112}$, $R^{c112}$ and $R^{d112}$ are each optionally substituted with 1, 2, 3, or 4 independently selected $R^M$ substituents;

or, any $R^{c112}$ and $R^{d112}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{e112}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f112}$ and $R^{g112}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h112}$ and $R^{i112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j112}$ and $R^{k112}$ is independently selected from OH, $C_{1-6}$ alkoxy, and $C_{1-6}$ haloalkoxy;

or any $R^{j112}$ and $R^{k112}$ attached to the same B atom, together with the B atom to which they are attached, form a 5- or 6-membered heterocycloalkyl group optionally substituted with 1, 2, 3, or 4 substituents independently selected from $C_{1-6}$ alkyl, $C_{1-6}$ haloalkyl, $C_{3-10}$ cycloalkyl, and 4-10 membered heterecycloalkyl.

In some embodiments, $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NOH)R^{b1}$, $C(=NCN)R^{b1}$, $NR^{c1}C(=NOH)NR^{c1}R^{d1}$, $NR^{c1}C(=NCN)NR^{c1}R^{d1}$, $NR^{c1}S(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, and $OS(O)_2R^{b1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, or 4 independently selected $R^{14}$ substituents; and each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, or 4, independently selected $R^{14}$ substituents.

In some embodiments, $R^1$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)$ $OR^{a1}$, $NR^{c1}C(O)NR^{c1}R^{d1}$, and $S(O)_2R^{b1}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^1$ are each optionally substituted with 1, 2, 3, or 4 independently selected $R^{1A}$ substituents; and each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{a1}$, $R^{b1}$, $R^{c1}$ and $R^{d1}$ are each optionally substituted with 1, 2, 3, or 4, independently selected $R^{1A}$ substituents.

In some embodiments, $R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$; and each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{1A}$ substituents.

In some embodiments, $R^1$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, and $S(O)_2R^{b1}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^1$ are each optionally substituted with 1, 2, 3, or 4 independently selected $R^{1A}$ substituents; and each $R^{a1}$, $R^{b1}$, $R^{c1}$, and $R^{d1}$ is independently selected from H, $C_{2-6}$ alkyl, $C_{1-6}$ haloalkyl, $C_{2-6}$ alkenyl, $C_{2-6}$ alkynyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{a1}$, $R^{b1}$, $R^{c1}$ and $R^{d1}$ are each optionally substituted with 1, 2, 3, or 4, independently selected $R^{1A}$ substituents.

In some embodiments, $R^1$ is selected from H, $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, and $NR^{c1}C(O)NR^{c1}R^{d1}$; and each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{1A}$ substituents.

In some embodiments, $R^1$ is selected from H, $C_{1-6}$ alkyl, $C_{1-6}$ haloalkyl, and $C(O)NR^{c1}R^{d1}$, wherein the $C_{1-6}$ alkyl is optionally substituted with 1, 2, 3, or 4 independently selected $R^{1A}$ substituents; and each $R^{c1}$ and $R^{d1}$ is independently selected from H, $C_{2-6}$ alkyl and 4-7 membered heterocycloalkyl.

In some embodiments, $R^1$ is selected from H, $C_{1-6}$ haloalkyl, and $C(O)NR^{c1}R^{d1}$.

In some embodiments, $R^1$ is selected from H, $C_{1-6}$ haloalkyl, and $C(O)NR^{c1}R^{d1}$; and each $R^{c1}$ and $R^{d1}$ is independently selected from H, $C_{1-6}$ alkyl, and 4-6 membered heterocycloalkyl, wherein the $C_{1-6}$ alkyl and 4-6 membered heterocycloalkyl of $R^{c1}$ and $R^{d1}$ are each optionally substituted with 1 or 2 independently selected $R^{1A}$ substituents.

In some embodiments, $R^1$ is selected from H, $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, $NR^{c1}C(O)NR^{c1}R^{d1}$, and 5-6 membered heteroaryl, wherein the $C_{1-6}$ alkyl and 5-6 membered heteroaryl are optionally substituted with 1 or 2 independently selected $R^{1A}$ substituents; and each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{1A}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents.

In some embodiments, $R^1$ is selected from H, $C_{1-6}$ alkyl, $C_{1-6}$ haloalkyl, $C(O)R^{b1}$, $C(O)NR^{c1}R^{d1}$, and 5-6 membered heteroaryl wherein the $C_{1-6}$ alkyl and 5-6 membered heteroaryl are optionally substituted with 1 or 2 independently selected $R^{1A}$ substituents; and each $R^{b1}$, $R^{c1}$ and $R^{d1}$ is independently selected from H, $C_{1-6}$ alkyl, $C_{3-6}$ cycloalkyl, and 4-6 membered heterocycloalkyl, wherein the $C_{1-6}$ alkyl, $C_{3-6}$ cycloalkyl, and 4-6 membered heterocycloalkyl of $R^{b1}$, $R^{c1}$ and $R^{d1}$ are each optionally substituted with 1 or 2 independently selected $R^{1A}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents.

In some embodiments, $R^1$ is selected from H, $C_{1-6}$ alkyl, $C_{1-6}$ haloalkyl, $C(O)R^{b1}$, $C(O)NR^{c1}R^{d1}$ and 5-6 membered heteroaryl, wherein the $C_{1-6}$ alkyl, and 5-6 membered heteroaryl are each optionally substituted with 1 or 2 independently selected $R^{1A}$ substituents;

$R^{b1}$ is 4-6 membered heterocycloalkyl, wherein the 4-6 membered heterocycloalkyl of $R^{b1}$ is optionally substituted with 1 or 2 independently selected $R^{1A}$ substituents;

each $R^{c1}$ and $R^{d1}$ is independently selected from H, $C_{1-6}$ alkyl, $C_{3-6}$ cycloalkyl, and 4-6 membered heterocycloalkyl, wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{14}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{14}$ substituents.

In some embodiments, each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{14}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{14}$ substituents.

In some embodiments, $R^{b1}$ is 4-6 membered heterocycloalkyl, wherein the 4-6 membered heterocycloalkyl of $R^{b1}$ is optionally substituted with 1 or 2 independently selected $R^{14}$ substituents.

In some embodiments, each $R^{c1}$ and $R^{d1}$ is independently selected from H, $C_{1-6}$ alkyl, $C_{3-6}$ cycloalkyl, and 4-6 membered heterocycloalkyl, wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{14}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{14}$ substituents.

In some embodiments, $R^{b1}$ is azetidinyl, optionally substituted with 1 or 2 independently selected $R^{14}$ substituents.

In some embodiments, $R^{b1}$ is selected from azetidin-1-yl, 3-hydroxyazetidin-1-yl, 3,3-dimethylazetidin-1-yl, and 3,3-difluoroazetidin-1-yl.

In some embodiments, each $R^{c1}$ and $R^{d1}$ is independently selected from H, isopropyl, tetrahydropyranyl, bicyclo[1.1.1]pentanyl, and cyclobutyl, wherein the tetrahydropyranyl, and cyclobutyl are each optionally substituted with 1 or 2 independently selected $R^{14}$ substituents;

or any $R^{c1}$ and $R^{d1}$, attached to the same N atom, together with the N atom to which they are attached, form an azetidinyl group, optionally substituted with 1 or 2 independently selected $R^{14}$ substituents.

In some embodiments, each $R^{c1}$ and $R^{d1}$ is independently selected from H, isopropyl, tetrahydro-2H-pyran-4-yl, 3-hydroxytetrahydro-2H-pyran-4-yl, 3-hydroxycyclobutyl, and bicyclo[1.1.1]pentan-1-yl;

or any $R^{c1}$ and $R^{d1}$, attached to the same N atom, together with the N atom to which they are attached, form an azetidinyl, 3-hydroxyazetidinyl, 3,3-dimethylazetidinyl, or 3,3-difluoroazetidin-1-yl group.

In some embodiments, each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{14}$ substituents.

In some embodiments, each $R^{c1}$ and $R^{d1}$ is independently selected from H, $C_{1-6}$ alkyl, and 4-6 membered heterocycloalkyl, wherein the $C_{1-6}$ alkyl and 4-6 membered heterocycloalkyl of $R^{c1}$ and $R^{d1}$ are each optionally substituted with 1 or 2 independently selected $R^{14}$ substituents.

In some embodiments, each $R^{c1}$ and $R^{d1}$ is independently selected from H, $C_{2-6}$ alkyl, and 4-6 membered heterocycloalkyl.

In some embodiments, each $R^{c1}$ and $R^{d1}$ is independently selected from H, isopropyl, and tetrahydropyranyl.

In some embodiments, each $R^{14}$ is independently selected from H, D, halo, $C_{1-6}$ alkyl, $C_{1-6}$ haloalkyl, phenyl, $C_{3-6}$ cycloalkyl, 5-6 membered heteroaryl, 4-6 membered heterocycloalkyl, and OH.

In some embodiments, each $R^{14}$ is independently selected from halo, $C_{1-6}$ alkyl, and OH.

In some embodiments, $R^1$ is selected from H, $C_{1-6}$ alkyl, $C_{1-6}$ haloalkyl, and $C(O)NR^{c1}R^{d1}$, wherein the $C_{1-6}$ alkyl is optionally substituted with 1, 2, 3, or 4 independently selected $R^{14}$ substituents; and each $R^{c1}$ and $R^{d1}$ is independently selected from H, $C_{1-6}$ alkyl and 4-7 membered heterocycloalkyl.

In some embodiments, $R^1$ is selected from H, $C_{1-6}$ haloalkyl, and $C(O)NR^{c1}R^{d1}$; and each $R^{c1}$ and $R^{d1}$ is independently selected from H, $C_{1-6}$ alkyl, and 4-6 membered heterocycloalkyl.

In some embodiments, $R^1$ is selected from H, $C_{1-6}$ haloalkyl, and $C(O)NR^{c1}R^{d1}$; and each $R^{c1}$ and $R^{d1}$ is independently selected from H, isopropyl, and tetrahydropyranyl.

In some embodiments, $R^1$ is selected from H, $CF_3$, and $C(O)NHR^{d1}$, wherein $R^{d1}$ is $C_{1-6}$ alkyl or 5-6 membered heterocycloalkyl.

In some embodiments, $R^1$ is selected from H, $CF_3$, $C(O)NHC(CH_3)_2$, and $C(O)NH$-tetrahydropyran.

In some embodiments, $R^1$ is 5-6 membered heteroaryl, optionally substituted with 1 or 2 independently selected $R^{14}$ substituents.

In some embodiments, $R^1$ is 5 membered heteroaryl, optionally substituted with 1 or 2 independently selected $R^{14}$ substituents.

In some embodiments, $R^1$ is selected from thiazolyl, and pyrazolyl, each optionally substituted with 1 or 2 independently selected $R^{14}$ substituents.

In some embodiments, $R^1$ is selected from, H, $CF_3$, isopropylcarbamoyl, (tetrahydro-2H-pyran-4-yl)carbamoyl, azetidine-1-carbonyl, bicyclo[1.1.1]pentan-1-ylcarbamoyl, 3,3-dimethylazetidine-1-carbonyl, 3,3-difluoroazetidine-1-carbonyl, 3-hydroxyazetidine-1-carbonyl, (3-hydroxycyclobutyl)carbamoyl, (3-hydroxytetrahydro-2H-pyran-4-yl)carbamoyl. 2-methylthiazol-5-yl, 1-methyl-1H-pyrazol-4-yl, 1-methyl-1H-pyrazol-5-yl, 5-methyl-1H-pyrazol-4-yl, and 1H-pyrazol-4-yl.

In some embodiments, $R^1$ is H.

In some embodiments, $R^1$ is $CF_3$.

In some embodiments, $R^1$ is $C(O)NHC(CH_3)_2$ or $C(O)NH$-tetrahydropyran.

In some embodiments, $R^1$ is $C(O)NHC(CH_3)_2$.

In some embodiments, $R^1$ is $C(O)NH$-tetrahydropyran.

In some embodiments, $R^1$ is 2-methylthiazol-5-yl, 1-methyl-1H-pyrazol-4-yl, 1-methyl-1H-pyrazol-5-yl, 5-methyl-1H-pyrazol-4-yl, or 1H-pyrazol-4-yl.

In some embodiments, $X^2$ is N.

In some embodiments, $X^2$ is $CR^2$.

In some embodiments, $R^2$ is selected from H, D, halo, CN, OH, $NH_2$, and $C_{1-6}$ alkyl.

In some embodiments, $R^2$ is selected from H, D, and $C_{1-6}$ alkyl.

In some embodiments, $R^2$ is H.

In some embodiments, $X^2$ is $CR^2$, wherein $R^2$ is selected from H, D, halo, CN, OH, $NH_2$, and $C_{1-6}$ alkyl.

In some embodiments, $X^2$ is $CR^2$, wherein $R^2$ is selected from H, D, and $C_{1-6}$ alkyl.

In some embodiments, $X^2$ is CH.

In some embodiments, $X^2$ is N or CH.

In some embodiments, when $X^2$ is N, $R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$.

In some embodiments, when $X^2$ is N, $R^1$ is selected from H, $CF_3$, $C(O)NHC(CH_3)_2$, and C(O)NH-tetrahydropyran.

In some embodiments, when $X^2$ is N, $R^1$ is H.

In some embodiments, when $X^2$ is $CR^2$, $R^1$ is selected from D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$.

In some embodiments, when $X^2$ is $CR^2$, $R^1$ is selected from $C_{1-6}$ alkyl, $C_{1-6}$ haloalkyl, $C(O)R^{b1}$, $C(O)NR^{c1}R^{d1}$ and 5-6 membered heteroaryl, wherein the $C_{1-6}$ alkyl, and 5-6 membered heteroaryl are each optionally substituted with 1 or 2 independently selected $R^{14}$ substituents.

In some embodiments, when $X^2$ is $CR^2$, $R^1$ is selected from $CF_3$, $C(O)NHC(CH_3)_2$, and C(O)NH-tetrahydropyran.

In some embodiments, when $X^2$ is $CR^2$, $R^1$ is selected from $CF_3$, isopropylcarbamoyl, (tetrahydro-2H-pyran-4-yl)carbamoyl, azetidine-1-carbonyl, bicyclo[1.1.1]pentan-1-ylcarbamoyl, 3,3-dimethylazetidine-1-carbonyl, 3,3-difluoroazetidine-1-carbonyl, 3-hydroxyazetidine-1-carbonyl, (3-hydroxycyclobutyl)carbamoyl, (3-hydroxytetrahydro-2H-pyran-4-yl)carbamoyl. 2-methylthiazol-5-yl, 1-methyl-1H-pyrazol-4-yl, 1-methyl-1H-pyrazol-5-yl, 5-methyl-1H-pyrazol-4-yl, and 1H-pyrazol-4-yl.

In some embodiments, $R^3$ is selected from H, D, halo, CN, OH, $NH_2$, and $C_{1-6}$ alkyl.

In some embodiments, $R^3$ is selected from H, D, and $C_{1-6}$ alkyl.

In some embodiments, $R^3$ is H.

In some embodiments, $X^4$ is N.

In some embodiments, $X^4$ is $CR^4$.

In some embodiments, $R^4$ is selected from H, D, halo, CN, OH, $NH_2$, $C_{1-6}$ alkyl, $C_{1-6}$ haloalkyl, $C_{2-6}$ alkenyl, and $C_{2-6}$ alkynyl.

In some embodiments, $R^4$ is selected from H, D, halo, CN, OH, $NH_2$, and $C_{1-6}$ alkyl.

In some embodiments, $R^4$ is selected from H, D, $C_{1-6}$ alkyl, $C_{1-6}$ haloalkyl, $C_{2-6}$ alkenyl, and $C_{2-6}$ alkynyl.

In some embodiments, $R^4$ is H or methyl.

In some embodiments, $R^4$ is H.

In some embodiments, $R^4$ is methyl.

In some embodiments, $X^4$ is $CR^4$, wherein $R^4$ is selected from H, D, halo, CN, OH, $NH_2$, and $C_{1-6}$ alkyl.

In some embodiments, $X^4$ is CH.

In some embodiments, $X^5$ is N.

In some embodiments, $X^5$ is $CR^5$.

In some embodiments, $R^5$ is selected from H, D, halo, CN, OH, $NH_2$, $C_{1-6}$ alkyl, $C_{1-6}$ haloalkyl, $C_{2-6}$ alkenyl, and $C_{2-6}$ alkynyl.

In some embodiments, $R^5$ is selected from H, D, halo, CN, OH, $NH_2$, and $C_{1-6}$ alkyl.

In some embodiments, $R^5$ is selected from H, D, $C_{1-6}$ alkyl, $C_{1-6}$ haloalkyl, $C_{2-6}$ alkenyl, and $C_{2-6}$ alkynyl.

In some embodiments, $R^5$ is H.

In some embodiments, $X^5$ is $CR^5$, wherein $R^5$ is selected from H, D, halo, CN, OH, $NH_2$, and $C_{1-6}$ alkyl.

In some embodiments, $X^5$ is CH.

In some embodiments, $X^6$ is N.

In some embodiments, $X^6$ is $CR^6$.

In some embodiments, $R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NOH)R^{b6}$, $C(=NCN)R^{b6}$, $NR^{c6}C(=NOH)NR^{c6}R^{d6}$, $NR^{c6}C(=NCN)NR^{c6}R^{d6}$, $NR^{c6}S(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2R^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{64}$ substituents;

each $R^{a6}$, $R^{b6}$, $R^{c6}$, and $R^{d6}$ is independently selected from H, $C_{1-6}$ alkyl, $C_{1-6}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, or 4 independently selected $R^{64}$ substituents;

each $R^{64}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NOH)R^{b61}$, $C(=NCN)R^{b61}$, $NR^{c61}C(=NOH)NR^{c61}R^{d61}$, $NR^{c61}C(=NCN)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{b61}$, and $OS(O)_2R^{b61}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{64}$ are each optionally substituted with 1, 2, 3, or 4 independently selected $R^M$ substituents; and wherein each $R^{a61}$, $R^{b61}$, $R^{c61}$, and $R^{d61}$ is independently selected from H and $C_{1-6}$ alkyl.

In some embodiments, $R^6$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, CN, $NO_2$, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}C(O)NR^{c6}R^{d6}$, and $S(O)_2R^{b6}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^6$ are each optionally substituted with 1, 2, 3, or 4 independently selected $R^{6A}$ substituents;

each $R^{a6}$, $R^{b6}$, $R^{c6}$, and $R^{d6}$ is independently selected from H, $C_{1-6}$ alkyl, $C_{1-6}$haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^{a6}$, $R^{b6}$, $R^{c6}$ and $R^{d6}$ are each optionally substituted with 1, 2, 3, or 4 independently selected $R^{6A}$ substituents; and each $R^{6A}$ is selected from H, D, halo, CN, OH, $NH_2$, and $C_{1-6}$ alkyl.

In some embodiments, $R^6$ is selected from H, D, halo, $C_{1-6}$ alkyl, $C_{1-6}$ haloalkyl, $SR^{a6}$, $C(O)NR^{c6}R^{d6}$, $C(O)R^{b6}$, and $S(O)_2R^{b6}$, wherein the $C_{1-6}$ alkyl is optionally substituted with 1, 2, 3, or 4 independently selected $R^{6A}$ substituents;

each $R^{a6}$, $R^{b6}$, $R^{c6}$ and $R^{d6}$ is independently selected from H and $C_{1-6}$ alkyl; and each $R^{6A}$ is selected from H, D, halo, CN, OH, $NH_2$, and $C_{1-6}$ alkyl.

In some embodiments, $R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1 or 2 independently selected $R^{6A}$ substituents.

In some embodiments, each $R^{6A}$ is independently selected from H, D, CN, $NO_2$, OH, halo, $C_{1-6}$ alkyl, $C_{1-6}$ haloalkyl, $C_{2-6}$ alkenyl, and $C_{2-6}$ alkynyl.

In some embodiments, each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl.

In some embodiments:

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1 or 2 independently selected $R^{6A}$ substituents;

each $R^{6A}$ is independently selected from H, D, CN, $NO_2$, OH, halo, $C_{1-6}$ alkyl, $C_{1-6}$ haloalkyl, $C_{2-6}$ alkenyl, and $C_{2-6}$ alkynyl; and each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl.

In some embodiments, $R^6$ is selected from H, halo, $C_{1-6}$ alkyl, $C(O)R^{b6}$, $S(O)R^{b6}$, and $S(O)_2R^{b6}$, wherein the $C_{1-6}$ alkyl is optionally substituted by 1 or 2 OH groups; and $R^{b6}$ is selected from H, $C_{1-6}$ alkyl, $C_{1-6}$ haloalkyl, $C_{2-6}$ alkenyl, and $C_{2-6}$ alkynyl.

In some embodiments:

In some embodiments, $R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 independently selected $R^{6A}$ substituents;

$R^{a6}$ and $R^{b6}$ are each independently selected from H and $C_{1-6}$ alkyl; and each $R^{6A}$ is selected from halo, OH, and $C_{1-6}$ haloalkyl.

In some embodiments, $R^6$ is selected from H, D, halo, methyl, $C(CH_3)_2OH$, $CH(CH_3)OH$, $C(O)CH_3$, $S(O)_2CH_3$, and $SCH_3$.

In some embodiments, $R^6$ is selected from H, chloro, methyl, hydroxyethyl, hydroxypropyl, thiomethyl, $C(O)CH_3$, and $S(O)_2CH_3$.

In some embodiments, $R^6$ is $CH(OH)—CH_2OH$.

In some embodiments, $R^6$ is $C(CH_3)(OH)—CH_2OH$.

In some embodiments, $R^6$ is $C(OH)(C_1\text{-haloalkyl})-CH_2OH$.

In some embodiments, $R^6$ is $C(OH)(S(=O)R^{b6})—CH_2OH$.

In some embodiments, $R^6$ is $C(OH)(C_1\text{-haloalkyl})-C(O)NH_2$.

In some embodiments, $R^6$ is $C(O)NH_2$.

In some embodiments, $R^6$ is methyl.

In some embodiments, $R^6$ is H.

In some embodiments, $R^6$ is selected from D, halo, methyl, $C(CH_3)_2OH$, $CH(CH_3)OH$, $C(O)CH_3$, $S(O)_2CH_3$, and $SCH_3$.

In some embodiments, $R^6$ is selected from H, methyl, chloro, $SCH_3$, $S(O)_2CH_3$, $C(O)CH_3$, $CH(CH_3)OH$, $C(CH_3)_2OH$, and 1,1,1-trifluoro-2,3-dihydroxypropan-2-yl.

In some embodiments, $R^6$ is a $C(OH)(R^{6A})_2$, wherein at least one $R^{6A}$ is $C_{1-6}$ haloalkyl. In some embodiments, each halogen is F. In some embodiments, the haloalkyl is optionally substituted with 1 or 2 independently selected $Y^2$ substituents.

In some embodiments, each $Y^2$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$alkoxy, $C_{1-6}$haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$alkyl)aminocarbonylamino.

In some embodiments, at least one $R^{6A}$ is selected from $CF_3$, $CCl_3$, $CF_2H$, $CCl_2H$, $CF_2Y^2$, $CCl_2Y^2$, $CFH_2$, $CClH_2$, $CFHY^2$, $CClHY^2$, $CF(Y^2)_2$ and $CCl(Y^2)_2$.

In some embodiments, at least one $R^{6A}$ is selected from $CF_3$, $CF_2H$, $CF_2Y^2$, $CFH_2$, $CFHY^2$, and $CF(Y^2)_2$.

In some embodiments, at least one $R^{6A}$ is $C_{1-6}$ haloalkyl, wherein each halogen is F.

In some embodiments, at least one $R^{6A}$ is $C_{1-6}$ haloalkyl, wherein each halogen is Cl.

In some embodiments, at least one $R^{6A}$ is selected from $CH_2F$, $CHF_2$, $CF_3$, and $CF_2CF_3$.

In some embodiments, at least one $R^{6A}$ is $CF_3$.

In some embodiments, at least one $R^{6A}$ is $CH_2F$.

In some embodiments, at least one $R^{6A}$ is $CHF_2$.

In some embodiments, at least one $R^{6A}$ is $CF_2CF_3$.

In some embodiments, $X^7$ is N.

In some embodiments, $X^7$ is C.

In some embodiments, $X^7$ is CH.

In some embodiments, $X^8$ is N.

In some embodiments, $X^8$ is C.

In some embodiments, $X^8$ is CH.

In some embodiments, both $X^7$ and $X^8$ are C.

In some embodiments, $X^7$ is N and $X^8$ is C.

In some embodiments, $X^7$ is C and $X^8$ is N.

In some embodiments, $X^9$ is $NR^{9N}$.

In some embodiments, $R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, or 4 independently selected $R^{9NA}$ substituents.

In some embodiments, $R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments, $R^{9N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl, $C_{3-6}$ cycloalkyl, and $C_{3-6}$ cycloalkyl-$C_{1-6}$ alkyl- of $R^{9N}$ are each optionally substituted with 1 or 2 independently selected $R^{9NA}$ substituents.

In some embodiments, $R^{9N}$ is selected from $C_{1-6}$ alkyl, $C_{3-6}$ cycloalkyl, and $C_{3-6}$ cycloalkyl-$C_{1-6}$ alkyl-.

In some embodiments, $R^{9N}$ is selected from $C_{1-6}$ alkyl, $C_{3-6}$ cycloalkyl, and $C_{3-6}$ cycloalkyl-$C_{1-6}$ alkyl-, wherein each are optionally substituted with $C_{3-6}$ cycloalkyl.

In some embodiments, $R^{9N}$ is $C_{3-6}$ cycloalkyl-$C_{1-6}$ alkyl-.

In some embodiments, $R^{9N}$ is cyclopropylethyl.

In some embodiments, $R^{9N}$ is 1-cyclopropylethyl.

In some embodiments, $X^9$ is N.

In some embodiments, $X^9$ is O.

In some embodiments, $X^9$ is S.

In some embodiments, $X^9$ is S(O).

In some embodiments, $X^9$ is $S(O)_2$.

In some embodiments, $X^9$ is $CR^9$.

In some embodiments, $X^9$ is $C(R^9)_2$.

In some embodiments, each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents;

or, alternatively, two $R^9$ groups together form an oxo group.

In some embodiments, $R^9$ is selected from H, D, halo, CN, OH, $NH_2$, and $C_{1-6}$ alkyl.

In some embodiments, each $R^9$ is H.

In some embodiments, two $R^9$ groups together form an oxo group.

In some embodiments, $X^9$ is $CR^9$; wherein $R^9$ is selected from H, D, halo, CN, OH, $NH_2$, and $C_{1-6}$ alkyl.

In some embodiments, $X^9$ is CH.

In some embodiments, $X^9$ is $CH_2$.

In some embodiments, $X^9$ is C(O).

In some embodiments, $X^{10}$ is $NR^{10N}$.

In some embodiments, $R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents.

In some embodiments, $R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments, $R^{10N}$ is selected from H, $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl- and (4-6 membered heterocycloalkyl)-$C_{1-6}$ alkyl- of $R^{10N}$ are each optionally substituted with 1 or 2 independently selected $R^{10NA}$ substituents.

In some embodiments, $R^{10N}$ is selected from H, $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-.

In some embodiments, $R^{10N}$ is selected from H, $C_{1-6}$ alkyl, phenyl, $C_{3-6}$ cycloalkyl, phenyl-$C_{1-6}$ alkyl-, and $C_{3-6}$ cycloalkyl-$C_{1-6}$ alkyl-, wherein the $C_{1-6}$ alkyl, phenyl, $C_{3-6}$ cycloalkyl, phenyl-$C_{1-6}$ alkyl-, and $C_{3-6}$ cycloalkyl-$C_{1-6}$ alkyl- of $R^{10N}$ are each optionally substituted with 1 or 2 independently selected $R^{10NA}$ substituents.

In some embodiments, $R^{10N}$ is selected from H, $C_{1-6}$ alkyl, phenyl, $C_{3-6}$ cycloalkyl, phenyl-$C_{1-6}$ alkyl-, and $C_{3-6}$ cycloalkyl-$C_{1-6}$ alkyl-.

In some embodiments, $R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, $C(O)R^{b10N}$, $C(O)NR^{c10N}R^{d10N}$, $C(O)OR^{a10N}$, $C(=NCN)NR^{c10N}R^{d10N}$, $C(=NOR^{a10N})NR^{c10N}$, $S(O)_2R^{b10N}$, $S(O)(=NR^{c10N})R^{d10N}$, and $S(O)_2NR^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, or 4 independently selected $R^{10NA}$ substituents;

each $R^{10NA}$ is selected from H, D, halo, CN, OH, NH$_2$, $C_{1-6}$ alkyl, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments, each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, $OR^{a10N2}$, $SR^{a10N2}$, $C(O)R^{b10N2}$, $C(O)NR^{c10N2}R^{d10N2}$, $C(O)OR^{a10N2}$, $OC(O)R^{b10N2}$, $OC(O)NR^{c10N2}R^{d10N2}$, $NR^{c10N2}R^{d10N2}$, $NR^{c10N2}NR^{c10N2}R^{d10N2}$, $NR^{c10N2}C(O)R^{b10N2}$, $NR^{c10N2}C(O)OR^{a10N2}$, and $NR^{c10N2}S(O)_2R^{b10N2}$;
wherein each $R^{a10N2}$, $R^{b10N2}$, $R^{c10N2}$, and $R^{d10N2}$ is independently selected from H and $C_{1-6}$ alkyl.

In some embodiments, each $R^{10NA}$ is selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$;
wherein each $R^{a10N2}$, $R^{b10N2}$, $R^{c10N2}$, and $R^{d10N2}$ is independently selected from H and $C_{1-6}$ alkyl.

In some embodiments, $R^{10N}$ is selected from H, $C_{1-6}$ alkyl, $C_{6-10}$ aryl-$C_{1-6}$ alkyl-, and $C_{3-10}$ cycloalkyl-$C_{1-6}$ alkyl-.

In some embodiments, $R^{10N}$ is selected from H, $C_{1-6}$ alkyl, phenyl-$C_{1-6}$ alkyl-, and $C_{3-6}$ cycloalkyl-$C_{1-6}$ alkyl-.

In some embodiments, $R^{10N}$ is selected from H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl.

In some embodiments, $R^{10N}$ is selected from H, ethyl, isopropyl, phenylethyl, and cyclopropylethyl.

In some embodiments, $R^{10N}$ is selected from H, ethyl, isopropyl, 1-phenylethyl, 1-cyclopropylethyl, 2-((tert-butoxycarbonyl)amino)-1-cyclopropylethyl, 2-amino-1-cyclopropylethyl, 1-cyclopropyl-2-(methylsulfonamido)ethyl, 2-acetamido-1-cyclopropylethyl, 1-cyclopropyl-2-(methylamino)-2-oxoethyl, 1-cyclopropyl-2-hydroxyethyl, and carboxy(cyclopropyl)methyl.

In some embodiments, $R^{10N}$ is 1-cyclopropylethyl.
In some embodiments, $R^{10N}$ is (A)-1-cyclopropylethyl.
In some embodiments, $X^{10}$ is N.
In some embodiments, $X^{10}$ is O.
In some embodiments, $X^{10}$ is S.
In some embodiments, $X^{10}$ is $CR^{10}$.
In some embodiments, $X^{10}$ is $C(R^{10})_2$.
In some embodiments, each $R^{10}$ is independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10}$ are each optionally substituted with 1, 2, 3, or 4 independently selected $R^{10A}$ substituents.

In some embodiments, each $R^{10}$ is independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments, each $R^{10}$ is independently selected from H, $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl- and (4-6 membered heterocycloalkyl)-$C_{1-6}$ alkyl- of $R^{10}$ are each optionally substituted with 1 or 2 independently selected $R^{10A}$ substituents.

In some embodiments, each $R^{10}$ is independently selected from H, $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-.

In some embodiments, each $R^{10}$ is independently selected from $C_{1-6}$ alkyl and $C_{3-6}$ cycloalkyl-$C_{1-6}$ alkyl-.

In some embodiments, each $R^{10}$ is independently selected from H, isopropyl, and cyclopropylethyl.

In some embodiments, each $R^{10}$ is independently selected from isopropyl and cyclopropylethyl.

In some embodiments, each $R^{10}$ is isopropyl.
In some embodiments, each $R^{10}$ is cyclopropylethyl.
In some embodiments, $R^{10}$ is 1-cyclopropylethyl.
In some embodiments, $R^{10}$ is (S)-1-cyclopropylethyl.
In some embodiments, $X^{10}$ is $CR^{10}$; wherein $R^{10}$ is selected from H, D, halo, CN, OH, NH$_2$, and $C_{1-6}$ alkyl.
In some embodiments, $X^{10}$ is $CR^{10}$; wherein $R^{10}$ is selected from $C_{1-6}$ alkyl and $C_{3-6}$ cycloalkyl-$C_{1-6}$ alkyl-.
In some embodiments, $X^{10}$ is $CR^{10}$; wherein $R^{10}$ is isopropyl or cyclopropylethyl.
In some embodiments, $X^{10}$ is CH.
In some embodiments, $X^{10}$ is CH$_2$.
In some embodiments, $X^{11}$ is $NR^{11N}$.
In some embodiments, $X^{11}$ is N.
In some embodiments, $X^{11}$ is O.
In some embodiments, $X^{11}$ is S.
In some embodiments, $X^{11}$ is $CR^{11}$.
In some embodiments, $X^{11}$ is $C(R^{11})_2$.
In some embodiments, each $R^{11}$ is independently selected from H, D, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl with 1 or 2 independently selected $R^{11A}$ substituents.

In some embodiments, each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments, each $R^{11}$ is independently selected from H, D, halo, CN, OH, NH$_2$, $C_{1-6}$ alkyl, $C_{1-6}$ haloalkyl, $C_{2-6}$ alkenyl, and $C_{2-6}$ alkynyl.

In some embodiments, each $R^{11}$ is independently selected from H, D, halo, CN, OH, NH$_2$, and $C_{1-6}$ alkyl.

In some embodiments, $X^{11}$ is $CR^{11}$; wherein $R^{11}$ is selected from H, D, halo, CN, OH, $NH_2$, and $C_{1-6}$ alkyl.

In some embodiments, $X^{11}$ is CH or $CH_2$.

In some embodiments, $X^{11}$ is $CH_2$.

In some embodiments, $X^{11}$ is CH.

In some embodiments:

each bond symbol represented by ══════ is independently a single or double bond;

$R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, $S(O)_2NR^{c1}R^{d1}$, and 5-6 membered heteroaryl, wherein the $C_{1-6}$ alkyl and 5-6 membered heteroaryl are optionally substituted with 1 or 2 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{1A}$ substituents;

each $R^{1A}$ is selected from H, D, halo, OH, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^2$ is N or $CR^2$;

$R^2$ is selected from H, D, and $C_{1-6}$ alkyl;

$R^3$ is selected from H, D, and $C_{1-6}$ alkyl;

$X^4$ is N or $CR^4$;

$X^5$ is N or $CR^5$;

$R^4$ is selected from H, D, $C_{1-6}$ alkyl, $C_{1-6}$ haloalkyl, $C_{2-6}$ alkenyl, and $C_{2-6}$ alkynyl;

$R^5$ is selected from H, D, $C_{1-6}$ alkyl, $C_{1-6}$ haloalkyl, $C_{2-6}$ alkenyl, and $C_{2-6}$ alkynyl;

$X^6$ is N or $CR^6$;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1, 2 or 3 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is selected from H, D, halo, OH, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^7$ is N or C;

$X^8$ is N or C;

$X^9$ is N, $NR^{9N}$, $CR^9$, or $C(R^9)_2$;

$X^{10}$ is N, $NR^{10N}$, $CR^{10}$, or $C(R^{10})_2$;

$X^{11}$ is N, $CR^{11}$ or $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents;

or, alternatively, two $R^9$ groups together form an oxo group;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, or 4 independently selected $R^{9NA}$ substituents;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

each $R^{10}$ is independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10}$ are each optionally substituted with 1, 2, 3, or 4 independently selected $R^{10A}$ substituents;

each $R^{10A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$alkyl-, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments:

$R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{1A}$ substituents;

each $R^{1A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^2$ is N or $CR^2$;

$R^2$ is selected from H, D, and $C_{1-6}$ alkyl;

$R^3$ is selected from H, D, and $C_{1-6}$ alkyl;

$X^4$ is N or $CR^4$;

$X^5$ is N or $CR^5$;

$R^4$ is selected from H, D, $C_{1-6}$ alkyl, $C_{1-6}$ haloalkyl, $C_{2-6}$ alkenyl, and $C_{2-6}$ alkynyl;

$R^5$ is selected from H, D, $C_{1-6}$ alkyl, $C_{1-6}$ haloalkyl, $C_{2-6}$ alkenyl, and $C_{2-6}$ alkynyl;

$X^6$ is N or $CR^6$;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1 or 2 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^7$ is N or C;

$X^8$ is N or C;

$X^9$ is N, $NR^{9N}$, $CR^9$, or $C(R^9)_2$;

$X^{10}$ is N, $NR^{10N}$, $CR^{10}$, or $C(R^{10})_2$;

$X^{11}$ is $CR^{11}$ or $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents;

or, alternatively, two $R^9$ groups together form an oxo group;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, or 4 independently selected $R^{9NA}$ substituents;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

each $R^{10}$ is independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10}$ are each optionally substituted with 1, 2, 3, or 4 independently selected $R^{10A}$ substituents;

each $R^{10A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments:

$R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$, and 5-6 membered heteroaryl wherein the $C_{1-6}$ alkyl and 5-6 membered heteroaryl are optionally substituted with 1 or 2 independently selected $R^{1A}$ substituents;

each $R^{b1}$, $R^{c1}$ and $R^{d1}$ is independently selected from H, $C_{1-6}$ alkyl, $C_{3-6}$ cycloalkyl, and 4-6 membered heterocycloalkyl, wherein the $C_{1-6}$ alkyl, $C_{3-6}$ cycloalkyl, and 4-6 membered heterocycloalkyl of $R^{b1}$, $R^{c1}$ and $R^{d1}$ are each optionally substituted with 1 or 2 independently selected $R^{1A}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;

each $R^{1A}$ is selected from halo, $C_{1-6}$ alkyl, and OH;

$X^2$ is N or $CR^2$;

$R^2$ is selected from H, D, and $C_{1-6}$ alkyl;

$R^3$ is selected from H, D, and $C_{1-6}$ alkyl;

$X^4$ is N or $CR^4$;

$X^5$ is N or $CR^5$;

$R^4$ is selected from H, D, $C_{1-6}$ alkyl, $C_{1-6}$ haloalkyl, $C_{2-6}$ alkenyl, and $C_{2-6}$ alkynyl;

$R^5$ is selected from H, D, $C_{1-6}$ alkyl, $C_{1-6}$ haloalkyl, $C_{2-6}$ alkenyl, and $C_{2-6}$ alkynyl;

$X^6$ is N or $CR^6$;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1, 2 or 3 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is independently selected from H, D, CN, $NO_2$, OH, halo, $C_{1-6}$ alkyl, $C_{1-6}$ haloalkyl, $C_{2-6}$ alkenyl, and $C_{2-6}$ alkynyl;

$X^7$ is N or C;

$X^8$ is N or C;

$X^9$ is N, $NR^{9N}$, $CR^9$, or $C(R^9)_2$;

$X^{10}$ is N, $NR^{10N}$, $CR^{10}$, or $C(R^{10})_2$;

$X^{11}$ is N, $CR^{11}$ or $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl;

or, alternatively, two $R^9$ groups together form an oxo group;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- are optionally substituted with 1 or 2 $R^{9NA}$ substituents independently selected from phenyl and $C_{3-7}$ cycloalkyl;

each $R^{10}$ is independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl;

each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments:

$R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl;

$X^2$ is N or $CR^2$;

$R^2$ is selected from H, D, and $C_{1-6}$ alkyl;

$R^3$ is selected from H, D, and $C_{1-6}$ alkyl;

$X^4$ is N or $CR^4$;

$X^5$ is N or $CR^5$;

$R^4$ is selected from H, D, $C_{1-6}$ alkyl, $C_{1-6}$ haloalkyl, $C_{2-6}$ alkenyl, and $C_{2-6}$ alkynyl;

$R^5$ is selected from H, D, $C_{1-6}$ alkyl, $C_{1-6}$ haloalkyl, $C_{2-6}$ alkenyl, and $C_{2-6}$ alkynyl;

$X^6$ is N or $CR^6$;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1 or 2 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is independently selected from H, D, CN, $NO_2$, OH, halo, $C_{1-6}$ alkyl, $C_{1-6}$ haloalkyl, $C_{2-6}$ alkenyl, and $C_{2-6}$ alkynyl;

$X^7$ is N or C;

$X^8$ is N or C;

$X^9$ is N, $NR^{9N}$, $CR^9$, or $C(R^9)_2$;
$X^{10}$ is N, $NR^{10N}$, $CR^{10}$, or $C(R^{10})_2$;
$X^{11}$ is $CR^{11}$ or $C(R^{11})_2$;
each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl;
or, alternatively, two $R^9$ groups together form an oxo group;
$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;
each $R^{10}$ is independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;
$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;
each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments:
$R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$, $S(O)R^{b1}$, $S(O)NR^{c1}R^{d1}$, $S(O)_2R^{b1}$, and $S(O)_2NR^{c1}R^{d1}$, and 5-6 membered heteroaryl, wherein the $C_{1-6}$ alkyl, and 5-6 membered heteroaryl are each optionally substituted with 1 or 2 independently selected $R^{1A}$ substituents;
each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{1A}$ substituents;
or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;
each $R^{1A}$ is independently selected from halo, $C_{1-6}$ alkyl, and OH;
$X^2$ is N or $CR^2$;
$R^2$ is selected from H, D, and $C_{1-6}$ alkyl;
$R^3$ is selected from H, D, and $C_{1-6}$ alkyl;
$X^4$ is N or $CR^4$;
$X^5$ is N or $CR^5$;
$R^4$ is selected from H, D, $C_{1-6}$ alkyl, $C_{1-6}$ haloalkyl, $C_{2-6}$ alkenyl, and $C_{2-6}$ alkynyl;
$R^5$ is selected from H, D, $C_{1-6}$ alkyl, $C_{1-6}$ haloalkyl, $C_{2-6}$ alkenyl, and $C_{2-6}$ alkynyl;
$X^6$ is N or $CR^6$;
$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1, 2 or 3 independently selected $R^{6A}$ substituents;
each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;
each $R^{6A}$ is independently selected from D, CN, $NO_2$, OH, halo, $C_{1-6}$ alkyl, $C_{1-6}$ haloalkyl, $C_{2-6}$ alkenyl, and $C_{2-6}$ alkynyl;
$X^7$ is N or C;
$X^8$ is N or C;
$X^9$ is N, $NR^{9N}$, $CR^9$, or $C(R^9)_2$;
$X^{10}$ is N, $NR^{10N}$, $CR^{10}$, or $C(R^{10})_2$;
$X^{11}$ is N, $CR^{11}$ or $C(R^{11})_2$;
each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl;
or, alternatively, two $R^9$ groups together form an oxo group;
$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- are each optionally substituted with 1 or 2 $R^{9NA}$ substituents independently selected from phenyl and $C_{3-7}$ cycloalkyl;
each $R^{10}$ is independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;
$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl;
each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments:
$R^1$ is selected from H, $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, and $NR^{c1}C(O)NR^{c1}R^{d1}$;

each $R^{a1}$, $R^{b1}$, $R^{c1}$, and $R^{d1}$ is independently selected from H, $C_{1-6}$ alkyl, $C_{1-6}$haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl;

$X^2$ is N or $CR^2$;

$R^2$ is selected from H, D, and $C_{1-6}$ alkyl;

$R^3$ is selected from H, D, and $C_{1-6}$ alkyl;

$X^4$ is N or $CR^4$;

$X^5$ is N or $CR^5$;

$R^4$ is selected from H, D, $C_{1-6}$ alkyl, $C_{1-6}$haloalkyl, $C_{2-6}$ alkenyl, and $C_{2-6}$ alkynyl;

$R^5$ is selected from H, D, $C_{1-6}$ alkyl, $C_{1-6}$ haloalkyl, $C_{2-6}$ alkenyl, and $C_{2-6}$ alkynyl;

$X^6$ is N or $CR^6$;

$R^6$ is selected from H, halo, $C_{1-6}$ alkyl, $C(O)R^{b6}$, $S(O)R^{b6}$, and $S(O)_2R^{b6}$, wherein the $C_{1-6}$ alkyl is optionally substituted by 1 or 2 OH groups;

$R^{b6}$ is selected from H, $C_{1-6}$ alkyl, $C_{1-6}$ haloalkyl, $C_{2-6}$ alkenyl, and $C_{2-6}$ alkynyl;

$X^7$ is N or C;

$X^8$ is N or C;

$X^9$ is N, $NR^{9N}$, $CR^9$, or $C(R^9)_2$;

$X^{10}$ is N, $NR^{10N}$, $CR^{10}$, or $C(R^{10})_2$;

$X^{11}$ is $CR^{11}$ or $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl;

or, alternatively, two $R^9$ groups together form an oxo group;

$R^{9N}$ is selected from $C_{1-6}$ alkyl, $C_{3-6}$ cycloalkyl, and $C_{3-6}$ cycloalkyl-$C_{1-6}$ alkyl-;

$R^{10}$ is selected from $C_{1-6}$ alkyl and $C_{3-6}$ cycloalkyl-$C_{1-6}$ alkyl-;

$R^{10N}$ is H, $C_{1-6}$ alkyl, phenyl-$C_{1-6}$ alkyl-, and $C_{3-6}$ cycloalkyl-$C_{1-6}$ alkyl-;

each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments:

each bond symbol represented by ══ is independently a single or double bond;

$R^1$ is selected from H, $C_{1-6}$ alkyl, $C_{1-6}$ haloalkyl, $C(O)R^{b1}$, $C(O)NR^{c1}R^{d1}$, and 5-6 membered heteroaryl, wherein the $C_{1-6}$ alkyl, and 5-6 membered heteroaryl are each optionally substituted with 1 or 2 independently selected $R^{1A}$ substituents;

$R^{b1}$ is 4-6 membered heterocycloalkyl, wherein the 4-6 membered heterocycloalkyl of $R^{b1}$ is optionally substituted with 1 or 2 independently selected $R^{1A}$ substituents;

each $R^{c1}$ and $R^{d1}$ is independently selected from H, $C_{1-6}$ alkyl, $C_{3-6}$ cycloalkyl, and 4-6 membered heterocycloalkyl, wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{1A}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;

each $R^{1A}$ is independently selected from halo, $C_{1-6}$ alkyl, and OH;

$X^2$ is N or CH;

$R^3$ is H;

$X^4$ is N or CH;

$X^5$ is N or CH;

$X^6$ is N or $CR^6$;

$R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 independently selected $R^{6A}$ substituents;

$R^{a6}$ and $R^{b6}$ are each independently selected from H and $C_{1-6}$ alkyl; and each $R^{6A}$ is selected from halo, OH, and $C_{1-6}$ haloalkyl;

$X^7$ is N or C;

$X^8$ is N or C;

$X^9$ is N, $NR^{9N}$, $CR^9$, or $C(R^9)_2$;

$X^{10}$ is N, $NR^{10N}$, $CR^{10}$, or $C(R^{10})_2$;

$X^{11}$ is N, CH or $CH_2$;

each $R^9$ is independently selected from H, and $C_{1-6}$ alkyl;

or, alternatively, two $R^9$ groups together form an oxo group;

$R^{9N}$ is selected from $C_{1-6}$ alkyl, $C_{3-6}$ cycloalkyl, and $C_{3-6}$ cycloalkyl-$C_{1-6}$ alkyl-, wherein the $C_{1-6}$ alkyl is optionally substituted with a $C_{3-6}$ cycloalkyl group;

$R^{10}$ is selected from $C_{1-6}$ alkyl and $C_{3-6}$ cycloalkyl-$C_{1-6}$ alkyl-; and $R^{10N}$ is H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl.

In some embodiments, the compound of Formula (I) is a compound of Formula (Ib):

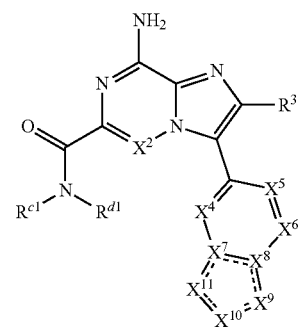

or a pharmaceutically acceptable salt thereof.

In some embodiments of Formula (Ib), $X^2$ is N.

In some embodiments of Formula (Ib), $X^2$ is N and $X^4$, $X^5$, and $X^6$ are each CH.

In some embodiments, the compound of Formula (I) is a compound of Formula (Ic):

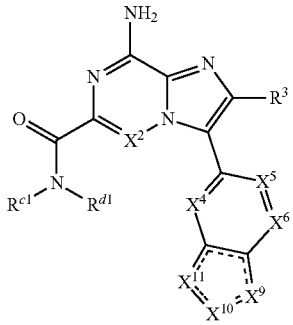

(Ic)

or a pharmaceutically acceptable salt thereof.

In some embodiments of Formula (Ic), $X^2$ is N.

In some embodiments of Formula (Ic), $X^2$ is N and $X^4$, $X^5$, and $X^6$ are each CH.

In some embodiments, the compound of Formula (I) is a compound of Formula (II):

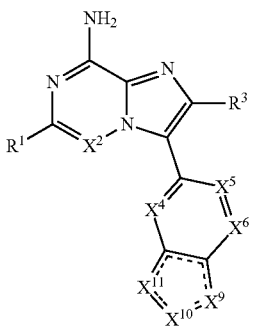

(II)

or a pharmaceutically acceptable salt thereof.

In some embodiments of Formula (II), $X^2$ is N.

In some embodiments of Formula (II), $X^2$ is N and $X^4$, $X^5$, and $X^6$ are each CH.

In some embodiments, the compound of Formula (I) is a compound of Formula (IIb):

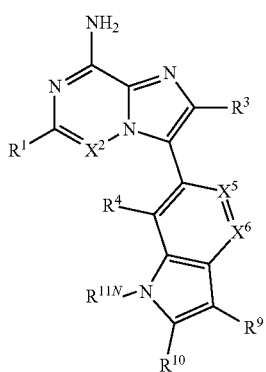

(IIb)

or a pharmaceutically acceptable salt thereof.

In some embodiments of Formula (IIb), $X^2$ is N.

In some embodiments of Formula (IIb), $X^2$ is N, $X^5$ is $CR^5$, and $X^6$ is $CR^6$.

In some embodiments of Formula (IIb), $X^2$ is N, $X^5$ is $CR^5$, and $X^6$ is N.

In some embodiments of Formula (IIb), $X^2$ is N, $X^5$ is N, and $X^6$ is $CR^6$.

In some embodiments of Formula (IIb), $X^2$ is N, $X^5$ is N, and $X^6$ is N.

In some embodiments of Formula (IIb), $X^2$ is $CR^2$.

In some embodiments of Formula (IIb), $X^2$ is $CR^2$, $X^5$ is $CR^5$, and $X^6$ is $CR^6$.

In some embodiments of Formula (IIb), $X^2$ is $CR^2$, $X^5$ is $CR^5$, and $X^6$ is N.

In some embodiments of Formula (IIb), $X^2$ is $CR^2$, $X^5$ is N, and $X^6$ is $CR^6$.

In some embodiments of Formula (IIb), $X^2$ is $CR^2$, $X^5$ is N, and $X^6$ is N.

In some embodiments, the compound of Formula (I) is a compound of Formula (IIc):

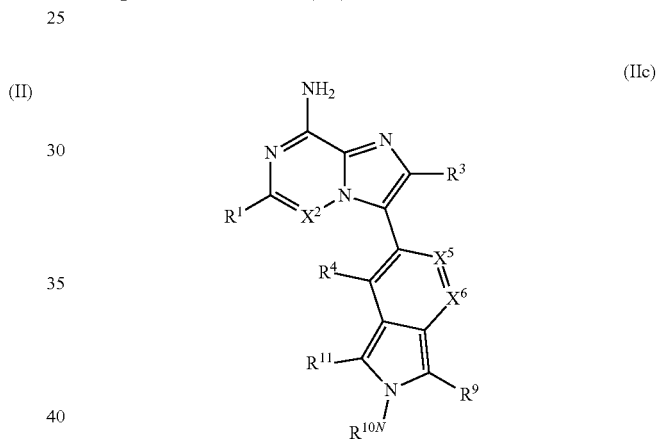

(IIc)

or a pharmaceutically acceptable salt thereof.

In some embodiments of Formula (IIc), $X^2$ is N.

In some embodiments of Formula (IIc), $X^2$ is N, $X^5$ is $CR^5$, and $X^6$ is $CR^6$.

In some embodiments of Formula (IIc), $X^2$ is N, $X^5$ is $CR^5$, and $X^6$ is N.

In some embodiments of Formula (IIc), $X^2$ is N, $X^5$ is N, and $X^6$ is $CR^6$.

In some embodiments of Formula (IIc), $X^2$ is N, $X^5$ is N, and $X^6$ is N.

In some embodiments of Formula (IIc), $X^2$ is $CR^2$.

In some embodiments of Formula (IIc), $X^2$ is $CR^2$, $X^5$ is $CR^5$, and $X^6$ is $CR^6$.

In some embodiments of Formula (IIc), $X^2$ is $CR^2$, $X^5$ is $CR^5$, and $X^6$ is N.

In some embodiments of Formula (IIc), $X^2$ is $CR^2$, $X^5$ is N, and $X^6$ is $CR^6$.

In some embodiments of Formula (IIc), $X^2$ is $CR^2$, $X^5$ is N, and $X^6$ is N.

In some embodiments, the compound of Formula (I) is a compound of Formula (IId):

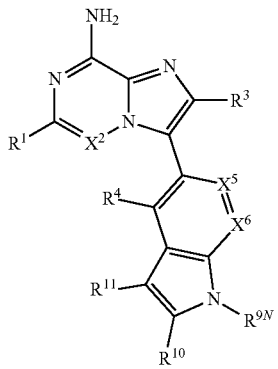

(IId)

or a pharmaceutically acceptable salt thereof.

In some embodiments of Formula (IId), $X^2$ is N.
In some embodiments of Formula (IId), $X^2$ is N, $X^5$ is $CR^5$, and $X^6$ is $CR^6$.
In some embodiments of Formula (IId), $X^2$ is N, $X^5$ is $CR^5$, and $X^6$ is N.
In some embodiments of Formula (IId), $X^2$ is N, $X^5$ is N, and $X^6$ is $CR^6$.
In some embodiments of Formula (IId), $X^2$ is N, $X^5$ is N, and $X^6$ is N.
In some embodiments of Formula (IId), $X^2$ is $CR^2$.
In some embodiments of Formula (IId), $X^2$ is $CR^2$, $X^5$ is $CR^5$, and $X^6$ is $CR^6$.
In some embodiments of Formula (IId), $X^2$ is $CR^2$, $X^5$ is $CR^5$, and $X^6$ is N.
In some embodiments of Formula (IId), $X^2$ is $CR^2$, $X^5$ is N, and $X^6$ is $CR^6$.
In some embodiments of Formula (IId), $X^2$ is $CR^2$, $X^5$ is N, and $X^6$ is N.

In some embodiments, the compound of Formula (I) is a compound of Formula (IIe):

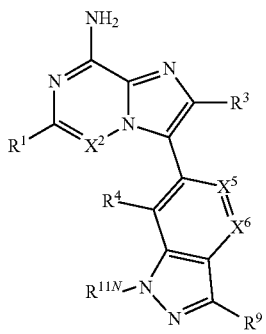

(IIe)

or a pharmaceutically acceptable salt thereof.

In some embodiments of Formula (IIc), $X^2$ is N.
In some embodiments of Formula (IIc), $X^2$ is N, $X^5$ is $CR^5$, and $X^6$ is $CR^6$.
In some embodiments of Formula (IIc), $X^2$ is N, $X^5$ is $CR^5$, and $X^6$ is N.
In some embodiments of Formula (IIc), $X^2$ is N, $X^5$ is N, and $X^6$ is $CR^6$.
In some embodiments of Formula (IIc), $X^2$ is N, $X^5$ is N, and $X^6$ is N.
In some embodiments of Formula (IIc), $X^2$ is $CR^2$.
In some embodiments of Formula (IIc), $X^2$ is $CR^2$, $X^5$ is $CR^5$, and $X^6$ is $CR^6$.
In some embodiments of Formula (IIc), $X^2$ is $CR^2$, $X^5$ is $CR^5$, and $X^6$ is N.
In some embodiments of Formula (IIc), $X^2$ is $CR^2$, $X^5$ is N, and $X^6$ is $CR^6$.
In some embodiments of Formula (IIc), $X^2$ is $CR^2$, $X^5$ is N, and $X^6$ is N.

In some embodiments, the compound of Formula (I) is a compound of Formula (IIf):

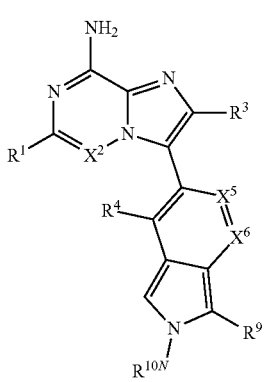

(IIf)

or a pharmaceutically acceptable salt thereof.

In some embodiments of Formula (IIf), $X^2$ is N.
In some embodiments of Formula (IIf), $X^2$ is N, $X^5$ is $CR^5$, and $X^6$ is $CR^6$.
In some embodiments of Formula (IIf), $X^2$ is N, $X^5$ is $CR^5$, and $X^6$ is N.
In some embodiments of Formula (IIf), $X^2$ is N, $X^5$ is N, and $X^6$ is $CR^6$.
In some embodiments of Formula (IIf), $X^2$ is N, $X^5$ is N, and $X^6$ is N.
In some embodiments of Formula (IIf), $X^2$ is $CR^2$.
In some embodiments of Formula (IIf), $X^2$ is $CR^2$, $X^5$ is $CR^5$, and $X^6$ is $CR^6$.
In some embodiments of Formula (IIf), $X^2$ is $CR^2$, $X^5$ is $CR^5$, and $X^6$ is N.
In some embodiments of Formula (IIf), $X^2$ is $CR^2$, $X^5$ is N, and $X^6$ is $CR^6$.
In some embodiments of Formula (IIf), $X^2$ is $CR^2$, $X^5$ is N, and $X^6$ is N.

In some embodiments, the compound of Formula (I) is a compound of Formula (IIg):

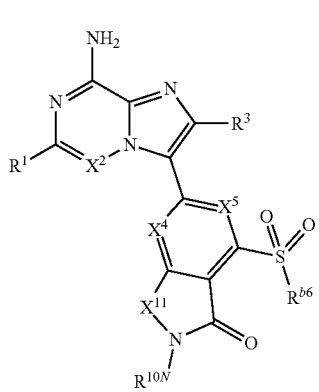

(IIg)

or a pharmaceutically acceptable salt thereof.

In some embodiments of Formula (IIg), $X^2$ is N.

In some embodiments of Formula (IIg), $X^2$ is N, $X^4$ is $CR^4$, and $X^5$ is $CR^5$.

In some embodiments of Formula (IIg), $X^2$ is N, $X^4$ is CH, and $X^5$ is CH.

In some embodiments of Formula (IIg), $X^2$ is N, $X^4$ is $CR^4$, and $X^5$ is N.

In some embodiments of Formula (IIg), $X^2$ is N, $X^4$ is N, and $X^5$ is $CR^5$.

In some embodiments of Formula (IIg), $X^2$ is N, $X^4$ is N, and $X^5$ is N.

In some embodiments of Formula (IIg), $X^2$ is $CR^2$.

In some embodiments of Formula (IIg), $X^2$ is $CR^2$, $X^4$ is $CR^4$, and $X^5$ is $CR^5$.

In some embodiments of Formula (IIg), $X^2$ is $CR^2$, $X^4$ is $CR^4$, and $X^5$ is N.

In some embodiments of Formula (IIg), $X^2$ is $CR^2$, $X^4$ is N, and $X^5$ is $CR^5$.

In some embodiments of Formula (IIg), $X^2$ is $CR^2$, $X^4$ is N, and $X^5$ is N.

In some embodiments, the compound of Formula (I) is a compound of Formula (IIh):

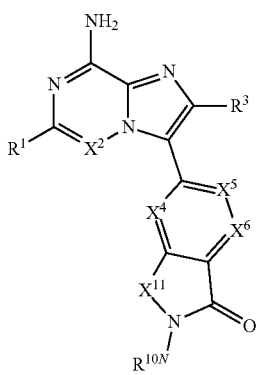

(IIh)

or a pharmaceutically acceptable salt thereof.

In some embodiments of Formula (IIh), $X^2$ is N.

In some embodiments of Formula (IIh), $X^2$ is N, $X^4$ is $CR^4$, $X^5$ is $CR^5$, and $X^6$ is $CR^6$.

In some embodiments of Formula (IIh), $X^2$ is N, $X^4$ is $CR^4$, $X^5$ is $CR^5$, and $X^6$ is N.

In some embodiments of Formula (IIh), $X^2$ is N, $X^4$ is $CR^4$, $X^5$ is N, and $X^6$ is $CR^6$.

In some embodiments of Formula (IIh), $X^2$ is N, $X^4$ is $CR^4$, $X^5$ is N, and $X^6$ is N.

In some embodiments of Formula (IIh), $X^2$ is N, $X^4$ is CH, $X^5$ is CH, and $X^6$ is $CR^6$.

In some embodiments of Formula (IIh), $X^2$ is $CR^2$.

In some embodiments of Formula (IIh), $X^2$ is $CR^2$, $X^4$ is $CR^4$, $X^5$ is $CR^5$, and $X^6$ is $CR^6$.

In some embodiments of Formula (IIh), $X^2$ is $CR^2$, $X^4$ is $CR^4$, $X^5$ is $CR^5$, and $X^6$ is N.

In some embodiments of Formula (IIh), $X^2$ is $CR^2$, $X^4$ is $CR^4$, $X^5$ is N, and $X^6$ is $CR^6$.

In some embodiments of Formula (IIh), $X^2$ is $CR^2$, $X^4$ is $CR^4$, $X^5$ is N, and $X^6$ is N.

In some embodiments of Formula (IIh), $X^2$ is CH, $X^4$ is CH, $X^5$ is CH, and $X^6$ is $CR^6$.

In some embodiments, the compound of Formula (I) is a compound of Formula (IIi):

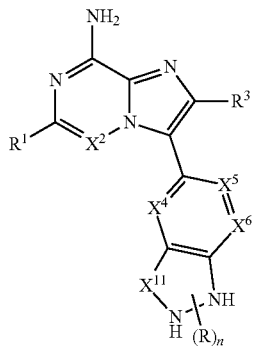

(IIi)

or a pharmaceutically acceptable salt thereof.

In some embodiments of Formula (IIi), $X^2$ is N.

In some embodiments of Formula (IIi), n is 0, 1, 2 or 3.

In some embodiments of Formula (IIi), $X^2$ is N, $X^4$ is $CR^4$, $X^5$ is $CR^5$, and $X^6$ is $CR^6$.

In some embodiments of Formula (IIi), $X^2$ is N, $X^4$ is $CR^4$, $X^5$ is $CR^5$, and $X^6$ is N.

In some embodiments of Formula (IIi), $X^2$ is N, $X^4$ is $CR^4$, $X^5$ is N, and $X^6$ is $CR^6$.

In some embodiments of Formula (IIi), $X^2$ is N, $X^4$ is $CR^4$, $X^5$ is N, and $X^6$ is N.

In some embodiments of Formula (IIi), $X^2$ is N, $X^4$ is CH, $X^5$ is CH, and $X^6$ is $CR^6$.

In some embodiments of Formula (IIi), $X^2$ is $CR^2$.

In some embodiments of Formula (IIi), $X^2$ is $CR^2$, $X^4$ is $CR^4$, $X^5$ is $CR^5$, and $X^6$ is $CR^6$.

In some embodiments of Formula (IIi), $X^2$ is $CR^2$, $X^4$ is $CR^4$, $X^5$ is $CR^5$, and $X^6$ is N.

In some embodiments of Formula (IIi), $X^2$ is $CR^2$, $X^4$ is $CR^4$, $X^5$ is N, and $X^6$ is $CR^6$.

In some embodiments of Formula (IIi), $X^2$ is $CR^2$, $X^4$ is $CR^4$, $X^5$ is N, and $X^6$ is N.

In some embodiments of Formula (IIi), $X^2$ is CH, $X^4$ is CH, $X^5$ is CH, and $X^6$ is $CR^6$.

In some embodiments, the compound of Formula (I) is a compound of Formula (IIj):

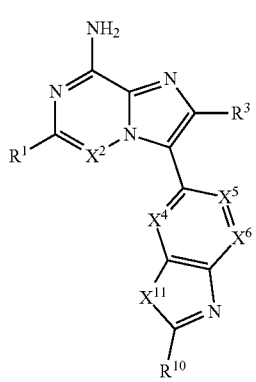

(IIj)

or a pharmaceutically acceptable salt thereof.

In some embodiments of Formula (IIj), $X^2$ is N.

In some embodiments of Formula (IIj), $X^2$ is N, $X^4$ is $CR^4$, $X^5$ is $CR^5$, and $X^6$ is $CR^6$.

In some embodiments of Formula (IIj), $X^2$ is N, $X^4$ is $CR^4$, $X^5$ is $CR^5$, and $X^6$ is N.

In some embodiments of Formula (IIj), $X^2$ is N, $X^4$ is $CR^4$, $X^5$ is N, and $X^6$ is $CR^6$.

In some embodiments of Formula (IIj), $X^2$ is N, $X^4$ is $CR^4$, $X^5$ is N, and $X^6$ is N.

In some embodiments of Formula (IIj), $X^2$ is N, $X^4$ is CH, $X^5$ is CH, and $X^6$ is $CR^6$.

In some embodiments of Formula (IIj), $X^2$ is $CR^2$.

In some embodiments of Formula (IIj), $X^2$ is $CR^2$, $X^4$ is $CR^4$, $X^5$ is $CR^5$, and $X^6$ is $CR^6$.

In some embodiments of Formula (IIj), $X^2$ is $CR^2$, $X^4$ is $CR^4$, $X^5$ is $CR^5$, and $X^6$ is N.

In some embodiments of Formula (IIj), $X^2$ is $CR^2$, $X^4$ is $CR^4$, $X^5$ is N, and $X^6$ is $CR^6$.

In some embodiments of Formula (IIj), $X^2$ is $CR^2$, $X^4$ is $CR^4$, $X^5$ is N, and $X^6$ is N.

In some embodiments of Formula (IIj), $X^2$ is CH, $X^4$ is CH, $X^5$ is CH, and $X^6$ is $CR^6$.

In some embodiments, the compound of Formula (I) is a compound of Formula (IIk):

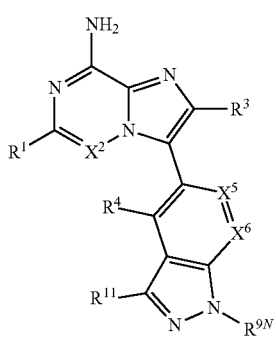

or a pharmaceutically acceptable salt thereof.

In some embodiments of Formula (IIk), $X^2$ is N.

In some embodiments of Formula (IIk), $X^2$ is N, $X^5$ is $CR^5$, and $X^6$ is $CR^6$.

In some embodiments of Formula (IIk), $X^2$ is N, $X^5$ is $CR^5$, and $X^6$ is N.

In some embodiments of Formula (IIk), $X^2$ is N, $X^5$ is N, and $X^6$ is $CR^6$.

In some embodiments of Formula (IIk), $X^2$ is N, $X^5$ is N, and $X^6$ is N.

In some embodiments of Formula (IIk), $X^2$ is $CR^2$.

In some embodiments of Formula (IIk), $X^2$ is $CR^2$, $X^5$ is $CR^5$, and $X^6$ is $CR^6$.

In some embodiments of Formula (IIk), $X^2$ is $CR^2$, $X^5$ is $CR^5$, and $X^6$ is N.

In some embodiments of Formula (IIk), $X^2$ is $CR^2$, $X^5$ is N, and $X^6$ is $CR^6$.

In some embodiments of Formula (IIk), $X^2$ is $CR^2$, $X^5$ is N, and $X^6$ is N.

In some embodiments, the compound of Formula (I) is a compound of Formula (III):

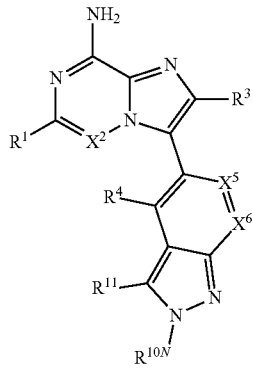

or a pharmaceutically acceptable salt thereof.

In some embodiments of Formula (III), $X^2$ is N.

In some embodiments of Formula (III), $X^2$ is N, $X^5$ is $CR^5$, and $X^6$ is $CR^6$.

In some embodiments of Formula (III), $X^2$ is N, $X^5$ is $CR^5$, and $X^6$ is N.

In some embodiments of Formula (III), $X^2$ is N, $X^5$ is N, and $X^6$ is $CR^6$.

In some embodiments of Formula (III), $X^2$ is N, $X^5$ is N, and $X^6$ is N.

In some embodiments of Formula (III), $X^2$ is $CR^2$.

In some embodiments of Formula (III), $X^2$ is $CR^2$, $X^5$ is $CR^5$, and $X^6$ is $CR^6$.

In some embodiments of Formula (III), $X^2$ is $CR^2$, $X^5$ is $CR^5$, and $X^6$ is N.

In some embodiments of Formula (III), $X^2$ is $CR^2$, $X^5$ is N, and $X^6$ is $CR^6$.

In some embodiments of Formula (III), $X^2$ is $CR^2$, $X^5$ is N, and $X^6$ is N.

In some embodiments, the compound of Formula (I) is a compound of Formula (IIm):

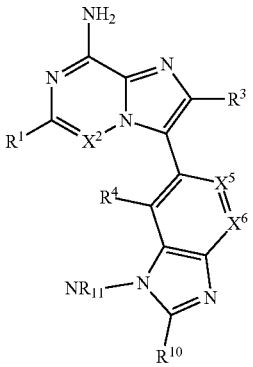

or a pharmaceutically acceptable salt thereof.

In some embodiments of Formula (IIm), $X^2$ is N.

In some embodiments of Formula (IIm), $X^2$ is N, $X^5$ is $CR^5$, and $X^6$ is $CR^6$.

In some embodiments of Formula (IIm), $X^2$ is N, $X^5$ is $CR^5$, and $X^6$ is N.

In some embodiments of Formula (IIm), $X^2$ is N, $X^5$ is N, and $X^6$ is $CR^6$.

In some embodiments of Formula (IIm), $X^2$ is N, $X^5$ is N, and $X^6$ is N.

In some embodiments of Formula (IIm), $X^2$ is $CR^2$.

In some embodiments of Formula (IIm), $X^2$ is $CR^2$, $X^5$ is $CR^5$, and $X^6$ is $CR^6$.

In some embodiments of Formula (IIm), $X^2$ is $CR^2$, $X^5$ is $CR^5$, and $X^6$ is N.

In some embodiments of Formula (IIm), $X^2$ is $CR^2$, $X^5$ is N, and $X^6$ is $CR^6$.

In some embodiments of Formula (IIm), $X^2$ is $CR^2$, $X^5$ is N, and $X^6$ is N.

In some embodiments, the compound of Formula (I) is a compound of Formula (IIn):

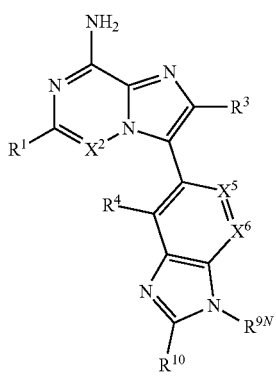

or a pharmaceutically acceptable salt thereof.

In some embodiments of Formula (IIn), $X^2$ is N.

In some embodiments of Formula (IIn), $X^2$ is N, $X^5$ is $CR^5$, and $X^6$ is $CR^6$.

In some embodiments of Formula (IIn), $X^2$ is N, $X^5$ is $CR^5$, and $X^6$ is N.

In some embodiments of Formula (IIn), $X^2$ is N, $X^5$ is N, and $X^6$ is $CR^6$.

In some embodiments of Formula (IIn), $X^2$ is N, $X^5$ is N, and $X^6$ is N.

In some embodiments of Formula (IIn), $X^2$ is $CR^2$.

In some embodiments of Formula (IIn), $X^2$ is $CR^2$, $X^5$ is $CR^5$, and $X^6$ is $CR^6$.

In some embodiments of Formula (IIn), $X^2$ is $CR^2$, $X^5$ is $CR^5$, and $X^6$ is N.

In some embodiments of Formula (IIn), $X^2$ is $CR^2$, $X^5$ is N, and $X^6$ is $CR^6$.

In some embodiments of Formula (IIn), $X^2$ is $CR^2$, $X^5$ is N, and $X^6$ is N.

In some embodiments, the compound of Formula (I) is a compound of Formula (IIo):

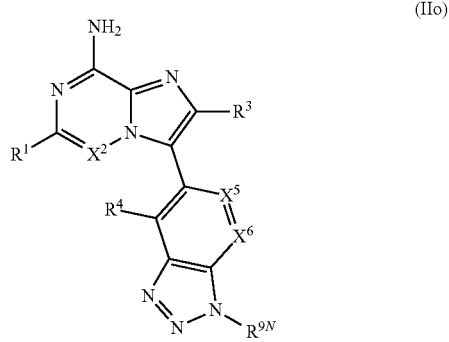

or a pharmaceutically acceptable salt thereof.

In some embodiments of Formula (IIo), $X^2$ is N.

In some embodiments of Formula (IIo), $X^2$ is N, $X^5$ is $CR^5$, and $X^6$ is $CR^6$.

In some embodiments of Formula (IIo), $X^2$ is N, $X^5$ is $CR^5$, and $X^6$ is N.

In some embodiments of Formula (IIo), $X^2$ is N, $X^5$ is N, and $X^6$ is $CR^6$.

In some embodiments of Formula (IIo), $X^2$ is N, $X^5$ is N, and $X^6$ is N.

In some embodiments of Formula (IIo), $X^2$ is $CR^2$.

In some embodiments of Formula (IIo), $X^2$ is $CR^2$, $X^5$ is $CR^5$, and $X^6$ is $CR^6$.

In some embodiments of Formula (IIo), $X^2$ is $CR^2$, $X^5$ is $CR^5$, and $X^6$ is N.

In some embodiments of Formula (IIo), $X^2$ is $CR^2$, $X^5$ is N, and $X^6$ is $CR^6$.

In some embodiments of Formula (IIo), $X^2$ is $CR^2$, $X^5$ is N, and $X^6$ is N.

In some embodiments, the compound of Formula (I) is a compound of Formula (IIp):

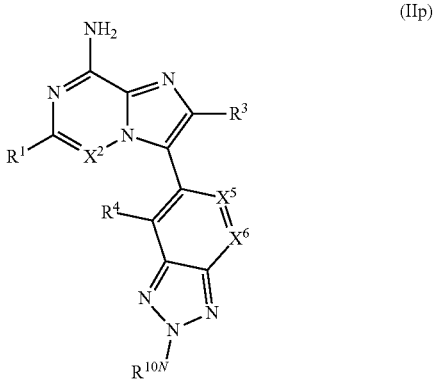

or a pharmaceutically acceptable salt thereof.

In some embodiments of Formula (IIp), $X^2$ is N.

In some embodiments of Formula (IIp), $X^2$ is N, $X^5$ is $CR^5$, and $X^6$ is $CR^6$.

In some embodiments of Formula (IIp), $X^2$ is N, $X^5$ is $CR^5$, and $X^6$ is N.

In some embodiments of Formula (IIp), $X^2$ is N, $X^5$ is N, and $X^6$ is $CR^6$.

In some embodiments of Formula (IIp), $X^2$ is N, $X^5$ is N, and $X^6$ is N.

In some embodiments of Formula (IIp), $X^2$ is $CR^2$.

In some embodiments of Formula (IIp), $X^2$ is $CR^2$, $X^5$ is $CR^5$, and $X^6$ is $CR^6$.

In some embodiments of Formula (IIp), $X^2$ is $CR^2$, $X^5$ is $CR^5$, and $X^6$ is N.

In some embodiments of Formula (IIp), $X^2$ is $CR^2$, $X^5$ is N, and $X^6$ is $CR^6$.

In some embodiments of Formula (IIp), $X^2$ is $CR^2$, $X^5$ is N, and $X^6$ is N.

In some embodiments, the compound of Formula (I) is a compound of Formula (IIq):

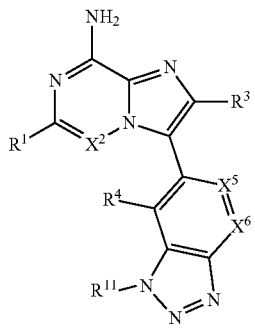

(IIq)

or a pharmaceutically acceptable salt thereof.

In some embodiments of Formula (IIq), $X^2$ is N.

In some embodiments of Formula (IIq), $X^2$ is N, $X^5$ is $CR^5$, and $X^6$ is $CR^6$.

In some embodiments of Formula (IIq), $X^2$ is N, $X^5$ is $CR^5$, and $X^6$ is N.

In some embodiments of Formula (IIq), $X^2$ is N, $X^5$ is N, and $X^6$ is $CR^6$.

In some embodiments of Formula (IIq), $X^2$ is N, $X^5$ is N, and $X^6$ is N.

In some embodiments of Formula (IIq), $X^2$ is $CR^2$.

In some embodiments of Formula (IIq), $X^2$ is $CR^2$, $X^5$ is $CR^5$, and $X^6$ is $CR^6$.

In some embodiments of Formula (IIq), $X^2$ is $CR^2$, $X^5$ is $CR^5$, and $X^6$ is N.

In some embodiments of Formula (IIq), $X^2$ is $CR^2$, $X^5$ is N, and $X^6$ is $CR^6$.

In some embodiments of Formula (IIq), $X^2$ is $CR^2$, $X^5$ is N, and $X^6$ is N.

In some embodiments, the compound of Formula (I) is a compound of Formula (IIr):

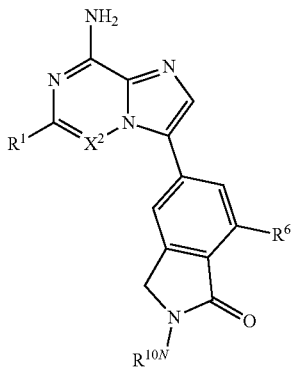

(IIr)

or a pharmaceutically acceptable salt thereof.

In some embodiments of Formula (IIr):

$R^1$ is selected from H, $C_{1-6}$ alkyl, $C_{1-6}$ haloalkyl, and $C(O)NR^{c1}R^{d1}$, wherein the $C_{1-6}$ alkyl is optionally substituted with 1, 2, 3, or 4 independently selected $R^{1A}$ substituents; each $R^{c1}$ and $R^{d1}$ is independently selected from H, $C_{1-6}$ alkyl and 4-7 membered heterocycloalkyl; and each $R^{1A}$ is selected from D, halo, CN, OH and $NH_2$;

$X^2$ is N or $CR^2$;

$R^6$ is selected from H, D, halo, $C_{1-6}$ alkyl, $SR^{a6}$, $C(O)R^{b6}$, and $S(O)_2R^{b6}$, wherein the $C_{1-6}$ alkyl is optionally substituted with 1, 2, 3, or 4 independently selected $R^{6A}$ substituents; each $R^{a6}$ and $R^{b6}$ is independently selected from H and $C_{1-6}$ alkyl; and each $R^{6A}$ is selected from D, halo, CN, OH, and $NH_2$; and $R^{10N}$ is selected from H, $C_{1-6}$ alkyl, $C_{6-10}$ aryl-$C_{1-6}$ alkyl-, and $C_{3-10}$ cycloalkyl-$C_{1-6}$ alkyl-.

In some embodiments, the compound of Formula (I) is a compound of Formula (IIs):

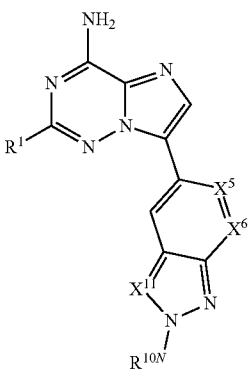

(IIs)

or a pharmaceutically acceptable salt thereof.

In some embodiments of Formula (IIs):

$R^1$ is selected from H, $C_{1-6}$ alkyl, $C_{1-6}$ haloalkyl, and $C(O)NR^{c1}R^{d1}$, wherein the $C_{1-6}$ alkyl is optionally substituted with 1, 2, 3, or 4 independently selected $R^{1A}$ substituents; each $R^{c1}$ and $R^{d1}$ is independently selected from H, $C_{1-6}$ alkyl and 4-7 membered heterocycloalkyl; and each $R^{1A}$ is selected from D, halo, CN, OH and $NH_2$;

$X^5$ is N or CH;

$X^6$ is N or $CR^6$;

$R^6$ is selected from H, D, halo, $C_{1-6}$ alkyl, $SR^{a6}$, $C(O)R^{b6}$, and $S(O)_2R^{b6}$, wherein the $C_{1-6}$ alkyl is optionally substituted with 1, 2, 3, or 4 independently selected $R^{6A}$ substituents; each $R^{a6}$ and $R^{b6}$ is independently selected from H and $C_{1-6}$ alkyl; and each $R^{6A}$ is selected from D, halo, CN, OH, and $NH_2$;

$R^{10N}$ is selected from H, $C_{1-6}$ alkyl, $C_{6-10}$ aryl-$C_{1-6}$ alkyl-, and $C_{3-10}$ cycloalkyl-$C_{1-6}$ alkyl-; and $X^{11}$ is N, C(O) or CH.

In some embodiments, the compound of Formula (I) is a compound of Formula (IIt):

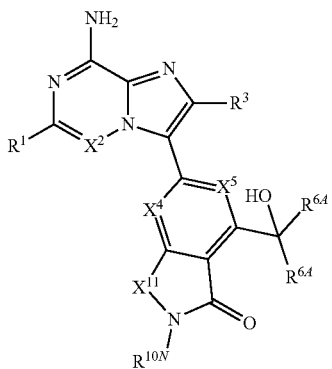

(IIt)

or a pharmaceutically acceptable salt thereof.

In some embodiments of Formula (IIt), $X^2$ is N.

In some embodiments of Formula (IIt), $X^2$ is N, $X^4$ is $CR^4$, and $X^5$ is $CR^5$.

In some embodiments of Formula (IIt), $X^2$ is N, $X^4$ is CH, and $X^5$ is CH.

In some embodiments of Formula (IIt), $X^2$ is N, $X^4$ is $CR^4$, and $X^5$ is N.

In some embodiments of Formula (IIt), $X^2$ is N, $X^4$ is N, and $X^5$ is $CR^5$.

In some embodiments of Formula (IIt), $X^2$ is N, $X^4$ is N, and $X^5$ is N.

In some embodiments of Formula (IIt), $X^2$ is $CR^2$.

In some embodiments of Formula (IIt), $X^2$ is $CR^2$, $X^4$ is $CR^4$, and $X^5$ is $CR^5$.

In some embodiments of Formula (IIt), $X^2$ is $CR^2$, $X^4$ is $CR^4$, and $X^5$ is N.

In some embodiments of Formula (IIt), $X^2$ is $CR^2$, $X^4$ is N, and $X^5$ is $CR^5$.

In some embodiments of Formula (IIt), $X^2$ is $CR^2$, $X^4$ is N, and $X^5$ is N.

In some embodiments, the compound of Formula (I) is a compound of Formula (IIu):

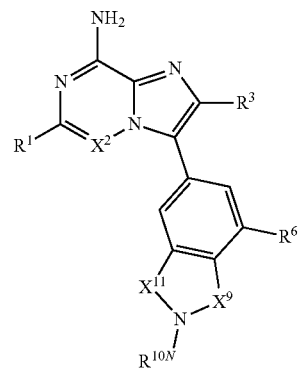

(IIu)

or a pharmaceutically acceptable salt thereof, wherein:

$X^2$ is N or $CR^2$;

$R^2$ is selected from H, D, halo, CN, OH, $NH_2$, $C_{1-6}$ alkyl, $C_{2-6}$ alkenyl, $C_{2-6}$ alkynyl, $C_{1-6}$ haloalkyl, and $C_{3-7}$ cycloalkyl;

provided that:

(a) when $X^2$ is N, then $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, and $NR^{c1}C(O)NR^{c1}R^{d1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{14}$ substituents; or (b) when $X^2$ is $CR^2$, then $R^1$ is selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, and $NR^{c1}C(O)NR^{c1}R^{d1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{14}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, 4, 5, 6, 7, or 8 independently selected $R^{14}$ substituents;

or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{14}$ substituents;

each $R^{14}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, OC(O)

$R^{b11}$, OC(O)NR$^{c11}$R$^{d11}$, NR$^{c11}$R$^{d11}$, NR$^{c11}$NR$^{c11}$R$^{d11}$, NR$^{c11}$C(O)R$^{b11}$, NR$^{c11}$C(O)OR$^{a11}$, and NR$^{c11}$C(O)NR$^{c11}$R$^{d11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{14}$ are each optionally substituted with 1, 2, 3, 4, 5, 6, 7, or 8 independently selected $R^M$ substituents;

each $R^{a11}$, $R^{b11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{b11}$, $R^{c11}$ and $R^{d11}$ are each optionally substituted with 1, 2, 3, 4, 5, 6, 7, or 8 independently selected $R^M$ substituents;

or, any $R^{c11}$ and $R^{d11}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^M$ is independently selected from D, OH, NO$_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^3$ is selected from H, D, halo, CN, OH, NH$_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and C(O)NR$^{a3}$R$^{b3}$;

each $R^{a3}$ and $R^{b3}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a3}$ and $R^{b3}$ are each optionally substituted with 1, 2, 3 or 4 independently selected $R^M$ substituents;

or, any $R^{a3}$ and $R^{b3}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a6}$, SR$^{a6}$, NHOR$^{a6}$, C(O)R$^{b6}$, C(O)NR$^{c6}$R$^{d6}$, C(O)NR$^{c6}$(OR$^{a6}$), C(O)OR$^{a6}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, C(=NR$^{c6}$)R$^{d6}$, C(=NOH)R$^{c6}$, C(=NCN)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NOH)NR$^{c6}$R$^{d6}$, NR$^{c6}$C(=NCN)NR$^{c6}$R$^{d6}$, NR$^{c6}$C(=NR$^{e6}$)R$^{b6}$, NR$^{c6}$S(O)NR$^{c6}$R$^{d6}$, NR$^{c6}$S(O)R$^{b6}$, NR$^{c6}$S(O)$_2$R$^{b6}$, NR$^{c6}$S(O)(=NR$^{e6}$)R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, S(O)(=NR$^{e6}$)R$^{b6}$, OS(O)(=NR$^{e6}$)R$^{b6}$, OS(O)$_2$R$^{b6}$, and SF$_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, 4, 5, 6, 7, or 8 independently selected $R^{6A}$ substituents;

or, any $R^{c6}$ and $R^{d6}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a61}$, SR$^{a61}$, NHOR$^{a61}$, C(O)R$^{b61}$, C(O)

$NR^{c61}R^{d61}$, $C(O)NR^{c61}(OR^{a61})$, $C(O)OR^{a61}$, $OC(O)$ $R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)$ $NR^{c61}R^{d61}$, $C(=NR^{e61})R^{b61}$, $C(=NOH)R^{b61}$, $C(=NCN)R^{b61}$, $C(=NR^{e61})NR^{c61}R^{d61}$, $NR^{c61}C$ $(=NR^{e61})NR^{c61}R^{d61}$, $NR^{c61}C(=NOH)NR^{c61}R^{d61}$, $NR^{c61}C(=NCN)NR^{c61}R^{d61}$, $NR^{c61}C(=NR^{e61})R^{b61}$, $NR^{c61}S(O)NR^{c61}R^{d61}$, $NR^{c61}S(O)R^{b61}$, $NR^{c61}$ $S(O)_2R^{b61}$, $NR^{c61}S(O)(=NR^{e61})R^{b61}$, $NR^{c61}$ $S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, $S(O)(=NR^{e61})R^{b61}$, $OS(O)(=NR^{e61})R^{b61}$, $OS(O)_2R^{b61}$, and $SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{64}$ are each optionally substituted with 1, 2, 3, 4, 5, 6, 7, or 8 independently selected $R^M$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{b61}$, $R^{c61}$ and $R^{d61}$ are each optionally substituted with 1, 2, 3, 4, 5, 6, 7, or 8 independently selected $R^M$ substituents;

or, any $R^{c61}$ and $R^{d61}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

$X^9$ is $NR^{9N}$ or $C(R^9)_2$;

$X^{11}$ is $NR^{11N}$ or $C(R^{11})_2$;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b9N}$, $C(O)NR^{c9N}R^{d9N}$, $C(O)OR^{a9N}$, $C(=NR^{e9N})R^{b9N}$, $C(=NR^{e9N})NR^{c9N}R^{d9N}$, $C(=NCN)NR^{c9N}R^{d9N}$, $C(=NOR^{a9N})NR^{c9N}$, $S(O)_2R^{b9N}$, $S(O)(=NR^{c9N})$ $R^{d9N}$, and $S(O)_2NR^{c9N}R^{d9N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, 4, 5, 6, 7, or 8 independently selected $R^{9NA}$ substituents;

each $R^{a9N}$, $R^{b9N}$, $R^{c9N}$, and $R^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9N}$, $R^{b9N}$, $R^{c9N}$, and $R^{d9N}$ are each optionally substituted with 1, 2, 3, 4, 5, 6, 7, or 8 independently selected $R^{9NA}$ substituents;

or, any $R^{c9N}$ and $R^{d9N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9NA}$ substituents;

each $R^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a9N2}$, $SR^{a9N2}$, $NHOR^{a9N2}$, $C(O)R^{b9N2}$, $C(O)$ $NR^{c9N2}R^{d9N2}$, $C(O)NR^{c9N2}(OR^{a9N2})$, $C(O)OR^{a9N2}$, $OC(O)R^{b9N2}$, $OC(O)NR^{c9N2}R^{d9N2}$, $NR^{c9N2}R^{d9N2}$, $NR^{C9N2}NR^{C9N2}R^{d9N2}$, $NR^{c9N2}C(O)R^{b9N2}$, $NR^{c9N2}C$ $(O)OR^{a9N2}$, and $NR^{c9N2}C(O)NR^{c9N2}R^{d9N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9NA}$ are each optionally substituted with 1, 2, 3, or 4 independently selected $R^M$ substituents;

each $R^{a9N2}$, $R^{b9N2}$, $R^{c9N2}$, and $R^{d9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a9N2}$, $R^{b9N2}$, $R^{c9N2}$ and $R^{d9N2}$ are each optionally substituted with 1, 2, 3, or 4 independently selected $R^M$ substituents;

or, any $R^{c9N2}$ and $R^{d9N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^9$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a91}$, SR$^{a91}$, NHOR$^{a91}$, C(O)R$^{b91}$, C(O)NR$^{c91}$R$^{d91}$, C(O)NR$^{c91}$(OR$^{a91}$), C(O)OR$^{a91}$, OC(O)R$^{b91}$, OC(O)NR$^{c91}$R$^{d91}$, NR$^{c91}$R$^{d91}$, NR$^{c91}$NR$^{c91}$R$^{d91}$, NR$^{c91}$C(O)R$^{b91}$, NR$^{c91}$C(O)OR$^{a91}$, and NR$^{c91}$C(O)NR$^{c91}$R$^{d91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^9$ are each optionally substituted with 1, 2, 3, 4, 5, 6, 7, or 8 independently selected R$^{9A}$ substituents;

or, alternatively, two R$^9$ groups together form an oxo group;

each R$^{a91}$, R$^{b91}$, R$^{c91}$, and R$^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{a91}$, R$^{b91}$, R$^{c91}$ and R$^{d91}$ are each optionally substituted with 1, 2, 3, 4, 5, 6, 7, or 8 independently selected R$^{9A}$ substituents;

or, any R$^{c91}$ and R$^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{9A}$ substituents;

each R$^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a92}$, SR$^{a92}$, NHOR$^{a92}$, C(O)R$^{b92}$, C(O)NR$^{c92}$R$^{d92}$, C(O)NR$^{c92}$(OR$^{a92}$), C(O)OR$^{a92}$, OC(O)R$^{b92}$, OC(O)NR$^{c92}$R$^{d92}$, NR$^{c92}$R$^{d92}$, NR$^{c92}$NR$^{c92}$R$^{d92}$, NR$^{c92}$C(O)R$^{b92}$, NR$^{c92}$C(O)OR$^{a92}$, and NR$^{c92}$C(O)NR$^{c92}$R$^{d92}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of R$^{9A}$ are each optionally substituted with 1, 2, 3, or 4 independently selected R$^M$ substituents;

each R$^{a92}$, R$^{b92}$, R$^{c92}$, and R$^{d92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of R$^{a92}$, R$^{b92}$, R$^{c92}$ and R$^{d92}$ are each optionally substituted with 1, 2, 3, or 4 independently selected R$^M$ substituents;

or, any R$^{c92}$ and R$^{d92}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected R$^M$ substituents;

R$^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, C(O)R$^{b10N}$, C(O)NR$^{c10N}$R$^{d10N}$, C(O)OR$^{a10N}$, C(=NR$^{e10N}$)R$^{b10N}$, C(=NR$^{e10N}$)NR$^{c10N}$R$^{d10N}$, C(=NCN)NR$^{c10N}$R$^{d10N}$, C(=NOR$^{a10N}$)NR$^{c10N}$, S(O)$_2$R$^{b10N}$, S(O)(=NR$^{c10N}$)R$^{d10N}$, and S(O)$_2$NR$^{c10N}$R$^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of R$^{10N}$ are each optionally substituted with 1, 2, 3, 4, 5, 6, 7, or 8 independently selected R$^{10NA}$ substituents;

each R$^{a10N}$, R$^{b10N}$, R$^{c10N}$, and R$^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R$^{a10N}$, R$^{b10N}$, R$^{c10N}$, and R$^{d10N}$ are each optionally substituted with 1, 2, 3, 4, 5, 6, 7, or 8 independently selected R$^{10NA}$ substituents;

or, any R$^{c10N}$ and R$^{d10N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected R$^{10NA}$ substituents;

each R$^{e10N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each R$^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a10N2}$, SR$^{a10N2}$, NHOR$^{a10N2}$, C(O)R$^{b10N2}$, C(O)NR$^{c10N2}$R$^{d10N2}$, C(O)NR$^{c10N2}$(OR$^{a10N2}$), C(O)OR$^{a10N2}$, OC(O)R$^{b10N2}$, OC(O)NR$^{c10N2}$R$^{d10N2}$, NR$^{c10N2}$R$^{d10N2}$, NR$^{c10N2}$NR$^{c10N2}$R$^{d10N2}$, NR$^{c10N2}$C(O)R$^{b10N2}$, NR$^{c10N2}$C(O)OR$^{a10N2}$, NR$^{c10N2}$C(O)NR$^{c10N2}$R$^{d10N2}$, and NR$^{c10N2}$S(O)$_2$R$^{b10N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl- $C_{1-6}$ alkyl-, (5-6 membered heteroaryl)-$C_{1-6}$ alkyl-, and (4-7 membered heterocycloalkyl)-$C_{1-6}$ alkyl- of $R^{10NA}$ are each optionally substituted with 1, 2, 3, or 4 independently selected $R^M$ substituents;

each $R^{a10N2}$, $R^{b10N2}$, $R^{c10N2}$, and $R^{d10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a10N2}$, $R^{b10N2}$, $R^{c10N2}$ and $R^{d10N2}$ are each optionally substituted with 1, 2, 3, or 4 independently selected $R^M$ substituents;

or, any $R^{c10N2}$ and $R^{d10N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b11N}$, $C(O)NR^{c11N}R^{d11N}$, $C(O)OR^{a11N}$, $C(=NR^{e11N})R^{b11N}$, $C(=NR^{e11N})NR^{c11N}R^{d11N}$, $C(=NCN)NR^{c11N}R^{d11N}$, $C(=NOR^{a11N})NR^{c11N}$, $S(O)_2R^{b11N}$, $S(O)(=NR^{e11N})R^{d11N}$, and $S(O)_2NR^{c11N}R^{d11N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{11N}$ are each optionally substituted with 1, 2, 3, 4, 5, 6, 7, or 8 independently selected $R^{11NA}$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^{11NA}$ substituents;

or, any $R^{c11N}$ and $R^{d11N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11NA}$ substituents;

each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11NA}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a11N2}$, $SR^{a11N2}$, $NHOR^{a11N2}$, $C(O)R^{b11N2}$, $C(O)NR^{c11N2}R^{d11N2}$, $C(O)NR^{c11N2}(OR^{a11N2})$, $C(O)OR^{a11N2}$, $OC(O)R^{b11N2}$, $OC(O)NR^{c11N2}R^{d11N2}$, $NR^{c11N2}R^{d11N2}$, $NR^{c11N2}NR^{c11N2}R^{d11N2}$, $NR^{c11N2}C(O)R^{b11N2}$, $NR^{c11N2}C(O)OR^{a11N2}$, and $NR^{c11N2}C(O)NR^{c11N2}R^{d11N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11NA}$ are each optionally substituted with 1, 2, 3, or 4 independently selected $R^M$ substituents;

each $R^{a11N2}$, $R^{b11N2}$, $R^{c11N2}$, and $R^{d11N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a11N2}$, $R^{b11N2}$, $R^{c11N2}$ and $R^{d11N2}$ are each optionally substituted with 1, 2, 3, or 4 independently selected $R^M$ substituents;

or, any $R^{c11N2}$ and $R^{d11N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{11}$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a111}$, $SR^{a111}$, $NHOR^{a111}$, $C(O)R^{b111}$, $C(O)NR^{c111}R^{d111}$, $C(O)NR^{c111}(OR^{a111})$, $C(O)OR^{a111}$, $OC(O)R^{b111}$, $OC(O)NR^{c111}R^{d111}$, $NR^{c111}R^{d111}$, $NR^{c111}NR^{c111}R^{d111}$, $NR^{c111}C(O)R^{b111}$, $NR^{c111}C(O)OR^{a111}$, and $NR^{c111}C(O)NR^{c111}R^{d111}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^{11A}$ substituents;

each $R^{a111}$, $R^{b111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a111}$, $R^{b111}$, $R^{c111}$ and $R^{d111}$ are each optionally substituted with 1, 2, 3, 4, 5, 6, 7, or 8 independently selected $R^{11A}$ substituents;

or, any $R^{c111}$ and $R^{d111}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11A}$ substituents; and each $R^{11A}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a112}$, $SR^{a112}$, $NHOR^{a112}$, $C(O)R^{b112}$, $C(O)NR^{c112}R^{d112}$, $C(O)NR^{c112}(OR^{a112})$, $C(O)OR^{a112}$, $OC(O)R^{b112}$, $OC(O)NR^{c112}R^{d112}$, $NR^{c112}R^{d112}$, $NR^{c112}NR^{c112}R^{d112}$, $NR^{c112}C(O)R^{b112}$, $NR^{c112}C(O)OR^{a112}$, and $NR^{c112}C(O)NR^{c112}R^{d112}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11A}$ are each optionally substituted with 1, 2, 3, or 4 independently selected $R^M$ substituents; and each $R^{a112}$, $R^{b112}$, $R^{c112}$, and $R^{d112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a112}$, $R^{b112}$, $R^{c112}$ and $R^{d112}$ are each optionally substituted with 1, 2, 3, or 4 independently selected $R^M$ substituents;

or, any $R^{c112}$ and $R^{d112}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents.

In some embodiments of Formula (IIu), $X^2$ is N, $X^9$ is $C(R^9)_2$ and $X^{11}$ is $C(R^{11})_2$.

In some embodiments of Formula (IIu), $X^2$ is N, $X^9$ is $NR^{9N}$ and $X^{11}$ is $C(R^{11})_2$.

In some embodiments of Formula (IIu), $X^2$ is N, $X^9$ is $C(R^9)_2$ and $X^{11}$ is $NR^{11N}$.

In some embodiments of Formula (IIu), $X^2$ is N, $X^9$ is $C(O)$ and $X^{11}$ is $C(R^{11})_2$.

In some embodiments of Formula (IIu), $X^2$ is N, $X^9$ is $C(O)$ and $X^{11}$ is $CH_2$.

In some embodiments of Formula (IIu), $X^2$ is N, $X^9$ is $C(R^9)_2$ and $X^{11}$ is $C(O)$.

In some embodiments of Formula (IIu), $X^2$ is N, $X^9$ is $CH_2$ and $X^{11}$ is $C(O)$.

In some embodiments of Formula (IIu), $X^2$ is $CR^2$, $X^9$ is $C(R^9)_2$ and $X^{11}$ is $C(R^{11})_2$.

In some embodiments of Formula (IIu), $X^2$ is $CR^2$, $X^9$ is $NR^{9N}$ and $X^{11}$ is $C(R^{11})_2$.

In some embodiments of Formula (IIu), $X^2$ is $CR^2$, $X^9$ is $C(R^9)_2$ and $X^{11}$ is $NR^{11N}$.

In some embodiments of Formula (IIu), $X^2$ is $CR^2$, $X^9$ is $C(O)$ and $X^{11}$ is $C(R^{11})_2$.

In some embodiments of Formula (IIu), $X^2$ is $CR^2$, $X^9$ is $C(O)$ and $X^{11}$ is $CH_2$.

In some embodiments of Formula (IIu), $X^2$ is $CR^2$, $X^9$ is $C(R^9)_2$ and $X^{11}$ is $C(O)$.

In some embodiments of Formula (IIu), $X^2$ is $CR^2$, $X^9$ is $CH_2$ and $X^{11}$ is $C(O)$.

In some embodiments of Formula (IIu):

$X^2$ is N or $CR^2$;

$R^2$ is selected from H, D, halo, CN, OH, $NH_2$, $C_{1-6}$ alkyl, $C_{2-6}$ alkenyl, $C_{2-6}$ alkynyl, $C_{1-6}$ haloalkyl, and $C_{3-7}$ cycloalkyl;

provided that:

(a) when $X^2$ is N, then $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, and $NR^{c1}C(O)NR^{c1}R^{d1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{1A}$ substituents; or (b) when $X^2$ is $CR^2$, then $R^1$ is selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, and $NR^{c1}C(O)NR^{c1}R^{d1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, 4, 5, 6, 7, or 8 independently selected $R^{1A}$ substituents;

or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{1A}$ substituents;

each $R^{1A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, and $NR^{c11}C(O)NR^{c11}R^{d11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^M$ substituents;

each $R^{a11}$, $R^{b11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{b11}$, $R^{c11}$ and $R^{d11}$ are each optionally substituted with 1, 2, 3, 4, 5, 6, 7, or 8 independently selected $R^M$ substituents;

or, any $R^{c11}$ and $R^{d11}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^3$ is selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^{a3}R^{b3}$;

each $R^{a3}$ and $R^{b3}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a3}$ and $R^{b3}$ are each optionally substituted with 1, 2, 3 or 4 independently selected $R^M$ substituents;

or, any $R^{a3}$ and $R^{b3}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NOH)NR^{c6}R^{d6}$, $NR^{c6}C(=NCN)NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $S(O)(=NR^{e6})R^{b6}$, $OS(O)(=NR^{e6})R^{b6}$, $OS(O)_2R^{b6}$, and $SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, 4, 5, 6, 7, or 8 independently selected $R^{6A}$ substituents;

or, any $R^{c6}$ and $R^{d6}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NR^{c61})R^{b61}$, $C(=NOH)R^{b61}$, $C(=NCN)R^{b61}$, $C(=NR^{e61})NR^{c61}R^{d61}$, $NR^{c61}C(=NR^{e61})NR^{c61}R^{d61}$, $NR^{c61}C(=NOH)NR^{c61}R^{d61}$, $NR^{c61}C(=NCN)NR^{c61}R^{d61}$, $NR^{c61}C(=NR^{e61})R^{b61}$, $NR^{c61}S(O)NR^{c61}R^{d61}$, $NR^{c61}S(O)R^{b61}$, $NR^{c61}S(O)_2R^{b61}$, $NR^{c61}S(O)(=NR^{e61})R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, $S(O)(=NR^{e61})R^{b61}$, $OS(O)(=NR^{e61})R^{b61}$, $OS(O)_2R^{b61}$, and $SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{6A}$ are each optionally substituted with 1, 2, 3, 4, 5, 6, 7, or 8 independently selected $R^M$ substituents;

each $R^{a61}$, $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{b61}$, $R^{c61}$ and $R^{d61}$ are each optionally substituted with 1, 2, 3, 4, 5, 6, 7, or 8 independently selected $R^M$ substituents;

or, any $R^{c61}$ and $R^{d61}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

$X^9$ is $NR^{9N}$ or $C(R^9)_2$;

$X^{11}$ is $NR^{11N}$ or $C(R^{11})_2$;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b9N}$, $C(O)NR^{c9N}R^{d9N}$, $C(O)OR^{a9N}$, $C(=NR^{e9N})R^{b9N}$, $C(=NR^{e9N})NR^{c9N}R^{d9N}$, $C(=NCN)NR^{c9N}R^{d9N}$, $C(=NOR^{a9N})NR^{c9N}$, $S(O)_2R^{b9N}$, $S(O)(=NR^{e9N})R^{d9N}$, and $S(O)_2NR^{c9N}R^{d9N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, 4, 5, 6, 7, or 8 independently selected $R^{9NA}$ substituents;

each $R^{a9N}$, $R^{b9N}$, $R^{c9N}$, and $R^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9N}$, $R^{b9N}$, $R^{c9N}$, and $R^{d9N}$ are each optionally substituted with 1, 2, 3, 4, 5, 6, 7, or 8 independently selected $R^{9NA}$ substituents;

or, any $R^{c9N}$ and $R^{d9N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9NA}$ substituents;

each $R^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a9N2}$, $SR^{a9N2}$, $NHOR^{a9N2}$, $C(O)R^{b9N2}$, $C(O)NR^{c9N2}R^{d9N2}$, $C(O)NR^{c9N2}(OR^{a9N2})$, $C(O)OR^{a9N2}$, $OC(O)R^{b9N2}$, $OC(O)NR^{c9N2}R^{d9N2}$, $NR^{c9N2}R^{d9N2}$, $NR^{c9N2}NR^{c9N2}R^{d9N2}$, $NR^{c9N2}C(O)R^{b9N2}$, $NR^{c9N2}C(O)OR^{a9N2}$, and $NR^{c9N2}C(O)NR^{c9N2}R^{d9N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9NA}$ are each optionally substituted with 1, 2, 3, or 4 independently selected $R^M$ substituents;

each $R^{a9N2}$, $R^{b9N2}$, $R^{c9N2}$, and $R^{d9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a9N2}$, $R^{b9N2}$, $R^{c9N2}$ and $R^{d9N2}$ are each optionally substituted with 1, 2, 3, or 4 independently selected $R^M$ substituents;

or, any $R^{c9N2}$ and $R^{d9N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^9$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, and $NR^{c91}C(O)NR^{c91}R^{d91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

or, alternatively, two $R^9$ groups together form an oxo group;

each $R^{a91}$, $R^{b91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a91}$, $R^{b91}$, $R^{c91}$ and $R^{d91}$ are each optionally substituted with 1, 2, 3, 4, 5, 6, 7, or 8 independently selected $R^{9A}$ substituents;

or, any $R^{c91}$ and $R^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9A}$ substituents;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, and $NR^{c92}C(O)NR^{c92}R^{d92}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a92}$, $R^{b92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a92}$, $R^{b92}$, $R^{c92}$ and $R^{d92}$ are each optionally substituted with 1, 2, 3, or 4 independently selected $R^M$ substituents;

or, any $R^{c92}$ and $R^{d92}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b10N}$, $C(O)NR^{c10N}R^{d10N}$, $C(O)OR^{a10N}$, $C(=NR^{e10N})R^{b10N}$, $C(=NR^{e10N})NR^{c10N}R^{d10N}$, $C(=NCN)NR^{c10N}R^{d10N}$, $C(=NOR^{a10N})NR^{c10N}$, $S(O)_2R^{b10N}$, $S(O)(=NR^{c10N})R^{d10N}$, and $S(O)_2NR^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, 4, 5, 6, 7, or 8 independently selected $R^{10NA}$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, 4, 5, 6, 7, or 8 independently selected $R^{10NA}$ substituents;

or, any $R^{c10N}$ and $R^{d10N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10NA}$ substituents;

each $R^{e10N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a10N2}$, $SR^{a10N2}$, $NHOR^{a10N2}$, $C(O)R^{b10N2}$, $C(O)NR^{c10N2}R^{d10N2}$, $C(O)NR^{c10N2}(OR^{a10N2})$, $C(O)OR^{a10N2}$, $OC(O)R^{b10N2}$, $OC(O)NR^{c10N2}R^{d10N2}$, $NR^{c10N2}R^{d10N2}$, $NR^{c10N2}NR^{c10N2}R^{d10N2}$, $NR^{c10N2}C(O)R^{b10N2}$, $NR^{c10N2}C(O)OR^{a10N2}$, and $NR^{c10N2}C(O)NR^{c10N2}R^{d10N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10NA}$ are each optionally substituted with 1, 2, 3, or 4 independently selected $R^M$ substituents;

each $R^{a10N2}$, $R^{b10N2}$, $R^{c10N2}$, and $R^{d10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a10N2}$, $R^{b10N2}$, $R^{c10N2}$ and $R^{d10N2}$ are each optionally substituted with 1, 2, 3, or 4 independently selected $R^M$ substituents;

or, any $R^{c10N2}$ and $R^{d10N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b11N}$, $C(O)NR^{c11N}R^{d11N}$, $C(O)OR^{a11N}$, $C(=NR^{e11N})R^{b11N}$, $C(=NR^{e11N})NR^{c11N}R^{d11N}$, $C(=NCN)NR^{c11N}R^{d11N}$, $C(=NOR^{a11N})NR^{c11N}$, $S(O)_2R^{b11N}$, $S(O)(=NR^{c11N})R^{d11N}$, and $S(O)_2NR^{c11N}R^{d11N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{11N}$ are each optionally substituted with 1, 2, 3, 4, 5, 6, 7, or 8 independently selected $R^{11NA}$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^{11NA}$ substituents;

or, any $R^{c11N}$ and $R^{d11N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11NA}$ substituents;

each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11NA}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a11N2}$, $SR^{a11N2}$, $NHOR^{a11N2}$, $C(O)R^{b11N2}$, $C(O)NR^{c11N2}R^{d11N2}$, $C(O)NR^{c11N2}(OR^{a11N2})$, $C(O)OR^{a11N2}$, $OC(O)R^{b11N2}$, $OC(O)NR^{c11N2}R^{d11N2}$, $NR^{c11N2}R^{d11N2}$, $NR^{c11N2}NR^{c11N2}R^{d11N2}$, $NR^{c11N2}C(O)R^{b11N2}$, $NR^{c11N2}C(O)OR^{a11N2}$, and $NR^{c11N2}C(O)NR^{c11N2}R^{d11N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11NA}$ are each optionally substituted with 1, 2, 3, or 4 independently selected $R^M$ substituents;

each $R^{a11N2}$, $R^{b11N2}$, $R^{c11N2}$, and $R^{d11N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a11N2}$, $R^{b11N2}$, $R^{c11N2}$ and $R^{d11N2}$ are each optionally substituted with 1, 2, 3, or 4 independently selected $R^M$ substituents;

or, any $R^{c11N2}$ and $R^{d11N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{11}$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a111}$, $SR^{a111}$, $NHOR^{a111}$, $C(O)R^{b111}$, $C(O)NR^{c111}R^{d111}$, $C(O)NR^{c111}(OR^{a111})$, $C(O)OR^{a111}$, $OC(O)R^{b111}$, $OC(O)NR^{c111}R^{d111}$, $NR^{c111}R^{d111}$, $NR^{c111}NR^{c111}R^{d111}$, $NR^{c111}C(O)R^{b111}$, $NR^{c111}C(O)OR^{a111}$, and $NR^{c111}C(O)NR^{c111}R^{d111}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^{11A}$ substituents;

each $R^{a111}$, $R^{b111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a111}$, $R^{b111}$, $R^{c111}$ and $R^{d111}$ are each optionally substituted with 1, 2, 3, 4, 5, 6, 7, or 8 independently selected $R^{11A}$ substituents;

or, any $R^{c111}$ and $R^{d111}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11A}$ substituents; and each $R^{11A}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a112}$, $SR^{a112}$, $NHOR^{a112}$, $C(O)R^{b112}$, $C(O)NR^{c112}R^{d112}$, $C(O)NR^{c112}(OR^{a112})$, $C(O)OR^{a112}$, $OC(O)R^{b112}$, $OC(O)NR^{c112}R^{d112}$, $NR^{c112}R^{d112}$, $NR^{c112}NR^{c112}R^{d112}$, $NR^{c112}C(O)R^{b112}$, $NR^{c112}C(O)OR^{a112}$, and $NR^{c112}C(O)NR^{c112}R^{d112}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11A}$ are each optionally substituted with 1, 2, 3, or 4 independently selected $R^M$ substituents;

each $R^{a112}$, $R^{b112}$, $R^{c112}$, and $R^{d112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a112}$, $R^{b112}$, $R^{c112}$ and $R^{d112}$ are each optionally substituted with 1, 2, 3, or 4 independently selected $R^M$ substituents;

or, any $R^{c112}$ and $R^{d112}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents.

In some embodiments of Formula (IIu):

$R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{1A}$ substituents;

each $R^{1A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^2$ is N;

$R^3$ is selected from H, D, and $C_{1-6}$ alkyl;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1 or 2 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^9$ is $NR^{9N}$ or $C(R^9)_2$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents;

or, alternatively, two $R^9$ groups together form an oxo group;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, or 4 independently selected $R^{9NA}$ substituents;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$ and 5-6 membered heteroaryl, wherein the $C_{1-6}$ alkyl, and 5-6 membered heteroaryl are each optionally substituted with 1 or 2 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{1A}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;

each $R^{1A}$ is selected from H, D, halo, OH, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^2$ is N;

$R^3$ is selected from H, D, and $C_{1-6}$ alkyl;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1, 2 or 3 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is selected from H, D, halo, OH, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^9$ is $NR^{9N}$ or $C(R^9)_2$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents;

or, alternatively, two $R^9$ groups together form an oxo group;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, or 4 independently selected $R^{9NA}$ substituents;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$ wherein each $R^{a10N2}$, $R^{b10N2}$, $R^{c10N2}$, and $R^{d10N2}$ is independently selected from H and $C_{1-6}$ alkyl; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{1A}$ substituents;

each $R^{1A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^2$ is $CR^2$;

$R^2$ is selected from H, D, and $C_{1-6}$ alkyl;

$R^3$ is selected from H, D, and $C_{1-6}$ alkyl;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1 or 2 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^9$ is $NR^{9N}$ or $C(R^9)_2$;

$X^{11}$ is $C(R^{11})_2$;

each $R^9$ is independently selected from H, D, $C_{1-6}$ alkyl, $C_{1-6}$ haloalkyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents;

or, alternatively, two $R^9$ groups together form an oxo group;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, or 4 independently selected $R^{9NA}$ substituents;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$ and 5-6 membered heteroaryl, wherein the $C_{1-6}$ alkyl, and 5-6 membered heteroaryl are each optionally substituted with 1 or 2 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl of $R^{a1}$, $R^{b1}$, $R^{c1}$ and $R^{d1}$ are each optionally substituted with 1 or 2 independently selected $R^{1A}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;

each $R^{1A}$ is selected from H, D, halo, OH, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^2$ is $CR^2$;

$R^2$ is selected from H, D, and $C_{1-6}$ alkyl;

$R^3$ is selected from H, D, and $C_{1-6}$ alkyl;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1, 2 or 3 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is selected from H, D, halo, OH, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-;

$X^9$ is $NR^{9N}$ or $C(R^9)_2$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl, of $R^9$ are each optionally substituted with 1, 2, 3, or 4 independently selected $R^{9A}$ substituents;

or, alternatively, two $R^9$ groups together form an oxo group;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, or 4 independently selected $R^{9NA}$ substituents;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl- $C_{1-6}$ alkyl-, (5-6 membered heteroaryl)-$C_{1-6}$ alkyl-, (4-7 membered heterocycloalkyl)-$C_{1-6}$ alkyl-;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, or 4 independently selected $R^{10NA}$ substituents;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$alkyl-, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from H, D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl;

$X^2$ is N;

$R^3$ is selected from H, D, and $C_{1-6}$ alkyl;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1 or 2 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is independently selected from H, D, CN, $NO_2$, OH, halo, $C_{1-6}$ alkyl, $C_{1-6}$ haloalkyl, $C_{2-6}$ alkenyl, and $C_{2-6}$ alkynyl;

$X^9$ is $NR^{9N}$ or $C(R^9)_2$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl;

or, alternatively, two $R^9$ groups together form an oxo group;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, and $NR^{c1}C(O)NR^{c1}R^{d1}$;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl;

$X^2$ is $CR^2$;

$R^2$ is selected from H, D, and $C_{1-6}$ alkyl;

$R^3$ is selected from H, D, and $C_{1-6}$ alkyl;

$R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1 or 2 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, and $C_{2-6}$ alkynyl;

each $R^{6A}$ is independently selected from H, D, CN, $NO_2$, OH, halo, $C_{1-6}$ alkyl, $C_{1-6}$ haloalkyl, $C_{2-6}$ alkenyl, and $C_{2-6}$ alkynyl;

$X^9$ is $NR^{9N}$ or $C(R^9)_2$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl;

or, alternatively, two $R^9$ groups together form an oxo group;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is H;

$X^2$ is N;

$R^3$ is selected from H, D, and $C_{1-6}$ alkyl;

$R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 $R^{6A}$ substituents independently selected from halo, OH, and $C_{1-6}$ haloalkyl;

$R^{a6}$ and $R^{b6}$ are selected from H, $C_{1-6}$ alkyl, $C_{1-6}$ haloalkyl, $C_{2-6}$ alkenyl, and $C_{2-6}$ alkynyl;

$X^9$ is C(O);

$X^{11}$ is $C(R^{11})_2$;

$R^{10N}$ is H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, $NR^{c1}C(O)NR^{c1}R^{d1}$ and 5-6 membered heteroaryl, wherein the $C_{1-6}$ alkyl, and 5-6 membered heteroaryl are each optionally substituted with 1 or 2 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{1A}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;

each $R^{1A}$ is independently selected from halo, $C_{1-6}$ alkyl, and OH;

$X^2$ is $CR^2$;

$R^2$ is selected from H, D, and $C_{1-6}$ alkyl;

$R^3$ is selected from H, D, and $C_{1-6}$ alkyl;

$R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 $R^{6A}$ substituents independently selected from halo, OH, and $C_{1-6}$ haloalkyl;

$R^{a6}$ and $R^{b6}$ are selected from H, $C_{1-6}$ alkyl, $C_{1-6}$ haloalkyl, $C_{2-6}$ alkenyl, and $C_{2-6}$ alkynyl;

$X^9$ is C(O);

$X^{11}$ is $C(R^{11})_2$;

$R^{10N}$ is H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from H, $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, $NR^{c1}C(O)NR^{c1}R^{d1}$ and 5-6 membered heteroaryl, wherein the $C_{1-6}$ alkyl, and 5-6 membered heteroaryl are each optionally substituted with 1 or 2 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{14}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{14}$ substituents;

each $R^{14}$ is independently selected from halo, $C_{1-6}$ alkyl, and OH;

$X^2$ is N or CH;

$R^3$ is selected from H, D, and $C_{1-6}$ alkyl;

$R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 $R^{6A}$ substituents independently selected from halo, OH, and $C_{1-6}$ haloalkyl;

$R^{a6}$ and $R^{b6}$ are selected from H, $C_{1-6}$ alkyl, $C_{1-6}$ haloalkyl, $C_{2-6}$ alkenyl, and $C_{2-6}$ alkynyl;

$X^9$ is C(O);

$X^{11}$ is $C(R^{11})_2$;

$R^{10N}$ is H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from H, $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, and $NR^{c1}C(O)NR^{c1}R^{d1}$;

each $R^{a1}$, $R^{b1}$, $R^{c1}$, and $R^{d1}$ is independently selected from H, $C_{1-6}$ alkyl, $C_{1-6}$haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl;

$X^2$ is N;

$R^3$ is selected from H, D, and $C_{1-6}$ alkyl;

$R^6$ is selected from H, halo, $C_{1-6}$ alkyl, $C(O)R^{b6}$, $S(O)R^{b6}$, and $S(O)_2R^{b6}$, wherein the $C_{1-6}$ alkyl is optionally substituted by 1 or 2 OH groups;

$R^{b6}$ is selected from H, $C_{1-6}$ alkyl, $C_{1-6}$ haloalkyl, $C_{2-6}$ alkenyl, and $C_{2-6}$ alkynyl;

$X^9$ is $NR^{9N}$ or $C(R^9)_2$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl;

or, alternatively, two $R^9$ groups together form an oxo group;

$R^{9N}$ is selected from $C_{1-6}$ alkyl, $C_{3-6}$ cycloalkyl, and $C_{3-6}$ cycloalkyl-$C_{1-6}$ alkyl-;

$R^{10N}$ is H, $C_{1-6}$ alkyl, phenyl-$C_{1-6}$ alkyl-, and $C_{3-6}$ cycloalkyl-$C_{1-6}$ alkyl-; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, and $NR^{c1}C(O)NR^{c1}R^{d1}$;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl;

$X^2$ is $CR^2$;

$R^2$ is selected from H, D, and $C_{1-6}$ alkyl;

$R^3$ is selected from H, D, and $C_{1-6}$ alkyl;

$R^6$ is selected from H, halo, $C_{1-6}$ alkyl, $C(O)R^{b6}$, $S(O)R^{b6}$, and $S(O)_2R^{b6}$, wherein the $C_{1-6}$ alkyl is optionally substituted by 1 or 2 OH groups;

$R^{b6}$ is selected from H, $C_{1-6}$ alkyl, $C_{1-6}$ haloalkyl, $C_{2-6}$ alkenyl, and $C_{2-6}$ alkynyl;

$X^9$ is $NR^{9N}$ or $C(R^9)_2$;

$X^{11}$ is $C(R^{11})_2$;

each $R^9$ is independently selected from H, D, $C_{1-6}$ alkyl, $C_{1-6}$ haloalkyl, $C_{2-6}$ alkenyl, $C_{2-6}$ alkynyl, wherein the $C_{1-6}$ alkyl, $C_{2-6}$ alkenyl, and $C_{2-6}$ alkynyl;

or, alternatively, two $R^9$ groups together form an oxo group;

$R^{9N}$ is selected from $C_{1-6}$ alkyl, $C_{3-6}$ cycloalkyl, and $C_{3-6}$ cycloalkyl-$C_{1-6}$ alkyl-;

$R^{10N}$ is H, $C_{1-6}$ alkyl, phenyl-$C_{1-6}$ alkyl-, and $C_{3-6}$ cycloalkyl-$C_{1-6}$ alkyl-; and each $R^{11}$ is independently selected from H, D, $C_{1-6}$ alkyl, $C_{1-6}$ haloalkyl, $C_{2-6}$ alkenyl, and $C_{2-6}$ alkynyl.

In some embodiments of Formula (IIu):

$R^1$ is selected from H, $C_{1-6}$ alkyl, $C_{1-6}$ haloalkyl, $C(O)R^{b1}$, $C(O)NR^{c1}R^{d1}$, and 5-6 membered heteroaryl, wherein the $C_{1-6}$ alkyl, and 5-6 membered heteroaryl are each optionally substituted with 1 or 2 independently selected $R^{14}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{3-6}$ cycloalkyl, and 4-6 membered heterocycloalkyl wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{14}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{14}$ substituents;

each $R^{14}$ is independently selected from halo, $C_{1-6}$ alkyl, and OH;

$X^2$ is N or CH;

$R^3$ is H;

$R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 $R^{6A}$ substituents independently selected from halo, OH, and $C_{1-6}$ haloalkyl;

$R^{a6}$ and $R^{b6}$ are selected from H, $C_{1-6}$ alkyl, $C_{1-6}$ haloalkyl, $C_{2-6}$ alkenyl, and $C_{2-6}$ alkynyl;

$X^9$ is C(O);

$X^{11}$ is $CH_2$;

$R^{10N}$ is H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl In some embodiments, the compound of Formula (I) is a compound of Formula (III):

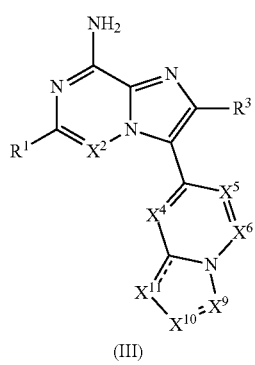

(III)

or a pharmaceutically acceptable salt thereof.

In some embodiments of Formula (III), $X^2$ is N.

In some embodiments of Formula (III), $X^2$ is N and $X^4$, $X^5$ and $X^6$ are each CH.

In some embodiments, the compound of Formula (I) is a compound of Formula (IIIb):

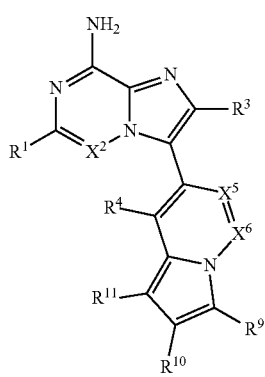

(IIIb)

or a pharmaceutically acceptable salt thereof.

In some embodiments of Formula (IIIb), $X^2$ is N.

In some embodiments of Formula (IIIb), $X^2$ is N, $X^5$ is $CR^5$, and $X^6$ is $CR^6$.

In some embodiments of Formula (IIIb), $X^2$ is N, $X^5$ is $CR^5$, and $X^6$ is N.

In some embodiments of Formula (IIIb), $X^2$ is N, $X^5$ is N, and $X^6$ is $CR^6$.

In some embodiments of Formula (IIIb), $X^2$ is N, $X^5$ is N, and $X^6$ is N.

In some embodiments of Formula (IIIb), $X^2$ is $CR^2$.

In some embodiments of Formula (IIIb), $X^2$ is $CR^2$, $X^5$ is $CR^5$, and $X^6$ is $CR^6$.

In some embodiments of Formula (IIIb), $X^2$ is $CR^2$, $X^5$ is $CR^5$, and $X^6$ is N.

In some embodiments of Formula (IIIb), $X^2$ is $CR^2$, $X^5$ is N, and $X^6$ is $CR^6$.

In some embodiments of Formula (IIIb), $X^2$ is $CR^2$, $X^5$ is N, and $X^6$ is N.

In some embodiments, the compound of Formula (I) is a compound of Formula (IIIc):

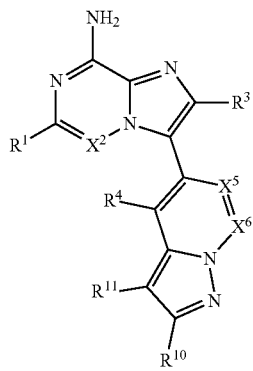

(IIIc)

or a pharmaceutically acceptable salt thereof.

In some embodiments of Formula (IIIc), $X^2$ is N.

In some embodiments of Formula (IIIc), $X^2$ is N, $X^5$ is $CR^5$, and $X^6$ is $CR^6$.

In some embodiments of Formula (IIIc), $X^2$ is N, $X^5$ is $CR^5$, and $X^6$ is N.

In some embodiments of Formula (IIIc), $X^2$ is N, $X^5$ is N, and $X^6$ is $CR^6$.

In some embodiments of Formula (IIIc), $X^2$ is N, $X^5$ is N, and $X^6$ is N.

In some embodiments of Formula (IIIc), $X^2$ is $CR^2$.

In some embodiments of Formula (IIIc), $X^2$ is $CR^2$, $X^5$ is $CR^5$, and $X^6$ is $CR^6$.

In some embodiments of Formula (IIIc), $X^2$ is $CR^2$, $X^5$ is $CR^5$, and $X^6$ is N.

In some embodiments of Formula (IIIc), $X^2$ is $CR^2$, $X^5$ is N, and $X^6$ is $CR^6$.

In some embodiments of Formula (IIIc), $X^2$ is $CR^2$, $X^5$ is N, and $X^6$ is N.

In some embodiments, the compound of Formula (I) is a compound of Formula (IIId):

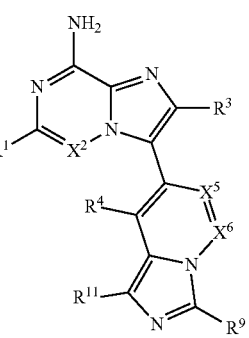

(IIId)

or a pharmaceutically acceptable salt thereof.

In some embodiments of Formula (IIId), $X^2$ is N.

In some embodiments of Formula (IIId), $X^2$ is N, $X^5$ is $CR^5$, and $X^6$ is $CR^6$.

In some embodiments of Formula (IIId), $X^2$ is N, $X^5$ is $CR^5$, and $X^6$ is N.

In some embodiments of Formula (IIId), $X^2$ is N, $X^5$ is N, and $X^6$ is $CR^6$.

In some embodiments of Formula (IIId), $X^2$ is N, $X^5$ is N, and $X^6$ is N.

In some embodiments of Formula (IIId), $X^2$ is $CR^2$.
In some embodiments of Formula (IIId), $X^2$ is $CR^2$, $X^5$ is $CR^5$, and $X^6$ is $CR^6$.
In some embodiments of Formula (IIId), $X^2$ is $CR^2$, $X^5$ is $CR^5$, and $X^6$ is N.
In some embodiments of Formula (IIId), $X^2$ is $CR^2$, $X^5$ is N, and $X^6$ is $CR^6$.
In some embodiments of Formula (IIId), $X^2$ is $CR^2$, $X^5$ is N, and $X^6$ is N.
In some embodiments, the compound of Formula (I) is a compound of Formula (IIIe):

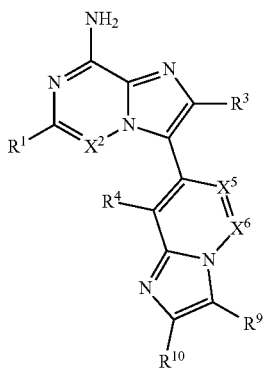

(IIIe)

or a pharmaceutically acceptable salt thereof.
In some embodiments of Formula (IIIe), $X^2$ is N.
In some embodiments of Formula (IIIe), $X^2$ is N, $X^5$ is $CR^5$, and $X^6$ is $CR^6$.
In some embodiments of Formula (IIIe), $X^2$ is N, $X^5$ is $CR^5$, and $X^6$ is N.
In some embodiments of Formula (IIIe), $X^2$ is N, $X^5$ is N, and $X^6$ is $CR^6$.
In some embodiments of Formula (IIIe), $X^2$ is N, $X^5$ is N, and $X^6$ is N.
In some embodiments of Formula (IIIe), $X^2$ is $CR^2$.
In some embodiments of Formula (IIIe), $X^2$ is $CR^2$, $X^5$ is $CR^5$, and $X^6$ is $CR^6$.
In some embodiments of Formula (IIIe), $X^2$ is $CR^2$, $X^5$ is $CR^5$, and $X^6$ is N.
In some embodiments of Formula (IIIe), $X^2$ is $CR^2$, $X^5$ is N, and $X^6$ is $CR^6$.
In some embodiments of Formula (IIIe), $X^2$ is $CR^2$, $X^5$ is N, and $X^6$ is N.
In some embodiments, the compound of Formula (I) is a compound of Formula (IIIf):

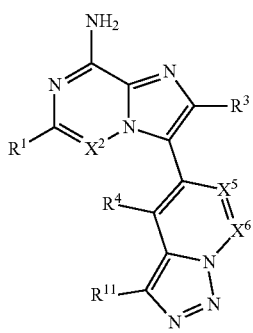

(IIIf)

or a pharmaceutically acceptable salt thereof.

In some embodiments of Formula (IIIf), $X^2$ is N.
In some embodiments of Formula (IIIf), $X^2$ is N, $X^5$ is $CR^5$, and $X^6$ is $CR^6$.
In some embodiments of Formula (IIIf), $X^2$ is N, $X^5$ is $CR^5$, and $X^6$ is N.
In some embodiments of Formula (IIIf), $X^2$ is N, $X^5$ is N, and $X^6$ is $CR^6$.
In some embodiments of Formula (IIIf), $X^2$ is N, $X^5$ is N, and $X^6$ is N.
In some embodiments of Formula (IIIf), $X^2$ is $CR^2$.
In some embodiments of Formula (IIIf), $X^2$ is $CR^2$, $X^5$ is $CR^5$, and $X^6$ is $CR^6$.
In some embodiments of Formula (IIIf), $X^2$ is $CR^2$, $X^5$ is $CR^5$, and $X^6$ is N.
In some embodiments of Formula (IIIf), $X^2$ is $CR^2$, $X^5$ is N, and $X^6$ is $CR^6$.
In some embodiments of Formula (IIIf), $X^2$ is $CR^2$, $X^5$ is N, and $X^6$ is N.
In some embodiments, the compound of Formula (I) is a compound of Formula (IIIg):

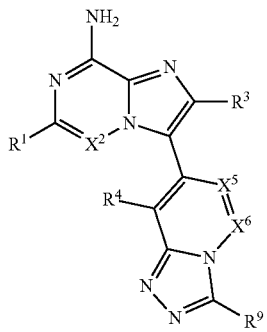

(IIIg)

or a pharmaceutically acceptable salt thereof.
In some embodiments of Formula (IIIg), $X^2$ is N.
In some embodiments of Formula (IIIg), $X^2$ is N, $X^5$ is $CR^5$, and $X^6$ is $CR^6$.
In some embodiments of Formula (IIIg), $X^2$ is N, $X^5$ is $CR^5$, and $X^6$ is N.
In some embodiments of Formula (IIIg), $X^2$ is N, $X^5$ is N, and $X^6$ is $CR^6$.
In some embodiments of Formula (IIIg), $X^2$ is N, $X^5$ is N, and $X^6$ is N.
In some embodiments of Formula (IIIg), $X^2$ is $CR^2$.
In some embodiments of Formula (IIIg), $X^2$ is $CR^2$, $X^5$ is $CR^5$, and $X^6$ is $CR^6$.
In some embodiments of Formula (IIIg), $X^2$ is $CR^2$, $X^5$ is $CR^5$, and $X^6$ is N.
In some embodiments of Formula (IIIg), $X^2$ is $CR^2$, $X^5$ is N, and $X^6$ is $CR^6$.
In some embodiments of Formula (IIIg), $X^2$ is $CR^2$, $X^5$ is N, and $X^6$ is N.

In some embodiments, the compound of Formula (I) is a compound of Formula (IIIh):

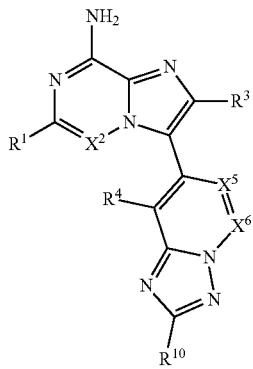

(IIIh)

or a pharmaceutically acceptable salt thereof.

In some embodiments of Formula (IIIh), $X^2$ is N.
In some embodiments of Formula (IIIh), $X^2$ is N, $X^5$ is $CR^5$, and $X^6$ is $CR^6$.
In some embodiments of Formula (IIIh), $X^2$ is N, $X^5$ is $CR^5$, and $X^6$ is N.
In some embodiments of Formula (IIIh), $X^2$ is N, $X^5$ is N, and $X^6$ is $CR^6$.
In some embodiments of Formula (IIIh), $X^2$ is N, $X^5$ is N, and $X^6$ is N.
In some embodiments of Formula (IIIh), $X^2$ is $CR^2$.
In some embodiments of Formula (IIIh), $X^2$ is $CR^2$, $X^5$ is $CR^5$, and $X^6$ is $CR^6$.
In some embodiments of Formula (IIIh), $X^2$ is $CR^2$, $X^5$ is $CR^5$, and $X^6$ is N.
In some embodiments of Formula (IIIh), $X^2$ is $CR^2$, $X^5$ is N, and $X^6$ is $CR^6$.
In some embodiments of Formula (IIIh), $X^2$ is $CR^2$, $X^5$ is N, and $X^6$ is N.

In some embodiments, the compound of Formula (I) is a compound of Formula (IIIi):

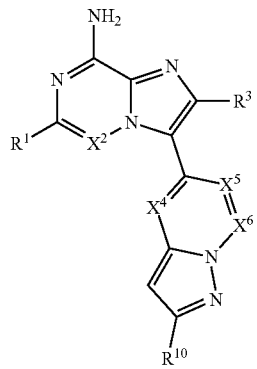

(IIIi)

or a pharmaceutically acceptable salt thereof.

In some embodiments of Formula (IIIi), $X^2$ is N.
In some embodiments of Formula (IIIi), $X^2$ is N, $X^4$ is $CR^4$, $X^5$ is $CR^5$, and $X^6$ is $CR^6$.
In some embodiments of Formula (IIIi), $X^2$ is N, $X^4$ is $CR^4$, $X^5$ is $CR^5$, and $X^6$ is N.
In some embodiments of Formula (IIIi), $X^2$ is N, $X^4$ is $CR^4$, $X^5$ is N, and $X^6$ is $CR^6$.
In some embodiments of Formula (IIIi), $X^2$ is N, $X^4$ is $CR^4$, $X^5$ is N, and $X^6$ is N.
In some embodiments of Formula (IIIi), $X^2$ is N, $X^4$ is CH, $X^5$ is CH, and $X^6$ is $CR^6$.
In some embodiments of Formula (IIIi), $X^2$ is $CR^2$.
In some embodiments of Formula (IIIi), $X^2$ is $CR^2$, $X^4$ is $CR^4$, $X^5$ is $CR^5$, and $X^6$ is $CR^6$.
In some embodiments of Formula (IIIi), $X^2$ is $CR^2$, $X^4$ is $CR^4$, $X^5$ is $CR^5$, and $X^6$ is N.
In some embodiments of Formula (IIIi), $X^2$ is $CR^2$, $X^4$ is $CR^4$, $X^5$ is N, and $X^6$ is $CR^6$.
In some embodiments of Formula (IIIi), $X^2$ is $CR^2$, $X^4$ is $CR^4$, $X^5$ is N, and $X^6$ is N.
In some embodiments of Formula (IIIi), $X^2$ is CH, $X^4$ is CH, $X^5$ is CH, and $X^6$ is $CR^6$.

In some embodiments, the compound of Formula (I) is a compound of Formula (IIIj):

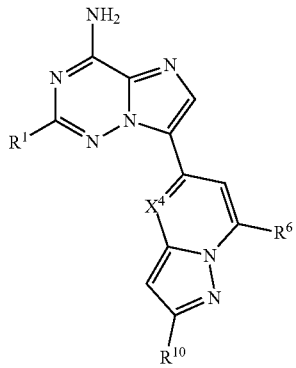

(IIIj)

or a pharmaceutically acceptable salt thereof.

In some embodiments of Formula (IIIj), $X^2$ is N.
In some embodiments of Formula (IIIj), $X^2$ is $CR^2$.
In some embodiments of Formula (IIIj), $X^2$ is CH.

In some embodiments, the compound of Formula (I) is a compound of Formula (IIIk):

(IIIk)

or a pharmaceutically acceptable salt thereof.

In some embodiments of Formula (IIIk):
$R^1$ is selected from H, $C_{1-6}$ alkyl, $C_{1-6}$ haloalkyl, and $C(O)NR^{c1}R^{d1}$, wherein the $C_{1-6}$ alkyl is optionally substituted with 1, 2, 3, or 4 independently selected $R^{14}$ substituents; each $R^{c1}$ and $R^{d1}$ is independently selected from H, $C_{1-6}$ alkyl and 4-7 membered heterocycloalkyl; and each $R^{14}$ is selected from D, halo, CN, OH and $NH_2$;

$X^4$ is N or CH;
$X^6$ is N or $CR^6$;
$R^6$ is selected from H, D, halo, $C_{1-6}$ alkyl, $SR^{a6}$, $C(O)R^{b6}$, and $S(O)_2R^{b6}$, wherein the $C_{1-6}$ alkyl is optionally substituted with 1, 2, 3, or 4 independently selected $R^{6A}$ substituents; each $R^{a6}$ and $R^{b6}$ is independently selected from H and $C_{1-6}$ alkyl; and each $R^{6A}$ is selected from D, halo, CN, OH, and $NH_2$;
$R^{10N}$ is selected from H, $C_{1-6}$ alkyl, $C_{6-10}$ aryl-$C_{1-6}$ alkyl-, and $C_{3-10}$ cycloalkyl-$C_{1-6}$ alkyl-; and
$X^{11}$ is N, C(O) or CH.

In some embodiments, the compound of Formula (I) is a compound of Formula (IV):

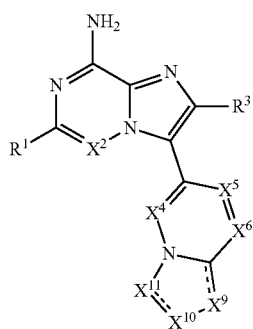

(IV)

or a pharmaceutically acceptable salt thereof.

In some embodiments of Formula (IV), $X^2$ is N.
In some embodiments of Formula (IV), $X^2$ is N and $X^4$, $X^5$ and $X^6$ are each CH.

In some embodiments, the compound of Formula (I) is a compound of Formula (IVb):

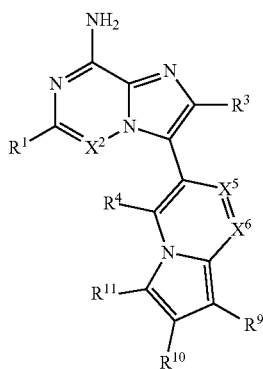

(IVb)

or a pharmaceutically acceptable salt thereof.

In some embodiments of Formula (IVb), $X^2$ is N.
In some embodiments of Formula (IVb), $X^2$ is N, $X^5$ is $CR^5$, and $X^6$ is $CR^6$.
In some embodiments of Formula (IVb), $X^2$ is N, $X^5$ is $CR^5$, and $X^6$ is N.
In some embodiments of Formula (IVb), $X^2$ is N, $X^5$ is N, and $X^6$ is $CR^6$.
In some embodiments of Formula (IVb), $X^2$ is N, $X^5$ is N, and $X^6$ is N.
In some embodiments of Formula (IVb), $X^2$ is $CR^2$.
In some embodiments of Formula (IVb), $X^2$ is $CR^2$, $X^5$ is $CR^5$, and $X^6$ is $CR^6$.
In some embodiments of Formula (IVb), $X^2$ is $CR^2$, $X^5$ is $CR^5$, and $X^6$ is N.
In some embodiments of Formula (IVb), $X^2$ is $CR^2$, $X^5$ is N, and $X^6$ is $CR^6$.
In some embodiments of Formula (IVb), $X^2$ is $CR^2$, $X^5$ is N, and $X^6$ is N.

In some embodiments, the compound of Formula (I) is a compound of Formula (IVc):

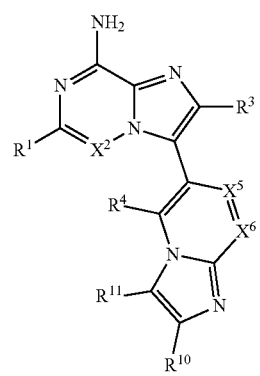

(IVc)

or a pharmaceutically acceptable salt thereof.

In some embodiments of Formula (IVc), $X^2$ is N.
In some embodiments of Formula (IVc), $X^2$ is N, $X^5$ is $CR^5$, and $X^6$ is $CR^6$.
In some embodiments of Formula (IVc), $X^2$ is N, $X^5$ is $CR^5$, and $X^6$ is N.
In some embodiments of Formula (IVc), $X^2$ is N, $X^5$ is N, and $X^6$ is $CR^6$.
In some embodiments of Formula (IVc), $X^2$ is N, $X^5$ is N, and $X^6$ is N.
In some embodiments of Formula (IVc), $X^2$ is $CR^2$.
In some embodiments of Formula (IVc), $X^2$ is $CR^2$, $X^5$ is $CR^5$, and $X^6$ is $CR^6$.
In some embodiments of Formula (IVc), $X^2$ is $CR^2$, $X^5$ is $CR^5$, and $X^6$ is N.
In some embodiments of Formula (IVc), $X^2$ is $CR^2$, $X^5$ is N, and $X^6$ is $CR^6$.
In some embodiments of Formula (IVc), $X^2$ is $CR^2$, $X^5$ is N, and $X^6$ is N.

In some embodiments, the compound of Formula (I) is a compound of Formula (IVd):

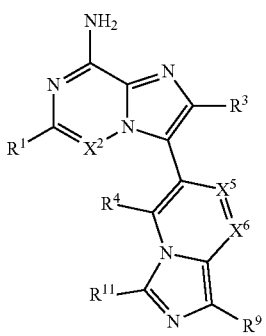

(IVd)

or a pharmaceutically acceptable salt thereof.

In some embodiments of Formula (IVd), $X^2$ is N.
In some embodiments of Formula (IVd), $X^2$ is N, $X^5$ is $CR^5$, and $X^6$ is $CR^6$.

In some embodiments of Formula (IVd), $X^2$ is N, $X^5$ is $CR^5$, and $X^6$ is N.

In some embodiments of Formula (IVd), $X^2$ is N, $X^5$ is N, and $X^6$ is $CR^6$.

In some embodiments of Formula (IVd), $X^2$ is N, $X^5$ is N, and $X^6$ is N.

In some embodiments of Formula (IVd), $X^2$ is $CR^2$.

In some embodiments of Formula (IVd), $X^2$ is $CR^2$, $X^5$ is $CR^5$, and $X^6$ is $CR^6$.

In some embodiments of Formula (IVd), $X^2$ is $CR^2$, $X^5$ is $CR^5$, and $X^6$ is N.

In some embodiments of Formula (IVd), $X^2$ is $CR^2$, $X^5$ is N, and $X^6$ is $CR^6$.

In some embodiments of Formula (IVd), $X^2$ is $CR^2$, $X^5$ is N, and $X^6$ is N.

In some embodiments, the compound of Formula (I) is a compound of Formula (IVe):

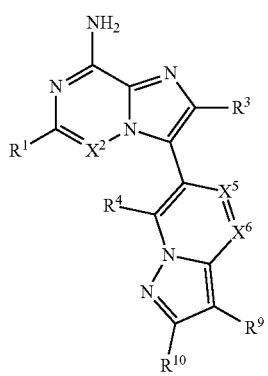

(IVe)

or a pharmaceutically acceptable salt thereof.

In some embodiments of Formula (IVe), $X^2$ is N.

In some embodiments of Formula (IVe), $X^2$ is N, $X^5$ is $CR^5$, and $X^6$ is $CR^6$.

In some embodiments of Formula (IVe), $X^2$ is N, $X^5$ is $CR^5$, and $X^6$ is N.

In some embodiments of Formula (IVe), $X^2$ is N, $X^5$ is N, and $X^6$ is $CR^6$.

In some embodiments of Formula (IVe), $X^2$ is N, $X^5$ is N, and $X^6$ is N.

In some embodiments of Formula (IVe), $X^2$ is $CR^2$.

In some embodiments of Formula (IVe), $X^2$ is $CR^2$, $X^5$ is $CR^5$, and $X^6$ is $CR^6$.

In some embodiments of Formula (IVe), $X^2$ is $CR^2$, $X^5$ is $CR^5$, and $X^6$ is N.

In some embodiments of Formula (IVe), $X^2$ is $CR^2$, $X^5$ is N, and $X^6$ is $CR^6$.

In some embodiments of Formula (IVe), $X^2$ is $CR^2$, $X^5$ is N, and $X^6$ is N.

In some embodiments, the compound of Formula (I) is a compound of Formula (IVf):

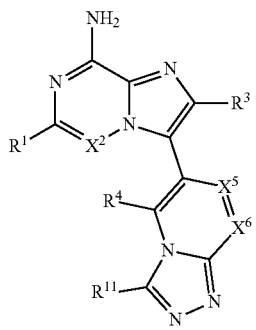

(IVf)

or a pharmaceutically acceptable salt thereof.

In some embodiments of Formula (IVf), $X^2$ is N.

In some embodiments of Formula (IVf), $X^2$ is N, $X^5$ is $CR^5$, and $X^6$ is $CR^6$.

In some embodiments of Formula (IVf), $X^2$ is N, $X^5$ is $CR^5$, and $X^6$ is N.

In some embodiments of Formula (IVf), $X^2$ is N, $X^5$ is N, and $X^6$ is $CR^6$.

In some embodiments of Formula (IVf), $X^2$ is N, $X^5$ is N, and $X^6$ is N.

In some embodiments of Formula (IVf), $X^2$ is $CR^2$.

In some embodiments of Formula (IVf), $X^2$ is $CR^2$, $X^5$ is $CR^5$, and $X^6$ is $CR^6$.

In some embodiments of Formula (IVf), $X^2$ is $CR^2$, $X^5$ is $CR^5$, and $X^6$ is N.

In some embodiments of Formula (IVf), $X^2$ is $CR^2$, $X^5$ is N, and $X^6$ is $CR^6$.

In some embodiments of Formula (IVf), $X^2$ is $CR^2$, $X^5$ is N, and $X^6$ is N.

In some embodiments, the compound of Formula (I) is a compound of Formula (IVg):

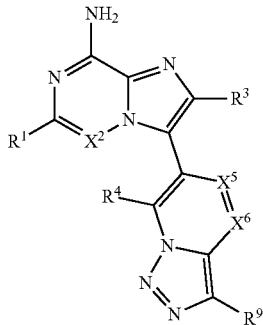

(IVg)

or a pharmaceutically acceptable salt thereof.

In some embodiments of Formula (IVg), $X^2$ is N.

In some embodiments of Formula (IVg), $X^2$ is N, $X^5$ is $CR^5$, and $X^6$ is $CR^6$.

In some embodiments of Formula (IVg), $X^2$ is N, $X^5$ is $CR^5$, and $X^6$ is N.

In some embodiments of Formula (IVg), $X^2$ is N, $X^5$ is N, and $X^6$ is $CR^6$.

In some embodiments of Formula (IVg), $X^2$ is N, $X^5$ is N, and $X^6$ is N.

In some embodiments of Formula (IVg), $X^2$ is $CR^2$.

In some embodiments of Formula (IVg), $X^2$ is $CR^2$, $X^5$ is $CR^5$, and $X^6$ is $CR^6$.
In some embodiments of Formula (IVg), $X^2$ is $CR^2$, $X^5$ is $CR^5$, and $X^6$ is N.
In some embodiments of Formula (IVg), $X^2$ is $CR^2$, $X^5$ is N, and $X^6$ is $CR^6$.
In some embodiments of Formula (IVg), $X^2$ is $CR^2$, $X^5$ is N, and $X^6$ is N.
In some embodiments, the compound of Formula (I) is a compound of Formula (IVh):

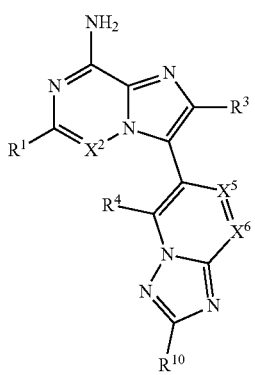

(IVh)

or a pharmaceutically acceptable salt thereof.
In some embodiments of Formula (IVh), $X^2$ is N.
In some embodiments of Formula (IVh), $X^2$ is N, $X^5$ is $CR^5$, and $X^6$ is $CR^6$.
In some embodiments of Formula (IVh), $X^2$ is N, $X^5$ is $CR^5$, and $X^6$ is N.
In some embodiments of Formula (IVh), $X^2$ is N, $X^5$ is N, and $X^6$ is $CR^6$.
In some embodiments of Formula (IVh), $X^2$ is N, $X^5$ is N, and $X^6$ is N.
In some embodiments of Formula (IVh), $X^2$ is $CR^2$.
In some embodiments of Formula (IVh), $X^2$ is $CR^2$, $X^5$ is $CR^5$, and $X^6$ is $CR^6$.
In some embodiments of Formula (IVh), $X^2$ is $CR^2$, $X^5$ is $CR^5$, and $X^6$ is N.
In some embodiments of Formula (IVh), $X^2$ is $CR^2$, $X^5$ is N, and $X^6$ is $CR^6$.
In some embodiments of Formula (IVh), $X^2$ is $CR^2$, $X^5$ is N, and $X^6$ is N.
In some embodiments, the compound of Formula (I) is a compound of Formula (IVi):

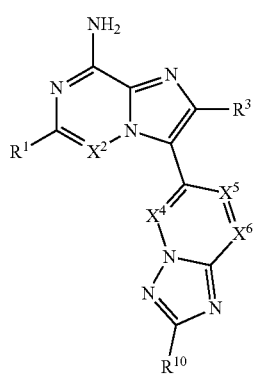

(IVi)

or a pharmaceutically acceptable salt thereof.
In some embodiments of Formula (IVi), $X^2$ is N.
In some embodiments of Formula (IVi), $X^2$ is N, $X^4$ is $CR^4$, $X^5$ is $CR^5$, and $X^6$ is $CR^6$.
In some embodiments of Formula (IVi), $X^2$ is N, $X^4$ is $CR^4$, $X^5$ is $CR^5$, and $X^6$ is N.
In some embodiments of Formula (IVi), $X^2$ is N, $X^4$ is $CR^4$, $X^5$ is N, and $X^6$ is $CR^6$.
In some embodiments of Formula (IVi), $X^2$ is N, $X^4$ is $CR^4$, $X^5$ is N, and $X^6$ is N.
In some embodiments of Formula (IVi), $X^2$ is N, $X^4$ is CH, $X^5$ is CH, and $X^6$ is $CR^6$.
In some embodiments of Formula (IVi), $X^2$ is $CR^2$.
In some embodiments of Formula (IVi), $X^2$ is $CR^2$, $X^4$ is $CR^4$, $X^5$ is $CR^5$, and $X^6$ is $CR^6$.
In some embodiments of Formula (IVi), $X^2$ is $CR^2$, $X^4$ is $CR^4$, $X^5$ is $CR^5$, and $X^6$ is N.
In some embodiments of Formula (IVi), $X^2$ is $CR^2$, $X^4$ is $CR^4$, $X^5$ is N, and $X^6$ is $CR^6$.
In some embodiments of Formula (IVi), $X^2$ is $CR^2$, $X^4$ is $CR^4$, $X^5$ is N, and $X^6$ is N.
In some embodiments of Formula (IVi), $X^2$ is CH, $X^4$ is CH, $X^5$ is CH, and $X^6$ is $CR^6$.
In some embodiments, the compound of Formula (I) is a compound of Formula (IVj):

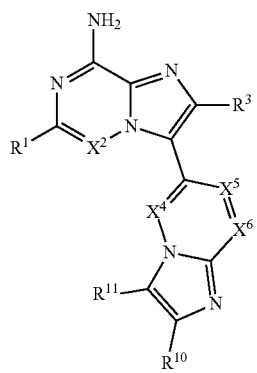

(IVj)

or a pharmaceutically acceptable salt thereof.
In some embodiments of Formula (IVj), $X^2$ is N.
In some embodiments of Formula (IVj), $X^2$ is N, $X^4$ is $CR^4$, $X^5$ is $CR^5$, and $X^6$ is $CR^6$.
In some embodiments of Formula (IVj), $X^2$ is N, $X^4$ is $CR^4$, $X^5$ is $CR^5$, and $X^6$ is N.
In some embodiments of Formula (IVj), $X^2$ is N, $X^4$ is $CR^4$, $X^5$ is N, and $X^6$ is $CR^6$.
In some embodiments of Formula (IVj), $X^2$ is N, $X^4$ is $CR^4$, $X^5$ is N, and $X^6$ is N.
In some embodiments of Formula (IVj), $X^2$ is N, $X^4$ is CH, $X^5$ is CH, and $X^6$ is $CR^6$.
In some embodiments of Formula (IVj), $X^2$ is $CR^2$.
In some embodiments of Formula (IVj), $X^2$ is $CR^2$, $X^4$ is $CR^4$, $X^5$ is $CR^5$, and $X^6$ is $CR^6$.
In some embodiments of Formula (IVj), $X^2$ is $CR^2$, $X^4$ is $CR^4$, $X^5$ is $CR^5$, and $X^6$ is N.
In some embodiments of Formula (IVj), $X^2$ is $CR^2$, $X^4$ is $CR^4$, $X^5$ is N, and $X^6$ is $CR^6$.
In some embodiments of Formula (IVj), $X^2$ is $CR^2$, $X^4$ is $CR^4$, $X^5$ is N, and $X^6$ is N.
In some embodiments of Formula (IVj), $X^2$ is CH, $X^4$ is CH, $X^5$ is CH, and $X^6$ is $CR^6$.

In some embodiments, the compound of Formula (I) is a compound of Formula (IVk):

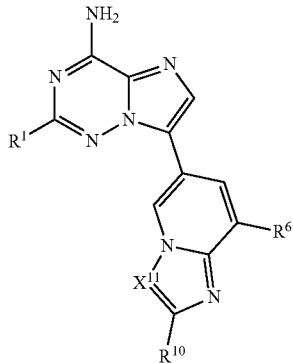

or a pharmaceutically acceptable salt thereof.

In some embodiments of Formula (IVk):

$R^1$ is selected from H, $C_{1-6}$ alkyl, $C_{1-6}$ haloalkyl, and $C(O)NR^{c1}R^{d1}$, wherein the $C_{1-6}$ alkyl is optionally substituted with 1, 2, 3, or 4 independently selected $R^{1A}$ substituents; each $R^{c1}$ and $R^{d1}$ is independently selected from H, $C_{1-6}$ alkyl and 4-7 membered heterocycloalkyl; and each $R^{1A}$ is selected from D, halo, CN, OH and $NH_2$;

$R^6$ is selected from H, D, halo, $C_{1-6}$ alkyl, $SR^{a6}$, $C(O)R^{b6}$, and $S(O)_2R^{b6}$, wherein the $C_{1-6}$ alkyl is optionally substituted with 1, 2, 3, or 4 independently selected $R^{6A}$ substituents; each $R^{a6}$ and $R^{b6}$ is independently selected from H and $C_{1-6}$ alkyl; and each $R^{6A}$ is selected from D, halo, CN, OH, and $NH_2$;

$R^{10}$ is selected from H, $C_{1-6}$ alkyl, $C_{6-10}$ aryl-$C_{1-6}$ alkyl-, and $C_{3-10}$ cycloalkyl-$C_{1-6}$ alkyl-; and $X^{11}$ is N, C(O) or CH.

In some embodiments, the compound of Formula (I) is a compound of Formula (V):

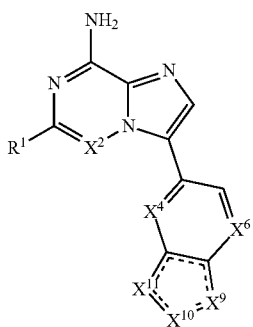

or a pharmaceutically acceptable salt thereof.

In some embodiments, the compound is the (S)-enantiomer of one of the preceding compounds, or a pharmaceutically acceptable salt thereof. In some embodiments, the compound is the (R)-enantiomer of one of the preceding compounds, or a pharmaceutically acceptable salt thereof.

It is further appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable subcombination. This present disclosure is intended to include all combinations of embodiments for each variable described hereinabove including salts thereof.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl. 3-pentyl, n-hexyl. 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., w-propoxy and isopropoxy), butoxy (e.g., w-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2 fused rings). The term "C$_{n-m}$ aryl" refers to an aryl group having from n to m ring carbon atoms.

Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "C$_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "C$_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include CF$_3$, C$_2$F$_5$, CHF$_2$, CH$_2$F, CCl$_3$, CHCl$_2$, C$_2$Cl$_5$ and the like.

As used herein, the term "C$_{n-m}$alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "C$_{n-m}$alkoxy carbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "C$_{n-m}$alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$ alkoxycarbonylamino" refers to a group of formula —NHC(O)O(C$_{n-m}$ alkyl), wherein the alkyl group has n to m carbon atoms. In some embodiments, the alkyl group has 1 to 6, 1 to 4, or 1 to 3 carbon atoms.

As used herein, the term "C$_{n-m}$alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "C$_{n-m}$alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "C$_{n-m}$alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "C$_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "C$_{n-m}$alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "C$_{n-m}$alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "C$_{n-m}$alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbamyl" to a group of formula —C(O)NH$_2$.

As used herein, the term "carbonyl", employed alone or in combination with other terms, refers to a —C(O)— group.

As used herein, the term "cyano-C$_{1-3}$ alkyl" refers to a group of formula —(C$_{1-3}$ alkylene)-CN.

As used herein, the term "HO—C$_{1-6}$ alkyl" refers to a group of formula —(C$_{1-6}$ alkylene)-OH.

As used herein, the term "HO—C$_{1-3}$ alkyl" refers to a group of formula —(C$_{1-3}$ alkylene)-OH.

As used herein, the term "C$_{1-6}$ alkoxy-C$_{1-6}$ alkyl" refers to a group of formula —(C$_{1-6}$ alkylene)-O(C$_{1-6}$ alkyl).

As used herein, the term "C$_{1-3}$ alkoxy-C$_{1-3}$ alkyl" refers to a group of formula —(C$_{1-3}$ alkylene)-O(C$_{1-3}$ alkyl).

As used herein, the term "carboxy" refers to a group of formula —C(O)OH.

As used herein, the term "di(C$_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "aminocarbonyloxy" refers to a group of formula —OC(O)NH$_2$.

As used herein, the term "$C_{1-3}$ alkylcarbonyloxy" refers to a group of formula —OC(O)($C_{1-3}$ alkyl).

As used herein, the term "$C_{1-3}$ alkylaminocarbonyloxy" refers to a group of formula —OC(O)NH($C_{1-3}$ alkyl).

As used herein, the term "di($C_{1-3}$ alkyl)aminocarbonyloxy" refers to a group of formula —OC(O)N($C_{1-3}$ alkyl)$_2$, wherein the two alkyl groups each has, independently, 1 to 3 carbon atoms.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., abridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclobutane, cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-10}$ monocyclic cycloalkyl which is optionally substituted by CH$_2$F, CHF$_2$, CF$_3$, and CF$_2$CF$_3$. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl (e.g. bicyclo[1.1.1]pentan-1-yl), bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B, wherein any ring forming N is optionally an N-oxide group. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-10 membered monocyclic or bicyclic heteroaryl having 1, 2, 3, or 4 heteroatom ring members independently selected from N, O, S and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S and B. In some embodiments, the heteroaryl is a 5-6 monocyclic heteroaryl ring having 1 or 2 heteroatom ring members independently selected from N, O or S. In some embodiments, the heteroaryl group contains 3 to 10, 4 to 10, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, isoxazole, thiophene, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, thieno[3,2-b]pyridine, imidazo[1,2-a]pyridine, 1,5-naphthyridine, 1H-pyrazolo[4,3-b]pyridine. 1,2,3-triazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, 1,2-dihydro-1,2-azaborine and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S and B, and wherein the ring-forming carbon atoms and heteroatoms of the heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2 fused rings) systems. Included in heterocycloalkyl are monocyclic and polycyclic 3-10-, 4-10-, 3-7-, 4-7-, and 5-6-membered heterocycloalkyl groups. Heterocycloalkyl groups can also include spirocycles and bridged rings (e.g., a 5-10 membered bridged biheterocycloalkyl ring having one or more of the ring-forming carbon atoms replaced by a heteroatom independently selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo [3.1.0]hexanyl, diazabicyclo[3.1.0]hexanyl, oxabicyclo [2.1.1]hexanyl, azabicyclo[2.2.1]heptanyl, diazabicyclo [2.2.1]heptanyl, azabicyclo[3.1.1]heptanyl, diazabicyclo [3.1.1]heptanyl, azabicyclo[3.2.1]octanyl, diazabicyclo [3.2.1]octanyl, oxabicyclo[2.2.2]octanyl, azabicyclo[2.2.2] octanyl, azaadamantanyl, diazaadamantanyl, oxaadamantanyl, azaspiro[3.3]heptanyl, diazaspiro[3.3] heptanyl, oxa-azaspiro[3.3]heptanyl, azaspiro[3.4]octanyl, diazaspiro[3.4]octanyl, oxa-azaspiro[3.4]octanyl, azaspiro [2.5]octanyl, diazaspiro[2.5]octanyl, azaspiro[4.4]nonanyl, diazaspiro[4.4]nonanyl, oxa-azaspiro[4.4]nonanyl, azaspiro [4.5]decanyl, diazaspiro[4.5]decanyl, diazaspiro[4.4] nonanyl, oxa-diazaspiro[4.4]nonanyl and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means that each occurrence of a variable or substituent are independently selected at each occurrence from the applicable list.

As used herein, a dashed bond (---) represents a single or double bond depending on the nature of the atoms in each ring and as required to complete the valencies of the atoms being linked by the bond.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein.

Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of Formula (I) can be prepared as shown in Scheme 1. Appropriately substituted starting materials 1-1 wherein $Y^B$ is a halogen (e.g., Cl, Br or I) or pseudohalogen (e.g., OTf or OMs) can be converted to an appropriately substituted metal 1-2 (e.g., $M^B$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or [1,1'-bis(diphenylphosphino)ferrocene]dichloropalladium(II), complex with dichloromethane, and a base, such as potassium acetate). Intermediate 1-3 wherein $Y^1$ and $Y^A$ are independently a halogen (e.g., Cl, Br or I) or pseudohalogen (e.g., OMs or OTf) can be selectively coupled with 1-2 under standard Suzuki conditions (e.g., in the presence of a palladium catalyst, such as tetrakis(triphenylphosphine)palladium(O), [1,1'-bis(diphenylphosphino)ferrocene]dichloropalladium (II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(O) catalyst, such as tetrakis(triphenylphosphine)palladium(O)) or standard Negishi conditions (e.g., in the presence of a palladium catalyst, such as tetrakis(triphenylphosphine)palladium(O) or [1,1'-bis(diphenylphosphino)ferrocene]dichloropalladium (II)) to give compound 1-4. Compound 1-4 can be coupled with a suitable partner $R^1$-M, where M is a boronic acid, boronate ester, potassium trifluoroborate, or an appropriately substituted metal such as $Sn(Bu)_3$ or Zn, under standard Suzuki conditions (e.g., in the presence of a palladium catalyst, such as [1,1'-bis(diphenylphosphino)ferrocene]dichloropalladium(II), complex with dichloromethane or bis(di-tert-butyl (4-dimethylaminophenyl)phosphine)dichloropalladium(II) and a base (e.g., a carbonate base or cesium fluoride)) or standard Stille conditions (e.g., in the presence of a palladium(O) catalyst, such as tetrakis(triphenylphosphine)palladium(O)) or standard Negishi conditions (e.g., in the presence of a palladium catalyst, such as tetrakis(triphenylphosphine)palladium(O) or [1,1'-bis(diphenylphosphino)ferrocene]dichloropalladium (II)) to afford compounds of Formula (I).

Alternatively, appropriately substituted starting materials 1-1 wherein $Y^B$ is a halogen (e.g., Cl, Br or I), can be coupled with an appropriately substituted metal 1-5 where $M^A$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(O), [1,1'-bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(O) catalyst, such as tetrakis(triphenylphosphine)palladium(O)) or standard Negishi conditions (e.g., in the presence of a palladium catalyst, such as tetrakis(triphenylphosphine)palladium(O) or [1,1'-bis(diphenylphosphino)ferrocene]dichloropalladium (II)), to give compounds of Formula (I).

Appropriately substituted starting materials are commercially available or can be synthesized based on the general procedures described in the art, e.g., in International Patent Application Publication Nos.: WO2011008487, WO2011075643, WO2011075630, WO2011130342, WO2013033569, WO2016130501, and WO2017223414, the disclosure of each of which is incorporated herein by reference in its entirety.

Scheme 1.

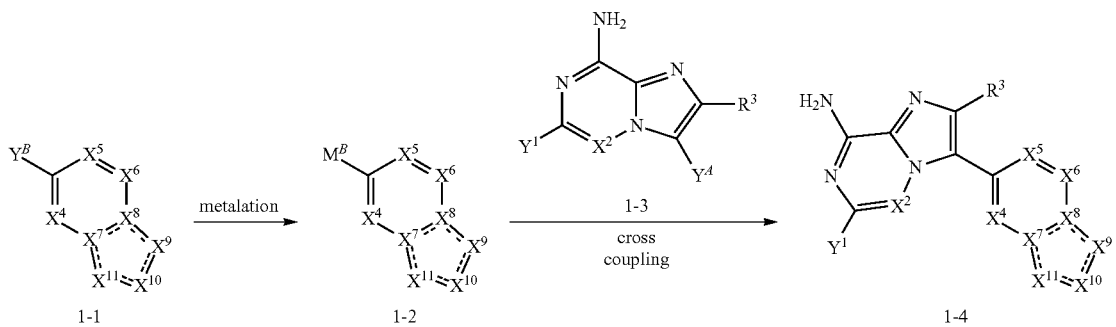

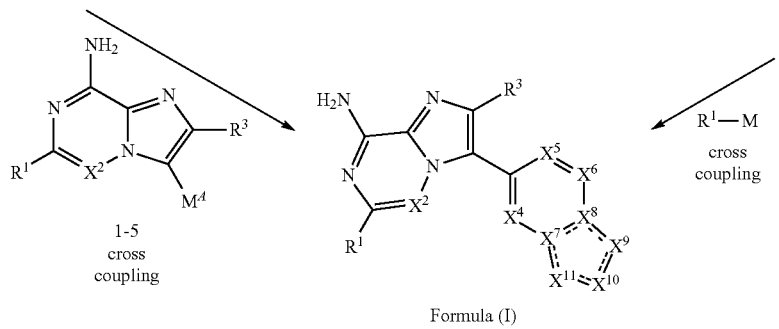

Formula (I)

Compounds of Formula (IIg) can be prepared as shown in Scheme 2. Appropriately substituted ester (e.g., R is —CH₃, or —CH₂CH₃) 2-1 can be halogenated on alkyl substitutent X¹¹ by treatment with a suitable halogenating reagent such as an N-halosuccinimide (e.g., N-chlorosuccinimide, N-bromosuccinimide or N-iodosuccinimide) to afford intermediate 2-3 wherein L¹¹ is a halogen (e.g., Cl, Br or I). Alternatively, intermediate 2-2 bearing an alcohol substituent on X¹¹ can be halogenated by treatment with a suitable halogenating reagent (e.g., SOCl₂ or PBr₃) to afford 2-3 wherein L¹¹ is a halogen (e.g., Cl or Br). The alcohol of intermediate 2-2 can also be converted to an alternative leaving group (e.g., OMs or OTs) by treatment with a sulfonyl chloride (e.g., p-toluenesulfonyl chloride or methanesulfonyl chloride) in the presence of a base (e.g., triethylamine or Hunig's base) to afford 2-3. Intermediate 2-3 can be converted to intermediate 2-4 via reaction with an amine (R¹⁰ᴺ NH₂) in the presence of acid (e.g., boric acid) and base (e.g., a carbonate base such as K₂CO₃, Cs₂CO₃ or Na₂CO₃). Intermediate 2-4 wherein Y⁶ is a suitable halogen (e.g., Cl, Br or I) can be converted to thioether 2-5 by heating in the presence of a suitable sulfur nucleophile Rᵇ⁶SM wherein M is a suitable metal such as sodium (e.g., sodium methanethiolate). Oxidation of intermediate 2-5 with a suitable oxidizing agent (e.g., m-CPBA) can provide sulfone intermediate 2-6. The Yᴮ halo (e.g., Cl, Br, or I) or pseudohalo group (e.g., OTf or OMs) of intermediate 2-6 can be converted to an appropriate substituted metal 2-7 (e.g., Mᴮ is B(OH)₂, Bpin, BF₃K, Sn(Bu)₃, or Zn) under standard conditions (e.g., in the presence of a diboron reagent such as bis(pinacolato)diboron, a palladium catalyst, such as dichloro[bis(triphenylphosphoranyl)]palladium or [1,1'-bis(diphenylphosphino)ferrocene]dichloropalladium(II), complex with dichloromethane, and a base, such as potassium acetate). Intermediate 2-7 can be used to prepare compounds of Formula (IIg) as shown in Scheme 1.

Scheme 2.

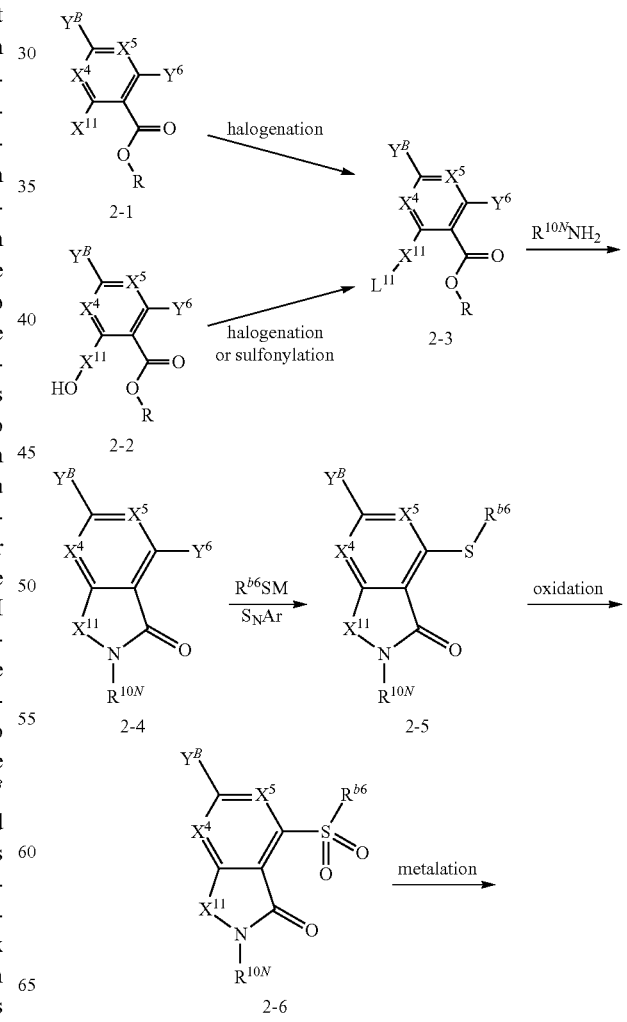

-continued

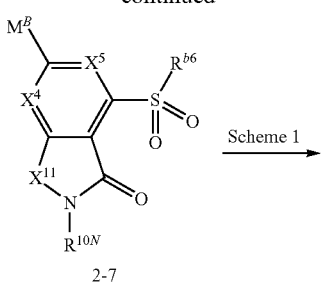

2-7

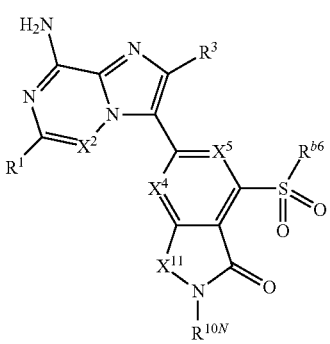

Formula (IIg)

Compounds of Formula (IIg) can be prepared as shown in Scheme 3. Suitably substituted intermediate 3-1 wherein $Y^B$ and $Y^6$ are independently halogen (e.g., Cl, Br, or I) or pseudohalo group (e.g., OTf or OMs) can be converted to an appropriate metal 3-2 (e.g., $M^B$ is B(OH)$_2$, Bpin, BF$_3$K, Sn(Bu)$_3$, or Zn) under standard conditions (e.g., in the presence of a diboron reagent such as bis(pinacolato)diboron, a palladium catalyst, such as dichloro[bis(triphenylphosphine)]palladium or [1,1'-bis(diphenylphosphino)ferrocene]dichloropalladium(II), complex with dichloromethane, and a base, such as potassium acetate). Intermediate 3-2 can be converted to compound 3-3 by methods outlined in Scheme 1. Compound 3-3 wherein $Y^6$ is a suitable halogen can be converted to thioether 3-4 by heating in the presence of a suitable sulfur nucleophile $R^{b6}$SM wherein M is a suitable metal such as sodium (e.g., sodium methanethiolate). Oxidation of intermediate 3-4 with a suitable oxidizing agent (e.g., m-CPBA) can provide compounds of Formula (I).

Scheme 3.

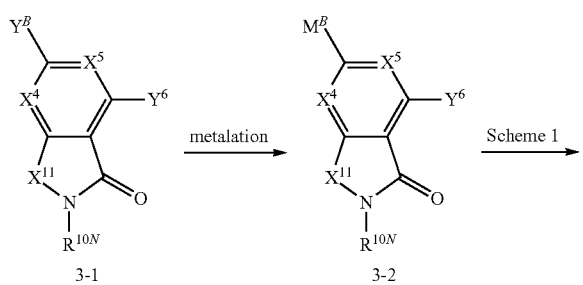

-continued

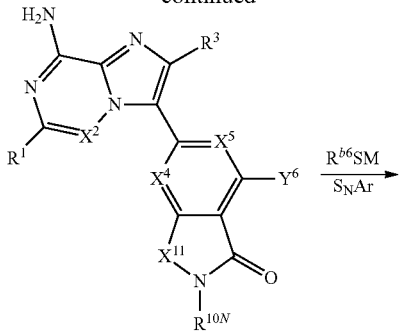

3-3

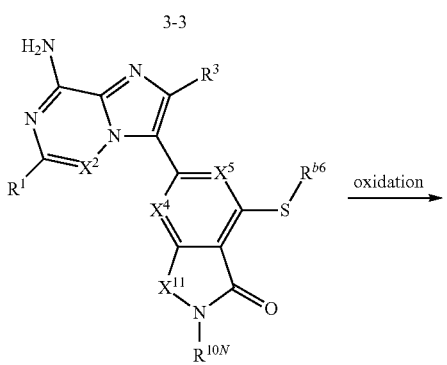

3-4

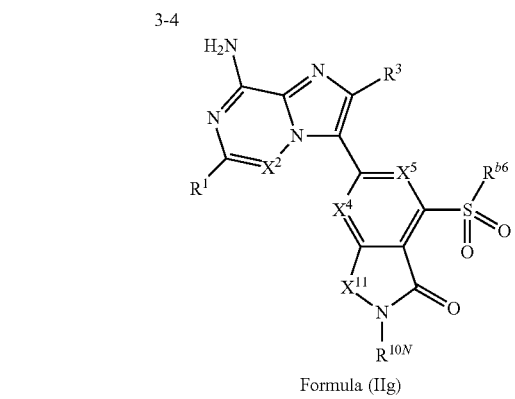

Formula (IIg)

Compounds of Formula (IIh) can be prepared as shown in Scheme 4. Intermediate 4-1 wherein $Y^B$ is a halogen (e.g., Cl, Br, or I) or pseudohalo group (e.g., OTf or OMs) can be converted to an appropriately substituted metal 4-2 (e.g., $M^B$ is B(OH)$_2$, Bpin, BF$_3$K, Sn(Bu)$_3$, or Zn) under standard conditions (e.g., in the presence of a diboron reagent such as bis(pinacolato)diboron, a palladium catalyst, such as dichloro[bis(triphenylphosphoranyl)]palladium or [1,1'-bis(diphenylphosphino)ferrocene]dichloropalladium(II), complex with dichloromethane, and a base, such as potassium acetate). Treatment of intermediate 4-2 with an alkylating agent $R^{10N}$-L wherein L is a suitable leaving group (e.g., a halogen (e.g., Cl, Br, or I)) or pseudohalo group (e.g., OTs or OMs) in the presence of a base (e.g., sodium hydride or carbonate base (e.g., cesium carbonate)) affords intermediate 4-3. Alternatively, the steps can be performed in reverse order (e.g., alkylation of 4-1 with $R^{10N}$-L in the presence of a base (e.g., sodium hydride or carbonate base (e.g., cesium carbonate)) to afford intermediate 4-4, followed by metalation of 4-4 as described above), to afford intermediate 4-3, which can be converted to compounds of Formula (IIh) as outlined in Scheme 1.

Scheme 4.

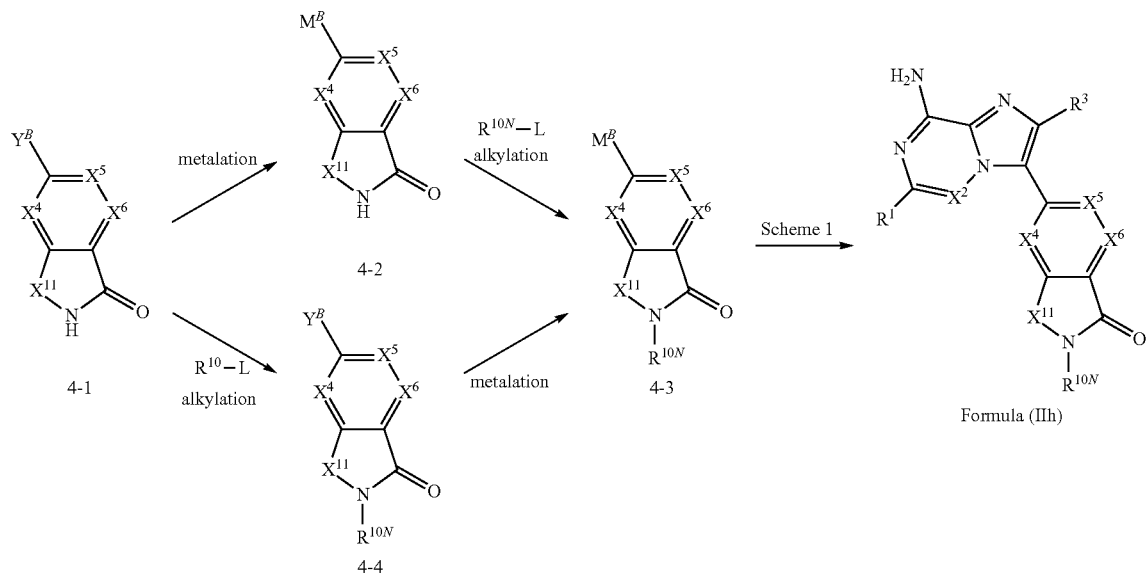

Compounds of Formula (Ib) can be prepared as shown in Scheme 5. Suitable starting material 5-1 wherein $Y^1$ is a halogen (e.g., Cl, Br, or I) or pseudohalo group (e.g., OTf or OMs) can be converted to an amide by reacting with CO gas in the presence of a suitable amine ($R^{c1}R^{d1}NH$) and a palladium catalyst (e.g., [1,1'-bis(diphenylphosphino)ferrocene]dichloropalladium) to afford compounds of Formula (Ib). Alternatively, the Pd-mediated carbonylation can be carried out in the absence of an amine and in a suitable alcohol solvent (e.g., methanol or ethanol) to provide an ester 5-2 (e.g., R=—CH$_3$ or —CH$_2$CH$_3$). Ester 5-2 can be hydrolyzed to a carboxylic acid under standard conditions (e.g., LiOH) to afford 5-3. Compound 5-3 can be coupled with an amine ($R^{c1}R^{d1}NH$) under standard amide coupling conditions (e.g., HATU or EDCI in the presence of a base such as triethylamine or Hunig's base) to afford compounds of Formula (Ib). Alternatively, ester 5-2 can be converted to compounds of Formula (Ib) by reacting with an appropriate amine ($R^{c1}R^{d1}NH$) in the presence of a lewis acid (e.g., AlMe$_3$).

Scheme 5.

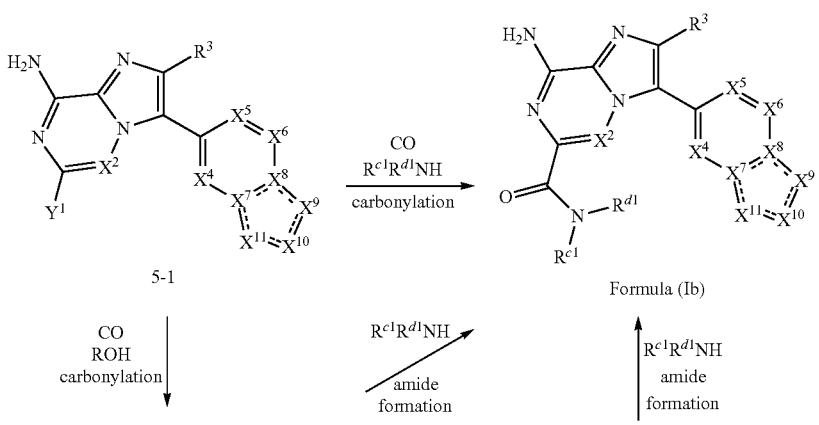

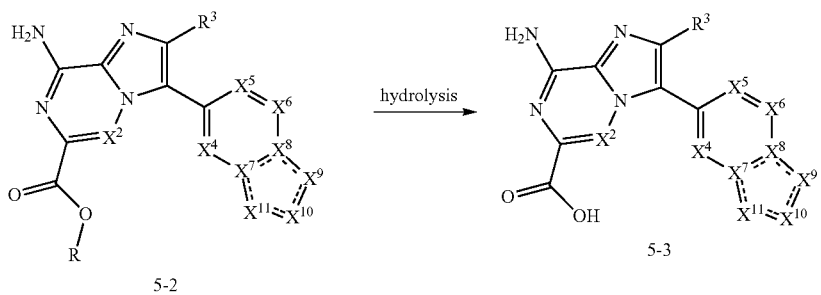

Compounds of the Formula (IIi) can be prepared as shown in Scheme 6. Heteroaromatic bicyclic starting materials 6-1 (wherein $Y^B$ is Cl, Br, or I) can be alkylated with electrophiles $R^{10N}$-L (wherein L=a leaving group such as Br, I, $OSO_2Me$, etc.) utilizing a base (e.g., $K_2CO_3$) in a suitable solvent such as DMF or MeCN. $R^{10N}$ can also be $R^{9N}$, $R^{11N}$ or $R^{11}$, depending on the substitution. Alkylation can also be accomplished with alcohols $R^{10}$—OH under Mitsunobu conditions (e.g., $PPh_3$, DEAD). Alkylated derivatives 6-2 can subsequently be converted to compounds of the Formula (IIi) by the methods outlined in Scheme 1.

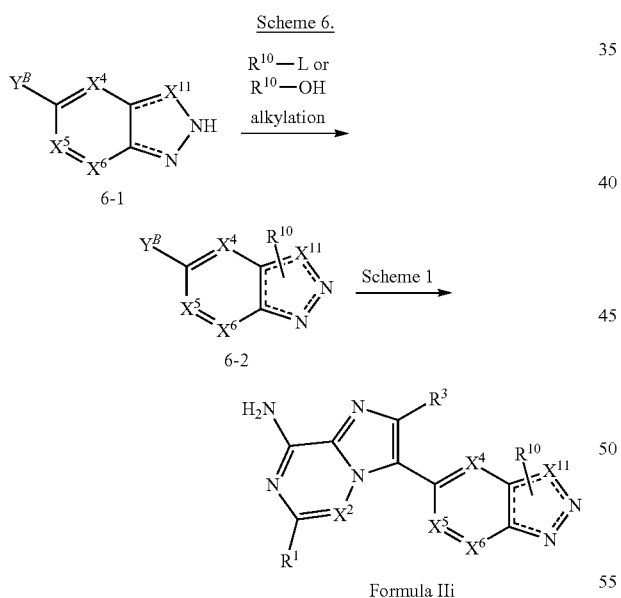

Compounds of the Formula (IIj) can also be synthesized as shown in Scheme 7. Amino containing starting materials 7-1 wherein $X^{11}$=a heteroatom (e.g., N, O, S) can undergo cyclization upon treatment with an ester or acid halide 7-2 (wherein Z=Cl, Br, OR, etc.) to afford bicyclic derivatives 7-3, which can subsequently be converted to compounds of the Formula (IIj) by the methods outlined in Scheme 1.

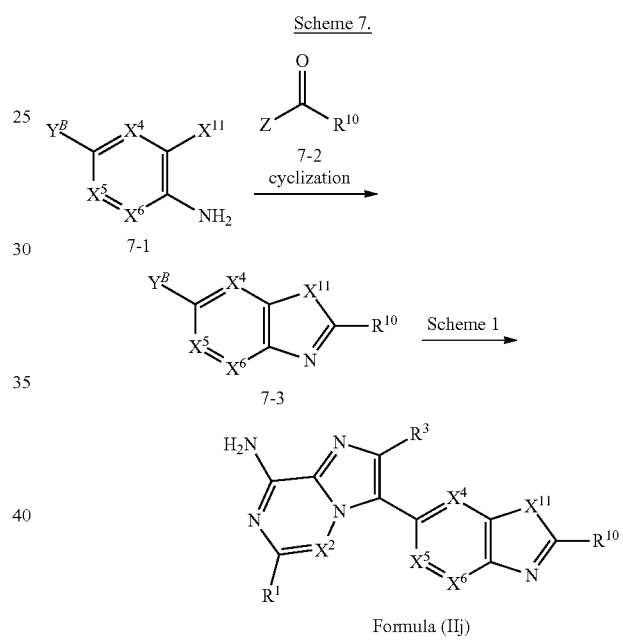

Compounds of the Formula (IVi) can also be synthesized as shown in Scheme 8. Treatment of amino containing starting materials 8-1 with an aminating reagent $H_2N$—OZ (8-2, wherein Z is a leaving group such as $SO_3H$, 2,4-dinitrophenyl, etc.) affords the aminated derivatives 8-3. Reaction with aldehydes 8-4 and a base such as DBU results in cyclization to afford triazoles 8-5, which can subsequently be converted to compounds of the Formula (IVi) by the methods outlined in Scheme 1.

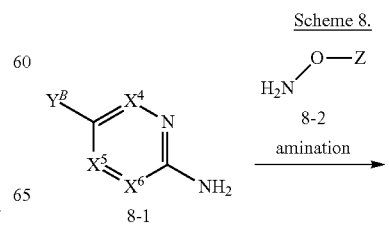

-continued

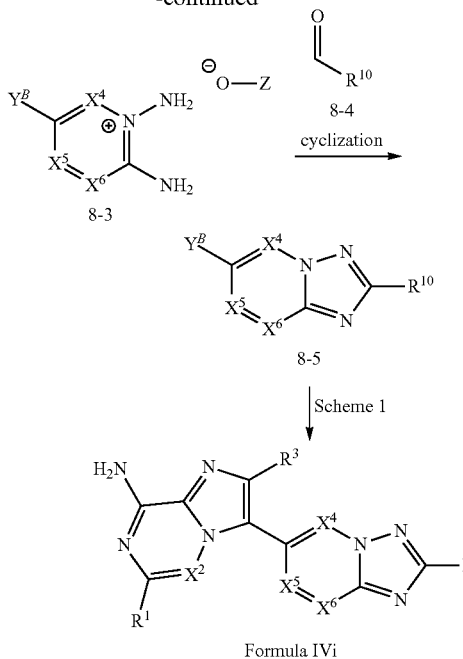

Compounds of the Formula (IVj) can also be prepared as shown in Scheme 9. Treatment of amino containing starting materials 9-1 with an α-halo ketone 9-2 at elevated temperature results in cyclization to provide imidazolo-fused derivatives 9-3. In turn, these intermediates can subsequently be converted to compounds of the Formula (IVj) by the methods outlined in Scheme 1.

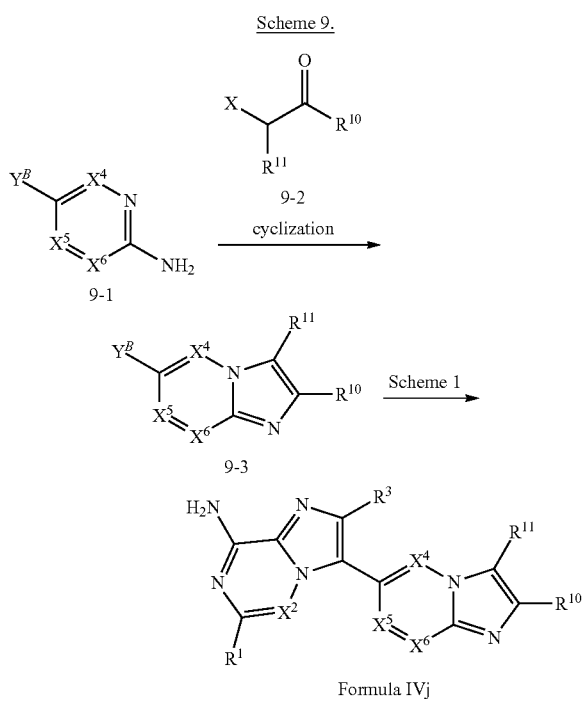

Compounds of the Formula (IIIi) can also be prepared as shown in Scheme 10. Treatment of amino containing starting materials 10-1 with an aminating reagent $H_2N-OZ$ (8-2, wherein Z is a leaving group such as $SO_3H$, 2,4-dinitrophenyl, etc.) affords the aminated derivatives 10-2. Reaction with alkynoates 10-3 results in cyclization to provide pyrazolo-fused products 10-4. The amino group in 10-4 can undergo diazotization (e.g., $NaNO_2$, t-$BuNO_2$, etc.) followed by displacement with a halogen utilizing a copper (I) source such as CuBr to afford intermediates 10-5. Heating under aqueous acidic conditions provides decarboxylated products 10-6, which can subsequently be converted to compounds of the Formula (IIIi) by the methods outlined in Scheme 1.

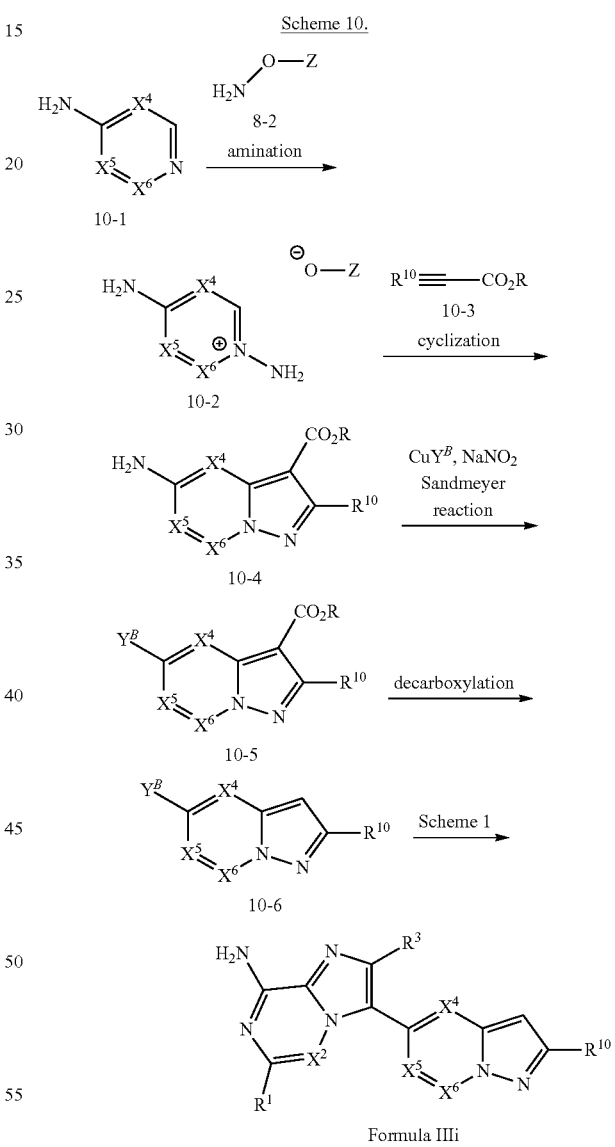

Compounds of the Formula (IIIj) can also be prepared as shown in Scheme 11. Reaction of 2-aminopyrazoles 11-1 with 3-alkoxyacrylates 11-2 affords pyridones 11-3. Deoxyhalogenation can be achieved with a dehydrating agent such as $POCl_3$ or $POBr_3$ to provide the halogenated derivatives 11-4, which can subsequently be converted to compounds of the Formula (IIIj) by the methods outlined in Scheme 1.

Scheme 11.

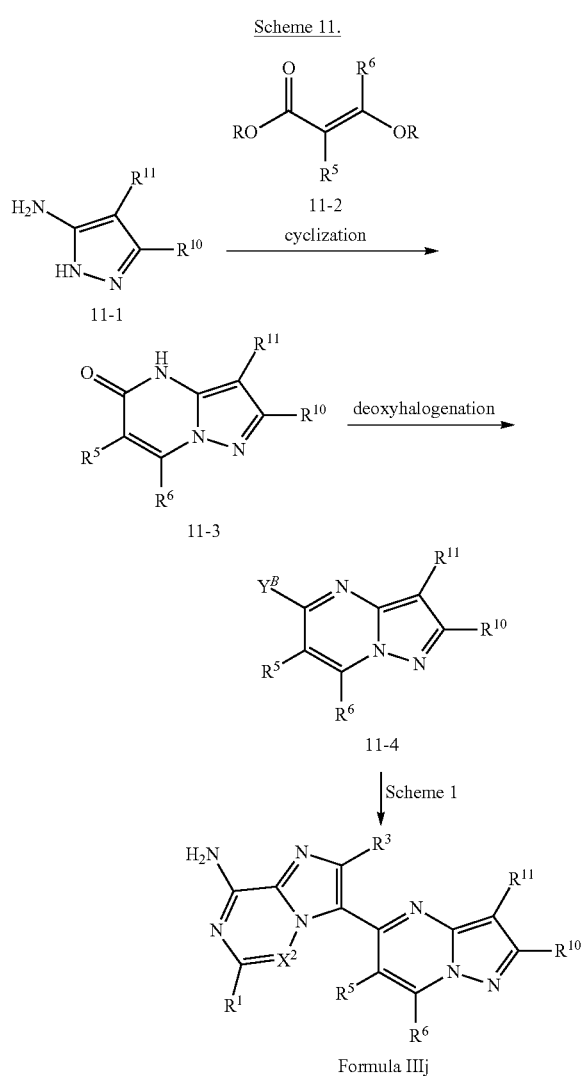

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds, salts or stereoisomers thereof described herein inhibit activity of PI3Kγ kinase. Accordingly, the compounds, salts or stereoisomers described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual/patient in need of the inhibition by administering an effective amount of a compound or salt of described herein. In some embodiments, modulating is inhibiting. In some embodiments, the contacting is in vivo. In some embodiments, the contacting is ex vivo. Advantageously, the compounds as described herein demonstrate better efficacy and favorable safety and toxicity profiles in animal studies.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3Kδ.

The compounds or salts described herein can be selective. By "selective" is meant that the compound binds to or inhibits PI3Kγ with greater affinity or potency, respectively, compared to at least one other kinase. In some embodiments, the compounds of the disclosure are selective inhibitors of PI3Kγ over PI3Kδ, PI3Kα, and PI3Kβ. In some embodiments, the compounds of the disclosure are selective inhibitors of PI3Kγ over PI3Kα and PI3Kβ. In some embodiments, selectivity can be at least about 2-fold, 3-fold, 5-fold, 10-fold, at or 20-fold over PI3Kδ as measured by the assays described herein. In some embodiments, selectivity can be tested at the 2 μM ATP concentration of each enzyme. In some embodiments, the selectivity of compounds of the disclosure can be determined by cellular assays associated with particular PI3K kinase activity.

Another aspect of the present disclosure pertains to methods of treating a kinase PI3Kγ-associated disease or disorder in an individual (e.g., patient) by administering to the individual in need of such treatment a therapeutically effective amount or dose of one or more compounds of the present disclosure or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, head and neck squamous cell carcinoma, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is mesothelioma or adrenocarcinoma. In some embodiments, the disease or disorder is mesothelioma. In some embodiments, the disease or disorder is adrenocarcinoma.

In some embodiments, the disease or disorder is acute myeloid leukemia (e.g., acute monocytic leukemia), small lymphocyctic lymphoma, chronic lymphocytic leukemia (CLL), chronic myelogenous leukemia (CML), multiple myeloma, T-cell actute lymphoblasic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xenoderoma pigmentosum, keratoctanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

MDSC (myeloid-derived suppressor cells) are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immunosuppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including Solid tumors with high basal level of macrophage and/or MDSC infiltration.

In some embodiments, the non-Hodgkin's lymphoma (NHL) is relapsed NHL, refractory NHL, recucurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma. In some embodiments, the Burkitt's lymphoma is endemic Burkitt's lymphoma, sporadic Burkitt's lymphoma, or Burkitt's-like lymphoma.

In some embodiments, the disease or disorder is rheumatoid arthritis, multiple sclerosis, systemic lupus erythematous, asthma, allergy (e.g., allergic rhinitis), pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, the disease or disorder is heart hypertrophy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), idiopathic pulmonary fibrosis, autoimmune hemolytic anemia, vasculitis, lupus nephritis, pemphigus, or membranous nephropathy.

In some embodiments, disease or disorder is heart hypertrophy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis *nodosa*, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, or anti-neutrophil cytoplasm antibody associated (ANCA) systemic vasculitis (AASV).

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the disclosure includes the administration of a compound of the present disclosure to an individual or patient, such as a human, having a PI3K, as well as, for example, introducing a compound of the disclosure into a sample containing a cellular or purified preparation containing the PI3K.

It is believed that compounds of provided herein (e.g., compounds of Formula (I), or pharmaceutically acceptable salts thereof) or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the present disclosure are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, the PI3Kγ inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the PI3Kγ inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti- CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the PI3Kγ inhibitors provided herein can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein. Examples of cancers include solid tumors and liquid tumors, such as blood cancers.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, and FAK kinase inhibitors such as, for example, those described in WO 2006/056399. Other agents such as therapeutic antibodies can be used in combination with the compounds of the present disclosure for treatment of PI3K-associated diseases, disorders or conditions. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the compounds of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADET™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumortargeted therapy, adjuvant therapy, immunotherapy, or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, streptozocin, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, the compounds of the disclosure can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia*, rhizophus), *Sporothrix schenkii, Blastomyces dermatitidis, Paracoccidioides brasiliensis, Coccidioides immitis* and *Histoplasma capsulatum*. Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma* gondi, and Nippostrongylus *brasiliensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable caterers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Substitution of one or more of the atoms of the compounds of the present disclosure can also be useful in generating differentiated ADME (Adsorption, Distribution, Metabolism and Excretion). Accordingly, the present disclosure includes PI3K assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups of the disclosed Formulas (e.g., Formula (I), (II), etc.), can be per-deuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1, 1-2, 1-3, 1-4, 1-5, 1-6, 1-7, 1-8 or 1-9 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of any alkyl, alkenyl, alkynyl, aryl, phenyl, cycloalkyl, heterocycloalkyl, or heteroaryl substituents, or —$C_{1-6}$ alkyl-, alkylene, alkenylene, and alkynylene linking groups, as described herein, are each optionally replaced by a deuterium atom.

Synthetic methods for including isotopes into organic compounds are known in the art (Deuterium Labeling in Organic Chemistry by Alan F. Thomas, New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-

7765; The Organic Chemistry of Isotopic Labelling by James R. Hanson, Royal Society of Chemistry, 2011).

Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro PI3K labeling and competition assays, compounds that incorporate $^3H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of PI3K-associated diseases or disorders, such as cancer, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004)).

The compounds separated were typically subjected to analytical liquid chromatography mass spectrometry (LCMS) for purity analysis under the following conditions: Instrument=Agilent 1100 series, LC/MSD; Column: Waters Sunfire™ $C_{18}$ 5 μm, 2.1×50 mm, Buffers: mobile phase A: 0.025% TFA in water and mobile phase B: acetonitrile; gradient 2% to 80% B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 30×100 mm or Waters XBridge™ $C_{18}$ 5 μm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g., "Preparative LCMS Purification: Improved Compound Specific Method Optimization", K. Blom, B. Glass, R. Sparks, A. Combs, J. Comb. Chem., 6, 874-883 (2004)).

pH=6.5 purifications: Waters XBridge™ $C_{18}$ 5 μm, 30×100 mm column, eluting with mobile phase A: 100 mM ammonium acetate ($NH_4OAc$) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, J. Comb. Chem., 6, 874-883 (2004)).

pH=10 purifications: Waters XBridge™ $C_{18}$ 5 μm, 30×100 mm column, eluting with mobile phase A: 0.10% $NH_4OH$ in water and mobile phase B: acetonitrile; the flow rate was 60 mL/minute, the separating gradient was optimized for each compound using the Compound Specific Method Optimization protocol as described in the literature (see e.g., "Preparative LCMS Purification: Improved Compound Specific Method Optimization", K. Blom, B. Glass, R. Sparks, A. Combs, *J. Comb. Chem.*, 6, 874-883 (2004)).
Stereochemical Rationale The Sharpless asymmetric dihydroxylation of olefins has been studied extensively, and its basis as a model for enantioselectivity is well established (Sharpless, K. B.; Amberg, W.; Bennani, Y. L.; Crispino, G. A.; Hartung, J.; Jeong, K.-S.; Kwong, H.-L.; Morikawa, K.; Wang, Z.-M.; Xu, D.; Zhang, X.-L. *J. Org. Chem.*, 1992, 57, 2768-2771; and Kolb, H. C.; VanNieuwenhze, M. S.; Sharpless, K. B. *Chem. Rev.*, 1994, 94, 2483-2547). Briefly, the application of AD-mix-α (containing (DHQ)$_2$-PHAL) in the dihydroxylation of prop-1-en-2-ylbenzene affords (S)-2-phenylpropane-1,2-diol. Application of AD-mix-β (containing (DHQD)$_2$-PHAL) in the dihydroxylation of prop-1-en-2-ylbenzene affords (R)-2-phenylpropane-1,2-diol (Sharpless and Kolb, supra). Moreno-Dorado et al. extended the method to the trifluoromethyl case (e.g., (3,3,3-trifluoroprop-1-en-2-yl)benzene affords (S)-3,3,3-trifluoro-2-phenylpropane-1,2-diol when treated with AD-mix-α and affords (R)-3,3,3-trifluoro-2-phenylpropane-1,2-diol when treated with AD-mix-3), and the stereochemical outcome was verified by subsequent conversion to well known compounds whose specific rotations were found to be in agreement with the literature values (Moreno-Dorado, F. J.; Guerra, F. M.; Ortega, M. J.; Zubia, E.; Massanet, G. M. *Tetrahedron: Asymmetry*, 2003, 14, 503-510). While not wishing to be bound by any one theory, in the dihydroxylations performed on vinyl arenes in the examples, we expect to obtain the (S)-configuration with AD-mix-α and the (R)-configuration with AD-mix-β.

Example 1. (S)-5-(8-Amino-6-(trifluoromethyl)imidazo[1,2-a]pyrazin-3-yl)-7-chloro-2-(1-cyclopropylethyl)isoindolin-1-one

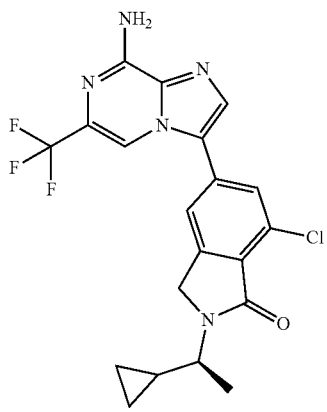 [SMILES: C[C@@H](C1CC1)N1Cc2cc(-c3cnc4c(N)nc(C(F)(F)F)cn34)cc(Cl)c2C1=O]

Step 1. Methyl 4-bromo-2-(bromomethyl)-6-chlorobenzoate

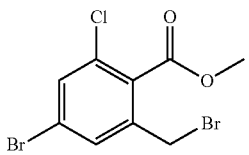

To methyl 4-bromo-2-chloro-6-methylbenzoate (1.5 g, 5.7 mmol, Astatech CL9176) in CCl$_4$ (28 mL) was added N-bromosuccinimide (1.1 g, 6.3 mmol) and benzoyl peroxide (0.028 g, 0.11 mmol), and the reaction was heated to reflux for 1.5 hours, and then stirred at room temperature overnight. A further portion of benzoyl peroxide (0.050 g, 0.20 mmol) was added, and the reaction was heated to reflux for 3 hours. The reaction mixture was washed with a solution of Na$_2$S2O$_3$ and the aqueous layer was extracted twice with EtOAc. The combined organic extracts were dried over Na$_2$SO$_4$, filtered, and concentrated. The product was purified via flash chromatography, eluting with a gradient from 0-50% EtOAc in hexanes, to afford the title compound (0.15 g, 67%).

Step 2. (S)-5-Bromo-7-chloro-2-(1-cyclopropylethyl)isoindolin-1-one

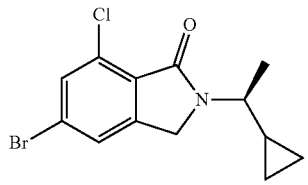

To a flask containing methyl 4-bromo-2-(bromomethyl)-6-chlorobenzoate (1.91 g, 5.58 mmol) in acetonitrile (19 mL) was added (S)-1-cyclopropylethan-1-amine (0.475 g, 5.58 mmol, Aldrich), followed by boric acid (0.345 g, 5.58 mmol). Potassium carbonate (1.54 g, 11.2 mmol) was added portionwise over 2 minutes, and the reaction was stirred overnight. The reaction mixture was filtered and solids were washed with acetonitrile. The solvent was evaporated from the filtrate in vacuo and the residue was purified via flash chromatography, eluting with a gradient from 0-30% EtOAc in hexanes (1.1 g, 62%). LCMS for C$_{13}$H$_{14}$BrClNO (M+H)$^+$: calculated m/z=314.0. found 314.0.

Step 3. (S)-7-Chloro-2-(I-cyclopropylethyl)-5-(4,4,5,5-tetramethyl-1,3,2-dioxaborolan-2-yl)isoindolin-1-one

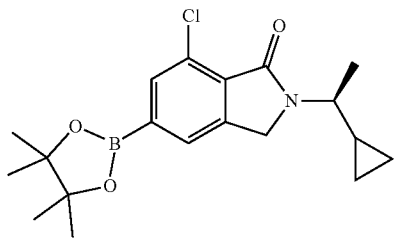 [SMILES: C[C@@H](C1CC1)N1Cc2cc(B3OC(C)(C)C(C)(C)O3)cc(Cl)c2C1=O]

A degassed mixture of (S)-5-bromo-7-chloro-2-(1-cyclopropylethyl)isoindolin-1-one (0.250 g, 0.795 mmol), bis(pinacolato)diboron (0.303 g, 1.19 mmol), potassium acetate (0.468 g, 4.77 mmol) and dichloro[1,1'-bis(diphenylphosphino)ferrocene]palladium(II) dichloromethane adduct (0.039 g, 0.048 mmol) in dioxane (4.0 mL) was heated to 80° C. overnight. Upon cooling to room temperature, water was added, and the mixture was extracted with EtOAc (3×). The combined organic extracts were dried over Na$_2$SO$_4$, filtered, and concentrated. The product was purified via flash chromatography, eluting with a gradient from 0-100% EtOAc in hexanes, to afford the title compound (0.25 g, 87%). LCMS for $C_{19}H_{26}BClNO_3$ (M+H)+: calculated m/z=362.1. found 362.1.

Step 4. (S)-5-(8-Amino-6-(trifluoromethyl)imidazo[1,2-a]pyrazin-3-yl)-7-chloro-2-(1-cyclopropylethyl)isoindolin-1-one A degassed mixture of (S)-7-chloro-2-(1-cyclopropylethyl)-5-(4,4,5,5-tetramethyl-1,3,2-dioxaborolan-2-yl)isoindolin-1-one (15 mg, 0.041 mmol), 3-bromo-6-(trifluoromethyl)imidazo[1,2-a]pyrazin-8-amine (Affinity Research Chemicals, Inc., ARI-0167, 17.5 mg, 0.0620 mmol) and dichloro[1,1'-bis(diphenylphosphino)ferrocene]palladium (II) dichloromethane adduct (6.8 mg, 8.3 µmol) in THF (2.0 mL) and 1.0 M $K_2CO_3$ (0.17 mL, 0.17 mmol) was heated in an microwave to 120° C. for 50 minutes. Upon cooling to room temperature, the reaction mixture was diluted with acetonitrile and filtered. The product was purified by preparative HPLC-MS (pH=2) and then repurified via preparative HPLC-MS (pH=10), to afford the title compound (8.0 mg, 44%). LCMS for $C_{20}H_{18}ClF_3N_5O$ (M+H)+: calculated m/z=436.1. found 436.1. 1H NMR (400 MHz, CDCl3) δ 8.03 (s, 1H), 7.76 (s, 1H), 7.57 (s, 1H), 7.52 (s, 1H), 5.90 (s, 2H), 4.63 (d, J=17.6 Hz, 1H), 4.51 (d, J=17.5 Hz, 1H), 3.86-3.76 (m, 1H), 1.39 (d, J=6.8 Hz, 3H), 1.11-0.99 (m, 1H), 0.73-0.62 (m, 1H), 0.55-0.36 (m, 3H).

Example 2. (S)-5-(8-Amino-6-(trifluoromethyl)imidazo[1,2-a]pyrazin-3-yl)-2-(1-cyclopropylethyl)-7-(methylthio)isoindolin-1-one

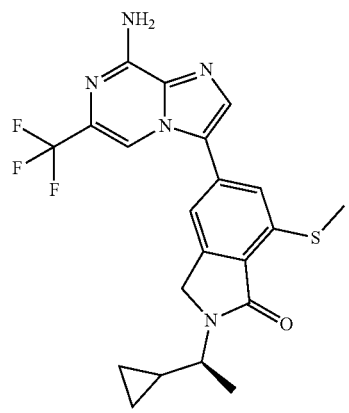 [SMILES: CSc1cc(-c2cnc3c(N)nc(C(F)(F)F)cn23)cc2c1C(=O)N([C@@H](C)C1CC1)C2]

Sodium methanethiolate (18 mg, 0.26 mmol) was added to a solution of (S)-5-(8-amino-6-(trifluoromethyl)imidazo[1,2-a]pyrazin-3-yl)-7-chloro-2-(1-cyclopropylethyl)isoindolin-1-one (51 mg, 0.12 mmol, from Example 1) in DMF (0.8 mL), and the mixture was heated to 110° C. for 2 hours. Upon cooling, the reaction mixture was partitioned between water and EtOAc. The organic layer was separated and the aqueous layer was extracted with two further portions of EtOAc. The combined organic extracts were washed with water, dried over $Na_2SO_4$, filtered and concentrated to afford a yellow solid (43 mg, 82%). A portion was further purified by preparative HPLC-MS (pH=10) to afford the title compound. LCMS for $C_{21}H_{21}F_3N_5OS$ (M+H)+: calculated m/z=448.1. found 448.0. 1H NMR (400 MHz, CDCl3) δ 8.05 (s, 1H), 7.76 (s, 1H), 7.30 (s, 1H), 7.25 (s, 1H), 6.02 (br s, 2H), 4.61 (d, J=17.5 Hz, 1H), 4.50 (d, J=17.4 Hz, 1H), 3.83-3.67 (m, 1H), 2.53 (s, 3H), 1.37 (d, J=6.9 Hz, 3H), 1.10-0.93 (m, 1H), 0.73-0.57 (m, 1H), 0.52-0.33 (m, 3H).

Example 3. (S)-5-(8-Amino-6-(trifluoromethyl)imidazo[1,2-a]pyrazin-3-yl)-2-(1-cyclopropylethyl)-7-(methylsulfonyl)isoindolin-1-one

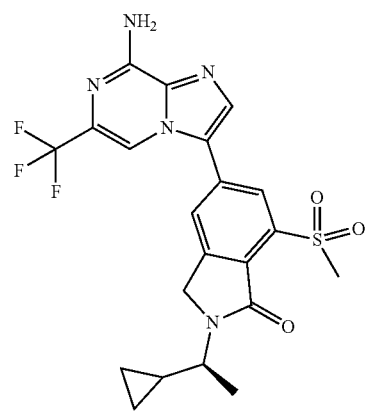 [SMILES: C[C@@H](C1CC1)N1Cc2cc(-c3cnc4c(N)nc(C(F)(F)F)cn34)cc(S(C)(=O)=O)c2C1=O]

To a solution of (S)-5-(8-amino-6-(trifluoromethyl)imidazo[1,2-a]pyrazin-3-yl)-2-(1-cyclopropylethyl)-7-(methylthio)isoindolin-1-one (0.040 g, 0.090 mmol, from Example 2) in DCM (1.6 mL) at 0° C. was added m-CPBA (0.041 g, 0.24 mmol). The reaction was warmed to room temperature over 3 hours. The reaction mixture then was partitioned between DCM and saturated aq. $NaHCO_3$. The organic layer was dried over $Na_2SO_4$, filtered, and concentrated. The residue was reconstituted in MeOH, and the product was purified by preparative HPLC-MS (pH=10) to afford the title compound (0.012 g, 26%). LCMS for $C_{21}H_{21}F_3N_5O_3S$ (M+H)+: calculated m/z=480.1. found 480.1. 1H NMR (400 MHz, CD3OD) δ 8.33 (s, 1H), 8.23 (s, 1H), 8.22 (s, 1H), 7.95 (s, 1H), 4.85 (d, J=18.2 Hz, 1H), 4.78 (d, J=18.8 Hz, 1H), 3.77-3.68 (m, 1H), 3.62 (s, 3H), 1.43 (d, J=6.8 Hz, 3H), 1.26-1.12 (m, 1H), 0.78-0.65 (m, 1H), 0.58-0.49 (m, 1H), 0.49-0.41 (m, 1H), 0.41-0.31 (m, 1H).

Example 4. 5-(8-Amino-6-(trifluoromethyl)imidazo[1,2-a]pyrazin-3-yl)isoindolin-1-one trifluoroacetate salt

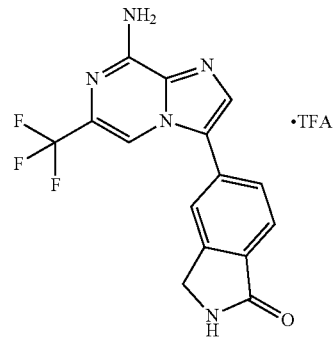 [SMILES: Nc1nc(C(F)(F)F)cn2c(-c3ccc4c(c3)CNC4=O)cnc12]

The title compound was prepared by the method of Example 1, Step 4, starting with 3-bromo-6-(trifluoromethyl)imidazo[1,2-a]pyrazin-8-amine (Affinity Research Chemicals, Inc., ARI-0167) and 5-(4,4,5,5-tetramethyl-1,3,2-dioxaborolan-2-yl)isoindolin-1-one (J&W PharmLab, 32R0096P). The product was purified by preparative HPLC-MS (pH=2) to afford the title compound. LCMS for $C_{15}H_{11}F_3N_5O$ (M+H)$^+$: calculated m/z=334.1. found 334.0. $^1$H NMR (400 MHz, DMSO-d$_6$) δ 8.67 (s, 1H), 8.15 (s, 1H), 7.92 (s, 1H), 7.91 (s, 1H), 7.85 (d, J=7.9 Hz, 1H), 7.78 (dd, J=7.9, 1.5 Hz, 1H), 7.66 (br s, 2H), 4.48 (s, 2H).

Example 5. (S)-5-(8-Amino-6-(trifluoromethyl)imidazo[1,2-a]pyrazin-3-yl)-2-(1-cyclopropylethyl)isoindolin-1-one

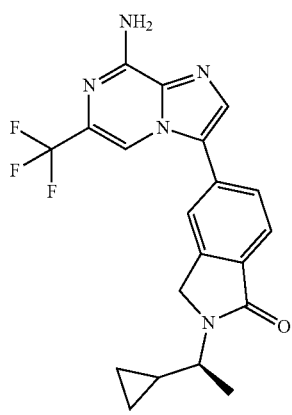 [SMILES: C[C@@H](C1CC1)N1Cc2cc(-c3cnc4c(N)nc(C(F)(F)F)cn34)ccc2C1=O]

The title compound was prepared according to the procedure of Example 1, Steps 2-4, using methyl 4-bromo-2-(bromomethyl)benzoate (Anichem, T10359) as the starting material in Step 2. LCMS for $C_{20}H_{19}F_3N_5O$ (M+H)$^+$: calculated m/z=402.2. found 402.1. $^1$H NMR (400 MHz, DMSO-d$_6$) δ 8.17 (s, 1H), 7.94 (s, 1H), 7.92 (s, 1H), 7.84 (d, J=7.9 Hz, 1H), 7.78 (dd, J=7.9, 1.5 Hz, 1H), 7.67 (br s, 2H), 4.65 (s, 2H), 3.70-3.54 (m, 1H), 1.31 (d, J=6.8 Hz, 3H), 1.21-1.11 (m, 1H), 0.63-0.55 (m, 1H), 0.46-0.35 (m, 2H), 0.29-0.20 (m, 1H). $^{19}$F NMR (376 MHz, DMSO-d$_6$) δ −66.55 (s).

Example 6

The compound in Table 1 was prepared by the method of Example 1, Steps 2-4, using methyl 4-bromo-2-(bromomethyl)benzoate (Anichem, T10359) as starting material in Step 2 and 7-bromoimidazo[2,1-f][1,2,4]triazin-4-amine (Affinity Research Chemicals, Inc., AP-3811) instead of 3-bromo-6-(trifluoromethyl)imidazo[1,2-a]pyrazin-8-amine in Step 4.

TABLE 1

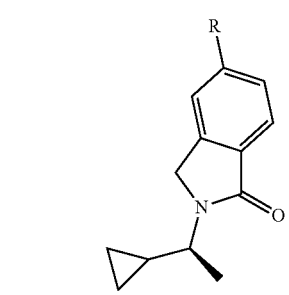

| Ex. No. | Name | R | LCMS [M + H]$^+$ | NMR Spectra |
|---|---|---|---|---|
| 6 | (S)-5-(4-Aminoimidazo[2,1-f][1,2,4]triazin-7-yl)-2-(1-cyclopropylethyl)isoindolin-1-one | | 335.1 | $^1$H NMR (400 MHz, DMSO-d$_6$) δ 8.43 (s, 1H), 8.29 (br s, 2H), 8.25 (d, J = 7.7 Hz, 1H), 8.22 (s, 1H), 8.18 (s, 1H), 7.78 (d, J = 8.0 Hz, 1H), 4.64 (s, 2H), 3.67-3.49 (m, 1H), 1.31 (d, J = 6.8 Hz, 3H), 1.22-1.09 (m, 1H), 0.65-0.51 (m, 1H), 0.47-0.34 (m, 2H), 0.30-0.18 (m, 1H). |

Example 7. (S)-5-(4-Aminoimidazo[2,1-f][1,2,4]triazin-7-yl)-7-chloro-2-(1-cyclopropylethyl)isoindolin-1-one

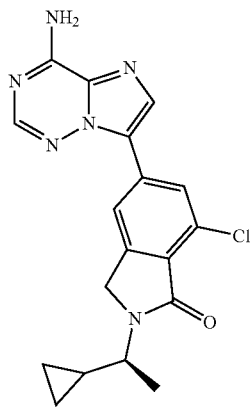 [SMILES: C[C@@H](C1CC1)N1Cc2cc(-c3cnc4c(N)ncnn34)cc(Cl)c2C1=O]

The title compound was prepared according to the procedure of Example 1, using 7-bromoimidazo[2,1-f][1,2,4]triazin-4-amine (Affinity Research Chemicals, Inc., AP-3811) instead of 3-bromo-6-(trifluoromethyl)imidazo[1,2-a]pyrazin-8-amine in Step 4. LCMS for $C_{18}H_{18}ClN_6O$ $(M+H)^+$: calculated m/z=369.1. found 369.1.

Example 8. (S)-5-(4-Aminoimidazo[2,1-f][1,2,4]triazin-7-yl)-2-(1-cyclopropylethyl)-7-(methylsulfonyl)isoindolin-1-one

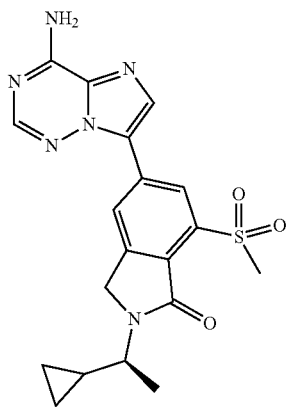 [SMILES: C[C@@H](C1CC1)N1Cc2cc(-c3cnc4c(N)ncnn34)cc(S(C)(=O)=O)c2C1=O]

(S)-5-(4-Aminoimidazo[2,1-f][1,2,4]triazin-7-yl)-7-chloro-2-(1-cyclopropylethyl)isoindolin-1-one (0.10 g, 0.27 mmol, prepared as in Example 7) was treated with sodium methanethiolate (0.076 g, 1.1 mmol) in DMF (1.8 mL) according to the procedure of Example 2 to provide (S)-5-(4-aminoimidazo[2,1-f][1,2,4]triazin-7-yl)-2-(1-cyclopropylethyl)-7-(methylthio)isoindolin-1-one. The crude product, (S)-5-(4-aminoimidazo[2,1-f][1,2,4]triazin-7-yl)-2-(1-cyclopropylethyl)-7-(methylthio)isoindolin-1-one, was treated with m-CPBA (0.054 g, 0.24 mmol) in DCM (1.1 mL) according to the procedure of Example 3, to afford the title compound (2.0 mg, 7%). LCMS for $C_{19}H_{21}N_6O_3S$ $(M+H)^+$: calculated m/z=413.1. found 413.1. $^1$H NMR (400 MHz, DMSO-$d_6$) δ 8.88 (s, 1H), 8.70 (s, 1H), 8.41 (br s, 1H), 8.35 (br s, 1H), 8.29 (s, 1H), 8.27 (s, 1H), 4.75 (s, 2H), 3.67-3.61 (m, 1H), 3.65 (s, 3H), 1.33 (d, J=6.8 Hz, 3H), 1.21-1.12 (m, 1H), 0.65-0.53 (m, 1H), 0.52-0.35 (m, 2H), 0.32-0.24 (m, 1H).

Example 9. 5-(8-Amino-6-(trifluoromethyl)imidazo[1,2-a]pyrazin-3-yl)-2-ethylisoindolin-1-one trifluoroacetate salt

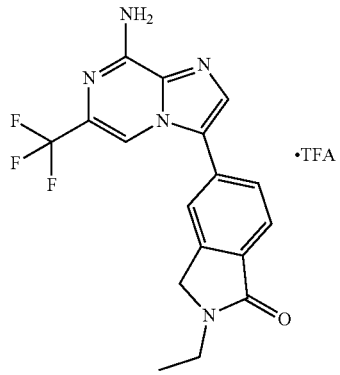 [SMILES: CCN1Cc2cc(-c3cnc4c(N)nc(C(F)(F)F)cn34)ccc2C1=O]

Step 1. 2-Ethyl-5-(4,4,5,5-tetramethyl-1,3,2-dioxaborolan-2-yl)isoindolin-1-one

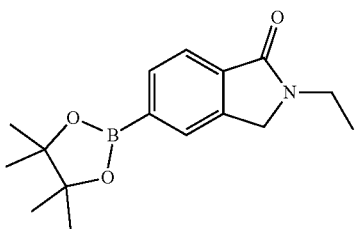 [SMILES: CCN1Cc2cc(B3OC(C)(C)C(C)(C)O3)ccc2C1=O]

To a solution of 5-(4,4,5,5-tetramethyl-1,3,2-dioxaborolan-2-yl)isoindolin-1-one (0.20 g, 0.77 mmol, J&W PharmLab, 32R0096P) in DMF (5.0 mL) at 0° C. was added sodium hydride (60% in mineral oil, 62 mg, 1.5 mmol). After stirring at room temperature for 30 minutes, the reaction mixture was once again cooled to 0° C. Iodoethane (0.12 mL, 1.5 mmol) was added, and the reaction mixture was warmed to room temperature and then was heated at 60° C. overnight. Additional iodoethane (0.062 mL, 0.77 mmol) was added, and heating was continued for 2 hours at 65° C. Upon cooling to room temperature, the reaction mixture was quenched with water. Brine was added, and the resulting mixture was extracted with EtOAc. The organic layer was washed twice with brine, dried over $Na_2SO_4$, filtered, and concentrated. The product was used without further purification in Step 2.

Step 2. 5-(8-Amino-6-(trifluoromethyl)imidazo[1,2-a]pyrazin-3-yl)-2-ethylisoindolin-1-one trifluoroacetate salt A degassed mixture of 2-ethyl-5-(4,4,5,5-tetramethyl-1,3,2-dioxaborolan-2-yl)isoindolin-1-one (35 mg, 0.061 mmol), 3-bromo-6-(trifluoromethyl)imidazo[1,2-a]pyrazin-8-amine (34 mg, 0.12 mmol, Affinity Research Chemicals, Inc., ARI-0167) and dichloro[1,1'-bis(diphenylphosphino)ferrocene]palladium(II) dichloromethane adduct (15 mg, 0.018 mmol) in THF (0.60 mL) and 1.0 M $K_2CO_3$ solution (0.24 mL, 0.24 mmol) was heated in the microwave at 120° C. for 30 minutes. Upon cooling to room temperature, the reaction mixture was diluted with acetonitrile, filtered, and then purified by preparative HPLC-MS (pH=2) to afford the title compound (5.2 mg, 21%). LCMS for $C_{17}H_{15}F_3N_5O$ (M+H)$^+$: calculated m/z=362.1. found 362.1. $^1$H NMR (400 MHz, DMSO-$d_6$) δ 8.14 (s, 1H), 7.93 (s, 2H), 7.84 (d, J=7.8 Hz, 1H), 7.78 (d, J=7.9 Hz, 1H), 7.67 (br s, 2H), 4.58 (s, 2H), 3.59 (q, J=7.2 Hz, 2H), 1.20 (t, J=7.2 Hz, 3H). $^{19}$F NMR (376 MHz, DMSO-$d_6$) δ −66.59 (s), −74.51 (s).

Example 10

The compound in Table 2 was prepared by the method of Example 9, using 7-bromoimidazo[2,1-f][1,2,4]triazin-4-amine (Affinity Research Chemicals, Inc., AP-3811) instead of 3-bromo-6-(trifluoromethyl)imidazo[1,2-a]pyrazin-8-amine in Step 2.

TABLE 2

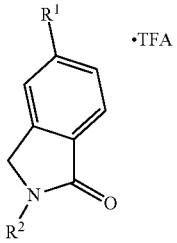

| Ex. No. | Name | R$^1$ | R$^2$ | LCMS [M + H]$^+$ | NMR Spectra |
|---|---|---|---|---|---|
| 10 | 5-(4-Aminoimidazo[2,1-f][1,2,4]triazin-7-yl)-2-ethylisoindolin-1-one trifluoroacetate salt |  | (ethyl) | 295.2 | $^1$H NMR (400 MHz, DMSO-$d_6$) δ 8.41 (s, 1H), 8.32 (br s, 1H), 8.27 (br s, 1H), 8.25 (dd, J = 8.0, 1.3 Hz, 1H), 8.22 (s, 1H), 8.18 (s, 1H), 7.78 (d, J = 8.0 Hz, 1H), 4.57 (s, 2H), 3.57 (q, J = 7.2 Hz, 2H), 1.20 (t, J = 7.2 Hz, 3H). |

Example 11. 5-(8-Amino-6-(trifluoromethyl)imidazo[1,2-a]pyrazin-3-yl)-2-(1-phenylethyl)isoindolin-1-one 1.4× trifluoroacetate salt (racemic mixture prepared)

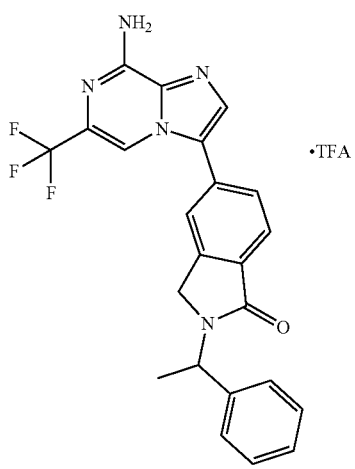 [SMILES: CC(c1ccccc1)N1Cc2cc(-c3cnc4c(N)nc(C(F)(F)F)cn34)ccc2C1=O]

Step 1. 5-Bromo-2-(1-phenylethyl)isoindolin-1-one (racemic mixture prepared)

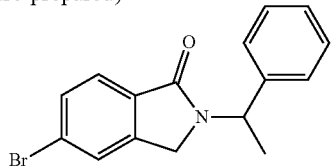

A solution of 5-bromoisoindolin-1-one (0.300 g, 1.42 mmol, Ark Pharm, AK-29385) in DMF (2.5 mL) was treated with (1-bromoethyl)benzene (314 mg, 1.70 mmol, Aldrich, 238104) and $Cs_2CO_3$ (1.38 g, 4.24 mmol). The reaction mixture was heated at 60° C. overnight. Upon cooling to room temperature, water was added, and the mixture was extracted with EtOAc. The organic layer was washed with water (2×) and brine (1×), dried over $Na_2SO_4$, filtered, and concentrated. The product was purified via flash chromatography, eluting with a gradient of 0-30% EtOAc in hexanes, to afford the title compound as a yellow solid (0.13 g, 30%). LCMS for $C_{16}H_{15}BrNO$ (M+H)$^+$: calculated m/z=316.0. found 316.0.

Step 2. 2-(1-Phenylethyl)-5-(4,4,5,5-tetramethyl-1,3,2-dioxaborolan-2-yl)isoindolin-1-one (racemic mixture prepared)

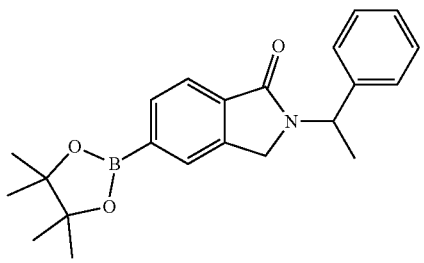 [SMILES: CC(c1ccccc1)N1Cc2cc(B3OC(C)(C)C(C)(C)O3)ccc2C1=O]

A mixture of 5-bromo-2-(1-phenylethyl)isoindolin-1-one (0.133 g, 0.421 mmol), bis(pinacolato)diboron (0.160 g, 0.631 mmol), potassium acetate (0.248 g, 2.52 mmol) and dichloro[1,1'-bis(diphenylphosphino)ferrocene]palladium (II) dichloromethane adduct (0.021 g, 0.025 mmol) in dioxane (2.1 mL) was degassed by sparging with $N_2$. The reaction mixture was heated at 80° C. overnight. Upon cooling to room temperature, the mixture was diluted with EtOAc and filtered over Celite®. The filtrate was concentrated in vacuo. The residue was purified via flash chromatography, eluting with a gradient from 0-30% EtOAc in hexanes, to afford the title compound as a yellow solid (0.11 g, 71%). LCMS for $C_{22}H_{27}BNO_3$ (M+H)$^+$: calculated m/z=364.2. found 364.2.

Step 3. 5-(8-Amino-6-(trifluoromethyl)imidazo[1,2-a]pyrazin-3-yl)-2-(1-phenylethyl)isoindolin-1-one 1.4× trifluoroacetate salt (racemic mixture prepared)

A microwave vial was charged with 2-(1-phenylethyl)-5-(4,4,5,5-tetramethyl-1,3,2-dioxaborolan-2-yl)isoindolin-1-one (0.010 g, 0.028 mmol), 3-bromo-6-(trifluoromethyl)imidazo[1,2-a]pyrazin-8-amine (Affinity Research Chemicals, Inc., ARI-0167, 9.3 mg, 0.033 mmol), and THF (275 µL), and 1.0 M $K_2CO_3$ (110 µL, 0.110 mmol) were added. The reaction mixture was degassed by sparging with $N_2$, and then dichloro[1,1'-bis(diphenylphosphino)ferrocene]palladium(II) dichloromethane adduct (4.5 mg, 5.5 µmol) was introduced. The mixture was again degassed and heated in the microwave at 120° C. for 35 minutes. Upon cooling to room temperature, the mixture was diluted with MeCN and MeOH and filtered. The product was purified via preparative HPLC-MS (pH=2) to afford the title compound (1.4×TFA salt, 11 mg, 66%). LCMS for $C_{23}H_{19}F_3N_5O$ (M+H)$^+$: calculated m/z=438.2. found 438.1. $^1$H NMR (400 MHz, DMSO-d$_6$) δ 8.16 (s, 1H), 7.91 (s, 1H), 7.90-7.84 (m, 2H), 7.79 (d, J=7.9 Hz, 1H), 7.75-7.51 (br, 2H), 7.43-7.34 (m, 4H), 7.34-7.24 (m, 1H), 5.58 (q, J=7.1 Hz, 1H), 4.64 (d, J=17.9 Hz, 1H), 4.21 (d, J=17.9 Hz, 1H), 1.68 (d, J=7.2 Hz, 3H). $^{19}$F NMR (376 MHz, DMSO-d$_6$) δ −66.55 (s), −74.63 (s).

Examples 12-14

The compounds in Table 3 were prepared by the method of Example 11, using (1-bromoethyl)benzene or the appropriate alkylating agent instead of (1-bromoethyl)benzene in Step 1, and using the appropriate bromide coupling partner in Step 3.

TABLE 3

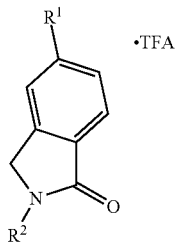

| Ex. No. | Name | R$^1$ | R$^2$ | LCMS [M +H]$^+$ | NMR Spectra |
|---|---|---|---|---|---|
| 12 | 5-(4-Aminoimidazo[2,1-f][1,2,4]triazin-7-yl)-2-(1-phenylethyl)isoindolin-1-one, trifluoroacetate salt (racemic mixture prepared) | 4-aminoimidazo[2,1-f][1,2,4]triazin-7-yl | 1-phenylethyl | 371.1 | $^1$H NMR (400 MHz, DMSO-d$_6$) δ 8.33 (br, 3H), 8.26 (d, J = 8.1 Hz, 1H), 8.21 (s, 1H), 8.16 (s, 1H), 7.82 (d, J = 8.0 Hz, 1H), 7.41-7.33 (m, 4H), 7.33-7.23 (m, 1H), 5.55 (q, J = 7.1 Hz, 1H), 4.65 (d, J = 17.8 Hz, 1H), 4.21 (d, J = 17.8 Hz, 1H), 1.67 (d, J = 7.2 Hz, 3H). |

TABLE 3-continued

| Ex. No. | Name | R¹ | R² | LCMS [M+H]⁺ | NMR Spectra |
|---|---|---|---|---|---|
| 13 | 5-(8-Amino-6-(trifluoromethyl)imidazo[1,2-a]pyrazin-3-yl)-2-isopropylisoindolin-1-one trifluoroacetate salt | (8-amino-6-(trifluoromethyl)imidazo[1,2-a]pyrazin-3-yl) | isopropyl | 376.1 | $^1$H NMR (400 MHz, DMSO-$d_6$) δ 8.15 (s, 1H), 7.93 (s, 2H), 7.84 (d, J = 7.8 Hz, 1H), 7.78 (dd, J = 7.8, 1.5 Hz, 1H), 7.66 (br s, 2H), 4.54 (s, 2H), 4.52-4.42 (m, 1H), 1.27 (d, J = 6.8 Hz, 6H). $^{19}$F NMR (376 MHz, DMSO-$d_6$) δ -66.58 (s), -74.89 (s). |
| 14 | 5-(4-Aminoimidazo[2,1-f][1,2,4]triazin-7-yl)-2-isopropylisoindolin-1-one trifluoroacetate salt | (4-aminoimidazo[2,1-f][1,2,4]triazin-7-yl) | isopropyl | 309.1 | $^1$H NMR (400 MHz, DMSO-$d_6$) δ 8.42 (s, 1H), 8.37 (br s, 1H), 8.31 (br s, 1H), 8.25 (dd, J = 8.1, 1.4 Hz, 1H), 8.23 (s, 1H), 8.18 (s, 1H), 7.78 (d, J = 8.0 Hz, 1H), 4.53 (s, 2H), 4.44 (h, J = 6.7 Hz, 1H), 1.26 (d, J = 6.8 Hz, 6H). |

Example 15. (S)-7-Acetyl-5-(4-aminoimidazo[2,1-f][1,2,4]triazin-7-yl)-2-(1-cyclopropylethyl)isoindolin-1-one trifluoroacetate salt

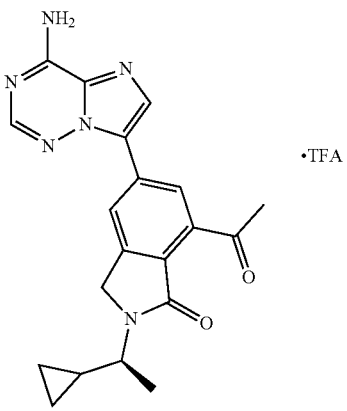 [SMILES: CC(=O)c1cc(-c2cnc3c(N)ncnn23)cc2c1C(=O)N([C@@H](C)C1CC1)C2]

A mixture of (S)-5-(4-aminoimidazo[2,1-f][1,2,4]triazin-7-yl)-7-chloro-2-(1-cyclopropylethyl)isoindolin-1-one (494 mg, 1.34 mmol, prepared as described in Example 7), tributyl(1-ethoxyvinyl)stannane (726 mg, 2.01 mmol), Pd$_2$(dba)$_3$ (307 mg, 0.335 mmol), 2-dicyclohexylphosphino-2',4',6'-triisopropylbiphenyl (XPhos, 160 mg, 0.34 mmol), copper(I) iodide (51.0 mg, 0.268 mmol), and cesium fluoride (407 mg, 2.68 mmol) in dioxane (15 mL) was degassed with a stream of nitrogen bubbled subsurface for 2 minutes. The reaction vial was sealed and heated in an oil bath held at 120° C. for 2.5 hours. Upon cooling, the reaction mixture was filtered over Celite©, and the Celite© was washed with 1:1 THF/MeOH (20 mL). To the filtrate was added 1.0 N HCl (20 mL), and the reaction mixture was stirred for 1 hour. The mixture was concentrated via rotary evaporation remove organic solvents, and the aqueous mixture was partitioned between MTBE and water. The aqueous layer was then separated. The precipitate-containing organic layer was stirred with 0.5 N HCl for 10 minutes, and the resulting aqueous layer was separated. Both separated aqueous layers were combined and filtered to remove insolubles. The aqueous filtrate was treated with solid NaHCO$_3$ to neutralize, then solid NaCl was added to saturate, and the aqueous solution was extracted with DCM (4×). The combined DCM extracts were dried over Na$_2$SO$_4$, filtered, and concentrated to give the title compound as a yellow solid (240 mg, 44%). A portion of the product was purified via preparative HPLC-MS (pH=2) to afford the title compound as the trifluoroacetate salt. LCMS for C$_{20}$H$_{21}$N$_6$O$_2$ (M+H)⁺: calculated m/z=377.2. found 377.1. $^1$H NMR (400 MHz, DMSO-$d_6$) δ 8.55 (d, J=1.5 Hz, 1H), 8.37 (br s, 1H), 8.32 (br s, 1H), 8.26 (s, 1H), 8.25 (s, 1H), 8.18 (d, J=1.5 Hz, 1H), 4.70 (s, 2H), 3.65-3.55 (m, 1H), 2.71 (s, 3H), 1.32 (d, J=6.8 Hz, 3H), 1.21-1.01 (m, 1H), 0.68-0.50 (m, 1H), 0.50-0.36 (m, 2H), 0.36-0.13 (m, 1H).

Example 16. 5-(4-Aminoimidazo[2,1-f][1,2,4]triazin-7-yl)-2-((S)-1-cyclopropylethyl)-7-(1-hydroxyethyl)isoindolin-1-one trifluoroacetate salt (mixture of two diastereomers prepared)

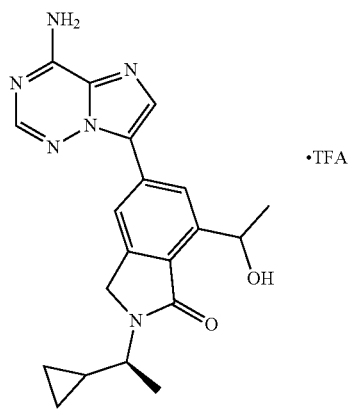 [SMILES: CC(O)c1cc(-c2cnc3c(N)ncnn23)cc2c1C(=O)N([C@@H](C)C1CC1)C2]

To a mixture of (S)-7-acetyl-5-(4-aminoimidazo[2,1-f][1,2,4]triazin-7-yl)-2-(1-cyclopropylethyl)isoindolin-1-one (8.0 mg, 0.021 mmol, from Example 15) in ethanol (0.4 mL) was added sodium borohydride (1.2 mg, 0.032 mmol). MeOH (0.2 mL) was added to give a clear solution. Additional portions of NaBH$_4$ (1.0 mg) were added four times over the course of 1 hour. After stirring overnight, the mixture was quenched with 1.0 N HCl, diluted with MeCN and MeOH, filtered and purified via preparative HPLC-MS (pH=2) to afford the title compound (2.5 mg). LCMS for C$_{20}$H$_{23}$N$_6$O$_2$ (M+H)$^+$: calculated m/z=379.2. found 379.2. $^1$H NMR (400 MHz, DMSO-d$_6$, mixture of diastereomers) δ 8.33 (br s, 1H), 8.30 (s, 1H), 8.27 (br s, 1H), 8.26-8.24 (m, 1H), 8.23 (s, 1H), 8.15 (s, 1H), 5.61-5.52 (m, 1H), 4.65 (s, 2H), 3.65-3.57 (m, 1H), 1.42 (d, J=6.5 Hz, 1.5H), 1.41 (d, J=6.5 Hz, 1.5H), 1.31 (d, J=6.9 Hz, 1.5H), 1.30 (d, J=6.9 Hz, 1.5H), 1.21-1.09 (m, 1H), 0.65-0.52 (m, 1H), 0.48-0.33 (m, 2H), 0.33-0.20 (m, 1H).

Example 17. (S)-5-(4-Aminoimidazo[2,1-f][1,2,4]triazin-7-yl)-2-(1-cyclopropylethyl)-7-(2-hydroxypropan-2-yl)isoindolin-1-one trifluoroacetate salt

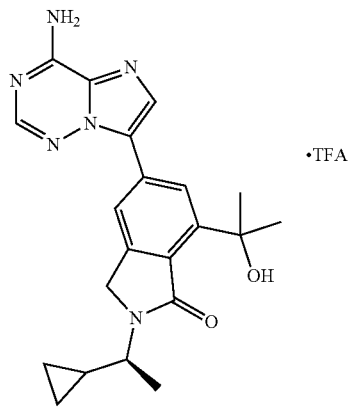 [SMILES: C[C@@H](C1CC1)N1Cc2cc(-c3cnc4c(N)ncnn34)cc(C(C)(C)O)c2C1=O]

To a mixture of (S)-7-acetyl-5-(4-aminoimidazo[2,1-f][1,2,4]triazin-7-yl)-2-(1-cyclopropylethyl)isoindolin-1-one (10. mg, 0.027 mmol, from Example 15) in THF (0.5 mL) was added methylmagnesium bromide (3.0 M in ether, 71 μl, 0.21 mmol) at room temperature. After stirring for 2 hours, the mixture was cooled in an ice bath, quenched by the addition of 0.5 N HCl, diluted with MeCN and MeOH, filtered and purified via preparative HPLC-MS (pH=2) to afford the title compound (2.6 mg). LCMS for C$_{21}$H$_{25}$N$_6$O$_2$ (M+H)$^+$: calculated m/z=393.2. found 393.2. $^1$H NMR (400 MHz, DMSO-d$_6$) δ 8.38-8.34 (m, 2H), 8.29 (br s, 1H), 8.24 (s, 1H), 8.24 (s, 1H), 8.14 (d, J=1.5 Hz, 1H), 4.73 (s, 2H), 3.71-3.58 (m, 1H), 1.61 (s, 3H), 1.60 (s, 3H), 1.34 (d, J=6.8 Hz, 3H), 1.25-1.10 (m, 1H), 0.68-0.54 (m, 1H), 0.50-0.36 (m, 2H), 0.36-0.22 (m, 1H).

Examples 18-19. 7-(2-(1-Cyclopropylethyl)-7-methyl-2H-indazol-5-yl)imidazo[2,1-f][1,2,4]triazin-4-amine trifluoroacetate salt (racemic mixture) & 7-(1-(1-Cyclopropylethyl)-7-methyl-1H-indazol-5-yl)imidazo[2,1-f][1,2,4]triazin-4-amine trifluoroacetate salt (racemic mixture)

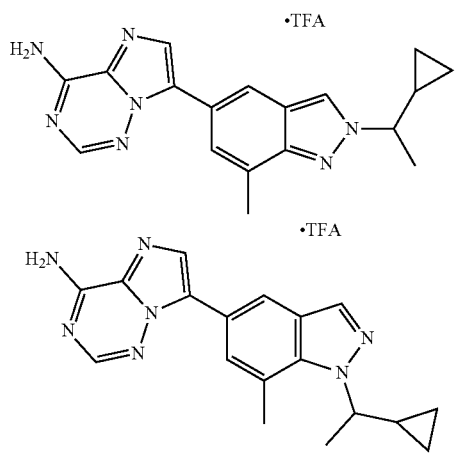

Step 1. 5-Bromo-2-(1-cyclopropylethyl)-7-methyl-2H-indazole & 5-Bromo-1-(1-cyclopropylethyl)-7-methyl-1H-indazole

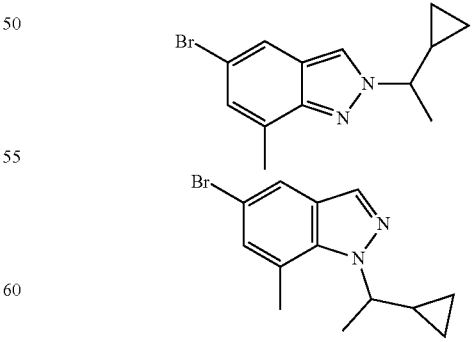

To a solution of 5-bromo-7-methyl-1H-indazole (50 mg, 0.24 mmol, Ark Pharm) in THF (1.5 ml) was added 1-cyclopropylethan-1-ol (34 μl, 0.36 mmol), triphenylphosphine (93 mg, 0.36 mmol) and DEAD (0.14 ml, 0.36 mmol)

sequentially, and the reaction mixture was stirred at room temperature for 1 h. More triphenylphosphine (93 mg, 0.36 mmol) and DEAD (0.14 mL, 0.36 mmol) were added, and the reaction mixture was stirred for an additional 1 h. The reaction mixture was concentrated and purified by flash chromatography (0-30% EtOAc/hexanes) to afford the title compounds (51 mg, 77%), which were carried forward as ~1:1 mixture.

LCMS peak 1: LCMS for $C_{13}H_{16}BrN_2$ (M+H)$^+$: m/z=279.0. Found: 279.0.

LCMS peak 2: LCMS for $C_{13}H_{16}BrN_2$ (M+H)$^+$: m/z=279.0. Found: 279.0.

Step 2. 2-(1-Cyclopropylethyl)-7-methyl-5-(4,4,5,5-tetramethyl-1,3,2-dioxaborolan-2-yl)-2H-indazole & 1-(1-Cyclopropylethyl)-7-methyl-5-(4,4,5,5-tetramethyl-1,3,2-dioxaborolan-2-yl)-1H-indazole

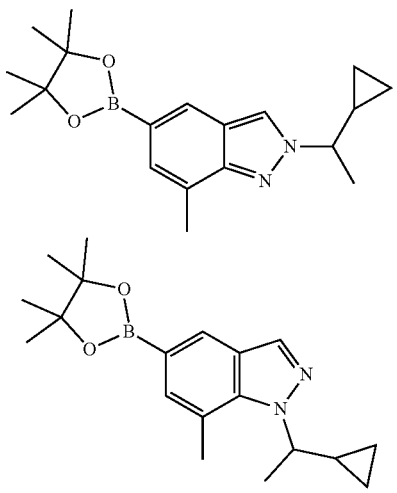

5-Bromo-2-(1-cyclopropylethyl)-7-methyl-2H-indazole and 5-bromo-1-(1-cyclopropylethyl)-7-methyl-1H-indazole (50 mg, 0.18 mmol, ~1:1 mixture) were combined with bis(pinacolato)diboron (68.2 mg, 0.27 mmol), dichloro[1,1'-bis(diphenylphosphino)ferrocene]palladium (II) dichloromethane adduct (8.8 mg, 0.01 mmol) and potassium acetate (52.7 mg, 0.54 mmol) in dioxane (2 ml) and the mixture was sparged with N$_2$. The reaction mixture was heated to 90° C. overnight. The reaction mixture was worked up by the addition of water and extraction with EtOAc. The combined organic extracts were dried over MgSO$_4$, filtered, and concentrated. Flash chromatography, eluting with a gradient from 0-100% EtOAc/hexanes afforded the title compounds, which were carried forward as ~1:1 mixture. Quantitative yield assumed.

LCMS peak 1: LCMS for $C_{19}H_{28}BN_2O_2$ (M+H)$^+$: m/z=327.2. Found: 327.2.

LCMS peak 2: LCMS for $C_{19}H_{28}BN_2O_2$ (M+H)$^+$: m/z=327.2. Found: 327.2.

Step 3. 7-(2-(1-Cyclopropylethyl)-7-methyl-2H-indazol-5-yl)imidazo[2,1-f][1,2,4]triazin-4-amine, trifluoroacetate & 7-(1-(1-Cyclopropylethyl)-7-methyl-1H-indazol-5-yl)imidazo[2,1-f][1,2,4]triazin-4-amine, trifluoroacetate A mixture of 7-bromoimidazo[2,1-f][1,2,4]triazin-4-amine (22.0 mg, 0.10 mmol), 2-(1-cyclopropylethyl)-7-methyl-5-(4,4,5,5-tetramethyl-1,3,2-dioxaborolan-2-yl)-2H-indazole, 1-(1-cyclopropylethyl)-7-methyl-5-(4,4,5,5-tetramethyl-1,3,2-dioxaborolan-2-yl)-1H-indazole (28 mg, 0.09 mmol, ~1:1 mixture), (1,1'-bis(diphenylphosphino)ferrocene)-dichloropalladium(II) dichloromethane adduct (3.1 mg, 4.3 µmol), and sodium carbonate (27.3 mg, 0.26 mmol) in dioxane (2 mL) and water (0.5 mL) was sparged with N$_2$ and heated to 100° C. overnight. The reaction mixture was cooled to room temperature, diluted with MeOH, and purified by prep HPLC (pH 2). Peak 2 was determined to be the N1 isomer by NMR.

LCMS peak 1 (N2 isomer; Example 18): LCMS for $C_{18}H_{20}N_7$ (M+H)$^+$: m/z=334.2. Found: 334.2.

LCMS peak 2 (N1 isomer; Example 19): LCMS for $C_{18}H_{20}N_7$ (M+H)$^+$: m/z=334.2. Found: 334.2. $^1$H NMR (600 MHz, DMSO) δ 8.49 (s, 1H), 8.28 (s, 1H), 8.21 (d, J=3.1 Hz, 2H), 8.05 (s, 1H), 7.76 (s, 1H), 4.44 (p, J=6.6 Hz, 1H), 2.70 (s, 3H), 1.60 (d, J=6.6 Hz, 3H), 1.56-1.50 (m, 1H), 0.62-0.58 (m, 1H), 0.41-0.31 (m, 2H), 0.30-0.23 (m, 1H).

Example 20. 7-(2-(1-cyclopropylethyl)-2H-benzo[d][1,2,3]triazol-5-yl)imidazo[2,1-f][1,2,4]triazin-4-amine trifluoroacetate salt (racemic mixture)

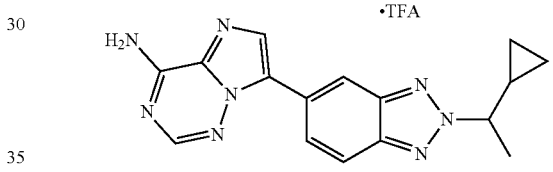

This compound was synthesized according to the procedure described for Examples 18-19, employing 6-bromo-1H-benzo[d][1,2,3]triazole instead of 5-bromo-7-methyl-1H-indazole in Step 1. LCMS for $C_{16}H_{17}N_8$ (M+H)$^+$: m/z=321.1. Found: 321.1. $^1$H NMR (600 MHz, DMSO) δ 8.85 (s, 1H), 8.36 (s, 1H), 8.29 (s, 1H), 8.24 (s, 1H), 8.20 (s, 1H), 8.11 (dd, J=8.8, 1.5 Hz, 1H), 8.05 (d, J=9.0 Hz, 1H), 4.36 (dq, J=9.2, 6.8 Hz, 1H), 1.75 (d, J=6.9 Hz, 3H), 1.52-1.44 (m, 1H), 0.68 (tdd, J=8.6, 5.9, 4.3 Hz, 1H), 0.53 (dq, J=9.7, 5.0 Hz, 1H), 0.47 (dt, J=10.0, 5.0 Hz, 1H), 0.42 (dt, J=9.8, 4.9 Hz, 1H).

Example 21. 7-(2-Isopropyl-[1,2,4]triazolo[1,5-a]pyridin-6-yl)imidazo[2,1-f][1,2,4]triazin-4-amine trifluoroacetate salt

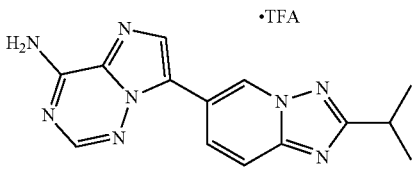 [SMILES: CC(C)c1nc2ccc(-c3cnc4c(N)ncnn34)cn2n1]

Step 1. 1,2-Diamino-5-bromopyridin-1-ium 2,4-dinitrophenolate

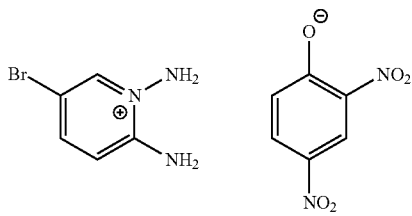 [SMILES: Nc1ccc(Br)c[n+]1N ; O=[N+]([O-])c1ccc([O-])c([N+](=O)[O-])c1]

To a solution of 5-bromopyridin-2-amine (200 mg, 1.16 mmol) in acetonitrile (3 ml) was added O-(2,4-dinitrophenyl)hydroxylamine (230 mg, 1.16 mmol) and the reaction mixture was stirred at 40° C. overnight. Diethyl ether was added and the resulting precipitate was filtered, washed with ether, and air dried to afford the title compound (310 mg, 72%). LCMS for $C_5H_7BrN_3$ (M+)$^+$: m/z=188.0. Found: 188.0.

Step 2. 6-Bromo-2-isopropyl-[1,2,4]triazolo[1,5-a]pyridine

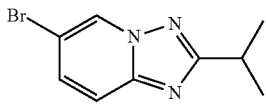

To a suspension of 1,2-diamino-5-bromopyridin-1-ium 2,4-dinitrophenolate (100 mg, 0.27 mmol) in EtOH (3 ml) was added isobutyraldehyde (74 µl, 0.81 mmol) and DBU (0.12 ml, 0.81 mmol). The resulting dark red solution was stirred at room temperature for 2 h. The reaction mixture was diluted with EtOAc and washed with water. The layers were separated and the aqueous layer was extracted with EtOAc. The combined organic layers were washed with brine, dried over $MgSO_4$, filtered and concentrated. The residue was purified by flash chromatography (0-50% EtOAc/hexanes) to afford the title compound (41 mg, 63%). LCMS for $C_9H_{11}BrN_3$ (M+H)$^+$: m/z=240.0. Found: 240.0.

Step 3. 2-Isopropyl-6-(4,4,5,5-tetramethyl-1,3,2-dioxaborolan-2-yl)-[1,2,4]triazolo[1,5-a]pyridine

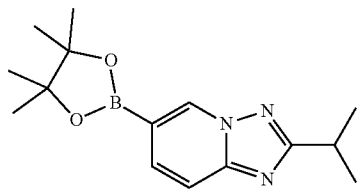 [SMILES: CC(C)c1nc2ccc(B3OC(C)(C)C(C)(C)O3)cn2n1]

6-Bromo-2-isopropyl-[1,2,4]triazolo[1,5-a]pyridine (40.7 mg, 0.17 mmol) was combined with bis(pinacolato)diboron (64.6 mg, 0.25 mmol), dichloro[1,1'-bis(diphenylphosphino)ferrocene]palladium (II) dichloromethane adduct (8.3 mg, 10 µmol) and potassium acetate (49.9 mg, 0.51 mmol) in dioxane (3 mL) and the mixture was sparged with $N_2$. The reaction was heated to 90° C. overnight. The reaction mixture was worked up by the addition of water and extraction with EtOAc. The combined organic extracts were washed with brine, dried over $MgSO_4$, filtered, and concentrated. Flash chromatography, eluting with a gradient from 0-100% EtOAc/hexanes afforded the title compound (33 mg, 68%). LCMS for $C_{15}H_{23}BN_3O_2$ (M+H)$^+$: m/z=288.2. Found: 288.1. (The product was also mainly detected as the corresponding boronic acid by LCMS: $C_9H_{13}BN_3O_2$ (M+H)$^+$: m/z=206.1. Found: 206.1.)

Step 4. 7-(2-isopropyl-[1,2,4]triazolo[1,5-a]pyridin-6-yl)imidazo[2,1-f][1,2,4]triazin-4-amine, trifluoroacetate A mixture of 7-bromoimidazo[2,1-f][1,2,4]triazin-4-amine (24.6 mg, 0.12 mmol), 2-isopropyl-6-(4,4,5,5-tetramethyl-1,3,2-dioxaborolan-2-yl)-[1,2,4]triazolo[1,5-a]pyridine (33 mg, 0.12 mmol), (1,1'-bis(diphenylphosphino)ferrocene)-dichloropalladium(II) dichloromethane adduct (4.2 mg, 5.8 µmol), and sodium carbonate (36.5 mg, 0.35 mmol) in dioxane (2 mL) and water (0.5 ml) was sparged with $N_2$ and heated to 100° C. for 4 h. The reaction mixture was diluted with MeOH, filtered, and purified by prep HPLC (pH 2). LCMS for $C_{14}H_{15}N_8$ (M+H)$^+$: m/z=295.1. Found: 295.1.

Example 22. 7-(2-isopropylimidazo[1,2-a]pyridin-6-yl)imidazo[2,1-f][1,2,4]triazin-4-amine

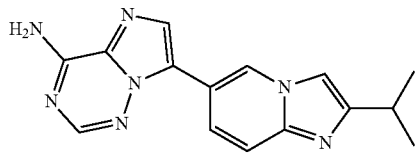 [SMILES: CC(C)c1cn2cc(-c3cnc4c(N)ncnn34)ccc2n1]

Step 1. 6-bromo-2-isopropylimidazo[1,2-a]pyridine

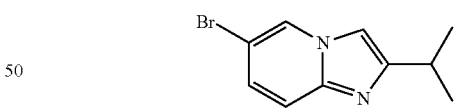

To a solution of 5-bromopyridin-2-amine (150 mg, 0.87 mmol) in EtOH (4 mL) was added 1-bromo-3-methylbutan-2-one (0.16 mL, 1.30 mmol) and sodium bicarbonate (146 mg, 1.73 mmol), and the reaction mixture was stirred at 70° C. overnight. The reaction mixture was partitioned between water and EtOAc, and the layers were separated. The aqueous layer was extracted with EtOAc and the combined extracts were washed with brine, dried over $MgSO_4$, filtered, and concentrated. The residue was purified by flash chromatography (0-100% EtOAc/hexanes) to afford the title compound (46 mg, 22%). LCMS for $C_{10}H_{12}BrN_2$ (M+H)$^+$: m/z=239.0. Found: 239.0.

181

Step 2. (2-isopropylimidazo[1,2-a]pyridin-6-yl)boronic acid

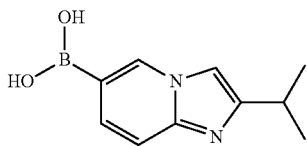

6-Bromo-2-isopropylimidazo[1,2-a]pyridine (137 mg, 0.57 mmol) was combined with bis(pinacolato)diboron (218 mg, 0.86 mmol), dichloro[1,1'-bis(diphenylphosphino)ferrocene]palladium (II) dichloromethane adduct (28.1 mg, 34 µmol) and potassium acetate (169 mg, 1.72 mmol) in dioxane (3 mL) and the mixture was sparged with $N_2$. The reaction was heated to 90° C. overnight. The reaction mixture was worked up by the addition of water and extraction with EtOAc. The combined organic extracts were dried over $MgSO_4$, filtered, and concentrated. Flash chromatography, eluting with a gradient from 0-100% EtOAc/hexanes, followed by 0-20% MeOH/DCM, afforded the title compound along with some inseparable impurities. Quantitative yield assumed. LCMS for $C_{10}H_{14}BN_2O_2$ $(M+H)^+$: m/z=205.1. Found: 205.1.

Step 3. 7-(2-isopropylimidazo[1,2-a]pyridin-6-yl)imidazo[2,1-f][1,2,4]triazin-4-amine A mixture of 7-bromoimidazo[2,1-f][1,2,4]triazin-4-amine (123 mg, 0.57 mmol), (2-isopropylimidazo[1,2-a]pyridin-6-yl)boronic acid (117 mg, 0.57 mmol), (1,1'-bis(diphenylphosphino)ferrocene)-dichloropalladium(II) dichloromethane adduct (30 mg, 29 mol), and sodium carbonate (182 mg, 1.72 mmol) in dioxane (2 mL) and water (0.5 mL) was sparged with $N_2$ and heated to 100° C. for 4 h. The reaction mixture was diluted with MeOH, filtered, and purified by prep HPLC (pH 10). LCMS for $C_{15}H_{16}N_7$ $(M+H)^+$: m/z=294.1. Found: 294.1. $^1$H NMR (600 MHz, DMSO) δ 9.38 (s, 1H), 8.32 (s, 1H), 8.26 (s, 1H), 8.22 (s, 1H), 8.10 (s, 1H), 7.86 (s, 1H), 7.77 (dd, J=9.4, 1.8 Hz, 1H), 7.59 (d, J=9.4 Hz, 1H), 3.01 (p, J=6.9 Hz, 1H), 1.30 (d, J=6.8 Hz, 6H).

Example 23. 7-(2-Isopropylpyrazolo[1,5-a]pyridin-5-yl)imidazo[2,1-f][1,2,4]triazin-4-amine trifluoroacetate salt

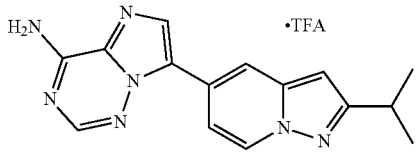 [SMILES: CC(C)c1cc2cc(-c3cnc4c(N)ncnn34)ccn2n1]

182

Step 1. 1,4-Diaminopyridin-1-ium 2,4-dinitrophenolate

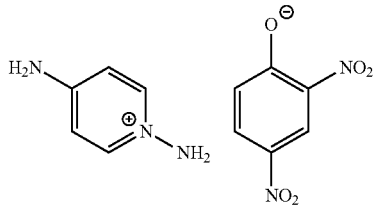 [SMILES: Nc1cc[n+](N)cc1 ; O=[N+]([O-])c1ccc([O-])c([N+](=O)[O-])c1]

To a solution of pyridin-4-amine (200 mg, 2.13 mmol) in acetonitrile (4 ml) was added O-(2,4-dinitrophenyl)hydroxylamine (423 mg, 2.13 mmol) and the reaction mixture was stirred at 40° C. overnight. Diethyl ether was added, and the resulting precipitate was filtered, washed with ether, and air dried to afford the title compound (563 mg, 90%). LCMS for $C_5H_8N_3$ $(M)^+$: m/z=110.1. Found: 110.1.

Step 2. ethyl 4-methylpent-2-ynoate

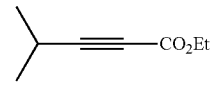

To a solution of 3-methylbut-1-yne (0.45 ml, 4.40 mmol) in THF (10 ml) at −78° C. was added n-butyllithium (2.5M/hexanes, 1.7 ml, 4.40 mmol) and the reaction mixture was stirred at −78° C. for 30 min. Ethyl chloroformate (0.42 mL, 4.40 mmol) was added and the reaction was allowed to warm to room temperature overnight. The reaction mixture was quenched with saturated $NH_4Cl$ and extracted with diethyl ether. The layers were separated and the organic layer was washed with brine, dried over $MgSO_4$, filtered and concentrated. The residue was purified by flash chromatography (0-5% EtOAc/hexanes) to afford the title compound (300 mg, 48%). $^1$H NMR (400 MHz, $CDCl_3$) δ 4.23 (q, J=7.1 Hz, 2H), 2.71 (sep, J=6.8 Hz, 1H), 1.33 (t, J=7.1 Hz, 3H), 1.25 (d, J=6.9 Hz, 6H).

Step 3. Ethyl 5-amino-2-isopropylpyrazolo[5-a]pyridine-3-carboxylate

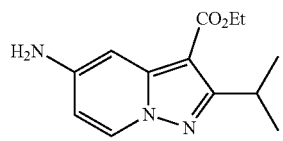 [SMILES: CCOC(=O)c1c(C(C)C)nn2ccc(N)cc12]

To a solution of 1,4-diaminopyridin-1-ium 2,4-dinitrophenolate (170 mg, 0.58 mmol) and ethyl 4-methylpent-2-ynoate (98 mg, 0.70 mmol) in DMF (5 mL) was added potassium carbonate (96 mg, 0.70 mmol) and the reaction mixture was stirred at 60° C. for 3 h. The reaction mixture was partitioned between water and EtOAc, and the layers were separated. The aqueous layer was extracted with EtOAc and the combined organic layers were washed with brine, dried over $MgSO_4$, filtered, and concentrated. The residue was purified by flash chromatography (0-100%

EtOAc/hexanes) to afford the title compound (85 mg, 59%). LCMS for $C_{13}H_{18}N_3O_2$ (M+H)+: m/z=248.1. Found: 248.2.

Step 4. Ethyl 5-bromo-2-isopropylpyrazolo[1,5-a]pyridine-3-carboxylate

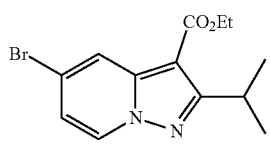 [SMILES: CCOC(=O)c1c(C(C)C)nn2ccc(Br)cc12]

To a solution of ethyl 5-amino-2-isopropylpyrazolo[1,5-a]pyridine-3-carboxylate (70 mg, 0.28 mmol) in HBr (33% in AcOH, 2.0 mL, 17.7 mmol) at 0° C. was added a solution of sodium nitrite (58.6 mg, 0.85 mmol) in water (1 mL) dropwise. The reaction mixture was stirred for 20 min at this temperature and copper(I) bromide (122 mg, 0.85 mmol) was added. The reaction mixture was warmed to room temperature and stirred for 1 h. The reaction mixture was partitioned between water and EtOAc, and the layers were separated. The aqueous layer was extracted with EtOAc and the combined organic layers were washed with brine, dried over MgSO₄, filtered, and concentrated. The residue was purified by flash chromatography (0-100% EtOAc/hexanes) to afford the title compound (50 mg, 57%). LCMS for $C_{13}H_{16}BrN_2O_2$ (M+H)+: m/z=311.0. Found: 311.0.

Step 5. 5-Bromo-2-isopropylpyrazolo[1,5-a]pyridine

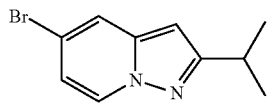

A solution of ethyl 5-bromo-2-isopropylpyrazolo[1,5-a]pyridine-3-carboxylate (46 mg, 0.15 mmol) in AcOH (2 mL) and 48% aqueous HBr (2 mL) was heated to 100° C. overnight. After cooling to room temperature, the reaction mixture was partitioned between water and EtOAc, and the layers were separated. The aqueous layer was extracted with EtOAc and the combined organic layers were washed with brine, dried over MgSO₄, filtered, and concentrated. The residue was purified by flash chromatography (0-100% EtOAc/hexanes) to afford the title compound (25 mg, 71%). LCMS for $C_{10}H_{12}BrN_2$ (M+H)+: m/z=239.0. Found: 239.0.

Step 6. 7-(4,4,5,5-Tetramethyl-1,3,2-dioxaborolan-2-yl)imidazo[2,1-f][1,2,4]triazin-4-amine

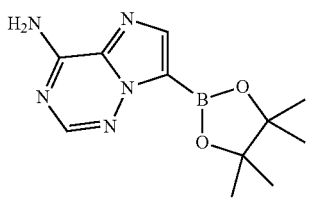 [SMILES: CC1(C)OB(c2cnc3c(N)ncnn23)OC1(C)C]

A mixture of 7-bromoimidazo[2,1-f][1,2,4]triazin-4-amine (1.0 g, 4.67 mmol), bis(pinacolato)diboron (1.42 g, 5.61 mmol), potassium acetate (1.38 g, 14.0 mmol), and dichloro[1,1'-bis(diphenylphosphino)ferrocene]palladium (II) dichloromethane adduct (153 mg, 0.19 mmol) in 1,4-dioxane (20 mL) was degassed for 5 min with N₂. The reaction mixture was heated to 100° C. for 4 h. The reaction mixture was cooled to room temperature, diluted with EtOAc (20 mL), and filtered through Celite® rinsing with EtOAc (3×40 mL). The filtrate was concentrated to afford the crude product (~1:1 along with deboronated product). This material was used without further purification. By LCMS, the product was mainly detected as the boronic acid. LCMS for $C_5H_7BN_5O_2$ (M+H)+: m/z=180.1. Found: 180.1.

Step 7. 7-(2-isopropylpyrazolo[1,5-a]pyridin-5-yl)imidazo[2,1-f][1,2,4]triazin-4-amine, trifluoroacetate A mixture of 7-(4,4,5,5-tetramethyl-1,3,2-dioxaborolan-2-yl)imidazo[2,1-f][1,2,4]triazin-4-amine (16.4 mg, 0.06 mmol), 5-bromo-2-isopropylpyrazolo[1,5-a]pyridine (10 mg, 0.04 mmol), (1,1'-bis(diphenylphosphino)ferrocene)-dichloropalladium(II) dichloromethane adduct (1.5 mg, 2.1 μmol), and sodium carbonate (13 mg, 0.13 mmol) in dioxane (2 mL) and water (0.5 ml) was sparged with N₂ and heated to 100° C. for 4 h. The reaction mixture was diluted with MeOH, filtered, and purified by prep HPLC (pH 2). LCMS for $C_{15}H_{16}N_7$ (M+H)+: m/z=294.1. Found: 294.1. ¹H NMR (500 MHz, DMSO) δ 8.67 (d, J=7.3 Hz, 1H), 8.59 (s, 1H), 8.36 (s, 1H), 8.31 (s, 1H), 8.26 (s, 1H), 8.24 (s, 1H), 7.46 (d, J=6.3 Hz, 1H), 6.55 (s, 1H), 3.11 (p, J=6.9 Hz, 1H), 1.32 (d, J=6.9 Hz, 6H).

Example 24. 7-(2-Isopropylpyrazolo[1,5-a]pyrimidin-5-yl)imidazo[2,1-f][1,2,4]triazin-4-amine trifluoroacetate salt

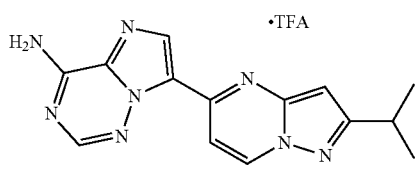 [SMILES: CC(C)c1cc2nc(-c3cnc4c(N)ncnn34)ccn2n1]

Step 1. 2-Isopropylpyrazolo[1,5-a]pyrimidin-5(4H)-one

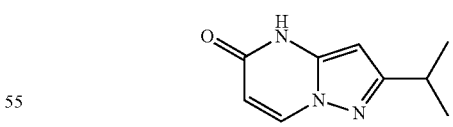

To a mixture of 5-isopropyl-1H-pyrazol-3-amine hydrochloride (150 mg, 0.93 mmol) and cesium carbonate (393 mg, 1.21 mmol) in DMF (4 mL) was added methyl (E)-3-methoxyacrylate (0.13 ml, 1.21 mmol) and the reaction mixture was stirred at 100° C. overnight. The reaction mixture was partitioned between water and EtOAc, and the layers were separated. The aqueous layer was extracted with EtOAc and the combined organic layers were washed with brine, dried over MgSO₄, filtered, and concentrated. The residue was purified by flash chromatography (0-50-100%

EtOAc/hexanes) to afford the title compound (20 mg, 12%). LCMS for $C_9H_{12}N_3O$ (M+H)$^+$: m/z=178.1. Found: 178.1.

Step 2. 5-Chloro-2-isopropylpyrazolo[1,5-a]pyrimidine

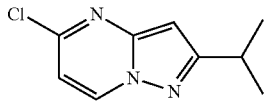

To a solution of 2-isopropylpyrazolo[1,5-a]pyrimidin-5(4H)-one (20 mg, 0.11 mmol) in MeCN (3 mL) was added POCl$_3$ (0.10 mL, 1.13 mmol) and the reaction mixture was heated to reflux for 3 h. After cooling to room temperature, the volatiles were removed in vacuo and the residue was purified by flash chromatography (0-100% EtOAc/hexanes) to afford the title compound (11 mg, 50%). LCMS for $C_9H_{11}ClN_3$ (M+H)$^+$: m/z=196.1. Found: 196.1.

Step 3. 7-(2-Isopropylpyrazolo[1,5-a]pyrimidin-5-yl)imidazo[2,1-f][1,2,4]triazin-4-amine, trifluoroacetate A mixture of 7-(4,4,5,5-tetramethyl-1,3,2-dioxaborolan-2-yl)imidazo[2,1-f][1,2,4]triazin-4-amine (15 mg, 0.06 mmol, Example 23, Step 6), 5-chloro-2-isopropylpyrazolo[1,5-a]pyrimidine (11 mg, 0.06 mmol), (1,1'-bis(diphenylphosphino)ferrocene)-dichloropalladium(II) dichloromethane adduct (2 mg, 2.8 μmol), and sodium carbonate (18 mg, 0.17 mmol) in dioxane (2 mL) and water (0.5 mL) was sparged with N$_2$ and heated to 100° C. for 4 h. The reaction mixture was diluted with MeOH, filtered, and purified by prep HPLC (pH 2). LCMS for $C_{14}H_{15}N_8$ (M+H)$^+$: m/z=295.1. Found: 295.1. $^1$H NMR (500 MHz, DMSO) δ 9.14 (d, J=7.4 Hz, 1H), 8.45 (s, 1H), 8.40 (s, 1H), 8.32 (s, 1H), 8.29 (s, 1H), 8.15 (d, J=7.4 Hz, 1H), 6.59 (s, 1H), 3.13 (p, J=6.9 Hz, 1H), 1.34 (d, J=6.9 Hz, 6H).

Example 25. 7-(2-(1-Cyclopropylethyl)-2H-pyrazolo[3,4-b]pyridin-5-yl)imidazo[2,1-f][1,2,4]triazin-4-amine trifluoroacetate salt

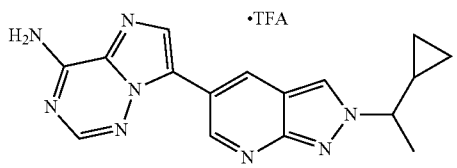 [SMILES: CC(C1CC1)n1cc2cc(-c3cnc4c(N)ncnn34)cnc2n1]

Step 1. 5-bromo-2-(I-cyclopropylethyl)-2H-pyrazolo[3,4-b]pyridine

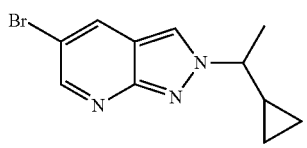

This compound was prepared by a procedure analogous to that described in Example 18, Step 1, utilizing 5-bromo-1H-pyrazolo[3,4-b]pyridine instead of 5-bromo-7-methyl-1H-indazole. Flash chromatography (0-50-100% EtOAc) afforded the title compound (117 mg, 58%), which eluted as the second peak. LCMS for $C_{11}H_{13}BrN_8$ (M+H)$^+$: m/z=266.0. Found: 266.0. LCMS and $^1$H NMR data for the N1 regioisomer: LCMS for $C_{11}H_{13}BrN_8$ (M+H)$^+$: m/z=266.0. Found: 266.0. $^1$H NMR (600 MHz, DMSO) δ 8.59 (d, J=2.2 Hz, 1H), 8.53 (d, J=2.2 Hz, 1H), 8.16 (s, 1H), 4.32 (dq, J=9.2, 6.8 Hz, 1H), 1.61 (d, J=6.9 Hz, 3H), 1.44-1.37 (m, 1H), 0.60 (tdd, J=8.6, 5.8, 4.4 Hz, 1H), 0.41 (dq, J=9.7, 4.9 Hz, 1H), 0.23 (dq, J=9.7, 4.8 Hz, 2H).

Step 2. 7-(2-(I-cyclopropylethyl)-2H-pyrazolo[3,4-b]pyridin-5-yl)imidazo[2,1-f][1,2,4]triazin-4-amine, trifluoroacetate This compound was prepared by a procedure analogous to that described in Example 23, Step 7, utilizing 5-bromo-2-(1-cyclopropylethyl)-2H-pyrazolo[3,4-b]pyridine instead of 5-bromo-2-isopropylpyrazolo[1,5-a]pyridine. LCMS for $C_{16}H_{17}N_8$ (M+H)$^+$: m/z=321.2. Found: 321.2. $^1$H NMR (600 MHz, DMSO) δ 9.20 (d, J=2.2 Hz, 1H), 9.02 (d, J=2.2 Hz, 1H), 8.65 (s, 1H), 8.35 (s, 1H), 8.27 (s, 1H), 8.22 (s, 1H), 8.19 (s, 1H), 4.02 (dq, J=9.1, 6.8 Hz, 1H), 1.69 (d, J=6.7 Hz, 3H), 1.45 (dtd, J=15.9, 9.5, 8.1, 4.8 Hz, 1H), 0.75-0.64 (m, 1H), 0.49-0.45 (m, 2H), 0.44-0.38 (m, 1H).

Example 26. 7-(2-(1-Cyclopropylethyl)-2H-pyrazolo[3,4-c]pyridin-5-yl)imidazo[2,1-f][1,2,4]triazin-4-amine, trifluoroacetate

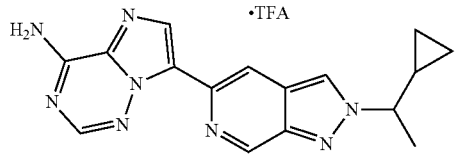 [SMILES: CC(C1CC1)n1cc2cc(-c3cnc4c(N)ncnn34)ncc2n1]

This compound was prepared utilizing a procedure analogous to that described in Example 25, starting from 5-bromo-1H-pyrazolo[3,4-c]pyridine instead of 5-bromo-1H-pyrazolo[3,4-b]pyridine. LCMS for $C_{16}H_{17}N_8$ (M+H)$^+$: m/z=321.2. Found: 321.1. $^1$H NMR (600 MHz, DMSO) δ 9.31 (s, 1H), 8.92 (d, J=1.4 Hz, 1H), 8.74 (s, 1H), 8.32 (s, 1H), 8.29 (s, 1H), 8.27 (s, 1H), 8.20 (s, 1H), 4.10 (ddd, J=13.5, 8.0, 4.7 Hz, 1H), 1.70 (d, J=6.8 Hz, 3H), 1.48-1.41 (m, 1H), 0.74-0.64 (m, 1H), 0.52-0.45 (m, 2H), 0.44-0.39 (m, 1H).

Example 27. 7-(2-(1-Cyclopropylethyl)imidazo[1,2-a]pyridin-6-yl)imidazo[2,1-f][1,2,4]triazin-4-amine trifluoroacetate salt

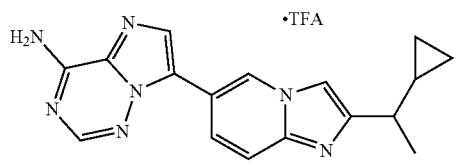 [SMILES: CC(c1cn2cc(-c3cnc4c(N)ncnn34)ccc2n1)C1CC1]

Step 1. 1-bromo-3-cyclopropylbutan-2-one

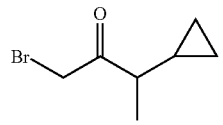

To a solution of 2-cyclopropylpropanoic acid (150 mg, 1.31 mmol, Enamine) in DCM (5 ml) at 0° C. was added oxalyl chloride (0.35 ml, 3.94 mmol) and 2 drops of DMF. The reaction mixture was stirred for 15 min and warmed to room temperature. Once gas evolution ceased (about 30 min), the volatiles were removed in vacuo and the residue was redissolved in DCM (5 mL). The solution was cooled to 0° C. and TMS-diazomethane (1.97 mL, 3.94 mmol) was added. The reaction mixture was warmed to room temperature and stirred for 2 h. The resulting solution was cooled back to 0° C. and HBr (33%/AcOH) (1 mL, 6.08 mmol) was added dropwise. After stirring for 1 h, the reaction was quenched with water and extracted with DCM. The organic layer was washed with saturated $NaHCO_3$, dried over $MgSO_4$, filtered, and concentrated. The residual dark oil was used without purification.

Step 2. 6-bromo-2-(1-cyclopropylethyl)imidazo[1,2-a]pyridine

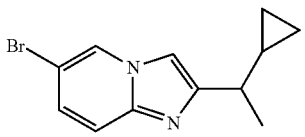

To a solution of 5-bromopyridin-2-amine (150 mg, 0.87 mmol) in EtOH (4 mL) was added 1-bromo-3-cyclopropylbutan-2-one (166 mg, 0.87 mmol, crude prepared in Step 1) and the reaction mixture was stirred at 80° C. overnight. The reaction mixture was partitioned between water and EtOAc, and the layers were separated. The aqueous layer was extracted with EtOAc and the combined organic layers were washed with brine, dried over $MgSO_4$, filtered, and concentrated. The residue was purified by flash chromatography (0-100% EtOAc/hexanes) to afford the title compound (38 mg, 18%). LCMS for $C_{12}H_{14}BrN_2$ $(M+H)^+$: m/z=265.0. Found: 265.0.

Step 3. 7-(2-(1-Cyclopropylethyl)imidazo[1,2-a]pyridin-6-yl)imidazo[2,1-f][1,2,4]triazin-4-amine, trifluoroacetate A mixture of 7-(4,4,5,5-tetramethyl-1,3,2-dioxaborolan-2-yl)imidazo[2,1-f][1,2,4]triazin-4-amine (47.3 mg, 0.18 mmol), 6-bromo-2-(1-cyclopropylethyl)imidazo[1,2-a]pyridine (12 mg, 45 mol), (1,1'-bis(diphenylphosphino)ferrocene)-dichloropalladium(II) (1.7 mg, 2.3 µmol), and sodium carbonate (14 mg, 0.14 mmol) in dioxane (2 mL) and water (0.5 mL) was sparged with $N_2$ and heated to 100° C. for 4 h. An additional ~5 eq of boronate was added and heating was continued for an additional 2 h. The reaction mixture was partitioned between water and EtOAc, and the layers were separated. The aqueous layer was extracted with EtOAc and the combined organic layers were washed with brine, dried over $MgSO_4$, filtered, and concentrated. The residue was purified by prep HPLC (pH 2). LCMS for $C_{17}H_{18}N_7$ $(M+H)^+$: m/z=320.2. Found: 320.1. $^1H$ NMR (500 MHz, DMSO) δ 9.72 (s, 1H), 8.46 (dd, J=9.4, 1.7 Hz, 1H), 8.39 (s, 1H), 8.28 (s, 1H), 8.28 (s, 1H), 8.03 (d, J=9.4 Hz, 1H), 2.41 (dq, J=9.2, 7.1 Hz, 1H), 0.63-0.58 (m, 1H), 0.57-0.51 (m, 1H), 0.41-0.36 (m, 1H), 0.36-0.30 (m, 1H).

Example 28. (S)-8-Amino-3-(2-(1-cyclopropylethyl)-7-(methylsulfonyl)-1-oxoisoindolin-5-yl)-N-isopropylimidazo[1,2-a]pyrazine-6-carboxamide trifluoroacetate salt (single enantiomer prepared)

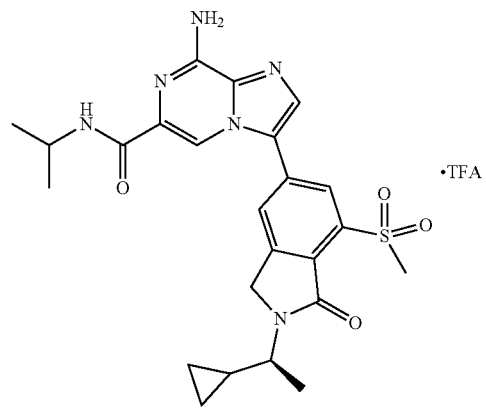 [SMILES: CC(C)NC(=O)c1cn2c(-c3cc4c(c(S(C)(=O)=O)c3)C(=O)N([C@@H](C)C3CC3)C4)cnc2c(N)n1]

Step 1. (S)-5-Bromo-2-(1-cyclopropylethyl)-7-(methylthio)isoindolin-1-one

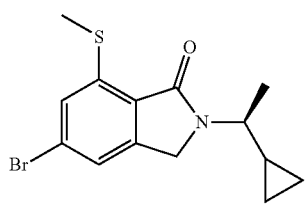 [SMILES: CSc1cc(Br)cc2c1C(=O)N([C@@H](C)C1CC1)C2]

Sodium methanethiolate (0.30 g, 4.3 mmol) was added to (S)-5-bromo-7-chloro-2-(1-cyclopropylethyl)isoindolin-1-one (0.45 g, 1.4 mmol, Example 1, Step 2) in acetonitrile (6.0 mL) and the mixture was heated to 120° C. overnight. Upon cooling to room temperature, the reaction mixture was filtered through Celite®, and the Celite® was washed with EtOAc. The organic solution was washed with water (2x), and brine, dried over $MgSO_4$, filtered, and concentrated to afford the title compound as a yellow solid (250 mg, 53%). LCMS for $C_{14}H_{17}BrNOS$ $(M+H)^+$: calculated m/z=326.0. found 326.1.

Step 2. (S)-5-Bromo-2-(1-cyclopropylethyl)-7-(methylsulfonyl)isoindolin-1-one

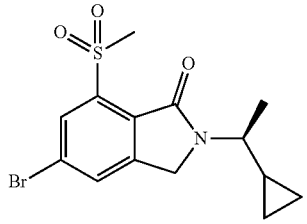 [SMILES: C[C@@H](C1CC1)N1Cc2cc(Br)cc(S(C)(=O)=O)c2C1=O]

To (S)-5-bromo-2-(1-cyclopropylethyl)-7-(methylthio)isoindolin-1-one (0.10 g, 0.31 mmol) in DCM (2.0 mL) at 0° C. was added m-CPBA (130 mg, 0.77 mmol). After stirring for 2 hours, the reaction mixture was diluted with DCM and washed with saturated NaHCO$_3$ solution and brine. The organic layer was dried over MgSO$_4$, filtered and concentrated. Purification via flash chromatography, eluting with a gradient from 0-80% EtOAc in hexanes provided the title compound as a yellow solid (0.080 g, 72%). LCMS for C$_{14}$H$_{17}$BrNO$_3$S (M+H)$^+$: calculated m/z=358.0. found 358.1.

Step 3. (S)-2-(I-Cyclopropylethyl)-7-(methylsulfonyl)-5-(4,4,5,5-tetramethyl-1,3,2-dioxaborolan-2-yl)isoindolin-1-one

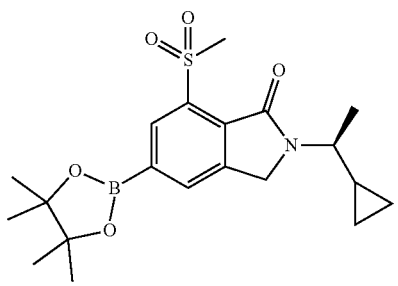 [SMILES: C[C@@H](C1CC1)N1Cc2cc(B3OC(C)(C)C(C)(C)O3)cc(S(C)(=O)=O)c2C1=O]

A degassed mixture of (S)-5-bromo-2-(1-cyclopropylethyl)-7-(methylsulfonyl)isoindolin-1-one (0.10 g, 0.28 mmol), bis(pinacolato)diboron (0.11 g, 0.42 mmol), potassium acetate (0.082 g, 0.84 mmol) and dichloro[1,1'-bis(diphenylphosphino)ferrocene]palladium(II) dichloromethane adduct (0.060 g, 0.017 mmol) in dioxane (3 mL) was degassed. The reaction mixture was heated to 80° C. for 2 hours. Upon cooling to room temperature, the reaction mixture was diluted with water and extracted with EtOAc. The combined organic extracts were dried over Na$_2$SO$_4$, filtered, and concentrated. The product was purified via flash chromatography, eluting with a gradient from 0-100% EtOAc in hexanes, to afford the title compound (0.080 g, 80%).

Step 4. (S)-5-(8-Amino-6-bromoimidazo[1,2-a]pyrazin-3-yl)-2-(1-cyclopropylethyl)-7-(methylsulfonyl)isoindolin-1-one

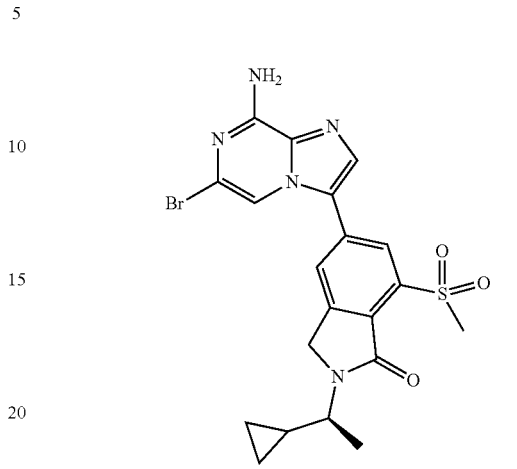

A mixture of (S)-2-(1-cyclopropylethyl)-7-(methylsulfonyl)-5-(4,4,5,5-tetramethyl-1,3,2-dioxaborolan-2-yl)isoindolin-1-one (0.40 g, 0.99 mmol), 6-bromo-3-iodoimidazo[1,2-a]pyrazin-8-amine (0.40 g, 1.2 mmol, Affinity ARI-0189) and dichloro[1,1'-bis(diphenylphosphino)ferrocene]palladium(II) dichloromethane adduct (0.16 g, 0.20 mmol) in THF (15 mL) and aq. K$_2$CO$_3$ solution (1.0 M, 4.0 mL, 4.0 mmol) was degassed by sparging with N$_2$ for 5 min. The reaction mixture was heated in a sealed vessel in an oil bath held at 100° C. for 2 h. Upon cooling to room temperature, the reaction mixture was partitioned between water and EtOAc. The aqueous layer was separated and was extracted with EtOAc (2×). The combined organic extracts were washed with brine, dried over Na$_2$SO$_4$, filtered and concentrated. Flash chromatography, eluting with a gradient from 0-100% EtOAc in hexanes, afforded the title compound (0.12 g, 25%). LCMS for C$_{20}$H$_{21}$BrN$_5$O$_3$S (M+H)$^+$: calculated m/z=490.1. found 490.0.

Step 5. (S)-8-Amino-3-(2-(I-cyclopropylethyl)-7-(methylsulfonyl)-1-oxoisoindolin-5-yl)-N-isopropylimidazo[1,2-a]pyrazine-6-carboxamide, trifluoroacetate salt (single enantiomer prepared)

To a solution of (S)-5-(8-amino-6-bromoimidazo[1,2-a]pyrazin-3-yl)-2-(1-cyclopropylethyl)-7-(methylsulfonyl)isoindolin-1-one (0.010 g, 0.020 mmol) in dioxane (0.41 mL) was added triethylamine (23 μL, 0.16 mmol), propan-2-amine (9.6 mg, 0.16 mmol) and dichloro[1,1'-bis(diphenylphosphino)ferrocene]palladium(II) dichloromethane adduct (3.3 mg, 4.1 μmol). Carbon monoxide gas was bubbled through the solution for 5 min. The reaction was heated at 100° C. under an atmosphere of CO for 2 h. Upon cooling to room temperature, the reaction mixture was diluted with MeOH and MeCN, and filtered. Purification via preparative HPLC-MS (pH=2) afforded the title compound (2.4 mg, 20%). LCMS for C$_{24}$H$_{29}$N$_6$O$_4$S (M+H)$^+$: calculated m/z=497.2. found 497.1. $^1$H NMR (400 MHz, DMSO-d$_6$) δ 8.30 (d, J=1.3 Hz, 1H), 8.30 (s, 1H), 8.19 (d, J=1.3 Hz, 1H), 8.01 (s, 1H), 7.93 (d, J=8.1 Hz, 1H), 7.42 (s, 2H), 4.79 (s, 2H), 4.14-3.98 (m, 1H), 3.71-3.62 (m, 1H), 3.68 (s, 3H), 1.35 (d, J=6.8 Hz, 3H), 1.21 (d, J=6.5 Hz, 6H), 0.67-0.57 (m, 1H), 0.52-0.38 (m, 2H), 0.35-0.24 (m, 1H).

Examples 29 and 29a-29d

The compounds in Table 4 were prepared by the method of Example 28 using the appropriate amine instead of propan-2-amine in Step 5.

TABLE 4

| Ex. No. | Name | R | LCMS [M + H]⁺ | NMR Spectra |
|---|---|---|---|---|
| 29 | (S)-8-Amino-3-(2-(1-cyclopropylethyl)-7-(methylsulfonyl)-1-oxoisoindolin-5-yl)-N-(tetrahydro-2H-pyran-4-yl)imidazo[1,2-a]pyrazine-6-carboxamide, trifluoroacetate salt (single enantiomer prepared) | tetrahydropyran-4-yl-NH- | 539.2 | ¹H NMR (400 MHz, DMSO-d$_6$) δ 8.32 (s, 1H), 8.30 (d, J = 1.5 Hz, 1H), 8.19 (d, J = 1.5 Hz, 1H), 8.11 (d, J = 8.0 Hz, 1H), 8.02 (s, 2H), 7.51 (br s, 2H), 4.79 (s, 2H), 4.05-3.93 (m, 1H), 3.93-3.84 (m, 2H), 3.73-3.54 (m, 1H), 3.67 (s, 3H), 3.42 (td, J = 11.6, 2.2 Hz, 2H), 1.87-1.74 (m, 2H), 1.58 (qd, J = 12.1, 4.3 Hz, 2H), 1.35 (d, J = 6.8 Hz, 3H), 1.27-1.12 (m, 1H), 0.67-0.57 (m, 1H), 0.52-0.38 (m, 2H), 0.35-0.21 (m, 1H). |
| 29a | (S)-5-(8-Amino-6-(azetidine-1-carbonyl)imidazo[1,2-a]pyrazin-3-yl)-2-(1-cyclopropylethyl)-7-(methylsulfonyl)isoindolin-1-one, trifluoroacetate salt (single enantiomer prepared) | azetidin-1-yl | 495.2 | |
| 29b | (S)-8-Amino-N-(bicyclo[1.1.1]pentan-1-yl)-3-(2-(1-cyclopropylethyl)-7-(methylsulfonyl)-1-oxoisoindolin-5-yl)imidazo[1,2-a]pyrazine-6-carboxamide, trifluoroacetate salt (single enantiomer prepared) | bicyclo[1.1.1]pentan-1-yl-NH- | 521.3 | |

TABLE 4-continued

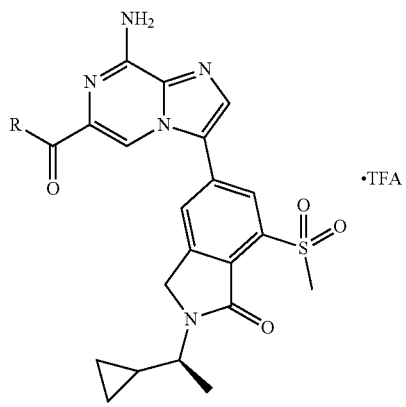

| Ex. No. Name | R | LCMS [M + H]+ | NMR Spectra |
|---|---|---|---|
| 29c (S)-5-(8-Amino-6-(3,3-dimethylazetidine-1-carbonyl)imidazo[1,2-a]pyrazin-3-yl)-2-(1-cyclopropylethyl)-7-(methylsulfonyl)isoindolin-1-one, trifluoroacetate salt (single enantiomer prepared) | 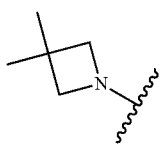 [SMILES: *N1CC(C)(C)C1] | 523.2 | |
| 29d (S)-5-(8-Amino-6-(3,3-difluoroazetidine-1-carbonyl)imidazo[1,2-a]pyrazin-3-yl)-2-(1-cyclopropylethyl)-7-(methylsulfonyl)isoindolin-1-one, trifluoroacetate salt (single enantiomer prepared) | 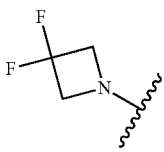 | 531.2 | $^1$H NMR (400 MHz, DMSO-d$_6$) δ 8.30 (s, 1H), 8.28 (d, J = 1.5 Hz, 1H), 8.18 (d, J = 1.5 Hz, 1H), 8.02 (s, 1H), 7.42 (br s, 2H), 5.06 (t, J = 12.5 Hz, 2H), 4.78 (s, 2H), 4.47 (t, J = 12.5 Hz, 2H), 3.73-3.58 (m, 1H), 3.67 (s, 3H), 1.34 (d, J = 6.8 Hz, 3H), 1.28-1.14 (m, 1H), 0.68-0.55 (m, 1H), 0.52-0.38 (m, 2H), 0.38-0.23 (m, 1H). |

Example 30. (S)-5-(8-Amino-6-(3-hydroxyazetidine-1-carbonyl)imidazo[1,2-a]pyrazin-3-yl)-2-(1-cyclopropylethyl)isoindolin-1-one, trifluoroacetate salt (single enantiomer prepared)

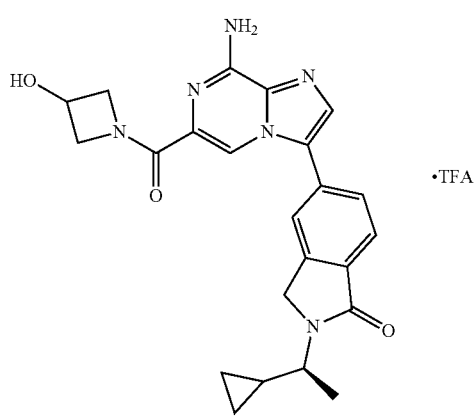 [SMILES: C[C@@H](C1CC1)N1Cc2cc(-c3cnc4c(N)nc(C(=O)N5CC(O)C5)cn34)ccc2C1=O]

Step 1. (S)-5-Bromo-2-(1-cyclopropylethyl)isoindolin-1-one

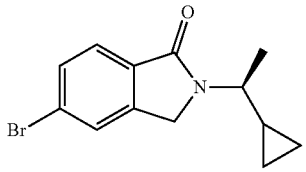 [SMILES: C[C@@H](C1CC1)N1Cc2cc(Br)ccc2C1=O]

A mixture of methyl 4-bromo-2-(bromomethyl)benzoate (1.00 g, 3.25 mmol, Ark Pharm, AK-26333), (S)-1-cyclopropylethan-1-amine (0.30 g, 3.6 mmol, Aldrich 727245), and K$_2$CO$_3$ (0.90 g, 6.5 mmol) in acetonitrile (8.1 mL) in a microwave vial was sealed and heated at 120° C. in a microwave oven for 30 min. The reaction mixture was filtered and solvent was removed in vacuo. The product was purified via flash chromatography, eluting with a gradient of 0-25% EtOAc in hexanes, to afford the title compound (0.42 g, 46%). LCMS for C$_{13}$H$_{15}$BrNO (M+H)+: calculated monoisotopic m/z=280.0. found 280.0.

Step 2. (S)-2-(1-Cyclopropylethyl)-5-(4,4,5,5-tetramethyl-1,3,2-dioxaborolan-2-yl)isoindolin-1-one

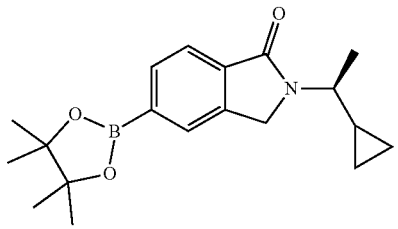 [SMILES: C[C@@H](C1CC1)N1Cc2cc(B3OC(C)(C)C(C)(C)O3)ccc2C1=O]

(S)-5-Bromo-2-(1-cyclopropylethyl)isoindolin-1-one (0.42 g, 1.5 mmol) was combined with bis(pinacolato)diboron (0.57 g, 2.3 mmol), potassium acetate (0.89 g, 9.0 mmol) and dichloro[1,1'-bis(diphenylphosphino)ferrocene]palladium (II) dichloromethane adduct (0.074 g, 0.090 mmol) in dioxane (7.5 mL), and the mixture was degassed. The reaction was heated to 80° C. for 3 hours. Upon cooling to room temperature, the mixture was diluted with EtOAc, filtered through Celite®, and concentrated. The product was purified via flash chromatography, eluting with a gradient from 0-20% EtOAc in hexanes, to afford the title compound (theoretical yield assumed). LCMS for $C_{19}H_{27}BNO_3$ (M+H)$^+$: calculated m/z=328.2. found 328.2.

Step 3. (S)-5-(8-Amino-6-bromoimidazo[1,2-a]pyrazin-3-yl)-2-(1-cyclopropylethyl)isoindolin-1-one

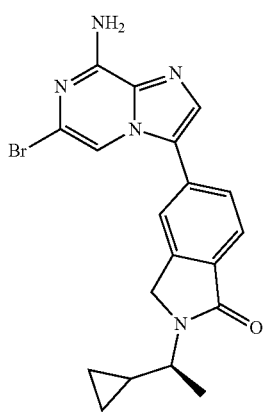 [SMILES: C[C@@H](C1CC1)N1Cc2cc(-c3cnc4c(N)nc(Br)cn34)ccc2C1=O]

The procedure of Example 28, Step 4 was followed, using (S)-2-(1-cyclopropylethyl)-5-(4,4,5,5-tetramethyl-1,3,2-dioxaborolan-2-yl)isoindolin-1-one (0.19 g, 0.58 mmol, from Step 1) instead of (S)-2-(1-cyclopropylethyl)-7-(methylsulfonyl)-5-(4,4,5,5-tetramethyl-1,3,2-dioxaborolan-2-yl)isoindolin-1-one, to afford the title compound (0.19 g, 79%).

LCMS for $C_{19}H_{19}BrN_5O$ (M+H)$^+$: calculated monoisotopic m/z=412.1. found 412.0.

Step 4. Ethyl (S)-8-amino-3-(2-(I-cyclopropylethyl)-1-oxoisoindolin-5-yl)imidazo[1,2-a]pyrazine-6-carboxylate

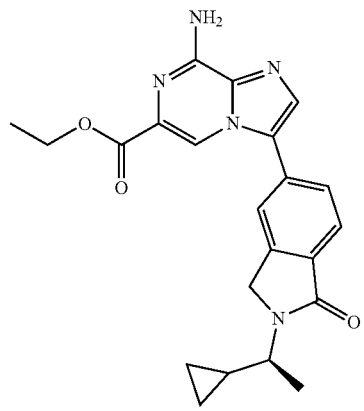 [SMILES: CCOC(=O)c1cn2c(-c3ccc4c(c3)CN([C@@H](C)C3CC3)C4=O)cnc2c(N)n1]

A mixture of (S)-5-(8-amino-6-bromoimidazo[1,2-a]pyrazin-3-yl)-2-(1-cyclopropylethyl)isoindolin-1-one (120 mg, 0.29 mmol), triethylamine (0.16 mL, 1.2 mmol) and dichloro[1,1'-bis(diphenylphosphino)ferrocene]palladium (II) dichloromethane adduct (24 mg, 0.029 mmol) in EtOH (8.0 mL) and DMF (2.0 mL) was degassed. Carbon monoxide was bubbled through the mixture for 5 min, then was heated to 80° C. under an atmosphere of CO for 2 hrs. The volatiles were removed in vacuo and the residue was purified via flash column chromatography, eluting with a gradient of 0-100% EtOAc in hexanes, followed by 5% MeOH in EtOAc, to provide the title compound (0.060 g, 50%). LCMS for $C_{22}H_{24}N_5O_3$ (M+H)$^+$: calculated m/z=406.0. found 406.2.

Step 5. (S)-8-Amino-3-(2-(1-cyclopropylethyl)-1-oxoisoindolin-5-yl)imidazo[1,2-a]pyrazine-6-carboxylic acid

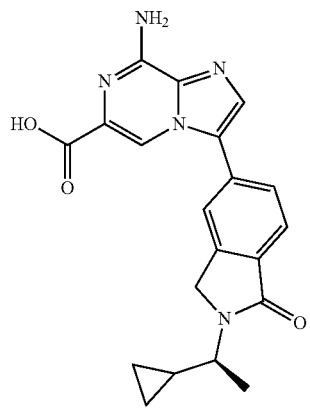 [SMILES: C[C@@H](C1CC1)N1Cc2cc(-c3cnc4c(N)nc(C(=O)O)cn34)ccc2C1=O]

Lithium hydroxide (35 mg, 1.5 mmol) was added to a mixture of ethyl (S)-8-amino-3-(2-(1-cyclopropylethyl)-1-oxoisoindolin-5-yl)imidazo[1,2-a]pyrazine-6-carboxylate (0.060 g, 0.15 mmol) in MeOH (3.0 mL) and water (3.0 mL). The suspension was stirred for 2.5 h, then MeOH was removed in vacuo. The aqueous solution was acidified by the addition of 1.0N HCl to a pH of 3, then was saturated with NaCl and extracted with EtOAc (6×). The combined organic extracts were dried over $Na_2SO_4$, filtered and concentrated to afford the title compound, which was used without further purification (48 mg, 87%). LCMS for $C_{20}H_{20}N_5O_3$ (M+H)$^+$: calculated m/z=378.2. found 378.2.

Step 6. (S)-5-(8-Amino-6-(3-hydroxyazetidine-1-carbonyl)imidazo[1,2-a]pyrazin-3-yl)-2-(1-cyclopropylethyl)isoindolin-1-one, trifluoroacetate salt (single enantiomer prepared)

To a solution of (S)-8-amino-3-(2-(1-cyclopropylethyl)-1-oxoisoindolin-5-yl)imidazo[1,2-a]pyrazine-6-carboxylic acid (8.0 mg, 0.021 mmol) in DMF (0.20 mL) was added HATU (0.010 g, 0.028 mmol) and DIEA (0.019 mL, 0.11 mmol). To this mixture was added azetidin-3-ol (1.9 mg, 0.025 mmol, ChemBridge #4002252). After stirring for 30 min, the reaction mixture was diluted with MeOH and MeCN, filtered and purified via preparative HPLC-MS (pH=2) to afford the title compound (3.0 mg, 26%). $^1$H NMR (400 MHz, DMSO-d$_6$) δ 8.21 (s, 1H), 7.91 (s, 1H), 7.90 (s, 1H), 7.86 (d, J=7.9 Hz, 1H), 7.76 (dd, J=7.9, 1.5 Hz, 1H), 7.35 (br s, 2H), 4.82 (dd, J=11.0, 6.7 Hz, 1H), 4.66 (s, 2H), 4.50 (tt, J=6.8, 4.4 Hz, 1H), 4.36 (dd, J=11.0, 4.2 Hz, 1H), 4.22 (dd, J=10.6, 6.9 Hz, 1H), 3.75 (dd, J=10.2, 4.1 Hz, 1H), 3.67-3.54 (m, 1H), 1.32 (d, J=6.8 Hz, 3H), 1.22-1.10 (m, 1H), 0.65-0.54 (m, 1H), 0.47-0.36 (m, 2H), 0.30-0.18 (m, 1H). LCMS for $C_{23}H_{25}N_6O_3$ (M+H)$^+$: calculated m/z=433.2. found 433.2.

Examples 31-32

The compounds in Table 5 were prepared by the method of Example 30 using the appropriate amines instead of azetidin-3-ol in Step 3.

TABLE 5

| Ex. No. | Name | R | LCMS [M + H]$^+$ |
|---|---|---|---|
| 31 | (S)-8-Amino-3-(2-(1-cyclopropylethyl)-1-oxoisoindolin-5-yl)-N-(3-hydroxycyclobutyl)imidazo[1,2-a]pyrazine-6-carboxamide, trifluoroacetate salt (mixture of two diastereomers prepared (cis and trans on cyclobutane)) | HO-cyclobutyl-NH- | 447.2 |
| 32 | 8-Amino-3-(2-((S)-1-cyclopropylethyl)-1-oxoisoindolin-5-yl)-N-(3-hydroxytetrahydro-2H-pyran-4-yl)imidazo[1,2-a]pyrazine-6-carboxamide, trifluoroacetate salt (mixture of two diastereomers, each of which is trans relative stereochemistry at tetrahydropyran) | OH-tetrahydropyran-NH- | 477.2 |

Example 33. (S)-5-(8-Amino-6-(2-methyloxazol-5-yl)imidazo[1,2-a]pyrazin-3-yl)-2-(1-cyclopropyl-ethyl)-7-(methylsulfonyl)isoindolin-1-one, trifluoroacetate salt (single enantiomer prepared)

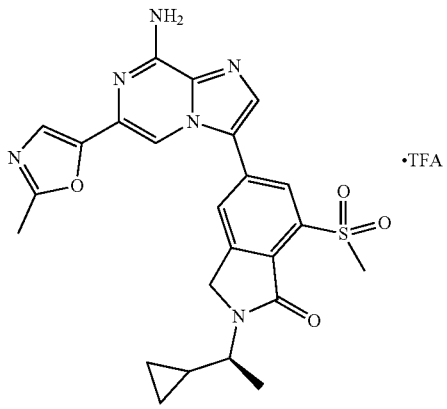 [SMILES: Cc1ncc(-c2cn3c(-c4cc5c(c(S(C)(=O)=O)c4)C(=O)N([C@@H](C)C4CC4)C5)cnc3c(N)n2)o1]

A degassed mixture of (S)-5-(8-amino-6-bromoimidazo[1,2-a]pyrazin-3-yl)-2-(1-cyclopropylethyl)-7-(methylsulfonyl)isoindolin-1-one (10.0 mg, 0.020 mmol, from Example 28, Step 4), 2-methyl-5-(4,4,5,5-tetramethyl-1,3,2-dioxaborolan-2-yl)oxazole (13 mg, 0.061 mmol, Ark Pharm #AK315370) and dichloro[1,1'-bis(diphenylphosphino)ferrocene]palladium(II) dichloromethane adduct (3.3 mg, 4.1 μmol) in THF (0.40 mL) and aq. $K_2CO_3$ (1.0 M, 0.051 mL, 0.051 mmol) was heated to 95° C. in a sealed vial for 2 h. Upon cooling to room temperature, the reaction mixture was diluted with MeOH and MeCN and filtered, then purified via preparative HPLC-MS (pH=2) to afford the title compound (6.0 mg, 49%). LCMS for $C_{24}H_{25}N_6O_4S$ (M+H)$^+$: calculated m/z=493.2. found 493.1.

Examples 34-38

The compounds in Table 6 were prepared by the method of Example 33 using the appropriate boronic esters instead of 2-methyl-5-(4,4,5,5-tetramethyl-1,3,2-dioxaborolan-2-yl)oxazole.

TABLE 6

| Ex. No. | Name | R | LCMS [M + H]$^+$ | NMR Spectra |
|---|---|---|---|---|
| 34 | (S)-5-(8-Amino-6-(2-methylthiazol-5-yl)imidazo[1,2-a]pyrazin-3-yl)-2-(1-cyclopropylethyl)-7-(methylsulfonyl)isoindolin-1-one, trifluoroacetate salt (single enantiomer prepared) | 2-methylthiazol-5-yl | 509.3 | $^1$H NMR (400 MHz, DMSO-d$_6$) δ 8.36-8.29 (m, 2H), 8.19 (d, J = 1.5 Hz, 1H), 8.17 (s, 1H), 7.96 (s, 1H), 7.38 (br s, 2H), 4.79 (s, 2H), 3.75-3.60 (m, 1H), 3.67 (s, 3H), 2.67 (s, 3H), 1.36 (d, J = 6.8 Hz, 3H), 1.29-1.11 (m, 1H), 0.68-0.58 (m, 1H), 0.54-0.37 (m, 2H), 0.37-0.21 (m, 1H). |
| 35 | (S)-5-(8-Amino-6-(1-methyl-1H-pyrazol-4-yl)imidazo[1,2-a]pyrazin-3-yl)-2-(1-cyclopropylethyl)-7-(methylsulfonyl)isoindolin-1-one, trifluoroacetate salt (single enantiomer prepared) | 1-methyl-1H-pyrazol-4-yl | 492.3 | $^1$H NMR (400 MHz, DMSO-d$_6$) δ 8.30 (d, J = 1.5 Hz, 1H), 8.19 (d, J = 1.5 Hz, 1H), 8.13 (s, 1H), 8.11 (s, 1H), 8.00 (s, 1H), 7.95-7.92 (m, 1H), 7.76 (br s, 2H), 4.80 (s, 2H), 3.89 (s, 3H), 3.75-3.57 (m, 1H), 3.67 (s, 3H), 1.36 (d, J = 6.8 Hz, 3H), 1.26-1.14 (m, 1H), 0.70-0.57 (m, 1H), 0.57-0.37 (m, 2H), 0.36-0.23 (m, 1H). |

TABLE 6-continued

| Ex. No. | Name | R | LCMS [M + H]+ | NMR Spectra |
|---|---|---|---|---|
| 36 | (S)-5-(8-Amino-6-(1-methyl-1H-pyrazol-5-yl)imidazo[1,2-a]pyrazin-3-yl)-2-(1-cyclopropylethyl)-7-(methylsulfonyl)isoindolin-1-one, trifluoroacetate salt (single enantiomer prepared) | 1-methyl-1H-pyrazol-5-yl | 492.3 | $^1$H NMR (400 MHz, DMSO-d$_6$) δ 8.32 (d, J = 1.5 Hz, 1H), 8.21 (d, J = 1.5 Hz, 1H), 8.13 (s, 1H), 8.04 (s, 1H), 7.56 (br s, 2H), 7.46 (d, J = 1.9 Hz, 1H), 6.57 (d, J = 1.9 Hz, 1H), 4.76 (s, 2H), 4.07 (s, 3H), 3.73-3.58 (m, 1H), 3.66 (s, 3H), 1.34 (d, J = 6.8 Hz, 3H), 1.28-1.09 (m, 1H), 0.69-0.54 (m, 1H), 0.52-0.35 (m, 2H), 0.35-0.15 (m, 1H). |
| 37 | (S)-5-(8-Amino-6-(5-methyl-1H-pyrazol-4-yl)imidazo[1,2-a]pyrazin-3-yl)-2-(1-cyclopropylethyl)-7-(methylsulfonyl)isoindolin-1-one, trifluoroacetate salt (single enantiomer prepared) | 5-methyl-1H-pyrazol-4-yl | 492.3 | $^1$H NMR (400 MHz, DMSO-d$_6$) δ 8.31 (d, J = 1.5 Hz, 1H), 8.25 (d, J = 1.5 Hz, 1H), 8.04 (s, 1H), 7.92 (s, 1H), 7.87 (s, 1H), 4.77 (s, 2H), 3.70-3.62 (m, 1H), 3.66 (s, 3H), 2.45 (s, 3H), 1.35 (d, J = 6.8 Hz, 3H), 1.27-1.12 (m, 1H), 0.68-0.58 (m, 1H), 0.53-0.38 (m, 2H), 0.37-0.25 (m, 1H). |
| 38 | (S)-5-(8-Amino-6-(1H-pyrazol-4-yl)imidazo[1,2-a]pyrazin-3-yl)-2-(1-cyclopropylethyl)-7-(methylsulfonyl)isoindolin-1-one, trifluoroacetate salt (single enantiomer prepared) | 1H-pyrazol-4-yl | 478.4 | |

Example 39. 5-(4-Aminoimidazo[2,1-f][1,2,4]tri-azin-7-yl)-2-((S)-1-cyclopropylethyl)-7-(1,1,1-trif-luoro-2,3-dihydroxypropan-2-yl)isoindolin-1-one, trifluoroacetate salt (mixture of two diastereomers prepared)

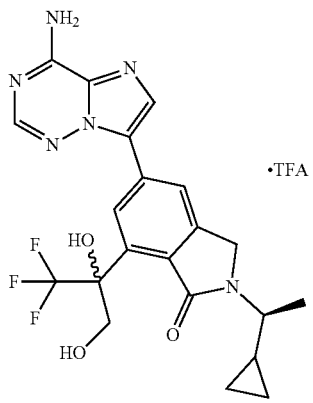 [SMILES: C[C@@H](C1CC1)N1Cc2cc(-c3cnc4c(N)ncnn34)cc(C(O)(CO)C(F)(F)F)c2C1=O]

Step 1. Methyl 2-(bromomethyl)-4-chloro-6-iodobenzoate

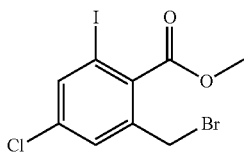

To methyl 4-chloro-2-iodo-6-methylbenzoate (6.8 g, 22 mmol, prepared as described in WO2011/006794) in CCl₄ (110 mL) was added NBS (4.7 g, 26 mmol) and benzoyl peroxide (0.53 g, 2.2 mmol) and the reaction was stirred at reflux for 23 hours. Additional NBS (0.78 g, 4.3 mmol) and benzoyl peroxide (0.25 g, 1.0 mmol) were added, and the mixture was stirred at reflux overnight. Upon cooling to room temperature, the reaction mixture was washed with dilute Na₂S₂O₃ solution and the aqueous layer was extracted with two portions of EtOAc. The combined organic extracts were dried over Na₂SO₄, filtered and concentrated. The product was purified via flash column chromatography, eluting with a gradient of 0-10% EtOAc/hexanes to afford the title compound (theoretical yield assumed). LCMS for C₉H₈BrClIO₂ (M+H)⁺: calculated monoisotopic m/z=388.8. found 388.8.

Step 2. (S)-5-Chloro-2-(I-cyclopropylethyl)-7-iodoi-soindolin-1-one

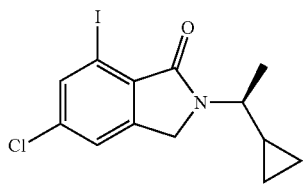

To a flask containing methyl 2-(bromomethyl)-4-chloro-6-iodobenzoate (7.3 g, 19 mmol) in acetonitrile (65 mL) was added (S)-1-cyclopropylethan-1-amine (1.6 g, 19 mmol, Aldrich #747245), followed by boric acid (1.2 g, 19 mmol). Solid K₂CO₃ (5.2 g, 38 mmol) was added portionwise over 2 minutes, and the reaction was stirred overnight. The reaction mixture was filtered, and the solid was washed with acetonitrile. The solvent was removed from the filtrate in vacuo, and the residue was purified via flash column chromatography, eluting with a gradient from 0-20% EtOAc in hexanes, to afford the title compound (3.3 g, 42% over 2 steps). LCMS for C₁₃H₁₄ClINO (M+H)⁺: calculated monoisotopic m/z=362.0. found 362.0.

Step 3. (S)-5-Chloro-2-(1-cyclopropylethyl)-7-(3,3,3-trifluoroprop-1-en-2-yl)isoindolin-1-one

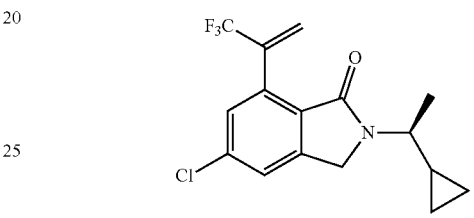

A degassed mixture of (S)-5-chloro-2-(1-cyclopropyl-ethyl)-7-iodoisoindolin-1-one (0.20 g, 0.55 mmol), (3,3,3-trifluoroprop-1-en-2-yl)boronic acid (0.12 g, 0.83 mmol, prepared as described in Tet. Lett., 43(24), 2001, pp. 4083-4085), tetrakis(triphenylphosphine)palladium(0) (0.013 g, 0.011 mmol), and aq. Na₂CO₃ (1.0 M, 1.7 mL, 1.7 mmol) in a mixture of toluene (5.0 mL) and MeOH (1.0 mL) was heated to 70° C. for 3 hours, then to 80° C. for 1 hour. Additional (3,3,3-trifluoroprop-1-en-2-yl)boronic acid (0.12 g, 0.83 mmol) and tetrakis(triphenylphosphine)palladium(0) (0.026 g, 0.022 mmol) were added. The mixture was again degassed and heated to 80° C. overnight. Upon cooling to room temperature, the reaction mixture was partitioned between EtOAc and water. The organic layer was dried over Na₂SO₄, filtered and concentrated. The product was purified via flash column chromatography, eluting with a gradient of 0-15% EtOAc in hexanes to afford the title compound (0.12 g, 65%). LCMS for C₁₆H₁₆ClF₃NO (M+H)⁺: calculated monoisotopic m/z=330.1. found 330.1.

Step 4. (5-Chloro-2-((S)-1-cyclopropylethyl)-7-(1,1,1-trifluoro-2,3-dihydroxypropan-2-yl)isoindolin-1-one (mixture of two diastereomers)

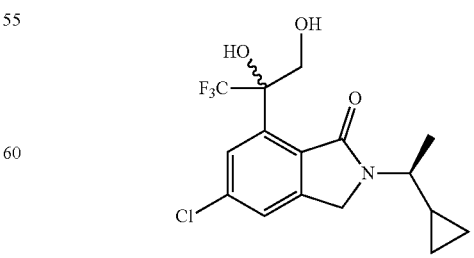

To a solution of (S)-5-chloro-2-(1-cyclopropylethyl)-7-(3,3,3-trifluoroprop-1-en-2-yl)isoindolin-1-one (0.12 g, 0.36 mmol) in acetone (1.0 mL) and water (1.0 mL) was added NMO (0.054 g, 0.46 mmol) and OsO₄ (4 wt % in water, 0.14 mL, 0.021 mmol). The mixture was stirred at 30° C. for 6 hours. To the reaction mixture was added sodium sulfite (0.090 g, 0.71 mmol), and the mixture was stirred for 10 min, then was filtered. The filtrate was partitioned between EtOAc and water. The aqueous layer was extracted with EtOAc (2×). The combined organic extracts were dried over Na₂SO₄, filtered and concentrated. The product was purified via flash column chromatography, eluting with a gradient of 0-60% EtOAc in hexanes to afford the title compound (65 mg, 50%). Partial separation of diastereomers was possible under these conditions, however the product was carried to the next step as a mixture of two diastereomers. LCMS for $C_{16}H_{18}ClF_3NO_3$ (M+H)⁺: calculated monoisotopic m/z=364.1. found 364.1.

Step 5. 2-((S)-1-Cyclopropylethyl)-5-(4,4,5,5-tetramethyl-1,3,2-dioxaborolan-2-yl)-7-(1,1,1-trifluoro-2,3-dihydroxypropan-2-yl)isoindolin-1-one (mixture of two diastereomers)

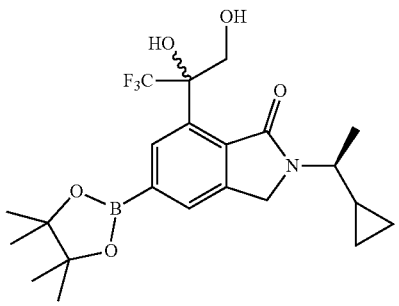 [SMILES: C[C@@H](C1CC1)N1Cc2cc(B3OC(C)(C)C(C)(C)O3)cc(C(O)(CO)C(F)(F)F)c2C1=O]

A degassed mixture of 5-chloro-2-((S)-1-cyclopropylethyl)-7-(1,1,1-trifluoro-2,3-dihydroxypropan-2-yl)isoindolin-1-one (65 mg, 0.18 mmol, a mixture of two diastereomers from Step 4), bis(pinacolato)diboron (0.14 g, 0.54 mmol), KOAc (0.11 g, 1.1 mmol), Pd₂(dba)₃ (8.2 mg, 8.9 µmol) and 2-dicyclohexylphosphino-2',4',6'-tri-iso-propyl-1,1'-biphenyl (17 mg, 0.036 mmol) in dioxane (1.5 mL) was heated in a sealed vial at 120° C. for one hour. Upon cooling to room temperature, the reaction mixture was diluted with EtOAc, filtered through Celite® and concentrated. The product was purified via flash column chromatography, eluting with a gradient of 0-60% EtOAc in hexanes to afford the title compound (63 mg, 77%). LCMS for $C_{22}H_{30}BF_3NO_5$ (M+H)⁺: calculated m/z=456.2. found 456.4.

Step 6. 5-(4-Aminoimidazo[2,1-f][1,2,4]triazin-7-yl)-2-((S)-1-cyclopropylethyl)-7-(1,1,1-trifluoro-2,3-dihydroxypropan-2-yl)isoindolin-1-one, trifluoroacetate salt (mixture of two diastereomers prepared)

A degassed mixture of 2-((S)-1-cyclopropylethyl)-5-(4,4,5,5-tetramethyl-1,3,2-dioxaborolan-2-yl)-7-(1,1,1-trifluoro-2,3-dihydroxypropan-2-yl)isoindolin-1-one (10.0 mg, 0.022 mmol, as a mixture of two diastereomers from Step 5), 7-bromoimidazo[2,1-f][1,2,4]triazin-4-amine (4.7 mg, 0.022 mmol, Affinity Research Chemicals, Inc. #AP-3811) and dichloro[1,1'-bis(diphenylphosphino)ferrocene]palladium (II) dichloromethane adduct (3.6 mg, 4.4 µmol) in THF (0.40 mL) and aq. K₂CO₃ (1.0 M, 0.066 mL, 0.066 mmol) was heated in the microwave at 120° C. for 25 min. Upon cooling to room temperature, the reaction mixture was diluted with MeCN and MeOH, then was filtered and purified via preparative HPLC-MS (pH=2) to afford the title compound (2.0 mg, 16%). ¹H NMR (400 MHz, DMSO-d₆) δ 10.08-10.02 (m, 1H), 8.55 (s, 1H), 8.40 (s, 1H), 8.35 (s, 1H), 8.31 (s, 1H), 8.28 (s, 1H), 8.24 (s, 1H), 4.83 (s, 2H), 4.31 (d, J=11.9 Hz, 1H), 3.93 (d, J=11.6 Hz, 1H), 3.72-3.60 (m, 1H), 1.35 (d, J=6.8 Hz, 3H), 1.28-1.12 (m, 1H), 0.68-0.55 (m, 1H), 0.52-0.37 (m, 2H), 0.34-0.24 (m, 1H). ¹⁹F NMR (376 MHz, DMSO-d₆) δ −73.99 (s), −76.45 (s). LCMS for $C_{21}H_{22}F_3N_6O_3$ (M+H)⁺: calculated m/z=463.2. found 463.1.

Example 40. 5-(8-Amino-6-(trifluoromethyl)imidazo[1,2-a]pyrazin-3-yl)-2-((S)-1-cyclopropylethyl)-7-(1,1,1-trifluoro-2,3-dihydroxypropan-2-yl)isoindolin-1-one, trifluoroacetate salt (mixture of two diastereomers prepared)

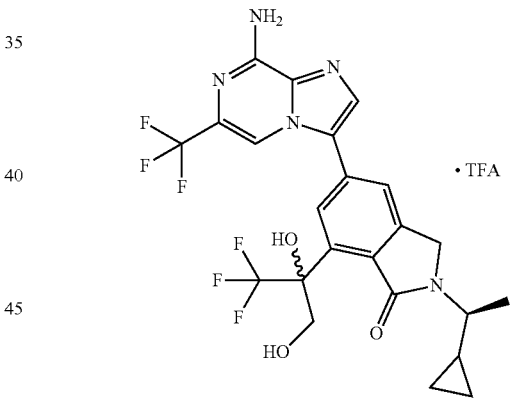

The method of Example 39, Step 6 was followed, using 3-bromo-6-(trifluoromethyl)imidazo[1,2-a]pyrazin-8-amine (6.2 mg, 0.022 mmol, Affinity Research Chemicals, Inc. #ARI-0167) instead of 7-bromoimidazo[2,1-f][1,2,4]triazin-4-amine to provide the title compound (2.2 mg, 13%). ¹H NMR (400 MHz, DMSO-d₆) δ 10.02 (d, J=2.0 Hz, 1H), 8.18 (s, 1H), 8.00-7.98 (m, 2H), 7.96 (s, 1H), 7.70 (s, 2H), 4.89-4.76 (m, 2H), 4.33-4.25 (m, 1H), 3.90 (d, J=11.7 Hz, 1H), 3.72-3.62 (m, 1H), 1.36 (d, J=6.7 Hz, 3H), 1.29-1.13 (m, 1H), 0.68-0.56 (m, 1H), 0.52-0.39 (m, 2H), 0.35-0.22 (m, 1H). ¹⁹F NMR (376 MHz, DMSO-d₆) δ −66.77 (s), −73.72 (s), −76.68 (s). LCMS for $C_{23}H_{22}F_6N_5O_3$ (M+H)⁺: calculated m/z=530.2. found 530.1.

Example 41. tert-Butyl (2-(5-(8-amino-6-(trifluoromethyl)imidazo[1,2-a]pyrazin-3-yl)-1-oxoisoindolin-2-yl)-2-cyclopropylethyl)carbamate (racemic mixture prepared)

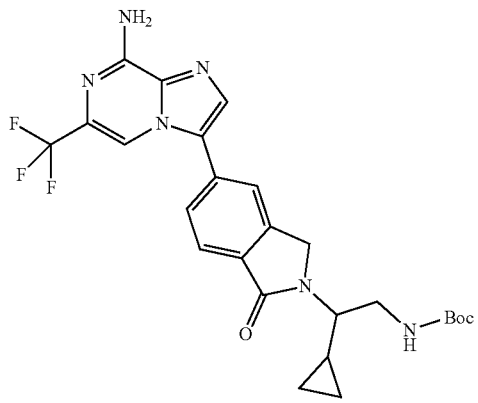 [SMILES: CC(C)(C)OC(=O)NCC(C1CC1)N1Cc2cc(-c3cnc4c(N)nc(C(F)(F)F)cn34)ccc2C1=O]

Step 1. tert-Butyl (2-(5-bromo-1-oxoisoindolin-2-yl)-2-cyclopropylethyl)carbamate

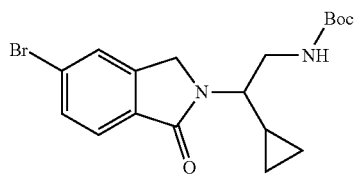 [SMILES: CC(C)(C)OC(=O)NCC(C1CC1)N1Cc2cc(Br)ccc2C1=O]

To methyl 4-bromo-2-(bromomethyl)benzoate (0.5 g, 1.6 mmol, Ark Pharm, #AK-26333) in acetonitrile (5.6 mL) was added tert-butyl(2-amino-2-cyclopropylethyl)carbamate (0.33 g, 1.6 mmol, Enamine, #EN300-84505), followed by boric acid (0.10 g, 1.6 mmol). $K_2CO_3$ (0.45 g, 3.3 mmol) was added portionwise over 2 minutes, and the reaction was stirred overnight. The reaction mixture was filtered, and the solid was washed with acetonitrile. The solvent was removed in vacuo, and the residue was purified via flash column chromatography, eluting with a gradient of 0-30% EtOAc in hexanes, to afford the title compound (0.30 g, 46%). LCMS for $C_{14}H_{16}BrN_2O_3$(M-tBu+H)$^+$: calculated monoisotopic m/z=339.0. found 339.1.

Step 2. 3-(4,4,5,5-Tetramethyl-1,3,2-dioxaborolan-2-yl)-6-(trifluoromethyl)imidazo[1,2-a]pyrazin-8-amine

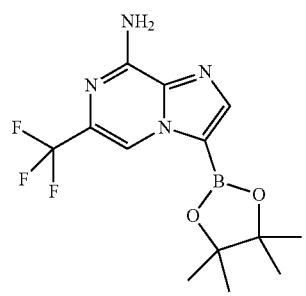 [SMILES: CC1(C)OB(c2cnc3c(N)nc(C(F)(F)F)cn23)OC1(C)C]

A degassed mixture of 3-bromo-6-(trifluoromethyl)imidazo[1,2-a]pyrazin-8-amine (0.40 g, 1.4 mmol, Affinity Research Chemicals, Inc. #ARI-0167), bis(pinacolato)diboron (430 mg, 1.7 mmol), KOAc (420 mg, 4.3 mmol), and dichloro[1,1'-bis(diphenylphosphino)ferrocene]palladium (II) dichloromethane adduct (46 mg, 0.057 mmol) in 1,4-dioxane (5.5 mL) was heated in the microwave at 110° C. overnight. Upon cooling to room temperature, the reaction mixture was filtered through Celite®, rinsing with EtOAc. The filtrate was concentrated to afford the crude product as a tan solid which was used without further purification.

Step 3. tert-Butyl (2-(5-(8-amino-6-(trifluoromethyl)imidazo[1,2-a]pyrazin-3-yl)-1-oxoisoindolin-2-yl)-2-cyclopropylethyl)carbamate (racemic mixture prepared)

A degassed mixture of 3-(4,4,5,5-tetramethyl-1,3,2-dioxaborolan-2-yl)-6-(trifluoromethyl)imidazo[1,2-a]pyrazin-8-amine (0.25 g, 0.76 mmol, crude from Step 2), tert-butyl (2-(5-bromo-1-oxoisoindolin-2-yl)-2-cyclopropylethyl)carbamate (0.10 g, 0.25 mmol, from Step 1), $Na_2CO_3$ (0.080 g, 0.76 mmol) and dichloro[1,1'-bis(diphenylphosphino)ferrocene]palladium (II) dichloromethane adduct (41 mg, 0.051 mmol) in THF (2.0 mL) and water (0.5 mL) was heated to 90° C. in a sealed vial for 1 hour. Upon cooling to room temperature, the reaction mixture was diluted with water and extracted with EtOAc (3×). The combined organic extracts were dried over $MgSO_4$, filtered and concentrated. The product was purified via flash column chromatography, eluting with a gradient from 0-100% EtOAc in hexanes, to afford the title compound (0.080 g, 61%). LCMS for $C_{15}H_{27}F_3N_6NaO_3$ (M+Na)$^+$: calculated m/z=539.2. found 539.2.

Example 42. 2-(2-Amino-1-cyclopropylethyl)-5-(8-amino-6-(trifluoromethyl)imidazo[1,2-a]pyrazin-3-yl)isoindolin-1-one, trifluoroacetate salt (racemic mixture prepared)

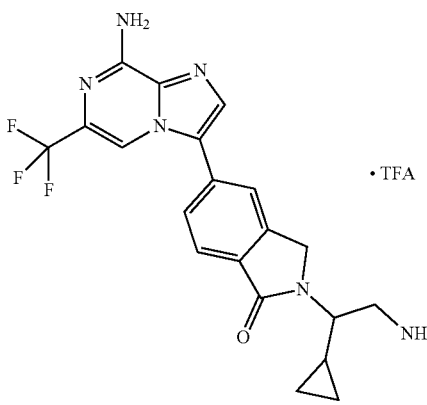

To a solution of tert-butyl (2-(5-(8-amino-6-(trifluoromethyl)imidazo[1,2-a]pyrazin-3-yl)-1-oxoisoindolin-2-yl)-2-cyclopropylethyl)carbamate (0.50 g, 0.097 mmol, from Example 41) in dioxane (1.0 mL) was added HCl (4.0 N in dioxane, 0.73 mL, 2.90 mmol), and the mixture was stirred for 2 h. Solvent was removed in vacuo to afford the title compound as the HCl salt (0.040 g). A portion of the material was purified via preparative HPLC-MS (pH=2) to afford the title compound. $^1$H NMR (400 MHz, DMSO-$d_6$) δ 8.12 (s, 1H), 8.01 (s, 1H), 7.95 (s, 1H), 7.89 (d, J=7.9 Hz, 1H), 7.83 (dd, J=7.8, 1.4 Hz, 1H), 7.81 (br s, 2H), 7.70 (br s, 2H), 4.70 (d, J=17.7 Hz, 1H), 4.64 (d, J=17.7 Hz, 1H), 3.74-3.63 (m, 1H), 3.43-3.11 (m, 2H), 1.32-1.19 (m, 1H), 0.76-0.65 (m, 1H), 0.59-0.42 (m, 2H), 0.33-0.21 (m, 1H). LCMS for $C_{20}H_{20}F_3N_6O$ (M+H)$^+$: calculated m/z=417.2. found 417.1.

Example 43. N-(2-(5-(8-Amino-6-(trifluoromethyl)imidazo[1,2-a]pyrazin-3-yl)-1-oxoisoindolin-2-yl)-2-cyclopropylethyl)methanesulfonamide, trifluoroacetate salt (racemic mixture prepared)

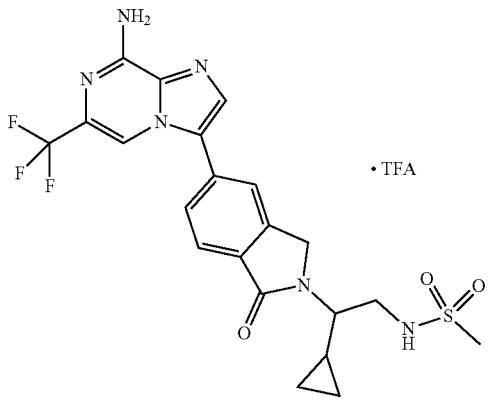 [SMILES: CS(=O)(=O)NCC(C1CC1)N1Cc2cc(-c3cnc4c(N)nc(C(F)(F)F)cn34)ccc2C1=O]

To a suspension of 2-(2-amino-1-cyclopropylethyl)-5-(8-amino-6-(trifluoromethyl)imidazo[1,2-a]pyrazin-3-yl)isoindolin-1-one, HCl salt (8.0 mg, 0.018 mmol, prepared as described in Example 42) in DCM (1.0 mL) was added triethylamine (7.4 µL, 0.053 mmol). The mixture was cooled to 0° C. and methanesulfonyl chloride (2.4 mg, 0.021 mmol) was added. The mixture was allowed to warm to room temperature. Solvent was removed in vacuo, and the crude product was dissolved in MeCN and MeOH and filtered. The product was purified via preparative HPLC-MS (pH=2) to afford the title compound (4.0 mg, 37%). $^1$H NMR (400 MHz, DMSO-$d_6$) δ 8.16 (s, 1H), 7.98-7.96 (m, 1H), 7.94 (s, 1H), 7.87 (d, J=7.8 Hz, 1H), 7.81 (dd, J=7.8, 1.4 Hz, 1H), 7.68 (s, 2H), 7.18 (t, J=6.3 Hz, 1H), 4.66 (s, 2H), 3.63-3.28 (m, 3H), 2.90 (s, 3H), 1.31-1.07 (m, 1H), 0.72-0.56 (m, 1H), 0.52-0.34 (m, 2H), 0.34-0.16 (m, 1H). LCMS for $C_{21}H_{22}F_3N_6O_3S$ (M+H)$^+$: calculated m/z=495.1. found 495.1.

Example 44. N-(2-(5-(8-Amino-6-(trifluoromethyl)imidazo[1,2-a]pyrazin-3-yl)-1-oxoisoindolin-2-yl)-2-cyclopropylethyl)acetamide, trifluoroacetate salt (racemic mixture prepared)

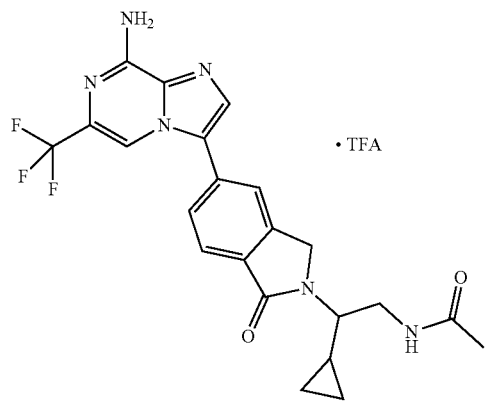 [SMILES: CC(=O)NCC(C1CC1)N1Cc2cc(-c3cnc4c(N)nc(C(F)(F)F)cn34)ccc2C1=O]

To a suspension of 2-(2-amino-1-cyclopropylethyl)-5-(8-amino-6-(trifluoromethyl)imidazo[1,2-a]pyrazin-3-yl)isoindolin-1-one, HCl salt (8.0 mg, 0.018 mmol, from Example 42) in DCM (1.0 mL) was added triethylamine (7.4 µl, 0.053 mmol) followed by acetyl chloride (1.6 mg, 0.021 mmol). After stirring for 1 hour, solvent was removed in vacuo, and the crude product was dissolved in MeCN and MeOH and filtered. The product was purified via preparative HPLC-MS (pH=2) to afford the title compound (3.0 mg, 27%). $^1$H NMR (400 MHz, DMSO-$d_6$) δ 8.16 (s, 1H), 7.97-7.95 (m, 1H), 7.94 (s, 1H), 7.92 (t, J=6.1 Hz, 1H), 7.85 (d, J=7.9 Hz, 1H), 7.79 (dd, J=7.9, 1.4 Hz, 1H), 7.68 (s, 2H), 4.70 (d, J=17.7 Hz, 1H), 4.62 (d, J=17.7 Hz, 1H), 3.77-3.65 (m, 1H), 3.58-3.40 (m, 2H), 1.71 (s, 3H), 1.23-1.08 (m, 1H), 0.71-0.60 (m, 1H), 0.47-0.36 (m, 2H), 0.25-0.14 (m, 1H). LCMS for $C_{22}H_{22}F_3N_6O_2$ (M+H)$^+$: calculated m/z=459.2. found 459.1.

Example 45. 2-(5-(8-Amino-6-(trifluoromethyl)imidazo[1,2-a]pyrazin-3-yl)-1-oxoisoindolin-2-yl)-2-cyclopropyl-N-methylacetamide, trifluoroacetate salt (racemic mixture prepared)

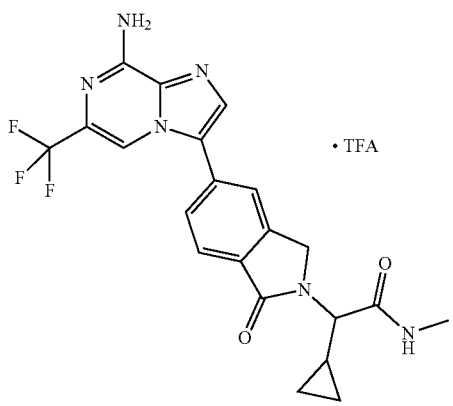 [SMILES: CNC(=O)C(C1CC1)N1Cc2cc(-c3cnc4c(N)nc(C(F)(F)F)cn34)ccc2C1=O]

Step 1. 4-bromo-2-(bromomethyl)benzoic acid

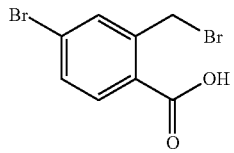

A solution of 4-bromo-2-methylbenzoic acid (0.30 g, 1.4 mmol, Aldrich #665126), NBS (250 mg, 1.4 mmol) and AIBN (11 mg, 0.070 mmol) in CCl$_4$ (10 mL) was heated to reflux for 6 h. The reaction mixture was filtered and purified via flash column chromatography, eluting with a gradient of 0-50% EtOAc in hexanes to afford the title compound (350 mg, 85%).

Step 2. 2-(5-Bromo-1-oxoisoindolin-2-yl)-2-cyclopropylacetic acid (racemic mixture)

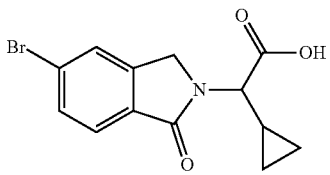 [SMILES: O=C(O)C(C1CC1)N1Cc2cc(Br)ccc2C1=O]

A mixture of 4-bromo-2-(bromomethyl)benzoic acid (0.050 g, 0.17 mmol, from Step 1) in DCM (3.0 mL) was treated with oxalyl chloride (0.016 mL, 0.13 mmol). A drop of DMF was added, and the reaction mixture was stirred for 1 h. Volatiles were removed in vacuo and the residue was dissolved in DCM (3.0 mL). Methyl 2-amino-2-cyclopropylacetate, HCl salt (28 mg, 0.17 mmol, Combi-Blocks #YC-1865) was added, and after stirring for 10 min, triethylamine (0.036 mL, 0.26 mmol) was added dropwise. Some hydrolysis of the ester occurred under the reaction conditions. After stirring overnight, the reaction mixture was concentrated and the product was used without purification in Step 3. LCMS for C$_{13}$H$_{13}$BrNO$_3$ (M+H)$^+$: calculated monoisotopic m/z=310.0. found 310.1.

Step 3. 2-(5-Bromo-1-oxoisoindolin-2-yl)-2-cyclopropyl-N-methylacetamide, trifluoroacetate salt (racemic mixture)

To a solution of 2-(5-bromo-1-oxoisoindolin-2-yl)-2-cyclopropylacetic acid (0.050 g, 0.16 mmol, crude product from Step 2) in DMF (3.0 mL) was added HATU (74 mg, 0.19 mmol) and DIEA (0.056 mL, 0.32 mmol), followed by methylamine (2.0 M in THF, Aldrich #395056, 6.0 µl, 0.012 mmol). After stirring for 1 h, the reaction was diluted with water and extracted with EtOAc. The organic layer was dried over MgSO$_4$, filtered and concentrated. Purification via preparative HPLC-MS (pH=2) provided the title compound (5 mg, 7% over 2 steps). LCMS for C$_{14}$H$_{16}$BrN$_2$O$_2$ (M+H)$^+$: calculated monoisotopic m/z=323.0. found 323.1.

Step 4. 2-(5-(8-Amino-6-(trifluoromethyl)imidazo[1,2-a]pyrazin-3-yl)-1-oxoisoindolin-2-yl)-2-cyclopropyl-N-methylacetamide, trifluoroacetate salt (racemic mixture prepared)

The procedure of Example 41, Step 3 was followed, using 2-(5-bromo-1-oxoisoindolin-2-yl)-2-cyclopropyl-N-methylacetamide, trifluoroacetate salt (5.0 mg, 0.015 mmol, racemic mixture prepared in Step 3) instead of tert-butyl (2-(5-bromo-1-oxoisoindolin-2-yl)-2-cyclopropylethyl)carbamate. Purification via preparative HPLC-MS (pH=2) afforded the title compound (2.0 mg, 23%). LCMS for C$_{21}$H$_{20}$F$_3$N$_6$O$_2$ (M+H)$^+$: calculated m/z=445.2. found 445.1.

Example 46. 5-(8-Amino-6-(trifluoromethyl)imidazo[1,2-a]pyrazin-3-yl)-2-(1-cyclopropyl-2-hydroxyethyl)isoindolin-L-one, trifluoroacetate salt (racemic mixture prepared)

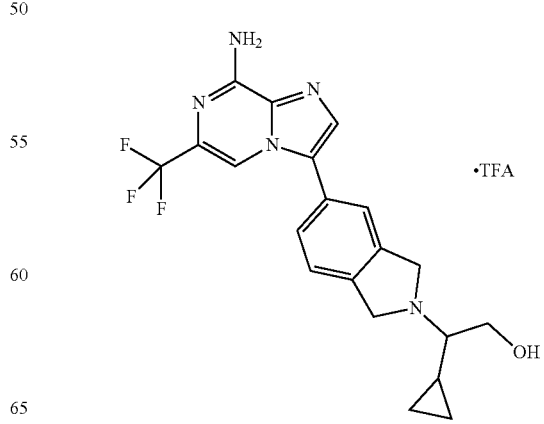

Step 1. 5-Bromo-2-(1-cyclopropyl-2-hydroxyethyl) isoindolin-1-one (racemic mixture prepared)

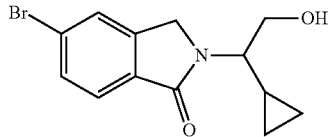 [SMILES: O=C1c2ccc(Br)cc2CN1C(CO)C1CC1]

To a mixture of methyl 4-bromo-2-(bromomethyl)benzoate (0.020 g, 0.065 mmol, Ark Pharm #AK-26333) and 2-amino-2-cyclopropylethan-1-ol, HCl salt (13 mg, 0.097 mmol, Enamine #EN300-77885) in toluene (2.0 mL) was added triethylamine (0.018 mL, 0.13 mmol). The mixture was heated at 110° C. overnight. Solvent was removed in vacuo and the product was used in Step 2 without further purification. LCMS for $C_{13}H_{15}BrNO_2$ (M+H)$^+$: calculated monoisotopic m/z=296.0. found 296.0.

Step 2. 5-(8-Amino-6-(trifluoromethyl)imidazo[1,2-a]pyrazin-3-yl)-2-(1-cyclopropyl-2-hydroxyethyl) isoindolin-1-one, trifluoroacetate salt (racemic mixture prepared)

The procedure of Example 41, Step 3 was followed, using 5-bromo-2-(1-cyclopropyl-2-hydroxyethyl)isoindolin-1-one (0.010 g, 0.034 mmol, racemic mixture prepared in Step 1) instead of tert-butyl (2-(5-bromo-1-oxoisoindolin-2-yl)-2-cyclopropylethyl)carbamate. Purification via preparative HPLC-MS (pH=2) afforded the title compound (4.0 mg, 28%). $^1$H NMR (400 MHz, DMSO-d$_6$) δ 8.18 (s, 1H), 7.97-7.95 (m, 1H), 7.94 (s, 1H), 7.85 (d, J=7.9 Hz, 1H), 7.79 (dd, J=7.9, 1.5 Hz, 1H), 7.67 (br s, 2H), 4.72 (d, J=18.2 Hz, 1H), 4.67 (d, J=18.2 Hz, 1H), 3.79-3.68 (m, 2H), 3.52-3.44 (m, 1H), 1.24-1.12 (m, 1H), 0.66-0.52 (m, 1H), 0.49-0.36 (m, 2H), 0.32-0.14 (m, 1H). $^{19}$F NMR (376 MHz, DMSO-d$_6$) δ −66.55 (s), −74.26 (s). LCMS for $C_{20}H_{19}F_3N_5O_2$ (M+H)$^+$: calculated m/z=418.1. found 418.1.

Example 47. 2-(5-(8-Amino-6-(trifluoromethyl) imidazo[1,2-a]pyrazin-3-yl)-1-oxoisoindolin-2-yl)-2-cyclopropylacetic acid, trifluoroacetate salt (racemic mixture prepared)

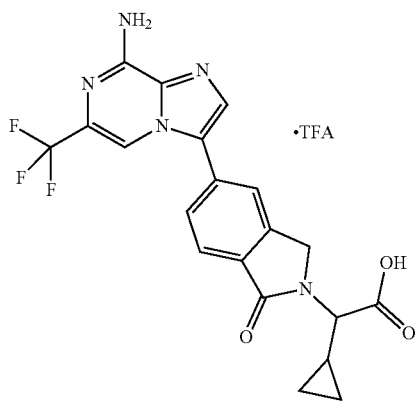 [SMILES: Nc1nc(C(F)(F)F)cn2c(-c3ccc4c(c3)CN(C(C(=O)O)C3CC3)C4=O)cnc12]

Step 1. Methyl 2-(5-bromo-1-oxoisoindolin-2-yl)-2-cyclopropylacetate (racemic mixture prepared)

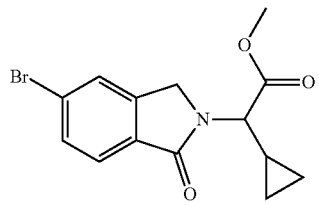 [SMILES: COC(=O)C(C1CC1)N1Cc2cc(Br)ccc2C1=O]

To a mixture of methyl 4-bromo-2-(bromomethyl)benzoate (0.020 g, 0.065 mmol, Ark Pharm #AK-26333) and methyl 2-amino-2-cyclopropylacetate, HCl salt (16 mg, 0.097 mmol, Combi-Block #YC-1865) in toluene (1.0 mL) was added triethylamine (0.027 mL, 0.20 mmol), and the reaction mixture was heated at 110° C. for 4 h, then was stirred at room temperature over three nights. Solvent was removed in vacuo, and the product was purified via flash column chromatography, eluting with a gradient from 0-80% EtOAc in hexanes to afford the title compound (15 mg, 71%). LCMS for $C_{14}H_{15}BrNO_3$ (M+H)$^+$: calculated monoisotopic m/z=324.0. found 324.1.

Step 2. 2-(5-(8-Amino-6-(trifluoromethyl)imidazo [1,2-a]pyrazin-3-yl)-1-oxoisoindolin-2-yl)-2-cyclopropylacetic acid, trifluoroacetate salt (racemic mixture prepared)

The procedure of Example 41, Step 3 was followed, using methyl 2-(5-bromo-1-oxoisoindolin-2-yl)-2-cyclopropylacetate (0.010 g, 0.031 mmol, racemic mixture prepared in Step 1) instead of tert-butyl (2-(5-bromo-1-oxoisoindolin-2-yl)-2-cyclopropylethyl)carbamate. The ester was hydrolyzed to the carboxylic acid under the reaction conditions. Purification via preparative HPLC-MS (pH=2) afforded the title compound (6.0 mg, 35%). $^1$H NMR (400 MHz, DMSO-d$_6$) δ 8.22 (s, 1H), 7.98 (s, 1H), 7.95 (s, 1H), 7.88 (d, J=7.9 Hz, 1H), 7.82 (dd, J=8.0, 1.4 Hz, 1H), 7.68 (br s, 2H), 4.80 (s, 2H), 4.02 (d, J=10.1 Hz, 1H), 1.52-1.35 (m, 1H), 0.85-0.72 (m, 1H), 0.71-0.64 (m, 1H), 0.64-0.53 (m, 1H), 0.35-0.20 (m, 1H). LCMS for $C_{20}H_{17}F_3N_5O_3$ (M+H)$^+$: calculated m/z=432.1. found 432.1.

Example A. THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, VA) and maintained in RPMI with 10% FBS (Gibco/Life Technologies, Carlsbad, CA). For the assay, THP-1 cells are serum starved overnight in RPMI, then plated in RPMI (2×10$^5$ cells/well in 90 μL) into 96-well flat-bottom tissue culture treated plates (Corning, Corning, NY), in the presence or absence of a concentration range of test compounds. Covered plates are incubated for 2 hours at 37° C., 5% CO$_2$ then treated with or without 10 nM MCP-1 (MYBioSource, San Diego, CA) for 15 minutes at 37° C., 5% CO$_2$. Plates are centrifuged at 1600 RPM and supernatants are removed. Cells are lysed in Lysis Buffer (Cell Signaling, Danvers, MA) with Protease Inhibitor (Calbiochem/EMD, Germany), PMSF (Sigma, St Louis MO), HALTS (Thermo Fisher, Rockford, IL) for 30 min on wet ice. Cell lysates are frozen at −80° C. before testing. The lysates are tested in the Human/Mouse/Rat Phospho-RPS6 ELISA (R&D Systems, Inc. Minn, MN). The plate is measured using a microplate reader (SpectraMax M5—Molecular Devices, LLC Sunnyvale, CA) set to 450 nm with a wavelength correction of 540. $IC_{50}$ determination is performed by fitting the curve of inhibitor percent inhibition versus the log of the inhibitor concentration using the GraphPad Prism 5.0 software.

Example B. PI3K-γ Scintillation Proximity Assay

Materials: [γ-$^{33}$P]ATP (10 mCi/mL) and Wheat Germ Agglutinin (WGA) YSi SPA Scintillation Beads was purchased from Perkin Elmer (Waltham, MA). Lipid kinase substrate, D-myo-Phosphatidylinositol 4,5-bisphosphate (PtdIns(4,5)P2)D (+)-sn-1,2-di-O-octanoylglycerol, 3-O-phospho linked (PIP2), CAS 204858-53-7, was purchased from Echelon Biosciences (Salt Lake City, UT). PI3Kγ (p110γ) Recombinant Human Protein was purchased from Life technology (Grand Island, NY). ATP, $MgCl_2$, DTT, EDTA, MOPS and CHAPS were purchased from Sigma Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P]ATP, 13 nM PI3Kγ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). $IC_{50}$ determination was performed by fitting the curve of percent of the solvent control activity versus the log of the inhibitor concentration using the GraphPad Prism 6.0 software.

Example C. PI3Kδ Scintillation Proximity Assay

Materials: [γ-$^{33}$P]ATP (10 mCi/mL) and Wheat Germ Agglutinin (WGA) YSi SPA Scintillation Beads was purchased from Perkin Elmer (Waltham, MA). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, UT). PI3Kδ (p110δ/p85α) Recombinant Human Protein was purchased from Eurofins (St Charles, MO). ATP, $MgCl_2$, DTT, EDTA, MOPS and CHAPS were purchased from Sigma Aldrich (St. Louis, MO).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 3.4 nM PI3Kδ. Reactions were incubated for 120 min and terminated by the addition of 40 μL SPA beads suspended in quench buffer: 163 mM potassium phosphate pH 7.8, 2000 glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (PerkinElmer). $IC_{50}$ determination was performed by fitting the curve of percent of the solvent control activity versus the log of the inhibitor concentration using the GraphPad Prism 6.0 software.

The compounds of the Examples were tested in the assays described in Examples A, B and C and found to have the $IC_{50}$s are shown in Table A.

TABLE A

| Ex. No. | PI3Kγ $IC_{50}$ (nM) | PI3Kδ $IC_{50}$ (nM) | PI3Kγ_THP1_RPS6_ELISA $IC_{50}$ (nM) |
|---|---|---|---|
| 1 | + | +++ | #### |
| 2 | + | ++ | #### |
| 3 | + | +++ | #### |
| 4 | +++ | +++ | NA |
| 5 | + | ++++ | #### |
| 6 | + | ++++ | #### |
| 7 | + | ++ | #### |
| 8 | + | ++ | ### |
| 9 | ++ | +++ | NA |
| 10 | ++ | +++ | NA |
| 11 | + | ++++ | NA |
| 12 | + | ++ | #### |
| 13 | + | ++++ | #### |
| 14 | + | ++++ | #### |
| 15 | + | ++ | #### |
| 16 | + | ++ | #### |
| 17 | + | +++ | ### |
| 18 | + | ++++ | #### |
| 19 | ++ | ++++ | NA |
| 20 | ++ | ++++ | NA |
| 21 | ++ | ++++ | NA |
| 22 | ++ | ++++ | NA |
| 23 | ++ | ++++ | NA |
| 24 | +++ | ++++ | NA |
| 25 | + | ++++ | #### |
| 26 | + | ++++ | NA |
| 27 | + | ++++ | NA |
| 28 | + | ++ | ## |
| 29 | + | ++ | ### |
| 29a | + | +++ | #### |
| 29b | + | ++ | ### |
| 29c | + | ++ | ### |
| 29d | + | ++ | ### |
| 30 | + | ++++ | NA |
| 31 | + | ++++ | #### |
| 32 | + | ++++ | #### |
| 33 | + | + | ## |
| 34 | + | + | # |
| 35 | + | ++ | ## |
| 36 | + | ++ | ## |
| 37 | + | ++ | ### |
| 38 | + | ++ | #### |
| 39 | + | +++ | #### |
| 40 | + | +++ | #### |
| 41 | ++ | ++++ | NA |
| 42 | +++ | ++++ | NA |
| 43 | +++ | ++++ | NA |

TABLE A-continued

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 44 | +++ | ++++ | NA |
| 45 | +++ | ++++ | NA |
| 46 | ++ | ++++ | NA |
| 47 | +++ | ++++ | NA |

+ refers to IC$_{50}$ of ≤100 nM;
++ refers to IC$_{50}$ of ≤500 nM;
+++ refers to an IC$_{50}$ of <2000 nM;
++++ refers to an IC$_{50}$ of ≥2000 nM.
# refers to IC$_{50}$ of ≤100 nM;
## refers to IC$_{50}$ of ≤500 nM;
### refers to IC$_{50}$ of <1000 nM;
#### refers to an IC$_{50}$ of ≥1000 nM.
NA refers to data not available.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a disease or disorder in a patient, wherein said disease or disorder is associated with abnormal expression or activity of PI3Kγ kinase, wherein the disease or disorder is lung cancer, melanoma, pancreatic cancer, breast cancer, prostate cancer, liver cancer, colon cancer, endometrial cancer, bladder cancer, skin cancer, cancer of the uterus, renal cancer, gastric cancer, seminoma, teratocarcinoma, astrocytoma, neuroblastoma, glioma, sarcoma, acute myeloid leukemia, acute monocytic leukemia, small lymphocytic lymphoma, chronic lymphocytic leukemia (CLL), chronic myelogenous leukemia (CML), multiple myeloma, T-cell acute lymphoblastic leukemia (T-ALL), cutaneous T-cell lymphoma, large granular lymphocytic leukemia, mature (peripheral) t-cell neoplasm (PTCL), anaplastic large cell lymphoma (ALCL), lymphoblastic lymphoma, Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xeroderma pigmentosum, keratoacanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smoldering myeloma (aka asymptomatic myeloma), monoclonal gammopathy of undetermined significance (MGUS), diffuse large B cell lymphoma, rheumatoid arthritis, multiple sclerosis, systemic lupus erythematous, asthma, allergy, allergic rhinitis, pancreatitis, psoriasis, anaphylaxis, glomerulonephritis, inflammatory bowel disease, thrombosis, meningitis, encephalitis, diabetic retinopathy, benign prostatic hypertrophy, myasthenia gravis, Sjögren's syndrome, osteoarthritis, restenosis, atherosclerosis, autoimmune hemolytic anemia, systemic lupus erythematosus, lupus nephritis, or pemphigus, the method comprising administering to said patient a therapeutically effective amount of a compound of Formula (IIu):

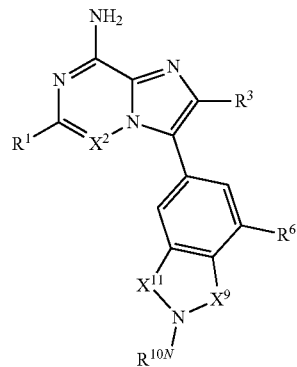

or a pharmaceutically acceptable salt thereof; wherein:
$X^2$ is N or $CR^2$;
$R^2$ is selected from H, D, halo, CN, OH, $NH_2$, $C_{1-6}$ alkyl, $C_{2-6}$ alkenyl, $C_{2-6}$ alkynyl, $C_{1-6}$ haloalkyl, and $C_{3-7}$ cycloalkyl;
provided that:
(a) when $X^2$ is N, then $R^1$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, and $NR^{c1}C(O)NR^{c1}R^{d1}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{1A}$ substituents; or
(b) when $X^2$ is $CR^2$, then $R^1$ is selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, and $NR^{c1}C(O)NR^{c1}R^{d1}$ wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{16}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^{1A}$ substituents;
each $R^{a1}$, $R^{b1}$, $R^{c1}$, and $R^{d1}$ is independently selected from H, $C_{1-6}$ alkyl, $C_{1-6}$ haloalkyl, $C_2$-6 alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a1}$, $R^{b1}$, $R^{c1}$ and $R^{d1}$ are each optionally substituted with 1, 2, 3, 4, 5, 6, 7, or 8 independently selected $R^{1A}$ substituents;

or, any $R^{c1}$ and $R^{d1}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{1A}$ substituents;

each $R^{1A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, and $NR^{c11}C(O)NR^{c11}R^{d11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^M$ substituents;

each $R^{a11}$, $R^{b11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{b11}$, $R^{c11}$ and $R^{d11}$ are each optionally substituted with 1, 2, 3, 4, 5, 6, 7, or 8 independently selected $R^M$ substituents;

or, any $R^{c11}$ and $R^{d11}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^M$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-6}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^3$ is selected from H, D, halo, CN, OH, $NH_2$, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkylamino, di($C_{1-6}$ alkyl)amino, and $C(O)NR^{a3}R^{b3}$;

each $R^{a3}$ and $R^{b3}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a3}$ and $R^{b3}$ are each optionally substituted with 1, 2, 3 or 4 independently selected $R^M$ substituents;

or, any $R^{a3}$ and $R^{b3}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{d6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NOH)R^{b6}$, $C(=NCN)R^{b6}$, $C(=NR^{e6})NR^{c6}R^{d6}$, $NR^{c6}C(=NR^{e6})NR^{c6}R^{d6}$, $NR^{c6}C(=NOH)NR^{c6}R^{d6}$, $NR^{c6}C(=NCN)NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $S(O)(=NR^{e6})R^{b6}$, $OS(O)(=NR^{e6})R^{b6}$, $OS(O)_2R^{b6}$, and $SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, 4, 5, 6, 7, or 8 independently selected $R^{6A}$ substituents;

or, any $R^{c6}$ and $R^{d6}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{6A}$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NR^{e61})R^{b61}$, $C(=NOH)R^{b61}$, $C(=NCN)R^{b61}$, $C(=NR^{e61})NR^{c61}R^{d61}$, $NR^{c61}C(=NR^{e61})NR^{c61}R^{d61}$, $NR^{c61}C(=NOH)NR^{c61}R^{d61}$, $NR^{c61}C(=NCN)NR^{c61}R^{d61}$, $NR^{c61}C(=NR^{e61})R^{b61}$, $NR^{c61}S(O)NR^{c61}R^{d61}$, $NR^{c61}S(O)R^{b61}$, $NR^{c61}S(O)_2R^{b61}$, $NR^{61}S(O)(=NR^{e61})R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, $S(O)(=NR^{e61})R^{b61}$, $OS(O)(=NR^{e61})R^{b61}$, $OS(O)_2R^{b61}$, and $SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{6A}$ are each optionally substituted with 1, 2, 3, 4, 5, 6, 7, or 8 independently selected $R^M$ substituents;

each $R^{a61}$ $R^{b61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a61}$, $R^{b6}$, $R^{c61}$ and $R^{d61}$ are each optionally substituted with 1, 2, 3, 4, 5, 6, 7, or 8 independently selected $R^M$ substituents;

or, any $R^{c61}$ and $R^{d61}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^M$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

$X^9$ is $NR^{9N}$, or $C(R^9)_2$;

$X^{11}$ is $NR^{11N}$, or $C(R^{11})_2$;

$R^{9N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b9N}$, $C(O)NR^{c9N}R^{d9N}$, $C(O)OR^{a9N}$, $C(=NR^{e9N})R^{b9N}C(=NR^{e9N})NR^{c9N}R^{d9N}$, $C(=NCN)NR^{c9N}R^{d9N}$, $C(=NOR^{a9N})NR^{c9N}$, $S(O)_2R^{b9N}$, $S(O)(=NR^{9N})R^{d9N}$, and $S(O)_2NR^{e9N}R^{d9N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{9N}$ are each optionally substituted with 1, 2, 3, 4, 5, 6, 7, or 8 independently selected $R^{9NA}$ substituents;

each $R^{a9N}$, $R^{b9N}$, $R^{c9N}$, and $R^{d9N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a9N}$, $R^{b9N}$, $R^{c9N}$, and $R^{d9N}$ are each optionally substituted with 1, 2, 3, 4, 5, 6, 7, or 8 independently selected $R^{9NA}$ substituents;

or, any $R^{e9N}$ and $R^{d9N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9NA}$ substituents;

each $R^{e9N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{9NA}$ is selected from H, D, halo, $C_{1-6}$ alkyl, $C_{1-6}$ haloalkyl, $C_{2-6}$ alkenyl, $C_{2-6}$ alkynyl, phenyl, C3.7 cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a9N2}$, $SR^{a9N2}$, $NHOR^{a9N2}$, $C(O)R^{b9N2}$, $C(O)NR^{9N2}R^{d9N2}$, $C(O)NR^{c9N2}(OR^{a9N2})$, $C(O)OR^{a9N2}$, $OC(O)R^{b9N2}$, $OC(O)NR^{9N2}R^{d9N2}$, $NR^{c9N2}R^{d9N2}$, $NR^{c9N2}NR^{c9N2}R^{d9N2}$, $NR^{c9N2}C(O)R^{b9N2}$, $NR^{e9N2}C(O)OR^{a9N2}$ and $NR^{c9N2}C(O)NR^{9N2}R^{d9N2}$ wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9NA}$ are each optionally substituted with 1, 2, 3, or 4 independently selected $R^M$ substituents;

each $R^{a9N2}$, $R^{b9N2}$, $R^{c9N2}$, and $R^{d9N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, C3.7 cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a9N2}$, $R^{b9N2}$ $R^{c9N2}$ and $R^{d9N2}$ are each optionally substituted with 1, 2, 3, or 4 independently selected $R^M$ substituents;

or, any $R^{c9N2}$ and $R^{d9N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^9$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c691}R^{d91}$, $NR^{c91}C(O)R^{b91}$, $NR^{c91}C(O)OR^{a91}$ and $NR^{c91}C(O)NR^{c91}R^{d91}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^9$ are each optionally substituted with 1, 2, 3, 4, 5, 6, 7, or 8 independently selected $R^{9A}$ substituents;

or, alternatively, two $R^9$ groups together form an oxo group;

each $R^{a91}$, $R^{b91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a91}$, $R^{b91}$, $R^{c91}$ and $R^{d91}$ are each optionally substituted with 1, 2, 3, 4, 5, 6, 7, or 8 independently selected $R^{9A}$ substituents;

or, any $R^{c91}$ and $R^{d91}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{9A}$ substituents;

each $R^{9A}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, and $NR^{c92}C(O)NR^{c92}R^{d92}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{9A}$ are each optionally substituted with 1, 2, 3, or 4 independently selected $R^M$ substituents;

each $R^{a92}$, $R^{b92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a92}$, $R^{b92}$, $R^{c92}$ and $R^{d92}$ are each optionally substituted with 1, 2, 3, or 4 independently selected $R^M$ substituents;

or, any $R^{c92}$ and $R^{d92}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{10N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b10N}$, $C(O)NR^{10N}R^{d10N}$, $C(O)OR^{a10N}$, $C(=NR^{e10N})R^{b10N}$, $C(=NR^{e10N})NR^{c10N}R^{d10N}$, $C(=NCN)NR^{c10N}R^{d10N}$, $C(=NOR^{a10N})NR^{c10N}$, $S(O)_2R^{b10N}$, $S(O)(=NR^{c10N})R^{d10N}$, and $S(O)_2NR^{c10N}R^{d10N}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{10N}$ are each optionally substituted with 1, 2, 3, 4, 5, 6, 7, or 8 independently selected $R^{10NA}$ substituents;

each $R^{a10N}$, $R^{b10N}$, $R^{c10N}$, and $R^{d10N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a10N}$, $R^{b10N}$, $R^{c10N}$, and $R^{d10N}$ are each optionally substituted with 1, 2, 3, 4, 5, 6, 7, or 8 independently selected $R^{10NA}$ substituents;

or, any $R^{c10N}$ and $R^{d10N}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{10NA}$ substituents;

each $R^{e10N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{10NA}$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a10N2}$, $SR^{a10N2}$, $NHOR^{a10N2}$, $C(O)R^{b10N2}$, $C(O)NR^{c10N2}R^{d10N2}$, $C(O)NR^{c10N2}(OR^{a10N2})$, $C(O)OR^{a10N2}$, $OC(O)R^{b10N2}$, $OC(O)NR^{c10N2}R^{d10N2}$, $NR^{c10N2}R^{d10N2}$, $NR^{c10N2}R^{c10N2}R^{c10N2}R^{d10N2}$, $NR^{c10N2}C(O)R^{b10N2}$, $NR^{e10N2}C(O)OR^{a10N2}$, $NR^{c10N2}C(O)NR^{c10N2}R^{d10N2}$, and $NR^{c10N2}S(O)_2R^{b10N2}$ wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{10}NA$ are each optionally substituted with 1, 2, 3, or 4 independently selected $R^M$ substituents;

each $R^{a10N2}$, $R^{b10N2}$, $R^{c10N2}$, and $R^{d10N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a10N2}$, $R^{b10N2}$, $R^{c10N2}$ and $R^{d10N2}$ are each optionally substituted with 1, 2, 3, or 4 independently selected $R^M$ substituents;

or, any $R^{c10N2}$ and $R^{d10N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

$R^{11N}$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b11N}$, $C(O)NR^{c11N}R^{d11N}$, $C(O)OR^{a11N}$, $C(=NR^{e11N})R^{b11N}$, $C(=NR^{e11N})NR^{c11N}R^{d11N}$, $C(=NCN)NR^{c11N}R^{d11N}$, $C(=NOR^{a11N})NR^{c11N}$ $S(O)_2R^{b11N}$, $S(O)(=NR^{c11N})R^{d11N}$ and $S(O)_2NR^{c11N}R^{d11N}$ wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl- of $R^{11N}$ are each optionally substituted with 1, 2, 3, 4, 5, 6, 7, or 8 independently selected $R^{11NA}$ substituents;

each $R^{a11N}$, $R^{b11N}$, $R^{c11N}$, and $R^{d11N}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11N}$, $R^{b11N}$, $R^{c11N}$, and $R^{d11N}$ are each optionally substituted with 1, 2, 3, 4, 5, 6, 7, or 8 independently selected $R^{11NA}$ substituents;

or, any $R^{c11N}$ and $R^{d11N}$ attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11NA}$ substituents;

each $R^{e11N}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{11NA}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a11N2}$, $SR^{a11N2}$, $NHOR^{a11N2}$, $C(O)R^{b11N2}$, $C(O)NR^{c11N2}R^{d11N2}$, $C(O)NR^{c11N2}(OR^{a11N2})$, $C(O)OR^{a11N2}$, $OC(O)R^{b11N2}$, $OC(O)NR^{c11N2}R^{d11N2}$, $NR^{c11N2}R^{d11N2}$, $NR^{c11N2}NR^{c11N2}R^{d11N2}$, $NR^{c11N2}C(O)R^{b11N2}$, $NR^{c11N2}C(O)OR^{a11N2}$ and $NR^{c11N2}C(O)NR^{c11N2}R^{d11N2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11NA}$ are each optionally substituted with 1, 2, 3, or 4 independently selected $R^M$ substituents;

each $R^{a11N2}$, $R^{b11N2}$, $R^{c11N2}$, and $R^{d11N2}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a11N2}$, $R^{b11N2}$, $R^{c11N2}$ and $R^{d11N2}$ are each optionally substituted with 1, 2, 3, or 4 independently selected $R^M$ substituents;

or, any $R^{c11N2}$ and $R^{d11N2}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents;

each $R^{11}$ is independently selected from H, D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a111}$, $SR^{a111}$, $NHOR^{a111}$, $C(O)R^{b111}$, $C(O)NR^{c111}R^{d111}$, $C(O)NR^{c111}(OR^{a111})$, $C(O)OR^{a111}$, $OC(O)R^{b111}$, $OC(O)NR^{c111}R^{d111}$, $NR^{c111}R^{d111}$, $NR^{c111}NR^{c111}R^{d111}$, $NR^{c111}C(O)R^{b111}$, $NR^{c111}C(O)OR^{a111}$, and $NR^{c111}C(O)NR^{c111}R^{d111}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{11}$ are each optionally substituted with 1, 2, 3, 4, 5, 6, 7, or 8 independently selected $R^{11A}$ substituents;

each $R^{a111}$, $R^{b111}$, $R^{c111}$, and $R^{d111}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a111}$, $R^{b111}$, $R^{c111}$ and $R^{d111}$ are each optionally substituted with 1, 2, 3, 4, 5, 6, 7, or 8 independently selected $R^{11A}$ substituents;

or, any $R^{c111}$ and $R^{d111}$, attached to the same N atom, together with the N atom to which they are attached, form a 5-10 membered heteroaryl group or a 4-10 membered heterocycloalkyl group, wherein the 5-10 membered heteroaryl group or 4-10 membered heterocycloalkyl group is optionally substituted with 1, 2, 3, 4, 5, 6, 7, or 8 independently selected $R^{11A}$ substituents; and each $R^{11A}$ is independently selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a112}$, $SR^{a112}$, $NHOR^{a112}$, $C(O)R^{b112}$, $C(O)NR^{c112}R^{d112}$, $C(O)NR^{c112}(OR^{a112})$, $C(O)OR^{a112}$, $OC(O)R^{b112}$, $OC(O)NR^{c112}R^{d112}$, $NR^{c112}R^{d112}$, $NR^{c112}NR^{c112}R^{d112}$, $NR^{c112}C(O)R^{b112}$, $NR^{c112}C(O)OR^{a112}$, and $NR^{c112}C(O)NR^{c112}R^{d112}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{11A}$ are each optionally substituted with 1, 2, 3, or 4 independently selected $R^M$ substituents; and each $R^{a112}$, $R^{b112}$, $R^{c112}$, and $R^{d112}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a112}$, $R^{b112}$, $R^{c112}$ and $R^{d112}$ are each optionally substituted with 1, 2, 3, or 4 independently selected $R^M$ substituents;

or, any $R^{c112}$ and $R^{d112}$, attached to the same N atom, together with the N atom to which they are attached, form a 5-6 membered heteroaryl group or a 4-7 membered heterocycloalkyl group, wherein the 5-6 membered heteroaryl group or 4-7 membered heterocycloalkyl group is optionally substituted with 1, 2, 3, or 4 independently selected $R^M$ substituents.

2. The method of claim 1, wherein $X^2$ is N.

3. The method of claim 2, wherein $R^1$ is H.

4. The method of claim 1, wherein $X^2$ is $CR^2$.

5. The method of claim 4, wherein $R^2$ is selected from H, D, and $C_{1-6}$ alkyl.

6. The method of claim 4, wherein $R^1$ is selected from D, halo, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}C(O)R^{b1}$, $NR^{c1}C(O)OR^{a1}$, $NR^{c1}C(O)NR^{c1}R^{d1}$ and 5-6 membered heteroaryl, wherein the $C_{1-6}$ alkyl and 5-6 membered heteroaryl are optionally substituted with 1 or 2 independently selected $R^{1A}$ substituents.

7. The method of claim 4, wherein each $R^{a1}$, $R^{b1}$, $R^{c1}$, and $R^{d1}$ is independently selected from H, $C_{1-6}$ alkyl, $C_{1-6}$ haloalkyl, $C_{3-6}$ cycloalkyl, and 4-6 membered heterocycloalkyl wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{1A}$ substituents.

8. The method of claim 4, wherein $R^1$ is selected from $CF_3$, isopropylcarbamoyl, (tetrahydro-2H-pyran-4-yl)carbamoyl, azetidine-1-carbonyl, bicyclo[1.1.1]pentan-1-ylcarbamoyl, 3,3-dimethylazetidine-1-carbonyl, 3,3-difluoroazetidine-1-carbonyl, 3-hydroxyazetidine-1-carbonyl, (3-hydroxycyclobutyl)carbamoyl, (3-hydroxytetrahydro-2H-pyran-4-yl)carbamoyl, 2-methylthiazol-5-yl, 1-methyl-1H-pyrazol-4-yl, 1-methyl-1H-pyrazol-5-yl, 5-methyl-1H-pyrazol-4-yl, and 1H-pyrazol-4-yl.

9. The method of claim 1, wherein $R^3$ is H.

10. The method of claim 1, wherein $R^6$ is selected from H, D, halo, $C_{1-6}$ alkyl, $C_{1-6}$ haloalkyl, $C_{2-6}$ alkenyl, $C_{2-6}$ alkynyl, $SR^{a6}$, $C(O)R^{b6}$, $S(O)R^{b6}$, $S(O)NR^{c6}R^{d6}$, $S(O)_2R^{b6}$, and $S(O)_2NR^{c6}R^{d6}$, wherein the $C_{1-6}$ alkyl, $C_{2-6}$ alkenyl, and $C_{2-6}$ alkynyl are each optionally substituted with 1, 2 or 3 independently selected $R^{6A}$ substituents.

11. The method of claim 1 wherein $R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 independently selected $R^{6A}$ substituents;

$R^{a6}$ and $R^{b6}$ are each independently selected from H and $C_{1-6}$ alkyl; and each $R^{6A}$ is selected from halo, OH, and $C_{1-6}$ haloalkyl.

12. The method of claim 1, wherein $R^6$ is selected from H, chloro, methyl, $SCH_3$, $S(O)_2CH_3$, $C(O)CH_3$, $CH(CH_3)OH$, $C(CH_3)_2OH$, and 1,1,1-trifluoro-2,3-dihydroxypropan-2-yl.

13. The method of claim 1, wherein $X^9$ is $C(R^9)_2$.

14. The method of claim 1, wherein two $R^9$ groups together form an oxo group.

15. The method of claim 1, wherein $R^{10N}$ is selected from H, $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl- and (4-6 membered heterocycloalkyl)-

$C_{1-6}$ alkyl- of $R^{10N}$ are each optionally substituted with 1 or 2 independently selected $R^{10NA}$ substituents.

16. The method of claim 1, or a pharmaceutically acceptable salt thereof, wherein $R^{10N}$ is selected from H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- of $R^{10N}$ are each optionally substituted with 1 or 2 independently selected $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl.

17. The method claim 1, wherein $R^{10N}$ is selected from H, ethyl, isopropyl, 1-phenylethyl, 1-cyclopropylethyl, 2-((tert-butoxycarbonyl)amino)-1-cyclopropylethyl, 2-amino-1-cyclopropylethyl, 1-cyclopropyl-2-(methylsulfonamido)ethyl, 2-acetamido-1-cyclopropylethyl, 1-cyclopropyl-2-(methylamino)-2-oxoethyl, 1-cyclopropyl-2-hydroxyethyl, and carboxy(cyclopropyl)methyl.

18. The method claim 1, wherein $X^{11}$ is $C(R^{11})_2$.

19. The method of claim 1, wherein each $R^{11}$ is independently selected from H, D, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl with 1 or 2 independently selected $R^{11A}$ substituents.

20. The method of claim 1, wherein $X^{11}$ is $CH_2$.

21. The method of claim 1, wherein:
$R^1$ is selected from H, $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, $NR^{c1}C(O)NR^{c1}R^{d1}$ and 5-6 membered heteroaryl, wherein the $C_{1-6}$ alkyl, and 5-6 membered heteroaryl are each optionally substituted with 1 or 2 independently selected $R^{1A}$ substituents;
each $R^{a1}$, $R^{b1}$, $R^{c1}$, and $R^{d1}$ is independently selected from H, $C_{1-6}$ alkyl, $C_{1-6}$ haloalkyl, $C_{3-6}$ cycloalkyl, and 4-6 membered heterocycloalkyl wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{1A}$ substituents;
or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;
each $R^{1A}$ is independently selected from halo, $C_{1-6}$ alkyl, and OH;
$X^2$ is N;
$R^3$ is selected from H, D, and $C_{1-6}$ alkyl;
$R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 $R^{6A}$ substituents independently selected from halo, OH, and $C_{1-6}$ haloalkyl;
$R^{a6}$ and $R^{b6}$ are selected from H, $C_{1-6}$ alkyl, $C_{1-6}$ haloalkyl, $C_{2-6}$ alkenyl, and $C_{2-6}$ alkynyl;
$X^9$ is $C(O)$;
$X^{11}$ is $C(R^{11})_2$;
$R^{10N}$ is H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl; and
each $R^{11}$ is independently selected from H, D, $C_{1-6}$ alkyl, $C_{1-6}$ haloalkyl, $C_{2-6}$ alkenyl, and $C_{2-6}$ alkynyl.

22. The method of claim 1, wherein:
$R^1$ is selected from $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, $NR^{c1}C(O)NR^{c1}R^{d1}$ and 5-6 membered heteroaryl, wherein the $C_{1-6}$ alkyl, and 5-6 membered heteroaryl are each optionally substituted with 1 or 2 independently selected $R^{1A}$ substituents;
each $R^{a1}$, $R^{b1}$, $R^{c1}$, and $R^{d1}$ is independently selected from H, $C_{1-6}$ alkyl, $C_{1-6}$ haloalkyl, $C_{3-6}$ cycloalkyl, and 4-6 membered heterocycloalkyl wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{1A}$ substituents;
or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;
each $R^{1A}$ is independently selected from halo, $C_{1-6}$ alkyl, and OH;
$X^2$ is $CR^2$;
$R^2$ is selected from H, D, and $C_{1-6}$ alkyl;
$R^3$ is selected from H, D, and $C_{1-6}$ alkyl;
$R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 $R^{6A}$ substituents independently selected from halo, OH, and $C_{1-6}$ haloalkyl;
$R^{a6}$ and $R^{b6}$ are selected from H, $C_{1-6}$ alkyl, $C_{1-6}$ haloalkyl, $C_{2-6}$ alkenyl, and $C_{2-6}$ alkynyl;
$X^9$ is $C(O)$;
$X^{11}$ is $C(R^{11})_2$;
$R^{10N}$ is H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl; and
each $R^{11}$ is independently selected from H, D, $C_{1-6}$ alkyl, $C_{1-6}$ haloalkyl, $C_{2-6}$ alkenyl, and $C_{2-6}$ alkynyl.

23. The method of claim 1, wherein:
$R^1$ is selected from H, $C_{1-6}$ alkyl, $C_{1-6}$ haloalkyl, $C(O)R^{b1}$, $C(O)NR^{c1}R^{d1}$, $NR^{c1}C(O)R^{b1}$, $NR^{c1}C(O)OR^{a1}$, $NR^{c1}C(O)NR^{c1}R^{d1}$ and 5-6 membered heteroaryl, wherein the $C_{1-6}$ alkyl, and 5-6 membered heteroaryl are each optionally substituted with 1 or 2 independently selected $R^{1A}$ substituents;
each $R^{a1}$, $R^{b1}$, $R^{c1}$, and $R^{d1}$ is independently selected from H, $C_{1-6}$ alkyl, $C_{1-6}$ haloalkyl, $C_{3-6}$ cycloalkyl, and 4-6 membered heterocycloalkyl wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{1A}$ substituents;
or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;

each $R^{1A}$ is independently selected from halo, $C_{1-6}$ alkyl, and OH;

$X^2$ is N or CH;

$R^3$ is selected from H, D, and $C_{1-6}$ alkyl;

$R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 $R^{6A}$ substituents independently selected from halo, OH, and $C_{1-6}$ haloalkyl;

$R^{a6}$ and $R^{b6}$ are selected from H, $C_{1-6}$ alkyl, $C_{1-6}$ haloalkyl, $C_{2-6}$ alkenyl, and $C_{2-6}$ alkynyl;

$X^9$ is C(O);

$X^{11}$ is $C(R^{11})_2$;

$R^{10N}$ is H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl; and each $R^{11}$ is independently selected from H, D, $C_{1-6}$ alkyl, $C_{1-6}$ haloalkyl, $C_{2-6}$ alkenyl, and $C_{2-6}$ alkynyl.

24. The method of claim 1, wherein:

$R^1$ is selected from H, $C_{1-6}$ alkyl, $C_{1-6}$ haloalkyl, $C(O)R^{b1}$, $C(O)NR^{c1}R^{d1}$, and 5-6 membered heteroaryl, wherein the $C_{1-6}$ alkyl, and 5-6 membered heteroaryl are each optionally substituted with 1 or 2 independently selected $R^{1A}$ substituents;

each $R^{a1}$, $R^{b1}$, $R^{c1}$, and $R^{d1}$ is independently selected from H, $C_{1-6}$ alkyl, $C_{1-6}$ haloalkyl, $C_{3-6}$ cycloalkyl, and 4-6 membered heterocycloalkyl wherein the $C_{1-6}$ alkyl, $C_{3-6}$ cycloalkyl, and 4-6 membered heterocycloalkyl of $R^{c1}$ and $R^{d1}$ are each optionally substituted with 1 or 2 independently selected $R^{1A}$ substituents;

or any $R^{c1}$ and $R^{d1}$, attached to the same N atom, together with the N atom to which they are attached, form a 4-6 membered heterocycloalkyl group, wherein the 4-6 membered heterocycloalkyl group is optionally substituted with 1 or 2 independently selected $R^{1A}$ substituents;

each $R^{1A}$ is independently selected from halo, $C_{1-6}$ alkyl, and OH;

$X^2$ is N or CH;

$R^3$ is H;

$R^6$ is selected from H, halo, $C_{1-6}$ alkyl, $SR^{a6}$, $C(O)R^{b6}$, $S(O)R^{b6}$, and $S(O)_2R^{b6}$, wherein the $C_{1-6}$ alkyl is optionally substituted by 1, 2 or 3 $R^{6A}$ substituents independently selected from halo, OH, and $C_{1-6}$ haloalkyl;

$R^{a6}$ and $R^{b6}$ are selected from H, $C_{1-6}$ alkyl, $C_{1-6}$ haloalkyl, $C_{2-6}$ alkenyl, and $C_{2-6}$ alkynyl;

$X^9$ is C(O);

$X^{11}$ is $CH_2$;

$R^{10N}$ is H, $C_{1-6}$ alkyl, phenyl-$C_{1-6}$ alkyl-, and $C_{3-6}$ cycloalkyl-$C_{1-6}$ alkyl-, wherein the $C_{1-6}$ alkyl, phenyl-$C_{1-6}$ alkyl-, and $C_{3-6}$ cycloalkyl-$C_{1-6}$ alkyl- are each optionally substituted with 1 or 2 $R^{10NA}$ substituents independently selected from phenyl, $C_{3-7}$ cycloalkyl, $OR^{a10N2}$, $NR^{c10N2}R^{d10N2}$, $C(O)NR^{c10N2}R^{d10N2}$, $C(O)OR^{a10N2}$, $NR^{c10N2}C(O)R^{b10N2}$, $NR^{c10N2}C(O)OR^{a10N2}$, and $NR^{c10N2}S(O)_2R^{b10N2}$, wherein each $R^{a10N2}$, $R^{b10N2}$, $R^{c10N2}$, and $R^{d10N2}$ is independently selected from H and $C_{1-6}$ alkyl.

25. The method of claim 1, wherein the compound of Formula (IIu) is selected from:
- (S)-5-(8-amino-6-(trifluoromethyl)imidazo[1,2-a]pyrazin-3-yl)-7-chloro-2-(1-cyclopropylethyl)isoindolin-1-one;
- (S)-5-(8-amino-6-(trifluoromethyl)imidazo[1,2-a]pyrazin-3-yl)-2-(1-cyclopropylethyl)-7-(methylthio)isoindolin-1-one;
- (S)-5-(8-amino-6-(trifluoromethyl)imidazo[1,2-a]pyrazin-3-yl)-2-(1-cyclopropylethyl)-7-(methylsulfonyl)isoindolin-1-one;
- 5-(8-amino-6-(trifluoromethyl)imidazo[1,2-a]pyrazin-3-yl)isoindolin-1-one;
- (S)-5-(8-amino-6-(trifluoromethyl)imidazo[1,2-a]pyrazin-3-yl)-2-(1-cyclopropylethyl)isoindolin-1-one;
- (S)-5-(4-aminoimidazo[2,1-f][1,2,4]triazin-7-yl)-2-(1-cyclopropylethyl)isoindolin-1-one;
- (S)-5-(4-aminoimidazo[2,1-f][1,2,4]triazin-7-yl)-7-chloro-2-(1-cyclopropylethyl)isoindolin-1-one;
- (S)-5-(4-aminoimidazo[2,1-f][1,2,4]triazin-7-yl)-2-(1-cyclopropylethyl)-7-(methylsulfonyl)isoindolin-1-one;
- 5-(8-amino-6-(trifluoromethyl)imidazo[1,2-a]pyrazin-3-yl)-2-ethylisoindolin-1-one;
- 5-(4-aminoimidazo[2,1-f][1,2,4]triazin-7-yl)-2-ethylisoindolin-1-one;
- 5-(8-amino-6-(trifluoromethyl)imidazo[1,2-a]pyrazin-3-yl)-2-(1-phenylethyl)isoindolin-1-one;
- 5-(4-aminoimidazo[2,1-f][1,2,4]triazin-7-yl)-2-(1-phenylethyl)isoindolin-1-one;
- 5-(8-amino-6-(trifluoromethyl)imidazo[1,2-a]pyrazin-3-yl)-2-isopropylisoindolin-1-one;
- 5-(4-aminoimidazo[2,1-f][1,2,4]triazin-7-yl)-2-isopropylisoindolin-1-one;
- (S)-7-acetyl-5-(4-aminoimidazo[2,1-f][1,2,4]triazin-7-yl)-2-(1-cyclopropylethyl)isoindolin-1-one;
- 5-(4-aminoimidazo[2,1-f][1,2,4]triazin-7-yl)-2-((S)-1-cyclopropylethyl)-7-(1-hydroxyethyl)isoindolin-1-one;
- (S)-5-(4-aminoimidazo[2,1-f][1,2,4]triazin-7-yl)-2-(1-cyclopropylethyl)-7-(2-hydroxypropan-2-yl)isoindolin-1-one;
- (S)-8-Amino-3-(2-(1-cyclopropylethyl)-7-(methylsulfonyl)-1-oxoisoindolin-5-yl)-N-isopropylimidazo[1,2-a]pyrazine-6-carboxamide; and
- (S)-8-Amino-3-(2-(1-cyclopropylethyl)-7-(methylsulfonyl)-1-oxoisoindolin-5-yl)-N-(tetrahydro-2H-pyran-4-yl)imidazo[1,2-a]pyrazine-6-carboxamide;

or a pharmaceutically acceptable salt thereof.

26. The method of claim 1, wherein the compound of Formula (IIu) is selected from:
- (S)-5-(8-Amino-6-(azetidine-1-carbonyl)imidazo[1,2-a]pyrazin-3-yl)-2-(1-cyclopropylethyl)-7-(methylsulfonyl)isoindolin-1-one;
- (S)-8-Amino-N-(bicyclo[1.1.1]pentan-1-yl)-3-(2-(1-cyclopropylethyl)-7-(methylsulfonyl)-1-oxoisoindolin-5-yl)imidazo[1,2-a]pyrazine-6-carboxamide;
- (S)-5-(8-Amino-6-(3,3-dimethylazetidine-1-carbonyl)imidazo[1,2-a]pyrazin-3-yl)-2-(1-cyclopropylethyl)-7-(methylsulfonyl)isoindolin-1-one;
- (S)-5-(8-Amino-6-(3,3-difluoroazetidine-1-carbonyl)imidazo[1,2-a]pyrazin-3-yl)-2-(1-cyclopropylethyl)-7-(methylsulfonyl)isoindolin-1-one;
- (S)-5-(8-Amino-6-(3-hydroxyazetidine-1-carbonyl)imidazo[1,2-a]pyrazin-3-yl)-2-(1-cyclopropylethyl)isoindolin-1-one;

(S)-8-Amino-3-(2-(1-cyclopropylethyl)-1-oxoisoindolin-5-yl)-N-(3-hydroxycyclobutyl)imidazo[1,2-a]pyrazine-6-carboxamide;
8-Amino-3-(2-((S)-1-cyclopropylethyl)-1-oxoisoindolin-5-yl)-N-(3-hydroxytetrahydro-2H-pyran-4-yl)imidazo[1,2-a]pyrazine-6-carboxamide;
(S)-5-(8-Amino-6-(2-methyloxazol-5-yl)imidazo[1,2-a]pyrazin-3-yl)-2-(1-cyclopropylethyl)-7-(methylsulfonyl)isoindolin-1-one;
(S)-5-(8-Amino-6-(2-methylthiazol-5-yl)imidazo[1,2-a]pyrazin-3-yl)-2-(1-cyclopropylethyl)-7-(methylsulfonyl)isoindolin-1-one;
(S)-5-(8-Amino-6-(1-methyl-1H-pyrazol-4-yl)imidazo[1,2-a]pyrazin-3-yl)-2-(1-cyclopropylethyl)-7-(methylsulfonyl)isoindolin-1-one;
(S)-5-(8-Amino-6-(1-methyl-1H-pyrazol-5-yl)imidazo[1,2-a]pyrazin-3-yl)-2-(1-cyclopropylethyl)-7-(methylsulfonyl)isoindolin-1-one;
(S)-5-(8-Amino-6-(5-methyl-1H-pyrazol-4-yl)imidazo[1,2-a]pyrazin-3-yl)-2-(1-cyclopropylethyl)-7-(methylsulfonyl)isoindolin-1-one;
(S)-5-(8-Amino-6-(1H-pyrazol-4-yl)imidazo[1,2-a]pyrazin-3-yl)-2-(1-cyclopropylethyl)-7-(methylsulfonyl)isoindolin-1-one;
5-(4-Aminoimidazo[2,1-f][1,2,4]triazin-7-yl)-2-((S)-1-cyclopropylethyl)-7-(1,1,1-trifluoro-2,3-dihydroxypropan-2-yl)isoindolin-1-one;
5-(8-Amino-6-(trifluoromethyl)imidazo[1,2-a]pyrazin-3-yl)-2-((S)-1-cyclopropylethyl)-7-(1,1,1-trifluoro-2,3-dihydroxypropan-2-yl)isoindolin-1-one;
tert-Butyl (2-(5-(8-amino-6-(trifluoromethyl)imidazo[1,2-a]pyrazin-3-yl)-1-oxoisoindolin-2-yl)-2-cyclopropylethyl)carbamate;
2-(2-Amino-1-cyclopropylethyl)-5-(8-amino-6-(trifluoromethyl)imidazo[1,2-a]pyrazin-3-yl)isoindolin-1-one;
N-(2-(5-(8-Amino-6-(trifluoromethyl)imidazo[1,2-a]pyrazin-3-yl)-1-oxoisoindolin-2-yl)-2-cyclopropylethyl)methanesulfonamide;
N-(2-(5-(8-Amino-6-(trifluoromethyl)imidazo[1,2-a]pyrazin-3-yl)-1-oxoisoindolin-2-yl)-2-cyclopropylethyl)acetamide;
2-(5-(8-Amino-6-(trifluoromethyl)imidazo[1,2-a]pyrazin-3-yl)-1-oxoisoindolin-2-yl)-2-cyclopropyl-N-methylacetamide;
5-(8-Amino-6-(trifluoromethyl)imidazo[1,2-a]pyrazin-3-yl)-2-(1-cyclopropyl-2-hydroxyethyl)isoindolin-1-one; and
2-(5-(8-Amino-6-(trifluoromethyl)imidazo[1,2-a]pyrazin-3-yl)-1-oxoisoindolin-2-yl)-2-cyclopropylacetic acid;
or a pharmaceutically acceptable salt thereof.

27. A method of treating a disease or disorder in a patient, wherein said disease or disorder is associated with abnormal expression or activity of PI3Kγ kinase, wherein the disease or disorder is lung cancer, melanoma, pancreatic cancer, breast cancer, prostate cancer, liver cancer, colon cancer, endometrial cancer, bladder cancer, skin cancer, cancer of the uterus, renal cancer, gastric cancer, seminoma, teratocarcinoma, astrocytoma, neuroblastoma, glioma, sarcoma, acute myeloid leukemia, acute monocytic leukemia, small lymphocytic lymphoma, chronic lymphocytic leukemia (CLL), chronic myelogenous leukemia (CML), multiple myeloma, T-cell acute lymphoblastic leukemia (T-ALL), cutaneous T-cell lymphoma, large granular lymphocytic leukemia, mature (peripheral) t-cell neoplasm (PTCL), anaplastic large cell lymphoma (ALCL), lymphoblastic lymphoma, Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xeroderma pigmentosum, keratoacanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smoldering myeloma (aka asymptomatic myeloma), monoclonal gammopathy of undetermined significance (MGUS), diffuse large B cell lymphoma, rheumatoid arthritis, multiple sclerosis, systemic lupus erythematous, asthma, allergy, allergic rhinitis, pancreatitis, psoriasis, anaphylaxis, glomerulonephritis, inflammatory bowel disease, thrombosis, meningitis, encephalitis, diabetic retinopathy, benign prostatic hypertrophy, myasthenia gravis, Sjögren's syndrome, osteoarthritis, restenosis, atherosclerosis, autoimmune hemolytic anemia, systemic lupus erythematosus, lupus nephritis, or pemphigus, the method comprising administering to said patient a therapeutically effective amount of a compound selected from:
7-(2-(1-Cyclopropylethyl)-7-methyl-2H-indazol-5-yl)imidazo[2,1-f][1,2,4]triazin-4-amine;
7-(1-(1-Cyclopropylethyl)-7-methyl-1H-indazol-5-yl)imidazo[2,1-f][1,2,4]triazin-4-amine;
7-(2-(1-cyclopropylethyl)-2H-benzo[d][1,2,3]triazol-5-yl)imidazo[2,1-f][1,2,4]triazin-4-amine;
7-(2-Isopropyl-[1,2,4]triazolo[1,5-a]pyridin-6-yl)imidazo[2,1-f][1,2,4]triazin-4-amine;
7-(2-isopropylimidazo[1,2-a]pyridin-6-yl)imidazo[2,1-f][1,2,4]triazin-4-amine;
7-(2-Isopropylpyrazolo[1,5-a]pyridin-5-yl)imidazo[2,1-f][1,2,4]triazin-4-amine;
7-(2-Isopropylpyrazolo[1,5-a]pyrimidin-5-yl)imidazo[2,1-f][1,2,4]triazin-4-amine;
7-(2-(1-Cyclopropylethyl)-2H-pyrazolo[3,4-b]pyridin-5-yl)imidazo[2,1-f][1,2,4]triazin-4-amine;
7-(2-(1-Cyclopropylethyl)-2H-pyrazolo[3,4-c]pyridin-5-yl)imidazo[2,1-f][1,2,4]triazin-4-amine; and
7-(2-(1-Cyclopropylethyl)imidazo[1,2-a]pyridin-6-yl)imidazo[2,1-f][1,2,4]triazin-4-amine;
or a pharmaceutically acceptable salt thereof.

28. The method of claim 1, wherein the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

29. The method of claim 1, wherein the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, anaplastic large cell lymphoma (T-cell type), enteropathy type T-cell lymphoma, adult T-cell leukemia/lymphoma, or angioimmunoblastic T-cell lymphoma.

30. The method of claim 1, wherein the anaplastic large cell lymphoma (ALCL) is systemic ALCL or primary cutaneous ALCL.

31. The method of claim 1, wherein the non-Hodgkin's lymphoma (NHL) is relapsed NHL, refractory NHL, recurrent follicular NHL, indolent NHL (iNHL), or aggressive NHL (aNHL).

32. The method of claim 1, wherein the diffuse large B cell lymphoma is activated B-cell like (ABC) diffuse large B cell lymphoma, or germinal center B cell (GCB) diffuse large B cell lymphoma.

33. The method of claim 1, wherein the Burkitt's lymphoma is endemic Burkitt's lymphoma, sporadic Burkitt's lymphoma, or Burkitt's-like lymphoma.

* * * * *